US007211601B2

(12) United States Patent
Halazy et al.

(10) Patent No.: US 7,211,601 B2
(45) Date of Patent: May 1, 2007

(54) PHARMACEUTICALLY ACTIVE PYRROLIDINE DERIVATIVES

(75) Inventors: Serge Halazy, Vétraz-Monthoux (FR); Anna Quattropani, Geneva (CH); Alexander Scheer, Versoix (CH); Matthias Schwarz, Geneva (CH); Russell J Thomas, Siena (IT); Anthony Baxter, Much Hadham (GB)

(73) Assignee: Applied Research Systems Ars Holding N.V., Curacao (AN)

( * ) Notice: Subject to any disclaimer, the term of this patent is extended or adjusted under 35 U.S.C. 154(b) by 394 days.

(21) Appl. No.: 10/239,912

(22) PCT Filed: Mar. 20, 2001

(86) PCT No.: PCT/EP01/03171

§ 371 (c)(1),
(2), (4) Date: Feb. 10, 2003

(87) PCT Pub. No.: WO01/72705

PCT Pub. Date: Oct. 4, 2001

(65) Prior Publication Data

US 2003/0212012 A1 Nov. 13, 2003

(30) Foreign Application Priority Data

Mar. 27, 2000 (EP) ................................. 00106034

(51) Int. Cl.
*A61K 31/40* (2006.01)
*C07D 207/10* (2006.01)
*C07D 207/14* (2006.01)

(52) U.S. Cl. ....................... 514/423; 548/536; 548/537

(58) Field of Classification Search ..................... None
See application file for complete search history.

(56) References Cited

U.S. PATENT DOCUMENTS

| | | | | |
|---|---|---|---|---|
| 3,555,007 | A | 1/1971 | Magerlein | |
| 3,674,647 | A | 7/1972 | Visser | |
| 5,756,497 | A | 5/1998 | Bell et al. | |
| 6,476,026 | B1 * | 11/2002 | Bryant et al. ............ | 514/235.8 |

FOREIGN PATENT DOCUMENTS

| | | |
|---|---|---|
| GB | 1118306 | 6/1968 |
| WO | WO 95/04718 | 2/1995 |
| WO | WO 96/22775 | 8/1996 |
| WO | WO 99/52868 | 10/1999 |
| WO | WO 00/08015 | 2/2000 |

OTHER PUBLICATIONS

Bryant et al., STN International (2005), CAPLUS Database, Columbus, OH, Accession No. 2000:666701, Registry No. 294621-30-0.*

Bryant et al., STN International (2005), CAPLUS Database, Columbus, OH, Accession No. 2000:666701).*

Sufrin et al. "Synthetic Approaches to Peptide Analogs Containing 4, 4-Difluoro-L-Proline and 4-Keto-L-Proline and4-L-proline." *Int. J. Pept. Protein Res.* (1982), 20(5), 438-42.

(Continued)

*Primary Examiner*—Kamal A. Saeed
*Assistant Examiner*—Andrew B. Freistein
(74) *Attorney, Agent, or Firm*—Browdy and Neimark, PLLC

(57) ABSTRACT

The present invention is related to pyrrolidine derivatives of formula (I). Said (I)

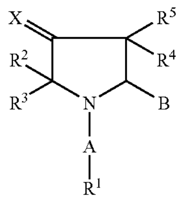

(a)

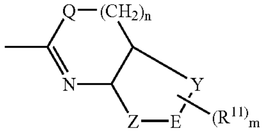

compounds are preferably for use as pharmaceutically active compounds. Specifically, pyrrolidine derivatives of formula (I) are useful in the treatment and/or prevention of premature labor, premature birth and dysmenorrhea. In particular, the present invention is related to pyrrolidine derivatives displaying a substantial modulatory, notably an antagonist activity of the oxytocin receptor. More preferably, said compounds are useful in the treatment and/or prevention of disease states mediated by oxytocin, including premature labor, premature birth and dysmenorrhea. The present invention is furthermore related to novel pyrrolidine derivatives as well as to methods of their preparation, wherein X is selected from the group consisting of CR6R7, NOR6, NNR6R7; A is selected from the group consisting of —(C═O)—, —(C═O)—O—, —C(═NH)—, —(C═O)—NH—, —(C═S)—NH, —SO22-, —SO2NH—, —CH2-, B is either a group —(C═O)—NR8R9 or represents a heterocyclic residue having the formula (a) wherein Q is NR10, O or S; n is an integer selected of 0, 1 or 2; Y, Z and E form together with the 2 carbons to which they are attached a 5–6 membered aryl or heteroaryl ring.

21 Claims, No Drawings

OTHER PUBLICATIONS

Komai et al. "Structure-activity Relationships of HIV-1 PR Inhibitors Containing AHPBA-II. Modification of Pyrrolidine Ring at P1' Proline" *Bioorg. Med. Chem.* (1996), 4(8), 1365-1377.

Narukawa et al. "General and Efficient Synthesis of 2-Alkylcarbapenems: Synthesis of Dethiacarba Analogs of Clinically Useful Carbapenems *via* Palladium-Catalyzed Cross-Coupling Reaction" *Tetrahedron* 1(1997) 53(2): 539-556.

Nicolaides et al. "Modified Di- and Tripeptides of the C-Terminal Portion of Oxytocini and Vasopressin as Possible Cognition Activation Agents" *Journal of Medicinal Chemistry, American Chemical Society* (1986) 29(6) 959-971.

Adlington et al. "A radical Route to 2(*S*)-4-Exomethylene Proline" *Tetrahedron* (1992) 48(31): 6529-6536.

Holmes et al. "The Design and Synthesis of Novel Hydroxyproline Inhibitors of HIV-1 Proteinase" *Bioorganic & Medical Chemistry Letters* (1993) 3(8): 1485-1491.

Maggi et al. "Human Myometrium during Pregnancy Contains and Responds to V1 Vasopressin Receptors as well as Oxytocin Receptors" *Journal of Clinical Endocrinology and Metabolism* (1990) 70(4): 1142-1154.

Evans et al. "Orally Active, Nonpeptide Oxytocin Antagonists" *J. Med. Chem.* (1992) 35: 3919-3927.

Pedersen et al. "Studies on Organophosphorus Compunds XX. Syntheses of Thioketones" *Bull. Soc., Chim. Belg.* vol. 87, No. 3, 1978.

* cited by examiner

PHARMACEUTICALLY ACTIVE PYRROLIDINE DERIVATIVES

This is a National filing under 35 U.S.C. § 371 of PCT/EP01/03171, filed Mar. 20, 2001.

FIELD OF THE INVENTION

The present invention is related to pyrrolidine derivatives. Said compounds are preferably for use as pharmaceutically active compounds. Specifically, pyrrolidine derivatives of formula I are useful in the treatment and/or prevention of premature labor, premature birth and dysmenorrhea. In particular, the present invention is related to pyrrolidine derivatives displaying a substantial modultatory notably an antagonist activity of the oxytocin eceptor. More preferably, said compounds are usefull in the treatment and/or prevention of disease states mediated by oxytocin, including premature labor, premature birth and dysmenorrhea. The present invention is furthermore related to novel pyrrolidine derivatives as well as to methods of their preparation.

BACKGROUND OF THE INVENTION

Oxytocin (OT) is a peptide hormone and causes the contraction of the uterus of mammals during labor. The corresponding Oxytocin receptor belongs to the family of G-protein-coupled receptors and is similar to $V_{1a}$ and $V_2$ vasopressin receptors. OT receptors increase dramatically during the course of pregnancy. The concentration of OT receptors has been shown to correlate with spontaneous uterine activity (M. Maggi et al. *J. Clin. Endocrinol Metabol;* 70; 1142, 1990). Premature labor, though, and premature birth is undesired as it represents a major cause of perinatal morbidity and mortality. Hence, the management of preterm labor represents a significant problem in the field of obstetrics.

In recent years, strong evidence has accumulated indicating that the hormone oxytocin plays a major role in initiating labor in mammals, notably in humans. Thereby, it is assumed that oxytocin exerts said effect in a direct as well as an indirect way, by contracting the uterine myometrium and by enhancing the synthesis and release of contractile prostaglandins from the uterine endometrium/decidua. These prostaglandins may furthermore play a role in the cervical ripening process. This "up-regulation" of oxytocin receptors and increased uterine sensitivity seems to be due to trophic effects of rising plasma levels of estrogen towards term. By down-regulating oxytocin, it is expected that both the direct (contractile) and indirect (increased prostaglandin synthesis) effects of oxytocin on the uterine could be blocked. An oxytocin modulator, e.g. blocker or antagonists would likely be more efficacious for treating preterm labor than current regimens. Moreover, as oxytocin at term has only an effect on the uterus, such an oxytocin modulator would have only few or no side effect.

A further condition being related to oxytocin is dysmenorrhea, which is characterised by cyclic pain associated with menses during ovulatory cycles. Said pain is believed to result from uterine contractions and ischemia, probably mediated by the effect of prostaglandins produced in the secretory endometrium. By blocking both the indirect and direct effects of oxytocin on the uterus, an oxytocin antagonost is believed more efficacious for treating dysmenorrhea than current regimens.

Some agents counteracting the action of Oxytocin (OT) are currently used in clinical studies. Such tocolytic agents (i.e. uterine-relaxing agents) include beta-2-adrenergic agonists, magnesium sulfate and ethanol. The leading beta-2-adrenergic agonists is Ritodrine, which causes a number of cardiovascular and metabolic side effects, including tachycardia, increased renin secretion, hyperglycemia and reactive hypoglycemia in the infant. Further beta-32-adrenergic agonists, including terbutaline and albuterol have side effects similar to those of ritodrine. Magnesium sulfate at plasma concentrations above the therapeutic range of 4 to 8 mg/dL can cause inhibition of cardiac conduction and neuromuscular transmission, respiratory depression and cardiac arrest, thus making this agent unsuitable when renal function is impaired. Ethanol is as effective as ritodrine in preventing premature labor, but it does not produce a corresponding reduction in the incidence of fetal respiratory distress that administration of ritodrine does.

The principal drawback to the use of peptide antagonists including also atosiban is the problem of low oral bioavailability resulting from intestinal degradation. Hence, they must be administered parenterally.

The development of non-peptide ligands for pepetide hormone receptors are expected to overcome this problem. The first to report small molecule selective oxytocin antagonists was Merck. Apart from cyclic hexapeptides, Merck suggested indanylpiperidines and tolylpiperazines as orally deliverable OT antagonists (Evans et al. *J. Med. Chem.,* 35, 3919 (1992). In WO 96/22775 and U.S. Pat. No. 5,756,497 Merck reported benzoxazinylpiperidines or benzoxazinones as OT receptor antagonists.

It is a purpose of this invention to provide substances which more effectively down-regulate—up to antagonizing—the function of OT in disease states in animals, preferably mammals, especially in humans. It is another purpose of this invention to provide a method of antagonizing the functions of oxytocin in disease states of mammals. It is also an objective of the present invention to provide small molecule chemical compounds for the modulation, preferably the down-regulation or even antagonisation of the Oxytocin receptor. Moreover, it is an objective of the present invention to provide methods for preparing said small molecule chemical compounds. It is furthermore an objective of the present invention to provide a new category of pharmaceutical formulations for the treatment of preterm labor and dysmenorrhea, and/or diseases mediated by the Oxytocin receptor. It is finally an objective of the present invention to provide a method of treating or prevent disorders mediated by the Oxytocin receptor, like preterm labor and dysmenorrhea by antagonising the binding of Oxytocin to its receptor.

DESCRIPTION OF THE INVENTION

The aforementioned objectives have been met according to the independent claims. Preferred embodiments are set out within the dependent claims which are incorporated herewith.

The following paragraphs provide definitions of the various chemical moieties that make up the compounds according to the invention and are intended to apply uniformly through-out the specification and claims unless an otherwise expressly set out definition provides a broader definition.

"$C_1$–$C_6$-alkyl" refers to monovalent alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g.

phenyl) or multiple condensed rings (e.g. naphthyl). Preferred aryl include phenyl, naphthyl, phenantrenyl and the like.

"$C_1$–$C_6$-alkyl aryl" refers to $C_1$–$C_6$-alkyl groups having an aryl substituent, including benzyl, phenethyl and the like.

"Heteroaryl" refers to a monocyclic heteromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl,1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrehydroisoquinolyl, purinyl, pteridinyl, carbazolyl, xanthenyl or benzoquinolyl.

"$C_1$–$C_6$-alkyl heteroaryl" refers to $C_1$–$C_6$-alkyl groups having a heteroaryl substituent, including 2-furylmethyl, 2-thienylmethyl, 2-(1H-indol-3-yl)ethyl and the like.

"Alkenyl" refers to alkenyl groups preferably having from 2 to 6 carbon atoms and having at least 1 or 2 sites of alkenyl unsaturation. Preferable alkenyl groups include ethenyl ($—CH{=}CH_2$), n-2-propenyl (allyl, $—CH_2CH{=}CH_2$) and the like.

"Alkynyl" refers to alkynyl groups preferably having from 2 to 6 carbon atoms and having at least 1–2 sites of alkynyl unsaturation, preferred alkynyl groups include ethynyl ($—C{\equiv}CH$), propargyl ($—CH_2C{\equiv}CH$), and the like.

"Acyl" refers to the group —C(O)R where R includes "$C_1$–$C_6$-alkyl", "aryl", "heteroaryl", "$C_1$–$C_6$-alkyl aryl" or "$C_1$–$C_6$-alkyl heteroaryl".

"Acyloxy" refers to the group —OC(O)R where R includes "$C_1$–$C_6$-alkyl", "aryl", "heteroaryl", "$C_1$–$C_6$-alkyl aryl" or "$C_1$–$C_6$-alkyl heteroaryl".

"Alkoxy" refers to the group —O—R where R includes "$C_1$–$C_6$-alkyl" or "aryl" or "heteroaryl" or "$C_1$–$C_6$-alkyl aryl" or "$C_1$–$C_6$-alkyl heteroaryl". Preferred alkoxy groups include by way of example, methoxy, ethoxy, phenoxy and the like.

"Alkoxycarbonyl" refers to the group —C(O)OR where R includes "$C_1$–$C_6$-alkyl" or "aryl" or "heteroaryl" or "$C_1$–$C_6$-alkyl aryl" or "$C_1$–$C_6$-alkyl heteroaryl".

"Aminocarbonyl" refers to the group —C(O)NRR' where each R, R' includes independently hydrogen or $C_1$–$C_6$-alkyl or aryl or heteroaryl or "$C_1$–$C_6$-alkyl aryl" or "$C_1$–$C_6$-alkyl heteroaryl".

"Acylamino" refers to the group —NR(CO)R' where each R, R' is independently hydrogen or "$C_1$–$C_6$-alkyl" or "aryl" or "heteroaryl" or "$C_1$–$C_6$-alkyl aryl" or "$C_1$–$C_6$-alkyl heteroaryl".

"Halogen" refers to fluoro, chloro, bromo and iodo atoms.

"Sulfonyl" refers to group "$—SO_2—R$" wherein R is selected from H, "aryl", "heteroaryl", "$C_1$–$C_6$-alkyl", "$C_1$–$C_6$-alkyl" substituted with halogens e.g. an $—SO_2—CF_3$ group, "$C_1$–$C_6$-alkyl aryl" or "$C_1$–$C_6$-alkyl heteroaryl".

"Sulfoxy" refers to a group "—S(O)—R" wherein R is selected from H, "$C_1$–$C_6$-alkyl", "$C_1$–$C_6$-alkyl" substituted with halogens e.g. an $—SO—CF_3$ group, "aryl", "heteroaryl", "$C_1$–$C_6$-alkyl aryl" or "$C_1$–$C_6$-alkyl heteroaryl".

"Thioalkoxy" refers to groups —S—R where R includes "$C_1$–$C_6$-alkyl" or "aryl" or "heteroaryl" or "$C_1$–$C_6$-alkyl aryl" or "$C_1$–$C_6$-alkyl heteroaryl". Preferred thioalkoxy groups include thiometioxy, thioethoxy, and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$–$C_6$-alkyl", "$C_1$–$C_6$-alkyl aryl", "$C_1$–$C_6$-alkyl heteroaryl", "$C_2$–$C_6$-alkenyl", "$C_2$–$C_6$-alkynyl", primary, secondary or tertiary amino groups or quaternary ammonium moieties "acyl", "acyloxy", "acylamino", "aminocarbonyl", "alkoxycarbonyl", "aryl", "heteroaryl", carboxyl, cyano, halogen, bydroxy, mercapto, nitro, sulfoxy, sulfonyl, alkoxy, thioalkoxy, trihalomethyl and the like. Alternatively said substitution could also comprise situations where neighboring substituents have undergone ring closure, notably when viccinal functional substituents are involved, thus forming e.g. lactams, lactons, cyclic anhydrides, but also acetals, thioacetals, aminals formed by ring closure for instance in an effort to obtain a protective group.

"Pharmaceutically acceptable salts or complexes" refers to salts or complexes of the below-identified compounds of formula I that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and polygalacturonic acid. Said compounds can also be administered as pharmaceutically acceptable quaternary salts known by a person skilled in the art, which specifically include the quaternary ammonium salt of the formula $—NR,R',R''^{+}Z^{-}$, wherein R, R', R'' is independently hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded. In the absence of an asymmetric synthesis, racemic products are usually obtained that do however also have the inventive set out activity as OT-R antagonists.

Quite surprisingly, it was now found that pyrrolidine derivatives according to formula I are suitable pharmaceutically active agents, by effectively modulating, in particular by effectively inhibiting the OT-R function and more specifically by antagonising the oxytocin receptor. When the oxytocin receptor is bound by the compounds according to formula I, oxytocin is antagonised by being blocked from its receptor and is therefore unable to exert its biologic or pharmacological effects. The compounds of the present invention are therefore in particular useful in the treatment and/or prevention of oxytocin-related disorders of mammals and in particular of humans. These disorders mediated by the oxytocin receptor, are primarily preterm labor and dysmenorrhea.

The compounds according to the present invention are those of formula I.

I

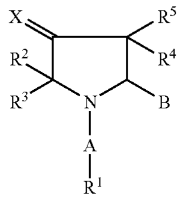

Said formula also comprises its geometrical isomers, its optically active forms as enantiomers, diastereomers and its racemate forms, as well as pharmaceutically acceptable salts thereof. Preferred pharmaceutically acceptable salts of the compound I, are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

In said formula I, X is selected from the group consisting of $CR^6R^7$, $NOR^6$, $NNR^6R^7$.

A is selected from the group consisting of —(C═O)—, —(C═O)—O—, —C(═NH)—,—(C—O)—NH—, —(C═S)—NH, $—SO_2—$, $—SO_2NH—$, $—CH_2—$.

B is either an amido group of the formula —(C═O)—$NR^8R^9$ or B represents a heterocyclic residue having the formula $B^1$

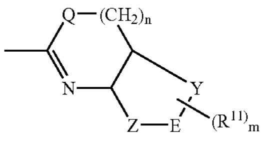

wherein Q is $NR^{10}$, O or S; n is an integer selected of 0, 1 or 2, preferably 0. m is an integer selected of 0, 1, 2 or 3, preferably 0 or 1.

Y, Z and E form together with the 2 carbons to which they are attached a 5–6 membered aryl is or heteroaryl ring.

$R^1$ is selected from the group comprising or consisting of unsubstituted or substituted $C_1$–$C_6$-alkyl, unsubstituted or substituted $C_2$–$C_6$-alkenyl, unsubstituted or substituted $C_2$–$C_6$-alkynyl, unsubstituted or substituted aryl, unsubstituted or substituted heteroaryl, unsubstituted or substituted saturated or unsaturated 3–8-membered cycloalkyl, acyl, unsubstituted or substituted $C_1$–$C_6$-alkyl aryl, unsubstituted or substituted $C_1$–$C_6$-alkyl heteroaryl, said cycloalkyl or aryl or heteroaryl groups may be fused with 1–2 ether cycloalkyl or aryl or heteroaryl group.

$R^2$, $R^3$, $R^4$ and $R^5$ are independently selected from each other from the group consisting of hydrogen, halogen, $C_1$–$C_6$-allyl, $C_1$–$C_6$-alkoxy, preferably they are all hydrogen.

$R^6$ and $R^7$ are independently selected from the group comprising or consisting of hydrogen, unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted alkoxy, unsubstituted or substituted thioalkoxy, halogen, cyano, nitro, acyl, alkoxycarbonyl, aminocarbonyl, unsubstituted or substituted saturated or unsaturated 3–8-membered cycloalkyl which may contain 1 to 3 heteroatoms selected of N, O, S, unsubstituted or substituted aryl, unsubstituted or substituted heteroaryl, unsubstituted or substituted $C_1$–$C_6$-alkyl aryl, unsubstituted or substituted $C_1$–$C_6$-alkyl heteroaryl.

$R^8$, $R^9$ and $R^{10}$ are independently selected from the group comprising or consisting of hydrogen, unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted saturated or unsaturated 3–8-membered cycloalkyl which may contain 1 to 3 heteroatoms selected of N, O, S, unsubstituted or substituted aryl, unsubstituted or substituted heteroaryl.

Alternatively, each pair $R^6$, $R^7$ and/or $R^8$, $R^9$ could form together with the N atom to which they are attached a 3–8 membered substituted or unsubstituted, saturated or unsaturated heterocyclic ring which may contain 1–2 further heteroatoms selected from N, S and O and which is optionally fused with an aryl, heteroaryl or 3–8 membered saturated or unsaturated cycloalkyl ring.

$R^{11}$ is selected from the group comprising or consisting of hydrogen, unsubstituted or substituted $C_1$–$C_6$-alkyl, unsubstituted or substituted alkenyl, unsubstituted or substituted alkynyl, hydroxy, mercapto, alkoxy, thioalkoxy, aryl, heteroaryl, halogen, nitro, cyano, acyl, acyloxy, acylamino, aminocarbonyl, alkoxycarbonyl, sulfonyl, sulfoxy, carboxyl, primary, secondary or tertiary amino groups or quaternary ammonium moieties, unsubstituted or substituted saturated or unsaturated 3–8-membered cycloalkyl.

Preferred pyrrolidine derivatives are those compounds according to formula I wherein B is a group —(C═O)—$NHR^9$, in which $R^9$ is selected from the group consisting of unsubstituted or substituted $C_1$–$C_6$ allyl, unsubstituted or substituted alkenyl, unsubstituted or substituted alkynyl, unsubstituted or substituted saturated or unsaturated 3–6-membered cycloalkyl which optionally contains a N atom, unsubstituted or substituted aryl, unsubstituted or substituted heteroaryl, unsubstituted or substituted $C_1$–$C_2$-alkyl aryl, unsubstituted or substituted $C_1$–$C_2$-alkyl heteroaryl.

Preferred heteroaryls are pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzo-thienyl, 2,1,3-benzothiadiazolyl, 2,1,3-benzoxadiazolyl, benzodioxolyl, indolyl, isoindolyl, 3H-indolyl, benzimidazolyl, imidazo[1,2-a]pyridyl, benzothiazolyl, benzoxazolyl, quinolizinyl, quinazolinyl, phthalazinyl, quinoxalinyl, cinnnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl, acridinyl or benzoquinolyl and whereby said heteroaryl could be fused with a 3–8-membered cycloalkyl containing optionally 1–3 heteroatoms selected from N, O, S.

According to a further preferred embodiment the pyrrolidine derivatives according to the present invention carry a residue $B^1$ which is a fused heterocycle of the formula

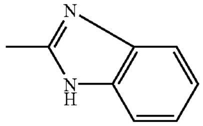

Particularly preferred pyrrolidine derivatives are those compounds according to formula I wherein X is $NOR^6$, and $R^6$ is selected from the group consisting of H, unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted acyl, unsubstituted or substituted aryl, unsubstituted or substituted heteroaryl, unsubstituted or substituted saturated or unsaturated 3–8-membered cycloalkyl, unsubstituted or substituted $C_1$–$C_6$-alkyl aryl, unsubstituted or substituted $C_1$–$C_6$-alkyl heteroaryl, said cycloalkyl or aryl or heteroaryl groups may be fused with 1–2 further cycloalkyl or aryl or heteroaryl groups. Particularly preferred $R^6$ is H, $CH_3$, unsubstituted or substituted $CH_2$-phenyl or allyl.

Under no circumstances B could be a group COOR or a group —(C═O)NR(OR), whereby R is H, alkyl or acyl. Such compounds, notably having a group B=hydroxamic acid are described in WO 99/52868 as being potent inhibitors of metalloproteases.

Further particularly preferred pyrrolidine derivatives are those compounds according to formula I wherein X is $CHR^6$, and $R^6$ is selected from the group consisting of halogen, cyano, unsubstituted or substituted $C_3$–$C_6$ alkyl, unsubstituted or substituted $C_2$–$C_6$ alkenyl, unsubstituted or substituted $C_2$–$C_6$ alkynyl, unsubstituted or substituted alkoxy, unsubstituted or substituted thioalkoxy, nitro, acyl, alkoxycarbonyl, aminocarbonyl, unsubstituted or substituted aryl, unsubstituted or substituted heteroaryl, unsubstituted or substituted saturated or unsaturated 3–8-membered cycloalkyl, unsubstituted or substituted $C_1$–$C_6$-alkyl aryl, unsubstituted or substituted $C_1$–$C_6$-alkyl heteroaryl, said cycloalkyl or aryl or heteroaryl groups may be fused with 1–2 further cycloalkyl or aryl or heteroaryl groups. Particularly preferred $R^6$ is halogen, cyano, $C_1$–$C_6$ alkyl or an unsubstituted or substituted phenyl group.

According to a further preferred embodiment the pyrrolidine derivatives have a substituent A being —(C═O)—, or —(C═O)—NH—, or —$SO_2$—, most preferred is —(C═O)—.

More preferred groups $R^1$ are substituted or unsubstituted $C_1$–$C_6$-alkyl, $C_2$–$C_6$-alkenyl, unsubstituted or substituted $C_2$–$C_6$-alkynyl, aryl, heteroaryl, saturated or unsaturated 3–8-membered cycloalkyl and still more preferred $R^1$ are $C_1$–$C_6$-alkyl or aryl. A particularly preferred substituent $R^1$ is biphenyl.

According to a most preferred embodiment, the pyrrolidine derivatives according to formula I are those wherein X is ═$NOR^6$ or ═CHCl, $R^6$ is a $C_1$–$C_6$-alkyl, e.g. a methyl group, or aryl or $C_1$–$C_6$-alkyl aryl group, A is —(C═O)— and $R^1$ is a $C_1$–$C_6$-alkyl or aryl or $C_1$–$C_6$-alkyl aryl group. Even more preferred are those pyrrolidine derivatives, wherein X is ═$NOR^6$, or ═CHCl, $R^6$ is methyl, B is an amido group of the formula —(C═O)$NHR^9$, wherein $R^9$ is an unsubstituted or substituted $C_1$–$C_6$-alkyl aryl group, e.g. a substituted phenylethyl group, A is —(C═O)— and $R^1$ is a substituted or unsubstituted biphenyl or an acetylmethyl group.

The compounds of formula I may contain one or more asymmetric centers and may therefore exist as enantiomers or diasteroisomers. It is to be understood that the invention includes both mixtures and separate individual isomers or enantiomers of the compounds of formula I. In a particularly preferred embodiment the pyrrolidine derivatives according to formula I are obtained in an enantiomeric excess of at least 52% ee, preferably of at least 92–98% ee. Also E/Z isomers with regard to pyrrolidine derivatives having residues X being ═$CR^6R^7$ whereby both $R^6R^7$ are different from each other, and/or with regard to pyrrolidine derivatives having residues X being ═$NOR^6$ or ═$NNR^6R^7$ are comprised by the present invention.

Specific examples of compounds of formula I include the following:

(2S,4EZ)-1-([1,1'-biphenyl]-4-ylcarbonyl)-N-(2-methoxyethyl)-4-(methoxyimino)-2-pyrrolidinecarboxamide (2S,4EZ)-1-([1,1'-biphenyl]-4-ylcarbonyl)-4-(chloromethylene)-N-[(2S)-2-hydroxy-2-phenethyl]-2-pyrrolidinecarboxamide (2S,4EZ)-1-([1,1'-biphenyl]-4-ylcarbonyl)-N-(2-hydroxyethyl)-4-(methoxyimino)-2-pyrrolidinecarboxamide (2S,4EZ)-1-([1,1'-biphenyl]-4-ylcarbonyl)-N-[(2RS)-2-hydroxy-2-phenethyl]-4-(methoxyimino)-2-pyrrolidinecarboxamide (3EZ,5S)-5-(1H-benzimidazol-2-yl)-1-([1,1'-biphenyl]4-ylcarbonyl)-3-pyrrolidinone O-methyloxime (2S,4EZ)-N-(2,1,3-benzothiadiazol-4-yl)-1-([1,1'-biphenyl]-4-ylcarbonyl)-4-(methoxyimino)-2-pyrrolidinecarboxamide (2S,4EZ)-1-([1,1'-biphenyl]-4-ylcarbonyl)-4-(methoxyimino)-N-(6-quinolinyl)-2-pyrrolidinecarboxamide (2S,4EZ)-1-acetoacetyl-N-benzyl-4-(methoxyimino)-2-pyrrolidinecarboxamide (2S,4EZ)-1-([1,1'-biphenyl]-4-ylcarbonyl)-4-(chloromethylene)-N-(2-furylmethyl)-2-pyrrolidinecarboxamide (2S,4EZ)-1-[(4chlorophenoxy)acetyl]-4-{[(3,4-dichlorobenzyl)oxy]imino}-N-[(2RS)-2-hydroxy-2-phenethyl]-2-pyrrolidinecarboxamide (2S,4EZ)-N-allyl-1-([1,1'-biphenyl]-4-ylcarbonyl)-4-(methoxyimino),2-pyrrolidinecarboxamide (2S,4EZ)-1-([1,1'-biphenyl]-4-ylcarbonyl)-4-(methoxyimino)-N-(2-thienylmethyl)-2-pyrrolidinecarboxamide (2S,4EZ)-4-(cyanomethylene)-N-(2-furylmethyl)-1-[(2-oxo-6-pentyl-2H-pyran-3-yl)carbonyl]-2-pyrrolidinecarboxamide (2S,4EZ)-1-([1,1'-biphenyl]-4-ylcarbonyl)-N-(2-furylmethyl)-4-(methoxyimino)-2-pyrrolidinecarboxamide (2S,4EZ)-1-acetyl-N-cyclopropyl-4-{[(3,4-dichlorobenzyl)oxy]imino}-2-pyrrolidinecarboxamide (2S,4EZ)-N-(2-furylmethyl)-4-(methoxyimino)-1-[(2-oxo-6-pentyl-2H-pyran-3-yl)carbonyl]-2-pyrrolidinecarboxamide (2S,4EZ)-N-benzyl-1-([1,1'-biphenyl]-4-ylcarbonyl)-4-(methoxyimino)-N-methyl-2-pyrrolidinecarboxamide (2S,4EZ)-1-(diphenylacetyl)-4-(methoxyimino)-N-(2-thienylmethyl)-2-pyrrolidinecarbox-amide (2S,4EZ)-N-(2,1,3-benzothiadiazol-4-yl)-4-(cyanomethylene)-1-(diphenylacetyl)-2-pyrrolidinecarboxamide (3EZ,5S)-5-(1H-benzimidazol-2-yl)-1-(diphenylacetyl)-3-pyrrolidinone O-methyloxime (2S)-2-[1-([1,1'-biphenyl]-4-ylcarbonyl)-4methylene-2-pyrrolidinyl]-1H-benzimidazole (2S,4EZ)-1-([1,1'-biphenyl]-4-ylcarbonyl)-4-(chloromethylene)-N-(2-methoxyethyl)-2-pyrrolidinecarboxamide (3EZ,5S)-5-(1H-benzimidazol-2-yl)-1-(diphenylacetyl)-3-pyrrolidinone O-allyloxime (2S,4EZ)-1-([1,1'-biphenyl]-4-ylcarbonyl)-N-[2-(diethylamino)ethyl]-4-(methoxyimino)-2-pyrrolidinecarboxamide
(2S,4EZ)-1-(diphenylacetyl)-4-{[(4-methoxybenzyl)oxy]imino}-N-(2-thienylmethyl)-2-pyrrolidinecarboxamide
(2S,4EZ)-1-([1,1'-biphenyl]-4-ylcarbonyl)-N-(3,4-dimethoxybenzyl)-4-(methoxyimino)-2-pyrrolidinecarboxamide
(2S,4EZ)-1-acetoacetyl-4-(methoxyimino)-N-(1-naphthylmethyl)-2-pyrrolidinecarboxamide
(2S,4EZ)-N-allyl-4-{[(3,4-dichlorobenzyl)oxy]imino}-1-(diphenylacetyl)-2-pyrrolidinecarboxamide
(2S,4EZ)-4-{[(3,4-dichlorobenzyl)oxy]imino}-$N^1$-pentyl-$N^2$-(6-quinolinyl)-1,2-pyrrolidinedicarboxamide
(2S,4EZ)-4-(chloromethylene)-1-(diphenylacetyl)-N-[(2RS)-2-hydroxy-2-phenethyl]-2-pyrrolidinecarboxamide
(2S)-1-([1,1'-biphenyl]-4-ylcarbonyl)-N-[(2RS)-2-hydroxy-2-phenethyl]-4-methylene-2-pyrrolidinecarboxamide
(2S,4EZ)-1-([1,1'-biphenyl]-4-ylcarbonyl)-4-(chloromethylene)-N-(6-quinolinyl)-2-pyrrolidinecarboxamide
(2S,4EZ)-4-benzylidene-N-[2-(diethylamino)ethyl]-1-(diphenylacetyl)-2-pyrrolidinecarboxamide
(2S,4EZ)-1-acetoacetyl-4-(methoxyimino)-N-(2-thienylmethyl)-2-pyrrolidinecarboxamide
(2S,4EZ)-1-acetyl-4-{[(3,4-dichlorobenzyl)oxy]imino}-N-[(2RS)-2-hydroxy-2-phenethyl]-2-pyrrolidinecarboxamide
(2S,4EZ)-4-{[(3,4-dichlorobenzyl)oxy]imino}-$N^1$-(3,5-dichlorophenyl)-$N^2$-(6-quinolinyl)-1,2-pyrrolidinedicarboxamide
(2S,4EZ)-4-(methoxyimino)-N-(1-naphthylmethyl)-1-(phenoxyacetyl)-2-pyrrolidinecarboxamide
(2S,4EZ)-4-(chloromethylene)-N-(3,4-dimethoxybenzyl)-1-[(2-oxo-6-pentyl-2H-pyran-3-yl)carbonyl]-2-pyrrolidinecarboxamide
(2S,4EZ)-1-(diphenylacetyl)-4-(methoxyimino)-N-(2-thienylmethyl)-2-pyrrolidinecarboxamide
(2S,4EZ)-N-benzyl-1-(diphenylacetyl)-4-(methoxyimino)-2-pyrrolidinecarboxamide
(2S,4EZ)-1-([1,1'-biphenyl]-4-ylcarbonyl)-4-{[(3,4-dichlorobenzyl)oxy]imino}-N-[2-(diethylamino)ethyl]-2-pyrrolidinecarboxamide
(2S,4EZ)-4-{[(3,4-dichlorobenzyl)oxy]imino}-1-[4-(dimethylamino)butanoyl]-N-(6-quinolinyl)-2-pyrrolidinecarboxamide
(2S,4EZ)-1-([1,1'-biphenyl]-4-ylcarbonyl)-N-(5-ethyl-1,3,4-thiadiazol-2-yl)-4-(methoxyimino)-2-pyrrolidinecarboxamide
(2S,4EZ)-N-benzyl-1-([1,1'-biphenyl]-4-ylcarbonyl)-4-(methoxyimino)-2-pyrrolidinecarboxamide
(2S,4EZ)-N-benzyl-1-(diphenylacetyl)-4-(eethoxyimino)-2-pyrrolidinecarboxamide
(2S,4EZ)-$N^2$-cyclopropyl-4-{[(3,4-dichlorobenzyl)oxy]imino}-$N^1$-(3-methoxyphenyl)-1,2-pyrrolidinedicarboxamide
(2S,4EZ)-1-(diphenylacetyl)-N-[(2RS)-2-hydroxy-2-phenethyl]-4-{[(4-methoxybenzyl)-oxy]imino}-2-pyrrolidinecarboxamide
(2S)-N-(2-furylmethyl)-4-methylene-1-[(2-oxo-6-pentyl-2H-pyran-3-yl)carbonyl]-2-pyrrolidinecarboxamide
(2S,4EZ)-N-(2,1,3-benzothiadiazol-4-yl)-1-(diphenylacetyl)-4-(methoxyimino)-2-pyrrolidinecarboxamide
(2S,4EZ)-N-benzyl-1-(diphenylacetyl)-4-{[(4-methoxybenzyl)oxy]imino}-2-pyrrolidinecarboxamide
(2S,4EZ)-1-benzoyl-4-{[(3,4-dichlorobenzyl)oxy]imino}-N-(6-quinolinyl)-2-pyrrolidinecarboxamide
(2S,4EZ)-1-acetoacetyl-N-cyclopropyl-4-{[(3,4-dichlorobenzyl)oxy]imino}-2-pyrrolidinecarboxamide
(2S,4EZ)-4 {[(3,4-dichlorobenzyl)oxy]imino}-$N^2$-[(2RS)-2-hydroxy-2-phenethyl]-$N^1$-pentyl-1,2-pyrrolidinedicarboxamide
(2S,4EZ)-4-[(benzyloxy)imino]-N-(1-naphthylmethyl)-1-(phenoxyacetyl)-2-pyrrolidinecarboxamide
(2S)-1-([1,1'-biphenyl]-4-ylcarbonyl)-4-methylene-N-(6-quinolinyl)-2-pyrrolidinecarboxamid
(2S,4EZ)-N-cyclopropyl-4-{[(3,4-dichlorobenzyl)oxy]imino}-1-(diphenylacetyl)-2-pyrrolidinecarboxamide
(2S,4EZ)-1-(4-cyanobenzoyl)-4-{[(3,4-dichlorobenzyl)oxy]imino}-N-(6-quinolinyl-2-pyrrolidinecarboxamide
(2S,4EZ)-N-cyclopropyl-4-{[(3,4-dichlorobenzyl)oxy]imino}-1-(methoxyacetyl)-2-pyrrolidinecarboxamide
(2S,4EZ)-N-(1,3-benzodioxol-5-ylmethyl)-1-([1,1'-biphenyl]-4-ylcarbonyl)-4-(methoxyimino)-2-pyrrolidinecarboxamide
(3EZ,5S)-5-[(4-acetyl-1-piperazinyl)carbonyl]-1-acryloyl-3-pyrrolidinone O-(3,4-dichlorobenzyl)oxime
(2)-1-([1,1'-biphenyl]-4-ylcarbonyl)-N-(2-furylmethyl)-4-methylene-2-pyrrolidinecarboxamid
(2S,4EZ)-4-(cyanomethylene)N-(3,4-dimethoxybenzyl)-1-[(2-oxo-6-pentyl-2H-pyran-3-yl)carbonyl]-2-pyrrolidinecarboxamide
(2S,4EZ)-N-[(2RS)-2-hydroxy-2-phenylethyl]-4-(methoxyimino)-1-[(2'-methyl[1,1'-biphenyl]-4-yl)carbonyl]-2-pyrrolidinecarboxamide
(2S,4EZ)-1-([1,1'-biphenyl]-3-ylcarbonyl)-N-[(2RS)-2-hydroxy-2-phenylethyl]-4-(methoxyimino)-2-pyrrolidinecarboxamide
(2S,4EZ)-1-(4-benzoylbenzyl)-N-[(2RS)-2-hydroxy-2-phenylethyl]-4-(methoxyimino)-2-pyrrolidinecarboxamide
(2S,4EZ)-N-[(2RS)-2-hydroxy-2-phenylethyl]-4-(methoxyimino)-1-(3-phenoxybenzoyl)-2-pyrrolidinecarboxamide
(2S,4EZ)-N-[(2RS)-2-hydroxy-2-phenylethyl]-4-(methoxyimino)-1-(2-phenoxybenzoyl)-2-pyrrolidinecarboxamide
(2S,4EZ)-N-[(2S)-2-hydroxy-2-phenylethyl]-4-(methoxyimino)-1-[(2'-methyl[1,1'-biphenyl]-4-yl)carbonyl]-2-pyrrolidinecarboxamide
(2S,4EZ)-N-[(2R)-2-hydroxy-2-phenylethyl]-4-(methoxyimino)-1-[(2'-methyl[1,1'-biphenyl]-4-yl)carbonyl]-2-pyrrolidinecarboxamide
(2S,4EZ)-N-(2-hydroxyethyl)-4-(methoxyimino)-1-[(2'-methyl[1,1'-biphenyl]-4-yl)carbonyl]-2-pyrrolidinecarboxamide
(2S,4EZ)-N-(2-hydroxyethyl)-4-(methoxyimino)-N-methyl-1-[(2'-methyl[1,1'-biphenyl]-4-yl)carbonyl]-2-pyrrolidinecarboxamide
(2S,4EZ)-1-([1,1'-biphenyl]-4-ylsulfonyl)-N-[(1S,2S,3R,4R)-3-(hydroxymethyl)bicyclo[2.2.1]hept-2-yl]-4-(methoxyimino)-2-pyrrolidinecarboxamide
(2S,4EZ)-1-([1,1'-biphenyl]-4-ylcarbonyl)-N-(trans-4-hydroxycyclohexyl)-4-(methoxyimino)-2-pyrrolidinecarboxamide
(2S,4EZ)-1-([1,1'-biphenyl]-4-ylcarbonyl)-N-[(1R,2R)-2-(hydroxymethyl)cyclohexyl],4-(methoxyimino)-2-pyrrolidinecarboxamide
(2S,4EZ)-1-([1,1'-biphenyl]-4-ylcarbonyl)-N-[(2RS)-2-hydroxy-3-phenoxypropyl]-4-(methoxyimino)-2-pyrrolidinecarboxamide
(2S,4EZ)-N-[(2RS)-2-hydroxy-3-phenoxypropyl]-4-(methoxyimino)-1-[4-(3-pyridinyl)benzoyl]-2-pyrrolidinecarboxamide
(2S,4EZ)-1-([1,1'-biphenyl]-4-ylsulfonyl)-N-[(2RS)-2-hydroxy-3-phenoxypropyl]-4-(methoxyimino)-2-pyrrolidinecarboxamide (2S,4EZ)-1-([1,1'-biphenyl]-4-ylcarbonyl)-N-[(2RS)-2-hydroxy-2-(4-hydroxyphenyl)ethyl]-4-(methoxyimino)-2-pyrrolidinecarboxamide (2S,4EZ)-1-([1,1'-biphenyl]-4-ylsulfonyl)-N-[(2RS)-2-hydroxy-2-(4-hydroxyphenyl)ethyl]-4-(methoxyimino)-2-pyrrolidinecarboxamide (2S,4EZ)-1-([1,1'-biphenyl]-4-ylcarbonyl)-N-[(1-hydroxycyclohexyl)methyl]-4-(methoxyimino)-2-pyrrolidinecarboxamide (2S,4EZ)-N-[(1-hydroxycyclohexyl)methyl]-4-(methoxyimino)-1-[4-(3-pyridinyl)benzoyl]-2-pyrrolidinecarboxamide (2S,4EZ)-1-([1,1'-biphenyl]-4-ylsulfonyl)-N-[(1-hydroxycyclohexyl)methyl]-4-(methoxyimino)-2-pyrrolidinecarboxamide (2S,4EZ)-1-([1,1'-biphenyl]-4-ylcarbonyl)-N-[(2RS)-2-(3,4-hydroxyphenyl)-2-hydroxyethyl]-4-(methoxyimino)-2-pyrrolidinecarboxamide (2S,4EZ)-N-[(2S)-2-hydroxy-2-phenylethyl]-4-(methoxyimino)-1-[4-(4-pyridinyl)benzoyl]-2-pyrrolidinecarboxamide (2S,4EZ)-N-[(2S)-2-hydroxy-2-phenylethyl]-4-(methoxyimino)-1-[4-(3-pyridinyl)benzoyl]-2-pyrrolidinecarboxamide (2S,4EZ)-N-[(2S)-2-hydroxy-2-phenylethyl]-4-(methoxyimino)-1-[4-(2-pyridinyl)benzoyl]-2-pyrrolidinecarboxamide (2S,4EZ)-1-([1,1'-biphenyl]-4-ylcarbonyl)-N-[(2RS)-2,3-dihydroxypropyl]-4-(methoxyimino)-2-pyrrolidinecarboxamide (2S,4EZ)-1-([1,1'-biphenyl]-4-ylsulfonyl-N-N[(2RS)-2,3-dihydroxypropyl]-4-(methoxyimino)-2-pyrrolidinecarboxamide (2S,4EZ)-1-([1,1'-biphenyl]-4-ylcarbonyl)-N-[(2RS)-2-hydroxy-3-(4-methoxyphenoxy)propyl]-4-(methoxyimino)-2-pyrrolidinecarboxamide (2S,4EZ)-N-[(2RS)-2-hydroxy-3-(4-methoxyphenoxy)propyl]-4-(methoxyimino)-1-[4-(3-pyridinyl)benzoyl]-2-pyrrolidinecarboxamide (2S,4EZ)-1-([1,1'-biphenyl]-4-ylsulfonyl)-N-[(2RS)-2-hydroxy-3-(4-methoxyphenoxy)-propyl]-4-(methoxyimino)-2-pyrrolidinecarboxamide (2S,4EZ)-1-([1,1'-biphenyl]-4-ylcarbonyl)-N-[(2RS)-2-hydroxypropyl]-4-(methoxyimino)-2-pyrrolidinecarboxamide (2S,4EZ)-1-([1,1'-biphenyl]-4-ylsulfonyl)-N-[(2RS)-2-hydroxypropyl]-4-(methoxyimino)-2-pyrrolidinecarboxamide (2S,4EZ)-1-([1,1'-biphenyl]-4-ylsulfonyl)-N-[(2RS)-2-hydroxy-2-(2-naphthyl)ethyl]-4-(methoxyimino)-2-pyrrolidinecarboxamide (2S,4EZ)-1-([1,1'-biphenyl]-4-ylcarbonyl)-N-[(2RS)-2-hydroxy-2-(4-nitrophenyl)ethyl]-4-(methoxyimino)-2-pyrrolidinecarboxamide (2S,4EZ)-N-[(2RS)-2-hydroxy-2-(4nitrophenyl)ethyl]-4-(methoxyimino)-1-[4-(4-pyridinyl)benzoyl]-2-pyrrolidinecarboxamide (2S,4EZ)-N-[(2RS)-2-hydroxy-2-(4-nitrophenyl)ethyl]-4-(methoxyimino)-1-[4-(3-pyridinyl)benzoyl]-2-pyrrolidinecarboxamide (2S,4EZ)-N-[(2RS)-2-hydroxy-2-(4-nitrophenyl)ethyl]-4-(methoxyimino)-1-[4-(2-pyridinyl)benzoyl]-2-pyrrolidinecarboxamide (2S,4EZ)-1-([1,1'-biphenyl]-4-ylsulfonyl)-N-[(2RS)-2-hydroxy-2-(4-nitrophenyl)ethyl]-4-(methoxyimino)-2-pyrrolidinecarboxamide (2S,4EZ)-N-{(2RS)-3-[4-(acetylamino)phenoxy]-2-hydroxypropyl}-1-([1,1'-biphenyl]-4-ylcarbonyl)-4-(methoxyimino)-2-pyrrolidinecarboxamide (2S,4EZ)-N-{(2RS)-3-[4-(acetylamino)phenoxy]-2-hydroxypropyl}-4-(methoxyimino)-1-[4-(4-pyridinyl)benzoyl]-2-pyrrolidinecarboxamide (2S,4EZ)-N-{(2RS)-3-[4-(acetylamino)phenoxy]-2-hydroxypropyl}-4-(methoxyimino)-1-[4-(3-pyridinyl)benzoyl]-2-pyrrolidinecarboxamide (2S,4EZ)-N-{(2RS)-3-[4-(acetylamino)phenoxy]-2-hydroxypropyl}-1-([1,1'-biphenyl]-4-ylsulfonyl)-4-(methoxyimino)-2-pyrrolidinecarboxamide (2S,4EZ)-1-([1,1'-biphenyl]-4-ylcarbonyl)-N-[(2R)-2-hydroxy-2-phenylethyl]-4-(methoxyimino)-2-pyrrolidinecarboxamide (2S,4EZ)-N-[(2R)-2-hydroxy-2-phenylethyl]-4-(methoxyimino)-1-[4-(4-pyridinyl)benzoyl]-2-pyrrolidinecarboxamide (2S,4EZ)-N-[(2R)-2-hydroxy-2-phenylethyl]-4-(methoxyimino)-1-[4-(3-pyridinyl)benzoyl]-2-pyrrolidinecarboxamide (2S,4EZ)-N-[(2R)-2-hydroxy-2-phenylethyl]-4-(methoxyimino)-1-[4-(2-pyridinyl)benzoyl]-2-pyrrolidinecarboxamide (2S,4EZ)-1-([1,1'-biphenyl]-4-ylsulfonyl)-N-[(2R)-2-hydroxy-2-phenylethyl]-4-(methoxyimino)-2-pyrrolidinecarboxamide (2S,4EZ)-1-([1,1'-biphenyl]-4-ylcarbonyl)-N-(3-hydroxypropyl)-4-(methoxyimino)-2-pyrrolidinecarboxamide (2S,4EZ)-1-([1,1'-biphenyl]-4-ylsulfonyl)-N-(3-hydroxypropyl)-4-(methoxyimino)-2-pyrrolidinecarboxamide (3EZ,5S)-1-([1,1'-biphenyl]-4-ylcarbonyl)-5-[(4-hydroxy-4-phenyl-1-piperidinyl)carbonyl]-3-pyrrolidinone O-methoxyimine (3EZ,5S)-5-[(4-hydroxy-4-phenyl-1-piperidinyl)carbonyl]-1-[4-(4-pyridinyl)benzoyl]-3-pyrrolidinone O-methyloxime (3EZ,5S)-5-[(4-hydroxy-4-phenyl-1-piperidinyl)carbonyl]-1-[4-(3-pyridinyl)benzoyl]-3-pyrrolidinone O-methyloxime (3EZ,5S)-1-([1,1'-biphenyl]-4-ylsulfonyl)-5-[(4-hydroxy4-phenyl-1-piperidinyl)carbonyl]-3-pyrrolidinone O-methyloxime (2S,4EZ)-1-([1,1'-biphenyl]-4-ylcarbonyl)-N-[(1S,2S)-2-hydroxycyclohexyl]-4-(methoxyimino)-2-pyrrolidinecarboxamide (2S,4EZ)-1-([1,1'-biphenyl]-4-ylsulfonyl)-N-[(1S,2S)-2-hydroxycyclohexyl]-4-(methoxyimino)-2-pyrrolidinecarboxamide (2S,4EZ)-N-benzyl-1-([1,1'-biphenyl]-4ylcarbonyl)-N-(2-hydroxyethyl)-4-(methoxyimino)-2-pyrrolidinecarboxamide (2S,4EZ)-N-benzyl-N-(2-hydroxyethyl)-4-(methoxyimino)-1-[4-(3-pyridinyl)benzoyl]-2-pyrrolidinecarboxamide (3EZ,5S)-1-([1,1'-biphenyl]-4-ylcarbonyl)-5-{[(3RS)-3-dihydroxypropyl]carbonyl}-3-pyrrolidinone O-methyloxime (3EZ,5S)-5-{[(3RS)-3-hydroxypiperidinyl]carbonyl}-1-[4-(4-pyridinyl)benzoyl]-3-pyrrolidinone O-methyloxime (3EZ,5S)-5-{[(3RS)-3-hydroxypiperidinyl]carbonyl}-4-[4-(3-pyridinyl)benzoyl]-3-pyrrolidinone O-methyloxime (3EZ,5S)-1-([1,1'-biphenyl]-4-ylsulfonyl)-5-{[(3RS)-3-hydroxypiperidinyl]carbonyl}-3-pyrrolidinone O-methyloxime (2S,4EZ)-1-([1,1'-biphenyl]-4-ylcarbonyl)-N-[(1S,2S)-2-hydroxy-1-(hydroxymethyl)-2-phenylethyl]-4-(methoxyimino)-2-pyrrolidinecarboxamide (2S,4EZ)-N-[(1S,2S)-2-hydroxy-1-(hydroxymethyl)-2-phenylethyl]-4-(methoxyimino)-1-[4-(4-pyridinyl)benzoyl]-2-pyrrolidinecarboxamide (2S,4EZ)-N-[(1S,2S)-2-hydroxy-1-(hydroxymethyl)-2-phenylethyl]-4-(methoxyimino)-1-[4-($_3$-pyridinyl)benzoyl]-2-pyrrolidinecarboxamide (2S,4EZ)-1-([1,1'-biphenyl]-4-ylsulfonyl)-N-[(1S,2S)-2-hydroxy-1-(hydroxymethyl)-2-phenylethyl]-4-(methoxyimino)-2-pyrrolidinecarboxamide (2S,4EZ)-N-(2-anilinoethyl)-1-([1,1'-biphenyl]-4-ylcarbonyl)-4-(methoxyimino)-2-pyrrolidinecarboxamide (2S,4EZ)-N-(2-anilinoethyl)-4-(methoxyimino)-1-[4-(4-pyridinyl)benzoyl]-2-pyrrolidinecarboxamide (2S,4EZ)-N-(2-anilinoethyl)-4-(methoxyimino)-1-[4-(3-pyridinyl)benzoyl]-2-pyrrolidinecarboxamide (2S,4EZ)-N-(2-anilinoethyl)-4-(methoxyimino)-1-[4-(2-pyridinyl)benzoyl]-2-pyrrolidinecarboxamide (2S,4EZ)-N-(2-anilinoethyl)-1-([1,1'-biphenyl]-4-ylsulfonyl)-4-(methoxyimino)-2-pyrrolidinecarboxamide (3EZ,5S)-1-([1,1-biphenyl]-4-ylcarbonyl)-5-[(4-hydroxy-1-piperidinyl)carbonyl]-3-pyrrolidinone O-methyloxime (3EZ,5S)-1-([1,1'-biphenyl]-4-ylsulfonyl)-5-[(4-hydroxy-1-piperidinyl)carbonyl]-3-pyrrolidinone O-methyloxime (2S,4EZ)-N-[(1S,2R,3S,4R)-3-(aminocarbonyl)bicyclo[2.2.1]hept-5-en-2-yl]-1-([1,1'-biphenyl]-4-ylsulfonyl)-4-(methoxyimino)-2-pyrrolidinecarboxamide (2S,4EZ)-N-(3-amino-3-oxopropyl)-1-([1,1'-biphenyl]-4-ylcarbonyl)-4-(methoxyimino)-2-pyrrolidinecarboxamide (2S,4EZ)-N-[(1S,2S,3R,4R)-3-(aminocarbonyl)bicyclo[2.2.1]hept-5-en-2-yl]-1-([1,1'-biphenyl]-4-ylsulfonyl)-4-(methoxyimino)-2-pyrrolidinecarboxamide (2S,4EZ)-1-([1,1 '-biphenyl]-4-ylcarbonyl)-N-(4-hydroxybutyl)-(methoxyimino)-2-pyrrolidinecarboxamide (2S,4EZ)-1-([1,1'-biphenyl]-4-ylsulfonyl)-N-(4-hydroxybutyl)-4-(methoxyimino)-2-pyrrolidinecarboxamide (2S,4EZ)-1-([1,1'-biphenyl]-4-ylsulfonyl)-N-[(1R,2R)-2-(hydroxymethyl)cyclohexyl]-4-(methoxyimino)-2-pyrrolidinecarboxamide (2S,4EZ)-1-([1,1'-biphenyl]-4-ylsulfonyl)-N-[(1R,2S,3R,4S)-3-(hydroxymethyl)bicyclo-[2.2.1 ]hept-2-yl]-4-(methoxyimino)-2-pyrrolidinecarboxamide (2S,4EZ)-1-([1,1'-biphenyl]-4-ylsulfonyl)-N-[(1R,2S)-2-(hydroxymethyl)cyclohexyl]-4-(methoxyimino)-2-pyrrolidinecarboxamide (2S,4E and 4Z)-N-[(2S)-2-hydroxy-2-phenylethyl]-4-(methoxyimino)-1-[(2'-methyl[1,1'-biphenyl]-4yl)carbonyl]-2-pyrrolidinecarboxamide (2S,4E and 4Z)-N-[(2S)-2-hydroxy-2-phenylethyl]-4-(methoxyimino)-1-[(2'-methyl[1,1'-biphenyl]-4-yl)carbonyl]-2-pyrrolidinecarboxamide (2S,4E and 4Z)-N-[(2R)-2-hydroxy-2-phenylethyl]-4-(methoxyimino)-1-[(2'-methyl[1,1'-biphenyl]-4-yl)carbonyl]-2-pyrrolidinecarboxamide (2S,4EZ)-1-([1,1'-biphenyl]-4-ylcarbonyl)-N-[(1R,2S)-2-(hydroxymethyl)cyclohexyl]-4-(methoxyimino)-2-pyrrolidinecarboxamide (2S,4EZ)-1-([1,1'-biphenyl]-4-ylcarbonyl)-N-[2-hydroxy-1-(hydroxymethyl)ethyl]-4-(methoxyimino)-2-pyrrolidinecarboxamide (2S,4EZ)-N-[(1S,2R,3S,4R)-3-(aminocarbonyl)bicyclo[2.2.1]hept-5-en-2-yl]-1-([1,1'-biphenyl]-4-ylcarbonyl)-4-(methoxyimino)-2-pyrrolidinecarboxamide (2S,4EZ)-N-[(1S,2S,3R,4R)-3-(aminocarbonyl)bicyclo[2.2.1]hept-5-en-2-yl]-1-([1,1'-biphenyl]-4-ylcarbonyl)-4-(methoxyimino)-2-pyrrolidinecarboxamide (2S,4EZ)-1-([1,1'-biphenyl]4-ylcarbonyl)-N-[(2S)-2-hydroxy-2-phenylethyl]-4-(methoxyimino)-2-pyrrolidinecarboxamide (2RS)-3-({[(2S,4EZ)-1-([1,1'-biphenyl]-4-ylcarbonyl)-4-(methoxyimino)pyrrolidinyl]-carbonyl}amino)-2-hydroxypropanoic acid (2S,4EZ)-N-[(1R,2S)-2-(aminocarbonyl)cyclohexyl]-1-([1,1'-biphenyl]-4-ylcarbonyl)-4-(methoxyimino)-2-pyrrolidinecarboxamide (2S,4EZ)-1-([1,1'-biphenyl]-4ylcarbonyl)-N-[(1RS)-2-hydroxy-1-methylethyl]-4-(methoxyimino)-2-pyrrolidinecarboxamide (2S,4EZ)-1-([1,1'-biphenyl]-4-ylcarbonyl)-N-[(1S,2S)-2-hydroxy-1-(hydroxymethyl)-2-(4-nitrophenyl)ethyl]-4-(methoxyimino)-2-pyrrolidinecarboxamide 4-({[(2S,4EZ)-1-([1,1'-biphenyl]-4-ylcarbonyl)-4-(methoxyimino)pyrrolidinyl]carbonyl}-amino)butanoic acid (2S,4EZ)-N-[(2S)-2-hydroxy-2-phenylethyl]-1-[(2'-methoxy[1,1'-biphenyl]-4-yl)carbonyl]-4-(methoxyimino)-2-pyrrolidinecarboxamide (2S,4EZ)-N-[(2RS)-2-hydroxy-2-(2-naphthyl)ethyl]-1-[(2'-methoxy[1,1'-biphenyl]-4-yl)carbonyl]-4-(methoxyimino)-2-pyrrolidinecarboxamide (2S,4EZ)-N-[(1RS)-2-hydroxy-1-methylethyl]-4-(methoxyimino)-1-[(2'-methyl[1,1'-biphenyl]-4-yl)carbonyl]-2-pyrrolidinecarboxamide (2S,4EZ)-N-[(1S,2S)-2-hydroxy-1-(hydroxymethyl)-2-(4-nitrophenyl)ethyl]-4-(methoxyimino)-1-[(2'-methyl[1,1'-biphenyl]-4-yl)carbonyl]-2-pyrrolidinecarboxamide (2S,4EZ)-N-[(1S,2S)-2-hydroxy-1-(hydroxymethyl)-2-(4-nitrophenyl)ethyl]-4-(methoxyimino)-1-[(2'-methoxy[1,1'-biphenyl]-4-yl)carbonyl]-2-pyrrolidinecarboxamide (3EZ,5S)-5-[(4-hydroxy-1-piperidinyl)carbonyl]-1-[(2'-methyl[1,1'-biphenyl]-4-yl)carbonyl]-3-pyrrolidinone O-methyloxime (2S,4EZ)-N-[(1S,2S,3R,4R)-3-(aminocarbonyl)bicyclo[2.2.1]hept-5-en-2-yl]-4-(methoxyimino)-1-[(2'-methyl[1,1'-biphenyl]-4-yl)carbonyl]-2-pyrrolidinecarboxamide (2S,4EZ)-N-[(2RS)-2-hydroxy-2-phenylethyl]-1-[(2'-methoxy[1 ,1'-biphenyl]-4-yl)carbonyl]-4-(methoxyimino)-2-pyrrolidinecarboxamide (2S,4EZ)-N-[(2RS)-2-hydroxypropyl]-4-(methoxyimino)-1-[(2'-methyl[1,1'-biphenyl]-4-yl)carbonyl]-2-pyrrolidinecarboxamide (2S,4EZ)-N-[(2RS)-2,3-dihydroxypropyl]-4-(methoxyimino)-1-[(2'-methyl[1,1'-biphenyl]-4-yl)carbonyl]-2-pyrrolidinecarboxamide (2S,4EZ)-N-(3-hydroxypropyl)-4-(methoxyimino)-1-[(2'-methyl[1,1-biphenyl]-4-yl)carbonyl]-2-pyrrolidinecarboxamide (2S,4EZ)-N-(2-amino-2-oxoethyl)-1-([1,1'-biphenyl]-4-ylcarbonyl)-4-(methoxyimino)-2-pyrrolidinecarboxamide (2S,4EZ)-N-(2-amino-2-oxoethyl)-4-(methoxyimino)-1-[(2'-methyl[1,1'-biphenyl]-4-yl)carbonyl]-2-pyrrolidinecarboxamide (2S,4EZ)-1-([1,1'-biphenyl]-4-ylcarbonyl)-N-[(2-RS)-2-hydroxy-2-(3-hydroxyphenyl)ethyl]-4-(methoxyimino)-2-pyrrolidinecarboxamide (2S,4EZ)-1-([1,1'-biphenyl]-4-ylcarbonyl)-N-[(1S,2R,3S,4R)-3-(hydroxymethyl)-bicyclo[2.2.1]hept-2-yl]-4-(methoxyimino)-2-pyrrolidinecarboxamide (2S,4EZ)-N-[(1R,2S,3R,45)-3-hydroxymethyl)bicyclo[2.2.1]hept-2-yl]-1-[(2'-methoxy[1,1'-biphenyl]-4-yl)carbonyl]-4-(methoxyimino)-2-pyrrolidinecarboxamide (2S,4EZ)-N-(trans-4-hydroxycyclohexyl)-1-[(2'-methoxy[1,1'-biphenyl]-4-yl)carbonyl]-4-(methoxyimino)-2-pyrrolidinecarboxamide (2S,4EZ)-N-[(1R,2R)-2-(hydroxymethyl)cyclohexyl]-1-[(2'-methoxy[1,1'-biphenyl]-4-yl)carbonyl]-4-(methoxyimino)-2-pyrrolidinecarboxamide (2S,4EZ)-N-[(2RS)-2-hydroxy-3-phenoxypropyl]-4-(methoxyimino)-1-[(2'-methyl[1,1'-biphenyl]-4-yl)carbonyl]-2-pyrrolidinecarboxamide (2S,4EZ)-N-[(2RS)-2-hydroxy-2-(4-hydroxyphenyl)ethyl]-4-(methoxyimino)-1-[(2'-methyl[1,1'-biphenyl]-4-yl)carbonyl]-2-pyrrolidinecarboxamide (2S,4EZ)-N-[(2RS)-2-hydroxy-2-(4-hydroxyphenyl)ethyl]-4-(methoxyimino)-1-[(2'-methoxy[1,1'-biphenyl]-4-yl)carbonyl]-2-pyrrolidinecarboxamide (2S,4EZ)-N-[(2RS)-2-hydroxy-2-(4-hydroxy-3-methoxyphenyl)ethyl]-1-[(2'-methyl[1,1'-biphenyl]-4-yl)carbonyl]-4-(methoxyimino)-2-pyrrolidinecarboxamide (2S,4EZ)-N-[(2RS)-2-hydroxy-2-(4-hydroxy-3-methoxyphenyl)ethyl]-1-[(2'-methoxy[1,1'-biphenyl]-4-yl)carbonyl]-4-(methoxyimino)-2-pyrrolidinecarboxamide (2S,4EZ)-N-[(2RS)-2-(3,4-dihydroxyphenyl)-2-hydroxyethyl]-1-[(2'-methoxy[1,1'-biphenyl]-4-yl)carbonyl]-4-(methoxyimino)-2-pyrrolidinecarboxamide (2R,4EZ)-1-([1,1'-biphenyl]-4-ylcarbonyl)-N-[(2RS)-2-hydroxy-2-phenylethyl]-4-(methoxyimino)-2-pyrrolidinecarboxamide (2R,4EZ)-N-[(2RS)-2-hydroxy-2-phenylethyl]-4-(methoxyimino)-1-[(2'-methyl[1,1'-biphenyl]-4-yl)carbonyl]-2-pyrrolidinecarboxamide (2S,4EZ)-1-[(2'-cyano[1,1'-biphenyl]-4-yl)carbonyl]-N-[(2RS)-2-hydroxy-2-phenylethyl]-4-(methoxyimino)-2-pyrrolidinecarboxamide (2S,4EZ)-1-[(3',4'-dichloro[1,1'-biphenyl]-4-yl)carbonyl]-N-[(2RS)-2-hydroxy-2-phenylethyl]-4-(methoxyimino)-2-pyrrolidinecarboxamide (2S,4EZ)-1-[(2'6'-dimethyl[1,1'-biphenyl]-4-yl)carbonyl]-N-[(2RS)-2-hydroxy-2-phenylethyl]-4-(methoxyimino)-2-pyrrolidinecarboxamide (2S,4EZ)-1-[(2',3-dimethyl[1,1'-biphenyl]-4-yl)carbonyl]-N-[(2RS)-2-hydroxy-2-phenylethyl]-4-(methoxyimino)-2-pyrrolidinecarboxamide (2S,4EZ)-N-[(2RS)-2-hydroxy-2-(3-hydroxyphenyl)ethyl]-4-(methoxyimino)-1-[(2'-methyl[1,1'-biphenyl]-4-yl)carbonyl]-2-pyrrolidinecarboxamide (2S,4EZ)-N-[(2RS)-2-hydroxy-2-(3-hydroxyphenyl)ethyl]-4-(methoxyimino)-1-[(2'-cyano[1,1'-biphenyl]-4-yl)carbonyl]-2-pyrrolidinecarboxamide (2S,4EZ)-N-[(2RS)-2-hydroxy-2-(3-hydroxyphenyl)ethyl] 4-(methoxyimino)-1-[(3',4'-dichloro[1,1'-biphenyl]-4-yl) carbonyl]-2-pyrrolidinecarboxamide (2S,4EZ)-N-[(2RS)-2-hydroxy-2-(3-hydroxyphenyl)ethyl]-4-(methoxyimino)-1-[(2',6'-dimethyl[1,1'-biphenyl]-4-yl) carbonyl]-2-pyrrolidinecarboxamide (2S,4EZ)-N-[(2RS)-2-hydroxy-2-(3-hydroxyphenyl)ethyl]-4-(methoxyimino)-1-[(2',3-dimethyl[1,1'-biphenyl]-4-yl) carbonyl]-2-pyrrolidinecarboxamide (2S,4EZ)-1-[(3',4'-dichloro[1,1'-biphenyl]-4-yl)carbonyl]-N-[(2RS)-2-hydroxy-2-(4-hydroxyphenyl)ethyl]-4-(methoxyimino)-2-pyrrolidinecarboxamide (2S,4EZ)-1-[(2',6'-dimethyl[1,1'-biphenyl]-4-yl)carbonyl]-N-[(2RS)-2-hydroxy-2-(4-hydroxyphenyl)ethyl]-4-(methoxyimino)-2-pyrrolidinecarboxamide (2S,4EZ)-1-[(2',3-dimethyl[1,1'-biphenyl]-4-yl)carbonyl]-N-[(2RS)-2-hydroxy-2-(4-hydroxyphenyl)ethyl]-4-(methoxyimino)-2-pyrrolidinecarboxamide (2S,4EZ-1-[(2',6'-dimethyl[1,1'-biphenyl]-4-yl)carbonyl]-N-[(2RS)-2-hydroxy-3-(4-methoxyphenoxy)propyl]-4-(methoxyimino)-2-pyrrolidinecarboxamide (2S,4EZ)-1-[(2',3-dimethyl[1,1'-biphenyl]-4-yl)carbonyl]-N-[(2RS)-2-hydroxy-3-(4-methoxyphenoxy)propyl]-4-(methoxyimino)-2-pyrrolidinecarboxamide (2S,4EZ)-N-(2-amino-2-oxoethyl)-1-[(2',6'-dimethyl[1,1'-biphenyl]-4-yl)carbonyl]-4-(methoxyimino)-2-pyrrolidinecarboxamide (2S,4EZ)-N-(2-amino-2-oxoethyl)-1-[(2',3-dimethyl[1,1'-biphenyl]-4yl)carbonyl]-4-(methoxyimino)-2-pyrrolidinecarboxamide (2S,4EZ)-N-(3-amino-3-oxopropyl)-1-[(2',6'-dimethyl[1,1'-biphenyl]-4yl)carbonyl]-4-(methoxyimino)-2-pyrrolidinecarboxamide (2S,4EZ)-N-(3-amino-3-oxopropyl)-1-[(2',3-dimethyl[1,1'-biphenyl]-4-yl)carbonyl]-4-(methoxyimino)-2-pyrrolidinecarboxamide (2S,4EZ)-1-[(2',6'-dimethyl[1,1'-biphenyl]-4-yl)carbonyl]-N-[2-hydroxy-1-(hydroxymethyl)ethyl]-4-(methoxyimino)-2-pyrrolidinecarboxamide (2S,4EZ)-1-[(2',3-dimethyl[1,1'-biphenyl]-4-yl)carbonyl]-N-[2-hydroxy-1-(hydroxymethyl)ethyl]-4-(methoxyimino)-2-pyrrolidinecarboxamide (2S,4EZ)-1-[(2'-cyano[1,1'-biphenyl]-4-yl)carbonyl]-N-[(1R,2R)-2-(hydroxymethyl)-cyclohexyl]-4-(methoxyimino)-2-pyrrolidinecarboxamide (3EZ,5S)-5-(3,4-dihydro-2(1H)-isoquinolinylcarbonyl)-1-[(2',3-dimethyl[1,1'-biphenyl]-yl)carbonyl]-3-pyrrolidinone O-methyloxime (2S,4EZ)-N-[(1R)-2-hydroxy-1-phenylethyl]-4-(methoxyimino)-1-[(2'-methyl[1,1'-biphenyl]-4-yl)carbonyl]-2-pyrrolidinecarboxamide (2S,4EZ)-1-[(2',6'-dimethyl[1,1'-biphenyl]-4-yl)carbonyl]-N-[2-(4-hydroxyphenyl)ethyl]-4-(methoxyimino)-2-pyrrolidinecarboxamide (2S,4EZ)-1-[(2',3-dimethyl[ 1,1'-biphenyl]-4-yl)carbonyl]-N-[2-(4-hydroxyphenyl)ethyl]-4-(methoxyimino)-2-pyrrolidinecarboxamide (2S,4EZ)-1-[(2',6'-dimethyl[1,1'-biphenyl]-4-yl)carbonyl]-N-[2-(3-hydroxyphenyl)ethyl]-4-(methoxyimino)-2-pyrrolidinecarboxamide (2S,4EZ)-1-[(2',3-dimethyl[1,1'-biphenyl]4-yl)carbonyl]-N-[2-(3-hydroxyphenyl)ethyl]-4-(methoxyimino)-2-pyrrolidinecarboxamide (2S,4EZ)-1-[(2',3-dimethyl[1,1'-biphenyl]-4-yl)carbonyl]-N-[(1R,23)-2-hydroxy-1,2-diphenylmethyl]-4-(methoxyimino)-2-pyrrolidinecarboxamide (2RS)-2-[({(2S,4EZ)-4-(methoxyimino)-1-[(2'-methyl[1,1'-biphenyl]-4-yl)carbonyl]-pyrrolidinyl}carbonyl)amino]-3-phenylpropane acid (2S,4EZ)-N-[(1R,2S)-2-(aminocarbonyl)cyclohexyl]-1-[(2',6'-dimethyl[1,1'-biphenyl]-4-yl)carbonyl]-4-(methoxyimino)-2-pyrrolidinecarboxamide (2S,4EZ)-N-[(1R,2S)-2-(aminocarbonyl)cyclohexyl]-1-[(2',3-dimethyl[1,1'-biphenyl]-4-yl)carbonyl]-4-(methoxyimino)-2-pyrrolidinecarboxamide 4'-{[(2S,4EZ)-2-{[4-(2-hydroxyethyl)-1-piperazinyl]carbonyl}-4-(methoxyimino)-pyrrolidinyl]carbonyl}[1,1'-biphenyl]-2-carbonitrile (3EZ,5S)-1-[(3',4'-dichloro[1,1'-biphenyl]-4yl)carbonyl]-5-{[4-(2-hydroxyethyl)-1-piperazinyl]carbonyl}-3-pyrrolidinone O-methyloxime (3EZ,5S)-1-[(2',6'-dimethyl[1,1'-biphenyl]-4-yl)carbonyl]-5-{[4-(2-hydroxyethyl)-1-piperazinyl]carbonyl}-3-pyrrolidinone O-methyloxime (3EZ,5S)-1-[(2',3-dimethyl[1,1'-biphenyl]-4-yl)carbonyl]-5-{[4-(2-hydroxyethyl)-1-piperazinyl]carbonyl}-3-pyrrolidinone O-methyloxime (3EZ,5S)-1-[(2'-methyl[1,1'-biphenyl]-4-yl)carbonyl]-5-({4-[4-(trifluoromethyl)phenyl]-1-piperazinyl}carbonyl)-3-pyrrolidinone O-methyloxime (3EZ,5S)-1-[(2'-methyl[1,1'-biphenyl]-4-yl)carbonyl]-5-({4-[3-(trifluoromethyl)phenyl]-1-piperazinyl}carbonyl)-3-pyrrolidinone O-methyloxime (2S,4EZ)-4-(methoxyimino)-1-[(2'-methyl[1,1'-biphenyl]-4-yl)carbonyl]-2-pyrrolidine-carboxamide (2S,4EZ)-4-(methoxyimino)-N-methyl-1-[(2'-methyl[1,1'-biphenyl]-4-yl)carbonyl]-2-pyrrolidinecarboxamide (2S,4EZ)-4-(methoxyimino)-N,N-dimethyl-1-[(2'-methyl[1,1'-biphenyl]-4yl)carbonyl]-2-pyrrolidinecarboxamide (2S,4EZ)-N-[(3R)-3-hydroxy-3-phenylpropyl]-4-(methoxyimino)-1-[(2'-methyl[1,1'-biphenyl]-4-yl)carbonyl]-2-pyrrolidinecarboxamide (2S,4EZ)-N-[(3S)-3-hydroxy-3-phenylpropyl]-4-(methoxyimino)-1-[(2'-methyl[1,1'-biphenyl]-4-yl)carbonyl]-2-pyrrolidinecarboxamide (2S,4EZ)-1-([1,1'-biphenyl]-4-ylcarbonyl)-N-[(3R)-3-hydroxy-3-phenylpropyl]-4-(methoxyimino)-2-pyrrolidinecarboxamide (2S,4EZ)-1-([1,1'-biphenyl]-4-ylcarbonyl)-N-[(3S)-3-hydroxy-3-phenylpropyl]-4-(methoxyimino)-2-pyrrolidinecarboxamide (2S,4EZ)-N-[(2S)-2-hydroxy-2-phenylethyl]-4-(methoxyimino)-1-{[2'-(trifluoro-methyl)[1,1'-biphenyl]-4-yl]carbonyl}-2-pyrrolidinecarboxamide (2S,4EZ)-N-[(2S)-2-hydroxy-2-phenylethyl]-4-(methoxyimino)-1-{[2'-chloro[1,1'-biphenyl]-4-yl]carbonyl}-2-pyrrolidinecarboxamide (2S,4EZ)-N-(2-hydroxyphenyl)-4-(methoxyimino)-1-[(2'-methyl[1,1'-biphenyl]-4-yl)carbonyl]-2-pyrrolidinecarboxamide (2S,4EZ)-N-[2-(hydroxymethyl)phenyl]-4-(methoxyimino)-1-[(2'-methyl[1,1'-biphenyl]-4-yl)carbonyl]-2-pyrrolidinecarboxamide (2S,4EZ)-N-[(2S)-2-hydroxy-2-phenylethyl]-4-(methoxyimino)-1-[(2-methyl[1,1'-biphenyl]-4-yl)carbonyl]-2-pyrrolidinecarboxamide (2S,4E and 4Z)-1-([1,1'-biphenyl]-4-ylcarbonyl)-N-[(2S)-2-hydroxy-2-phenylethyl]-4-(methoxyimino)-2-pyrrolidinecarboxamide (2S,4EZ)-4-(methoxyimino)-1-[(2-methyl[1,1'-biphenyl]-4-yl)carbonyl]-N-(2-phenylethyl)-2-pyrrolidinecarboxamide Thereby, the most preferred compounds are those which are selected from the group consisting of:

(2S,4EZ)-1-([1,1'-biphenyl]-4-ylcarbonyl)-4-(chloromethylene)-N-[(2RS)-2-hydroxy-2-phenethyl]-2-pyrrolidinecarboxamide (2S,4EZ)-1-([1,1'-biphenyl]-4-ylcarbonyl)-N-(2-hydroxyethyl)-4-(methoxyimino-2-pyrrolidinecarboxamide (2S,4EZ)-1-([1,1'-biphenyl]-4-ylcarbonyl)-N-[(2RS)-2-hydroxy-2-phenethyl]-4-(methoxyimino)-2-pyrrolidinecarboxamide (3EZ,5S)-5-(1H-benzimidazol-2-yl)-1-([1,1'-biphenyl]-4-ylcarbonyl)-3-pyrrolidinone O-methyloxime (2S,4EZ)-N-(2,1,3-benzothiadiazol-4-yl)-1-([1,1'-biphenyl]-4-ylcarbonyl)-4-(methoxyimino)-2-pyrrolidinecarboxamide (2S,4EZ)-1-([1,1'-biphenyl]-4-ylcarbonyl)-4-(methoxyimino)-N-(6-quinolinyl)-2-pyrrolidine-carboxamide (2S,4Z-N-[(2S)-2-hydroxy-2-phenylethyl]-4-(methoxyimino)-1-[(2'-methyl[1,1'-biphenyl]-4-yl)carbonyl]-2-pyrrolidinecarboxamide (2S,4E)-N-[(2S)-2-hydroxy-2-phenylethyl]-4-(methoxyimino)-1-[(2'-methyl[1,1'-biphenyl]-4-yl)carbonyl]-2-pyrrolidinecarboxamide A further aspect of the present invention is related to the use of the pyrrolidine derivatives according to formula I for the preparation of pharmaceutical compositions for the treatment and/or prevention of premature labor, premature birth, for stopping labor prior to cesarean delivery and dysmenorrhea Preferably, the compounds according to formula I are suitable for the modulation of the OT function, thus specifically allowing the treatment and/or prevention of disorders which are mediated by the oxytocin receptor. Said treatment involves the modulation—notably the down regulation or the antagonisation—of the oxytocin receptor.

More specifically, the compounds of the present invention are useful for the treatment of preterm labor, premature birth, dysmenorrhea and for stopping labor prior to cesarean delivery.

Still a further aspect of the present invention is related to the actually novel pyrrolidine compounds of formula I. Some very few compounds have actually been disclosed prior to the filing of the present application, without any medical use though. Said known compounds of formula I are those, wherein X is (=$CH_2$), A is —(C=O)—O—, $R^1$ is a t-butyl group and B is —(C=O)-$NMe_2$ (*Tetrahedron* 53(2), 539, 1997); —(C=O)—NHMe (WO 95/47718); —(C=O)—NH—CH(Me)—(C=O)—NH—CH(Me)-COOH (WO 95/47718); or —(C=O)—NH—CH($COOCH_2$-Ph)-$CH_2$—COOPh (*Tetrahedron* 48(31), 6529, 1992).

X is (=$CHR^6$) with $R^6$ being cyclohexylmethyl, A is —(C=O)—O—, $R^1$ is a t-butyl group and is —(C=O)-NH-t-butyl (*Biorg. Chem. Lett.* 3(8), 1485, 1993).

X is $C_1$–$C_{20}$ alkylidene, A is —(C=O)—O—, $R^1$ is a t-butyl and B is

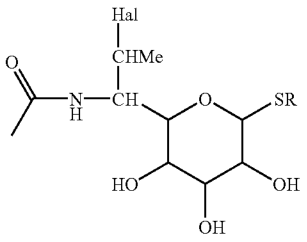

wherein R is $C_1$–$C_{12}$ alkyl and Hal is Cl, Br, J. Said compounds are disclosed in DE-1,932,823 as intermediates.

X is $C_1$–$C_{20}$ alkylidene, A-$R^1$ is a protective group and B is

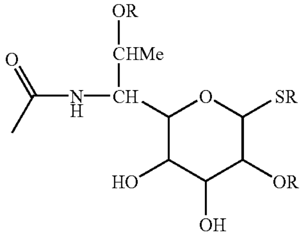

with R being H or $C_1$–$C_{12}$ alkyl (GB-1,118,306)

Hence, the novel compounds are those of the formula I, wherein the above mentioned known compounds are excluded.

Still a further object of the present invention is a process for preparing the pyrrolidine derivatives according to formula I.

The pyrrolidine derivatives exemplified in this invention can be prepared from readily available starting materials using the following general methods and procedures. It will be appreciated that where typical or preferred experimental conditions (i.e. reaction temperatures, time, moles of reagents, solvents, etc.) are given, other experimental conditions can also be used unless otherwise stated. Optimum reaction conditions may vary with the particular reactants or solvents used, but such conditions can be determined by one skilled in the art by routine optimisation procedures.

Generally, the pyrrolidine derivatives according to the general formula I could be obtained by several processes, using both solution-phase and solid-phase chemistry protocols. Depending on the nature of A, B, and X, certain processes will, in some instances, be preferred over others, and it is assumed that the choice of the most suitable process will be known to the practitioner skilled in the art.

According to one process, pyrrolidine derivatives according to the general formula I, whereby the substituent B is C(O)—$NR^8R^9$, with $R^8$ and $R^9$ being defined as above, are prepared from the corresponding suitably N-protected 4-substituted pyrrolidine derivatives II, whereby the substituent X is as above defined, by solution-phase chemistry protocols such as described in the Examples and shown in Scheme 1, below. The suitably N-protected 4-substituted pyrrolidine derivatives II are first reacted with primary or secondary amines III, whereby the substituents $R^8$ and $R^9$ are as above defined, using conditions and methods well known to those skilled in the art to prepare an amide from an amine and a carboxylic acid or a carboxylic acid derivative, using standard peptide coupling agents, such as e.g. DIC, EDC, TBTU, DECP, or others, to yield compounds of formula IV. Removal of the N-protecting group using the appropriate deprotection agents produces derivatives of formula V. These can be treated with acylating agents of general formula VI, whereby the substituent $R^1$ is as above defined, while LG could be any appropriate leaving group. Preferred acylating agents VI are acid chlorides (VIa), used in conjunction with a tertiary amine base, or carboxylic acids (VIb), used in conjunction with a peptide coupling agent, e.g. from the above mentioned group, to yield the products of general formula I, with B being defined as $C(O)N^8R^9$ (Ia).

Scheme 1

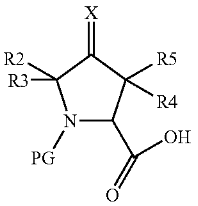

II

+

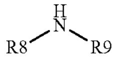

III

-continued

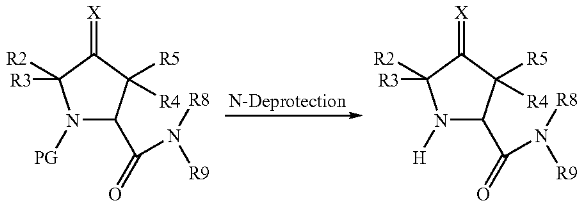

IV

V

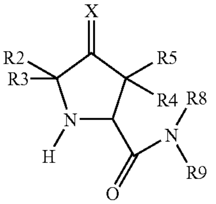

V

+

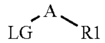

VIa (e.g., A = C(O); LG = Cl)
VIb (e.g., A = C(O); LG = OH)

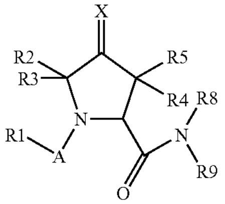

Ia

Other derivatives of formula I are prepared using known modifications to the Scheme 1 reaction sequence. Compounds of formula I wherein A is different from the carbonyl functionality are prepared by replacing formula VI compounds with compounds containing the appropriate functional groups, e.g. sulfonyl chlorides, isocyanates, isothiocyanate, chloroformates, substituted alkyl halides, or others to yield sulfonamide, urea, thiourea, carbamate, substituted alkyl derivatives, or others, respectively.

Compounds of formula II, whereby the substituent X is $CR^6R^7$, and $R^6$ and $R^7$ are as above defined, can be prepared from compounds of general formula VII by Wittig-type reactions with anions of phosphoranes such as VIIIa and/or of phosphonates such as VIIIb, followed by saponification of the ester function using standard synthetic techniques, as hereinafter described in the Examples and shown in Scheme 2.

Scheme 2

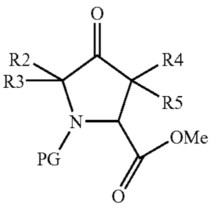

VII

+

-continued

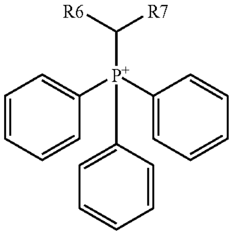

VIIIa or

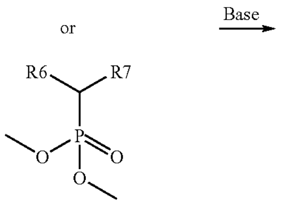

VIIIb

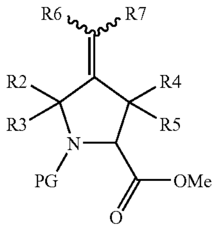

IX

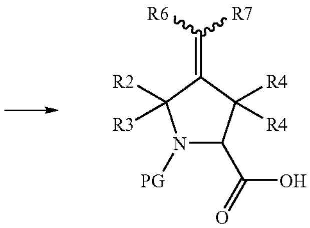

IIa

Compounds of general formula VII can be prepared from commercially available, suitably N-protected 4-hydroxyproline X, by a reaction sequence consisting of oxidation and esterification, using standard synthetic techniques as hereinafter described in the Examples and shown in Scheme 3.

Scheme 3

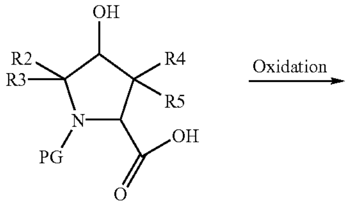

X

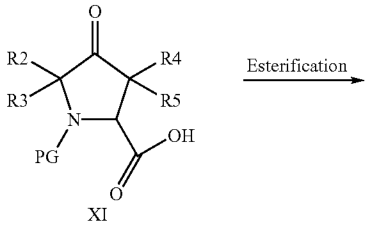

XI

-continued

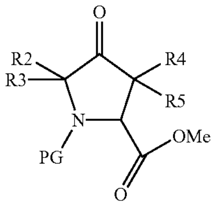

VII

Compounds of formula II, wherein the substituent X is $NOR^6$ or $NNR^6R^7$, and $R^6$ and $R^7$ are as above defined, can be prepared from compounds of general formula XI by reaction with substituted hydroxylamines XIIa and/or substituted hydrazines and/or hydrazides XIIb using standard synthetic techniques as hereinafter described in the Examples and shown in Scheme 4.

Scheme 4

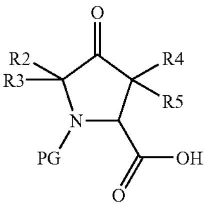

XI

+

$XH_2$

XIIa (X=N—O—R6)
XIIb (X=N—N—R6R7)

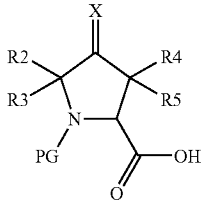

II

Compounds of formula XIIa are commercially available or prepared by standard synthetic techniques as hereinafter described in the Examples. Compounds of formula II with X═S are accessible from the corresponding suitably protected ketopyrrolidine intermediates VII through standard functional group interconversion methods well known to the person skilled in the art, such as, e.g., by treatment with Lawesson's reagent or others (Pedersen, B. S. et al.; *Bull. Soc. Chim. Belg.* 1978, 87, 223), followed by saponification.

According to another process, pyrrolidine derivatives according to the general formula I, whereby the substituent B is a heterocyclic residue B1 as above defined, and the substituents are as above defined, are prepared from the corresponding suitably N-protected 4-substituted pyrrolidine derivatives II, whereby the substituent X is as above defined, by solution-phase chemistry protocols such as described in the Examples and shown in Scheme 5, below. The starting suitably N-protected 4-substituted pyrrolidine derivatives II are first reacted with ortho-substituted primary anilines of general formula XI, whereby the substituents Q, Z, E, Y, and $R^{11}$ are as above defined, using standard peptide coupling agents, such as DIC, EDC, TBTU, DECP, or others, followed by exposure to dilute weak acid, such as acetic acid, in a suitable organic solvent, such as DCM, to promote cyclisation yielding compounds of formula XIV. Removal of the N-protecting group using the appropriate deprotection agents produces cyclic derivatives of formula XV. These can be treated with acylating agents of general formula VI, whereby the substituent $R^1$ is as above defined, while LG could be any appropriate leaving group. Preferred acylating agents VI are acid chlorides (VIa), used in conjunction with a tertiary amine base, or carboxylic acids (VIb), used in conjunction with a peptide coupling agent, e.g. from the above mentioned group, to yield the products of general formula I, with B being defined as B1 (Ib).

Scheme 5

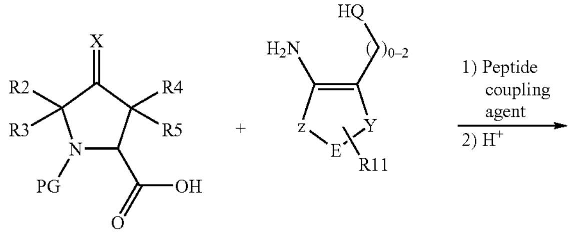

II XIII

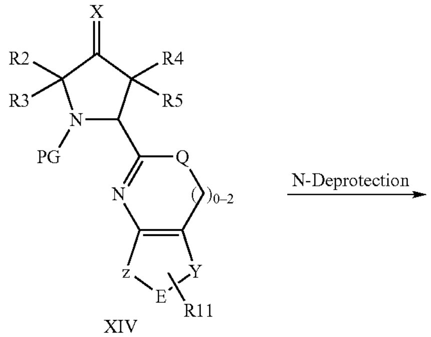

XIV

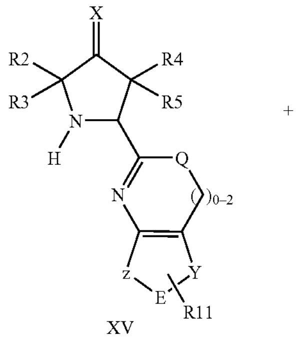

XV

-continued

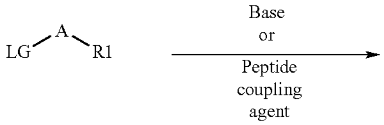

VIa (e.g., A = C(O); LG = Cl)
VIb (e.g., A = C(O); LG = OH)

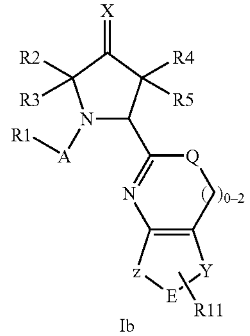

Ib

Other derivatives of formula I are prepared using known modifications to the Scheme S reaction sequence. Compounds of formula I wherein A is different from the carbonyl functionality are prepared by replacing formula VI with compounds containing the appropriate functional groups, e.g. sulfonyl chlorides, isocyanates, isothiocyanate, chloroformates, substituted alkyl halides, or others to yield sulfonamide, urea, thiourea, carbamate, substituted alkyl derivatives, or others, respectively.

According to another general process, summarized in Scheme 6, pyrrolidine derivatives according to the general formula I, whereby the substituents A, B, X, and $R^1$ are as above defined, are prepared from compounds of formula XVI, using the synthetic techniques as outlined in Schemes 2 and 4. As further shown in Scheme 6, compounds of formula XVI are accessible either from XI, following, e.g., the synthetic methodologies introduced in Schemes 1 and 5, or from Ic through hydrolysis of the methyloxime moiety, e.g. under mild hydrolysis conditions as described hereinafter in the Examples. This present synthetic strategy is most preferred when X is NOH or $NNR^6R^7$, whereby the substituents $R^6$ and $R^7$ are as above defined.

Scheme 6

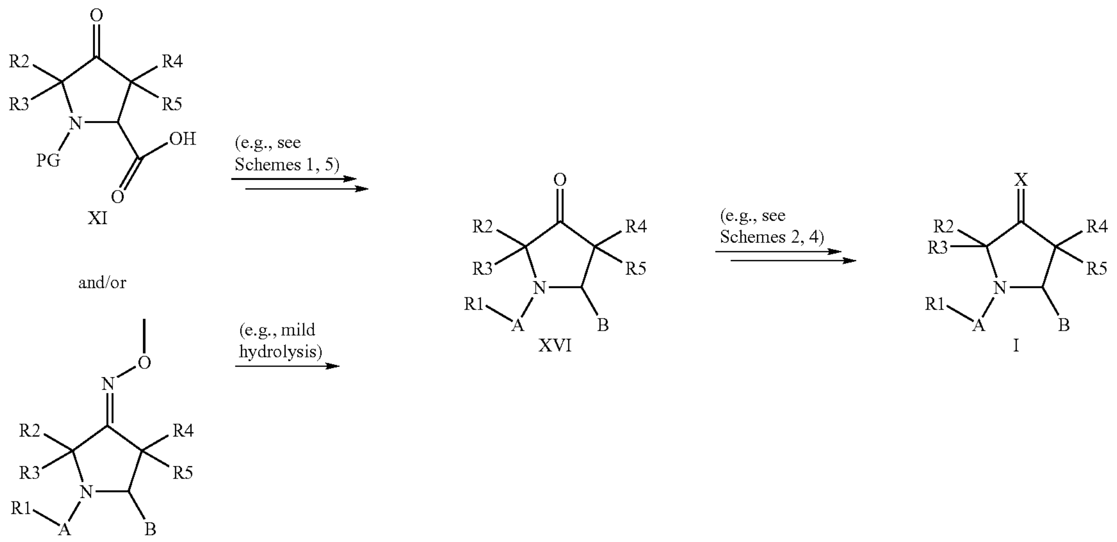

XI and/or

Ic

XVI

I

According to yet another process, pyrrolidine derivatives according to the general formula I, whereby the substituents A, B, X, and $R^1$ are as above defined, are prepared from the corresponding suitably N-protected 4substituted pyrrolidine derivatives II, whereby the substituent X is above defined, by a solid-phase protocol such as described in the examples and shown in Scheme 7, below. The N-Boc-protected 4-substituted pyrrolidine derivative II is reacted e.g. with Kaiser oxime resin using standard carbodiimide-mediated coupling conditions well known to the practitioner skilled in the art, followed by Boc-deprotection with dilute TFA in DCM, or with $BF_3.OEt_2$ in dilute HOAc in DCM, to give compound XIX. The latter compound can be treated with acylating agents of general formula VI, whereby the substituent $R^1$ is as above defined, while LG could be any appropriate leaving group. Preferred acylating agents VI are acid chlorides (VIa), used in conjunction with a tertiary amine base, or carboxylic acids (VIb), used in conjunction with a peptide coupling agent, e.g. DIC or EDC, to yield products of general formula XX.

Compounds of formula I wherein A is different from the carbonyl functionality are prepared by replacing formula VI with compounds containing the appropriate functional groups, e.g. sulfonyl chlorides, isocyanates, isothiocyanate, chloroformates, substituted alkyl halides, or others to yield sulfonamide, urea, thiourea, carbamate, substituted alkyl derivatives, or others respectively.

In order to obtain the final compounds of general formula I, the linkage to the resin is cleaved by prolonged treatment with amines of general formulae III or XIII and low percentages of a weak acid, such as HOAc. The cycles within the below Scheme 7 illustrate the resign beads to which the corresponding compounds are linked during the solid phase synthesis. Other is derivatives of formula I are prepared using known modifications to, or variations of, the Scheme 7 reaction sequence. Further to the above mentioned Kaiser oxime resin, other suitable reagents, notably resins, known to a person skilled in the art, could be employed for the solid-phase synthesis of compounds of general formula I.

Scheme 7

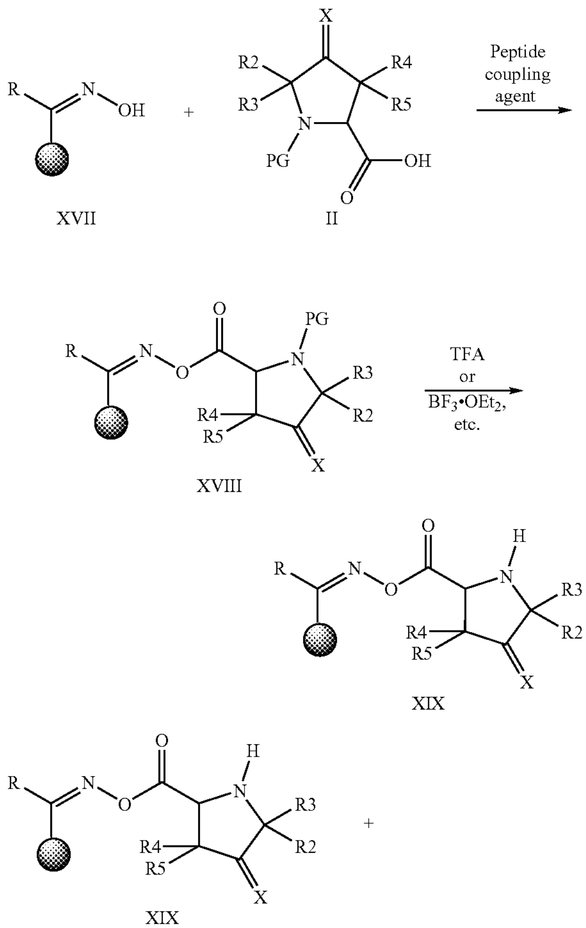

XVII

II

XVIII

XIX

XIX

-continued

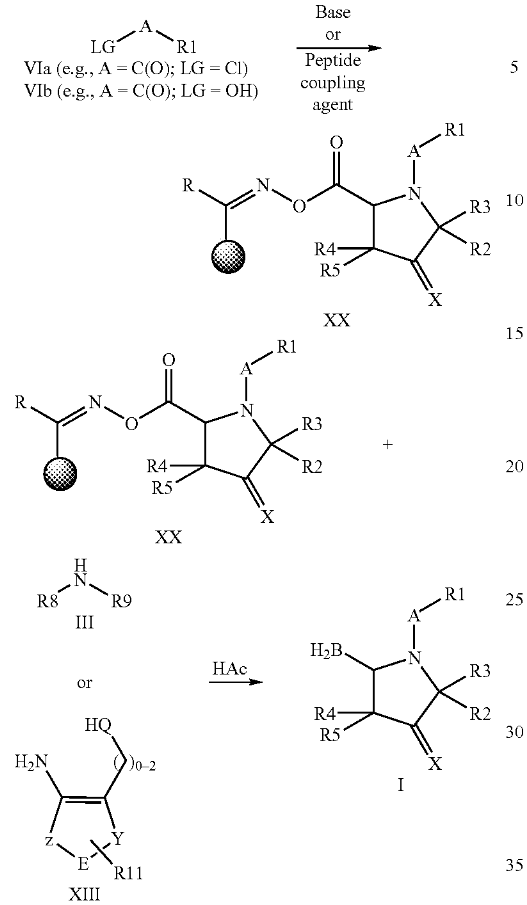

VIa (e.g., A = C(O); LG = Cl)
VIb (e.g., A = C(O); LG = OH)

XX

XX

III or

XIII

I

The reaction sequences outlined in the above Schemes provides enantiomerically pure compounds of formula I, if enantiomerically pure starting materials are used. (R) as well as (S) enantiomers can be obtained depending upon whether (R) or (S) forms of commercially available compounds of formulas II, III, VI, and/or X were used as the starting materials.

However, the reaction sequences outlined in the above Schemes usually provide mixtures of (E) and (Z) isomers with respect to the substituents on the exocyclic double bond of the pyrrolidine ring. In all cases studied, these (E)/(Z)-isomers could be separated by standard chromatography techniques well known to the person skilled in the art, such as by reversed phase high-pressure liquid chromatography (HPLC) or silica gel flash chromatography (FC). The assignment of the absolute configuration of the exocyclic double bond was performed using NMR-techniques well described in the literature as will be known to the practitioner skilled in the art (for configurationnal assignements of e.g. oxime functionalities, see e.g. E. Breitmaier, W. Voelter Carbon-13 NMR Spectroscopy, 3rd Ed, VCH, 1987, p. 240).

According to a further general process, compounds of formula I can be converted to alternative compounds of formula I, employing suitable interconversion techniques such as hereinafter described in the Examples.

If the above set out general synthetic methods are not applicable for obtaining compounds according to formula I and/or necessary intermediates for the synthesis of compounds of formula I, suitable methods of preparation known by a person skilled on the art should be used. In general, the synthesis pathways for any individual compound of formula I will depend on the specific substitutents of each molecule and upon the ready availability of intermediates necessary, again such factors being appreciated by those of ordinary skill in the art. For all the protection, deprotection methods, see Philip J. Kocienski, in "*Protecting Groups*", Georg Thieme Verlag Stuttgart, New York, 1994 and, Theodora W. Greene and Peter G. M. Wuts in "*Protective Groups in Organic Synthesis*", Wiley-Interscience, 1991.

Compounds of this invention can be isolated in association with solvent molecules by crystallization from evaporation of an appropriate solvent. The pharmaceutically acceptable acid addition salts of the compounds of formula I, which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of formula I with a suitable base. Both types of salt may be formed or interconverted using ion-exchange resin techniques.

If the above set out general synthetic methods are not applicable for the obtention of compounds of formula I, suitable methods of preparation known by a person skilled in the art should be used.

A final aspect of the present invention is related to the use of the compounds according to formula I for the modulation of the Oxytocin receptor, the use of said compounds for the preparation of pharmaceutical compositions for the modulation of the oxytocin receptor as well as the formulations containing the active compounds according to formula I. Said modulation of the oxytocin receptor is viewed as a suitable approach for the treatment of preterm labor, premature birth and dysmenorrhea. Hence, the compounds of the present invention are suitable for the treatment of preterm labor, premature birth and dysmenorrhea.

When employed as pharmaceuticals, the pyrrolidine derivatives of the present invention are typically administered in the form of a pharmaceutical composition. Hence, pharmaceutical compositions comprising a compound of formula I and a pharmaceutically acceptable carrier, diluent or excipient therefore are also within the scope of the present invention. A person skilled in the art is aware of a whole variety of such carrier, diluent or excipient compounds suitable to formulate a pharmaceutical composition. Also, the present invention provides compounds for use as a medicament. In particular, the invention provides the compounds of formula I for use as antagonists of the oxytocin receptor, for the treatment or prevention of disorders mediated by the oxytocin receptor in mammals, notably of humans, either alone or in combination with other medicaments, e.g. in combination with a further OT antagonist.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the pyrrolidine derivatives of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, and intranasal. Depending on the intended route of delivery, the compounds are preferably formulated as either injectable or oral compositions. The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the pyrrolidine compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gun tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As above mentioned, the pyrrolidine derivatives of formula I in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 8 of *Remington's Pharmaceutical Sciences,* 17$^{th}$ Edition, 1985, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences.*

In the following the present invention shall be illustrated by means of some examples which are not construed to be viewed as limiting the scope of the invention. The HPLC, NMR and MS data provided in the examples described below were obtained as followed. The following abbreviations are hereinafter used in the accompanying examples: min (minute), hr (our), g (gram), mmol (millimole), m.p. (melting point), eq (equivalents), mL (milliliter), μL (microliters), mL (milliliters), ACN (Acetonitrile), $CDCl_3$ (deuterated chloroform), cHex (Cyclohexanes), DCM (Diclloromethane), DECP (Diethylcyanophos-phonate), DIC (Diisopropyl carbodiimide), DMAP (4-Dimethylaminopyridine) DMF (Dimethylformamide), DMSO (Dimethylsulfoxide), DMSO-$d_6$ (deuterated dimethylsulfoxide), EDC (1-(3-Dimethylaminopropyl)-3-ethylcarbodiimide), EtOAc (Ethyl acetate), $Et_2O$ (Diethyl ether), HOBt (1-Hydroxybenzotriazole), $K_2CO_3$ (potassium carbonate), NaH (Sodium hydride), $NaHCO_3$ (Sodium bicarbonate), nBuLi (n Butyllithium), TBTU (O-Benzotziazolyl-N,N,N',N'-tetramethyluronium-tetrafluoroborate), TEA (Triethyl amine), TFA (Trifluoro-acetic acid), THF (Tetrahydrofuran), $MgSO_4$ Magnesium sulfate), PetEther (Petroleum ether), rt (room temperature).

EXAMPLES

Intermediate 1: (2S)-1-(tert-butoxycarbonyl)-4-oxo-2-pyrrolidinecarboxylic acid Commercial (2S,4R)-1-(tert-butoxycarbonyl)-4-hydroxy-2-pyrrolidinecarboxylic acid (30 g, 0.13 mol) was dissolved in acetone (1500 ml). A mechanical stirrer was placed in the flask and the solution stirred vigorously. A freshly made solution of 8N chromic acid was prepared by dissolving chromium trioxide (66.7 g, 0.667 mol) in water (40 ml), adding concentrated sulphuric acid (53.3 ml) and adding enough water to bring the solution volume to 115 ml. The 8N chromic acid solution (115 ml) was then added dropwise over a period of 30 minutes with continued vigorous stirring, the reaction's exotherm being maintained at the optimal temperature of 25° C. by the use of an ice bath. After the complete addition of the chromic acid, the reaction mixture was stirred for a further 15 minutes—maintaining the optimal temperature of 25° C. The reaction mixture was then quenched by the addition of methanol (20 ml). Exotherm controlled by the use of an ice bath and, if necessary, direct addition of a small amount of crushed ice to the reaction mixture itself. The reaction mixture was filtered through a Celite pad and then concentrated in vacuo. The resulting acidic solution was then extracted with ethyl acetate (3×300 ml) and the combined organic layers washed with brine (2×100 ml). Organics then dried with magnesium sulfate and concentrated in vacuo. Crude product recrystallised from ethyl acetate to give the white crystalline product, (2S)-1-(tert-butoxycarbonyl)-4-oxo-2-pyrrolidinecarboxylic acid (22.55 g, 76%). The antipodal intermediate, (2-R)-1-(tert-butoxycarbonyl)-4oxo-2-pyrrolidinecarboxylic acid, was made according to the same protocol, starting from commercial (2R,4S)-1-(tert-butoxycarbonyl)-4-hydroxy-2-pyrrolidinecarboxylic acid.

1H NMR (360 MHz, CDCl3); 1.4 (m, 9H), 2.5–3.0 (m, 2H), 3.7–3.9 (m, 2H), 4.75 (dd, 1H)

Intermediate 2: 1-tert-butyl 2-methyl (2S)-4-oxo-1,2-pyrrolidinedicarboxylate

A solution of (2S)-1-(tert-butoxycarbonyl)-4-oxo-2-pyrrolidinecarboxylic acid (1 g, 4.3 mmol) in a 1:1 mixture of methanol and toluene (60 ml) was made. Trimethylsilyl diazomethane (6.5 ml of a 2M solution in hexanes, 13 mmol) was then added dropwise to the stirred solution at room temperature under nitrogen. After completion of the evolution of nitrogen gas, the resulting yellow solution was evaporated in vacuo, and the residue filtered through a pad of silica gel, eluting with ethyl acetate. Removal of solvent from the filtrate gave a yellow oil (1.05 g, near quantitative yield).

$^1$H NMR (400 MHz, $CDCl_3$); 1.4 (m, 9H), 2.5 (m, 1H), 2.8–2.9 (m, 1H), 3.7 ((s, 3H), 3.9 (m, 2H), 4.6–4.8 (m, 1H).

Intermediate 3: 1-tert-butyl 2-methyl (2S,4EZ)-4-(chloromethylene)-1,2-pyrrolidinedicarboxylate Chloromethyltriphenylphosphonium iodide (270 mg, 0.62 mmol) was added to a solution of potassium tert-butoxide (67 mg, 0.59 mmol) in anhydrous diethyl ether (5 ml) under nitrogen and the resulting bright yellow mixture stirred for 30 minutes at ambient temperature. The reaction was then cooled to 0° C. and a solution of 1-tert-butyl 2-methyl (2S)-4-oxo-1,2-pyrrolidinedicarboxylate (100 mg, 0.41 mmol in 2 ml anhydrous diethyl ether) was added dropwise. The reaction was then warmed to room temperature and stirred for 30 minutes before adding saturated aqueous ammonium chloride solution (0.5 ml). The organic layer was removed in vacuo, and the aqueous washed with diethyl ether (3×5 ml). The combined organic layers were dried with brine and magnesium sulfate before filtering and removal of solvent. The desired product was isolated by silica gel chromatography, eluting with 15% ethyl acetate in hexanes to give 105 mg (93% yield) as a off-white wax.

$^1$H NMR (400 MHz, $CDCl_3$); 1.4 (9H, m), 2.6–2.75 (m, 1H), 2.8–3.0 (m, 1H), 3.65 (s, 3H), 4.1 (m, 2H), 4.4–4.5 (m, 1H)5.9–6.0 (m, 1H).

Intermediate 4: 1-tert-butyl 2-methyl (2S)-4-methylene-1,2-pyrrolidinedicarboxylate Methyltriphenylphosphonium bromide (22 g, 61.6 mmol) was added to a solution of potassium tert-butoxide (6.5 g, 57.6 mmol) in anhydrous diethyl ether (450 ml) at 0° C. under nitrogen and the resulting bright yellow mixture stirred for 30 minutes. A solution of 1-tert-butyl 2-methyl (2S)-4-oxo-1,2-pyrrolidinedicarboxylate (10 g, 41.1 mmol in 150 ml anhydrous diethyl ether) was added slowly to the reaction mixture, which was then warmed at 35° C. for 3 h. Saturated aqueous ammonium chloride solution (0.5 ml) was then added. The organic layer was removed, and the aqueous washed with diethyl ether (3×5 ml). The combined organic layers were dried with brine and magnesium sulfate before filtering and removal of solvent. Silica gel chromatography, eluting with 15% ethyl acetate in hexanes gave the desired product 6.9 g (70% yield) as a off-white wax.

$^1$H NMR (400 MHz, $CDCl_3$); 1.4 (9H, m), 2.5 (m, 1H), 2.8 (m, 1H), 3.65 (s, 3H), 4.0 (m, 2H), 4.3–4.5 (m, 1H), 4.9 (m, 2H).

Intermediate 5:1-tert-butyl 2-methyl (2S,4EZ)-4-(cyanomethylene)-1,2-pyrrolidinedicarboxylate Diethyl cyanomethyl phosphonate (0.86 ml, 4.4 mmol) was dissolved in dry THF (50 ml) and the solution cooled to 0° C. Sodium hydride (205 mg of a 60% suspension in parrafin oil, 5.1 mmol) was then added cautiously and the reaction stirred for 30 min. The reaction mixture was then cooled to −78° C. and a solution of 1-tert-butyl 2-methyl (25)-4-oxo-1,2-pyrrolidinedicarboxylate (1.0 g, 4.1 mmol) in dry THF (5 ml) was added dropwise. The reaction was then allowed to reach room temperature. Saturated aqueous ammonium chloride solution (15 ml) was then added, followed by ethyl acetate (100 ml). (The organic layer was removed, and the aqueous washed with ethyl acetate (3×5 ml). The combined organic layers were dried with brine and magnesium sulfate before filtering and removal of solvent. Silica gel chromatography, eluting with 35% ethyl acetate in hexanes gave the desired compound (860 mg, 80%) as an off-white wax.

$^1$H NMR (360 MHz, $CDCl_3$); 1.4 (m, 9H), 2.7–3.0 (m, 1H), 3.1–3.3 (m, 1H), 3.7 (m, 3H), 4.2–4.4 (m, 2H), 4.5–4.7 (m, 1H), 5.4 (m, 1H).

Intermediate 6: 1-tert-butyl 2-methyl (2S,4EZ)-4-benzylidene-1,2-pyrrolidinedicarboxylate Potassium tert-butoxide (6.1 g, 54 mmol) was added portionwise to a solution of benzyl-triphenylphosphonium chloride (22.45 g, 58 mmol) in anhydrous dichloromethane (400 ml) and the reaction stirred at ambient temperature for 1 h. The solution was then cooled to 0° C. and a solution of 1-tert-butyl 2-methyl (2S)-4-oxo-1,2-pyrrolidinedicarboxylate (9.36 g, 38.5 mmol) in dry dichloromethane (30 ml) was added dropwise. After stirring for a further 1 h at 0° C. the reaction was stirred for a further 3 h at ambient temperature. Saturated aqueous ammonium chloride solution (30 ml) was then added. The organic layer was removed, and the aqueous washed with dichloromethane (3×20 ml). The combined organic layers were dried with brine and magnesium sulfate before filtering and removal of solvent. Silica gel chromatography, eluting with 30% ether in hexanes gave the desired product 8.65 g (71% yield) as a pale yellow wax.

$^1$H NMR (400 MHz, $CDCl_3$);1.5 (m, 91), 2.8–3.0 (m, 1H), 3.2 (m, 1H), 3.7 (m, 31), 4.2–4.4 (m, 2H), 4.5–4.6 (m, 1H), 6.3–6.4 (m, 1H), 7.1–7.5 (m, 5H).

Intermediate 7: (2S,4EZ)-1-(tert-butoxycarbonyl-)-4-(methoxyimino)-2-pyrrolidinecarboxylic acid A solution was made containing (2S)-1-(tert-butoxycarbonyl)-4-oxo-2-pyrrolidinecarboxylic acid (5.0 g, 21 mmol) and O-methylhydroxylamine hydrochloride (2.7 g, 32.8 mmol) in chloroform (100 ml) containing triethylamine (5.5 g, 55 mmol). The reaction mixture was then stirred at ambient temperature overnight, prior to removal of solvent. The resultant crude reaction mixture was dissolved in ethyl acetate (150 ml) and washed rapidly with 1N HCl (40 ml). The acidic layer was then extracted with ethyl acetate (3×20 ml) and the combined organic layers washed with brine before drying over magnesiom sulfate, filtering and removal of solvent in vacuo. The desired product (5.3 g, 94%) was isolated as a pale yellow oil.

$^1$H NMR (400 MHz, $CDCl_3$); 1.45 (m, 9H), 2.8–3.2 (m, 2H), 3.9 (s, 3H), 4.2 (m, 2H), 4.5–4.7 (m, 1H).

Intermediate 8: (2S,4EZ)-1-(tert-butoxycarbonyl)-4-(ethoxyimino)-2-pyrrolidinecarboxylic acid A solution was made containing (2S)-1-(tert-butoxycarbonyl)-4-oxo-2-pyrrolidinecarboxylic acid (5.0 g, 22 mmol) and O-ethylhydroxylamine hydrochloride (6.4 g, 65.5 mmol) in a 1:1 mixture of pyridine and ethanol (100 ml). The reaction was heated to reflux for 2.5 h before cooling and removal of solvent. The residue was dissolved in ethyl acetate and washed rapidly with 1.3N HCl (40 ml). The acidic layer was then extracted with ethyl acetate (3×20 ml) and the combined organic layers washed with brine before drying over magnesiom sulfate, filtering and removal of solvent in vacuo. The desired product (5.5 g, 93%) was isolated as a pale yellow oil.

$^1$H NMR (400 MHz, DMSO); 1.3 (t, 3H), 1.55 (m, 9H), 2.9–2.7 (m, 1H), 3.4–3.1 (m, 1H), 4.1–4.3 (m, 4H), 4.6 (m, 1H), 12–13.5 (br, 1H).

Intermediate 9: (2S,4EZ)-4-[(allyloxy-imino]-1-(tert-butoxycarbonyl)-2-pyrrolidine-carboxylic acid A solution was made containing (2S)-1-(tert-butoxycarbonyl)-4-oxo-2-pyrrolidinecarbocylic acid (5.0 g, 22 mmol) and O-allylhydroxylamine hydrochloride monohydrate (7.2 g, 65.5 mmol) in a 1:1 mixture of pyridine and ethanol (100 ml). The reaction was heated to reflux for 2.5 h before cooling and removal of solvent. The residue was dissolved in ethyl acetate and washed rapidly with 1.3N HCl (40 ml). The acidic layer was then extracted with ethyl acetate (3×20 ml) and the combined organic layers washed with brine before drying over magnesium sulfate, filtering and removal of solvent in vacuo. The desired product (5.9 g, 94%) was isolated as a pale yellow oil.

$^1$H NMR (400 MHz, $CDCl_3$); 1.5 (m, 9H), 2.8–3.2 (m, 2H), 4.2 (m, 2H), 4.5–4.7 (m, 3H), 5.25 (m, 2H), 5.9 (m, 1H), 11.1 (broad S, 1H).

Intermediate 10: 1-[(aminooxy)methyl]-4-methoxybenzene

A solution was made of Boc hydroxylamine (2.0 g, 17.1 mmol) in dry TBF (60 ml). Sodium hydride (1.1 g of a 60% suspension in paraffin oil, 25.7 mmol) was then added and the suspension stirred. A catalytic amount of KI was then added to the reaction prior to the cautious addition of 4-methoxybenzyl chloride (3.2 g, 20.4 mmol). The reaction was then allowed to stir overnight before removal of solvent in vacuo. The residue was taken up with diethyl ether (100 ml) and HCl gas bubbled in for 20 minutes, causing the start of precipitation of the product. The flask was stoppered and left to stand overnight. The product was then filtered off as a off-white wax (39–52% yield according to varying batches).

$^1$H NMR (400 MHz, $D_2O$); 3.8 (s, 3H), 5 (s, 2H), 7.0 (d, 2H), 7.4 (d, 2H).

Intermediate 11: (2S,4EZ)-1-(tert-butoxycarbonyl)-4-{[(4-methoxybenzyl)oxy]imino}-2-pyrrolidinecarboxylic acid The same method as employed in the preparation of Intermediate 7, but starting from (2S)-1-(tert-butoxycarbonyl)-4-oxo-2-pyrrolidinecarboxylic acid (Intermediate 1) and 1-[(aminooxy)methyl]4-methoxy-benzene (Intermediate 10) gave the title compound as a gum in a 85% yield.

$^1$H NMR (400 MHz, DMSO); 1.5 (m, 9H), 2.7–2.9 (m, 1H) 3.9 (s, 3H), 4.2 (m, 3H), 4.6 (m, 1H), 5.15 (s, 2H), 7.1 (d, 2H), 7.45 (d, 2H).

Intermediate 12: 2-aminoethyl acetate TFA-salt

A solution was made containing ethanolamine (36.5 ml, 0.6 mol) in chloroform (1000 ml). The $Boc_2O$ (13.1 g, 60 mmol) dissolved in chloroform (600 ml) was slowly added dropwise at 0° C. over a 6-hours period (the temperature was maintained all over this period). The reaction was allowed to reach room temperature and was stirred overnight. The organic layer was washed with water (2×500 ml), brine and dried over magnesium sulfate before being concentrated in vacuo. The desired product (9.5 g,>95%) was isolated as a colourless oil and was used without further purification. A solution was made containing the Boc-ethanolamine (1.92 g, 12 mmol) with potassium carbonate (5 g, 36 mmol) in DCM (40 ml). Acetyl chloride (30 ml, 0.42 mol) was added and the reaction stirred for 6 hours at room temperature. The excess of acetyl chloride was removed in vacuo and the crude dissolved in DCM (100 ml). The organic layer was washed with water (50 ml), brine and dried over magnesium sulfate before being concentrated in vacuo. The desired product (1.86 g, 77%) was isolated as a colourless oil and was used without further purification. A solution was made containing the O-acyl, Boc-ethanolamine (1.65 g, 8.1 mmol) in DCM (20 ml) and TFA (20 ml) was added. After one hour at room temperature, the solvent was removed in vacuo. The crude was concentrated from methanol (2–3 times) and from DCM (2–3 times) to give the expected compound (1.75 g, quant.) as an oil used without further purification.

$^1$H NMR (400 MHz, $D_2O$); 2.0 (m, 9H), 3.1–3.2 (m, 2H), 4.15–4.25 (m, 2H).

Intermediate 13: 2'-methyl[1,1'-biphenyl]-4-carboxylic acid

To a mixture of 4-bromobenzoic acid (30 g, 0.15 mol), 2-methylphenylboronic acid (24 g, 0.15 mol), sodium carbonate (250 g) in toluene (500 mL) and water (500 mL) was added tetrakistriphenylphosphine palladium(0) (9 g, 0.0074 mol) under nitrogen atmosphere. The reaction mixture was refluxed for 10 h. After this time, 100 ml of 10% NaOH were added to the reaction mixture, the aqueous layer was separated and washed with toluene (2×200 mL). Acidification of the aqueous layer with 3N HCl solution gave a solid product, which was filtered, washed with water and dried. The crude product was then crystallized from toluene to yield 2'-methyl [1,1'-biphenyl]-4-carboxylic acid (20 g, 62.5%). Conversely, the product could also be obtained from 1-bromo-2-methylbenzene and 4-carboxybenzeneboronic acid, using analogous conditions.

$^1$H NMR (300 MHz, DMSO); 2.2 (s, 3H), 7.2–7.4 (m, 4H), 7.43 (d, J=9 Hz, 2H), 7.99 (d, J=9 Hz, 2H), 13 (b, 1H).

Similarly, using the appropriate commercial boronic acids and arylbromides, the following, related 1,1'-biphenyl intermediates 13 may be obtained: 4'-methyl[1,1'-biphenyl]-4-carboxylic acid; 2',3-dimethyl[1,1'-biphenyl]-4-carboxylic acid; 2',6'-dimethyl[1,1'-biphenyl]-4-carboxylic acid; 2-methyl[1,1'-biphenyl]-4-carboxylic acid; 3-methyl[1,1'-biphenyl]-4-carboxylic acid; 2,2'-dimethyl[1,1'-biphenyl]-4-carboxylic acid; 2'-methoxy[1,1'-biphenyl]-4-carboxylic acid; 3'-methoxy[1,1'-biphenyl]-4-carboxylic acid; 4'-methoxy[1,1'-biphenyl]-4-carboxylic acid; 2'-chloro[1,1'-biphenyl]-4-carboxylic acid; 3'-chloro[1,1'-biphenyl]-4-carboxylic acid; 4'-chloro[1,1'-biphenyl]-4-carboxylic acid; 3',4'-dichloro[1,1'-biphenyl]-4-carboxylic acid; 2'-(trifluoromethyl)[1,1'-biphenyl]-4-carboxylic acid; 3'-(trifluoromethyl)[1,1'-biphenyl]-4-carboxylic acid; 2'-cyano[1,1'-biphenyl]-4-carboxylic acid; 2',4'-difluoro[1,1'-biphenyl]-4-carboxylic acid; 4-(2-pyridinyl)benzoic acid; 4-(3-pyridinyl)benzoic acid; 4-(4-pyridinyl)benzoic acid; 4-(5-pyrimidinyl)benzoic acid.

Intermediate 14: 4-(3-methyl-2-pyridinyl)benzoic acid

A mixture of 2-bromo-3-methylpyridine (22.5 g, 0.1312 mol), 4-(hydroxymethyl)phenylboronic acid (25 g, 0.164 mol), $Pd(PPh_3)_4$ (9.5 g, 0.0082 mol), and sodium carbonate (200 g in 500 ml of water) in toluene (750 ml) were refluxed under nitrogen atmosphere for 15 h. Separated the toluene layer and distilled under reduced pressure to give a residue. The residue was then purified by column chromatography to yield [4-(3-methyl-2-pyridinyl)-phenyl]methanol (12 g, 47%).

To a solution of [4-(3-methyl-2-pyridinyl)phenyl]methanol (12 g, 0.06 mol) in dry DMF (150 mL) was added pyridiniumdichromate (91 g, 0.24 mol) and stirred at RT for 3 days. The reaction mixture was poured into water and extracted with ethyl acetate (250 mL). The organic layer was washed with water, brine, dried and concentrated. The crude was purified by column chromatography over silica gel to give 4-(3-methyl-2-pyridinyl)benzoic acid (3 g, 25%) as white solid.

$^1$H NMR (300 MHz, DMSO); 2.3 (s, 3H), 7.33 (dd, J=7.5 Hz, 5 Hz, 1H), 7.67 (d, J=8 Hz, 2H), 7.75 (d, J=7.5 Hz, 1H), 8.01 (d, J=8 Hz, 2H), 8.50 (d, J=5 Hz, 1H), 13 (b, 1H).

Intermediate 15: 4-(1-oxido-3-pyridinyl)benzoic acid

To a mixture of 4-tolylboronic acid (38 g, 0.28 mol), 3-bromopyridine (44 g, 0.28 mol), $Na_2CO_3$ (200 g) in toluene (500 ml) and water (500 ml) was added $Pd(PPh_3)_4$ (16 g, 0.014 mol), and refluxed for 16 h. The reaction mixture was cooled, and the separated organic layer was washed with water and brine, and dried. The solvent was removed to give 4-(3-pyridyl)toluene (42 g, 90%).

To a mixture of 4-(3-pyridyl)toluene (35 g, 0.207 mol) in pyridine (400 ml) and water (400 ml) was added KMnO4 (163 g, 1.03 mol) in portions and refiuxed for 12 h. The reaction mixture was filtered through celite and acidified with cone. HCl. The product was washed with water and dried to give 4-(3pyridyl)benzoic acid (32 g, 76%) as a white solid. To a mixture of 4-(3-pyridyl)benzoic acid (22 g, 0.11 mol) in THF (2.51), mCPBA (152 g 0.44 mol, 50%) was added and stirred at RT for 12 h. The solid was filtered, and washed with TBF to give 4-(1-oxido-3-pyridinyl)benzoic acid (20 g, 86%).

$^1$H NMR (300 MHz, DMSO); 7.5–7.8 (m, 5H), 7.9 (d, J=8 Hz, 2H), 8.33 (d, J=5Hz, 2H).

Similarly, starting from 4-tolylboronic acid (45 g, 0.33 mol) and 2-bromopyridine (52 g, 0.33 mol), the related intermediate 4-(1-oxido-2-pyridinyl)benzoic acid was obtained.

Example 1

General Procedure for the Saponification of the Olefin-Type Proline Methyl Esters, Such as Intermediates 3–6

A solution of sodium hydroxide (4.5 g, 112 mmol) in water (70 ml) was added to the relevant proline olefin methyl ester (66 mmol) in 3:1 dioxane:water (500 ml) and the reaction stirred for 3 h. The reaction mixture was then washed with diethyl ether (2×50 ml), and the aqueous phase acidified to pH 2 (0.1N HCl) and extracted into ethyl acetate. The ethyl acetate layer was then dried over magnesium sulfate, filtered and the solvent was then removed in vacuo to give the desired product in near quantitative yields as an oil which was used without fiber purification.

Example 2

General Protocol for the Solution-Phase Synthesis of Oximether Prolidine Derivatives of General Formula Ia (Scheme 1)

Method A: e.g. (2S,4EZ)-1-([1,1'-biphenyl]-4-ylcarbonyl)-N-(2-methoxyethy)-4-(methoxmyimino)-2-pyrrolidinecarboxamide a) Protocol for the Formation of the Amide Bond A solution was made containing the central building block, e.g. (2S,4EZ)-1-(tert-butoxycarbonyl)-4-(methoxyimino)-2-pyrrolidinecarboxylic acid (Intermediate 7) (1.5 g, 5.8 mmol), an amine or an amine salt, e.g. 2-methoxyethylamine (0.51 ml, 5.81 mmol) and DMAP (780 mg, 5.8 mmol) in DCM (30 ml). At 0° C., EDC (1.1 g, 5.8 mmol) was slowly added portion-wise. The reaction was slowly allowed to reach room temperature and was stirred overnight. The DCM was evaporated and the crude purified by column chromatography using EtOAc (100%) to collect the desired product, e.g. tert-butyl (2S,4EZ)-2-{[(2-meth-oxyethyl)amino]carbonyl}-4-(methoxyimino)-1-pyrrolidinecarboxylate (1.5 g, 80%) as a colourless oil.

$^1$H NMR (400 MHz, $CDCl_3$); 1.25 (m, 9H), 2.5–2.9 (m, 2H), 3.1 (s, 3H), 3.2–3.3 (m, 4H), 3.65 (s, 3H), 3.8–4.4 (m, 3H), 6.7 (s broad, 1H).

b) Protocol for the N-Deprotection Step

A solution was made containing the amide compounds from the previous step, e.g. tert-butyl (2S,4EZ)-2-{[(2-methoxyethyl)amino]carbonyl}-4-(methoxyimino)-1-pyrrolidine-carboxylate (1.5 g, 0.4 mmol), in anhydrous ether (35 ml). HCl gas was bubbled slowly through the reaction and the deprotection was followed by TLC. After approximately 20 minutes, the ether was evaporated. The product was concentrated in vacuo from DCM (2–3 times) to remove the HCl. The desired product, e.g. (2S,4EZ)-N-(2-methoxyethyl)-4-(methoxyimino)-2-pyrrolidinecarboxamide (1.2 g, quant.) was isolated as a yellow oil and used without further purification.

c) Protocol for the N-Capping Step

A solution was made containing the free NH-compound from the previous step, e.g. (2S,4EZ)-N-(2-methoxyethyl)-4-(methoxyimino)-2-pyrrolidinecarboxamide (940 mg, 3.7 mmol), a carboxylic acid, e.g. [1,1'-biphenyl]-4-carboxylic acid (740 mg, 3.7 mmol) and DMAP (960 mg, 7.8 mmol) in DCM (30 ml). At 0° C., EDC (715 mg, 3.7 mmol) was slowly added portionwise. The reaction was slowly allowed to reach room temperature and was stirred overnight. The DCM was evaporated and the crude purified by column chromatography using EtOAc (100%) to collect the desired product, e.g. (2S,4EZ)-1-([1,1'-biphe-nyl]-4-ylcarbonyl)-N-(2-methoxyethyl)-4-(methoxyimino)-2-pyrrolidinecarboxamide as a mixture of two isomers as an off-white solid.

1H NMR (400 MHz, CDCl3); 2.75–2.85 (m, 1H), 3.1–3.3 (m, 4H), 3.4–3.5 (m, 4H), 3.8 (m, 3H), 4.1–4.3 (m, 2H), 5.1 (m, 1H), 6.9 (m, 1H), 7.2–7.7 (m, 10H). $M^+$($APCI^+$); 396.

Method B: e.g. (2S,4E and 4Z)-N-[(2S)-2-hydroxy-2-phenylethyl]-4-(methoxyimino)-1-[(2'-methyl[1,1'-biphenyl]-4-yl)carbonyl]-2-pyrrolidinecarboxamide a) Protocol for the Formation of the Amide Bond To a solution of the central building block, e.g. (2S,4EZ)-1-(tert-butoxycarbonyl)-4-(methoxyimino)-2-pyrrolidinecarboxylic acid (Intermediate 7) (24.2 mmol, 6.24 g) in dry THF (125 ml) at −25° C. was added NMM (2.5 eq, 60.4 mmol, 6.64 ml) followed by isobutylchloroformate (1.05 eq, 25.4 mmol, 3.3 ml). The resulting mixture was stirred at −25° C. for 30 min and an amine or an amine salt, e.g. (S)-2-amino-1-phenylethanol (1.51 eq, 36.5 mmol, 5 g) was then added. The mixture was allowed to gradually warm to rt. After 16 h, the solvents were removed. The residue was dissolved in AcOEt, washed twice with $NH_4Cl$ saturated solution, then twice with 10% $NaHCO_3$ solution. The organic layer was dried over $Na_2SO_4$, filtrated and concentrated to afford the desired product, e.g. tert-butyl (2S,4EZ)-2-({[(2S)-2-hydroxy-2-phenylethyl]amino}carbonyl)-4-(methoxyimino)-1-pyrrolidine-carboxylate (8.76 g, 96%) as a pale yellow oil in 88.5% purity by HPLC.

$^1$H NMR ($CDCl_3$: 300 MHz) δ1.44 (s, 9H, N-Boc), 3.23–2.85 (m, 4H), 3.72 (m, 1H), 3.85 (s, 3H, O—$CH_3$), 4.10 (m, 2H), 4.49 (m, 1H), 4.83 (m, 1H), 7.34 (m, 5H, Ar—H); [M+$Na^+$] ($ESI^+$): 400.

b) Protocol for the N-Deprotection Step

A solution was made containing the amide compounds from the previous step, e.g. tert-butyl (2S,4EZ)-2-({[(2S)-2-hydroxy-2-phenylethyl]amino}carbonyl)-4-(methoxyimino)-1-pyrrolidinecarboxylate (2.64 g, 7 mmol), in anhydrous DCM (35 ml). At 0° C., HCl gas was bubbled slowly through the reaction and the deprotection was followed by TLC. After approximately 20 minutes, the DCM was evaporated. The product was concentrated in vacuo from DCM (2–3 times) to remove the HCl. The desired product, e.g. (2S,4EZ)-N-[(2S)-2-hydroxy-2-phenylethyl]-4-(methoxyimino)-2-pyrrolidinecarboxamide (1.94 g, quant.) was isolated as a yellow solid and used without further purification.

c) Protocol for the N-Capping Step

To a suspension of 4-(2-methylphenyl)benzoic acid (1.49 g, 7 mmol.) in 35 ml DCM, was added oxalyl chloride and DMF (3 ml) under ice cooling. The mixture was stirred for 2 h at rt. The solvent was removed affording the corresponding acyl chloride as a yellow solid. It was dissolved in DCM (30 mL) and added slowly on a 0° C. solution containing the free NH-compound from the previous step, e.g. (2S,4EZ)-N-[(2S)-2-hydroxy-2-phenylethyl]-4-(methoxyimino)-2-pyrrolidinecarboxamide (1.94 g, 7 mmol), and triethylamime (5 eq, 35 mmol, 4.9 ml) in dry DCM (35 ml). The reaction mixture was stirred overnight at r.t. Poltrisamine was added (2.12 g, 3.45 mmol/g) in order to scavenge excess of acyl chloride. The mixture was shaken 3 h, filtered and the resulting solution was washed with $NH_4Cl$ sat, brine, and dried over $Na_2SO_4$. After filtration and evaporation of the solvents, the resulting dark oil (3.26 g) was purified by flash chromatography (Biotage system, column 40M, 90 g SiO2, with gradients of DCM and MeOH as eluent), affording (2S,4E2)-N-[(2S)-2-hydroxy-2-phenylethyl]-4-(methoxyimino)-1-[(2'-methyl[1,1'-biphenyl]-4-yl)carbonyl]-2-pyrrolidinecarboxamide. Separation of the E/Z-isomers was achieved by several chromatographies, affording (2S,4E)-N-[(2S)-2-hydroxy-2-phenylethyl]-4-(methoxyimino)-1-[(2'-methyl[1,1'-biphenyl]-4-yl)carbonyl]-2-pyrrolidinecarboxamide (230 mg, colorless powder, 98.7% purity by HPLC) and (2S,4Z)-N-[(2S)-2-hydroxy-2-phenylethyl]-4-(methoxyimino)-1-[(2'-methyl[1,1'-biphenyl]-4-yl)carbonyl]-2-pyrrolidinecarboxamide (266 mg, colorless powder, 98.3% purity by HPLC).

(2S,4E)-N-[(2S)-2-hydroxy-2-phenylethyl]-4-(methoxyimino)-1-[(2'-methyl[1,1'-biphenyl]-4-yl)carbonyl]-2-pyrrolidinecarboxamide: M.p. 74° C.; IR (neat) ν3318, 2932, 1613, 1538, 1416, 1239, 1047, 848 $cm^{-1}$; $^1H$ NMR (300 MHz, $CDCl_3$): 2.27 (s, 3H, $ArCH_3$), 2.89 (dd, J=6, 12 Hz, 1H),3.18 (br d, J=12 Hz, 1H), 3.27 (m, 1H), 3.76 (m, 1H), 3.88 (s, 3H, $NOCH_3$), 4.28 (d, J=10 Hz, 1H), 4.47 (d, J=10 Hz, 1H), 4.59 (br s, 1H), 4.88 (m, 1H), 5.20 (m, 1H), 7.03–7.42 (m, 11H, H arom.),7.45–7.54 (m, 2H, H arom.); $M^+(APCI^+)$: 472; $M^-(APCI^-)$: 470. analysis calculated for $C_{28}H_{29}N_3O_4$ 0.3 $H_2O$: C, 70.51; H, 6.26; N, 8.81. Found: C, 70.53; H, 6.30; N, 8.87.

(2S,4Z)-N-[(2S)-2-hydroxy-2-phenylethyl]-4-(methoxyimino)-1-[(2'-methyl[1,1'-biphenyl]-4-yl)carbonyl]-2-pyrrolidinecarboxamide: M.p. 78° C.; IR (neat) ν3318, 2938, 1622, 1538, 1416, 1233, 1045, 852 $cm^{-1}$; $^1H$ NMR (300 MHz, $CDCl_3$): 2.28 (s, 3H, $ArCH_3$), 2.69 (dd, J=6, 10 Hz, 1H), 3.02–3.22 (m, 2H), 3.25 (br s, 1H), 3.60 (m, 1H), 3.86 (s, 3H, $NOCH_3$), 4.14 (m, 2H), 4.71 (m, 1H), 4.96 (m, 1H), 7.03–7.42 (m, 1H, H arom.), 7.45–7.54 (m, 2H, H arom.); $M^+(APCI^+)$: 472; $M^-(APCI^-)$: 470. Analysis calculated for $C_{28}H_{29}N_3O_4$ 0.9 $H_2O$: C, 68.95; H, 6.36; N, 8.61. Found: C, 68.87; H, 6.25; N, 8.77.

d) E/Z-Isomerisation

The pure E-isomer was isomerized to a mixture of the E/Z-isomers by the following procedure: the E-isomer was dissolved in dioxane/water 3:1 mixture. NaOH (1.7 eq; 0.52 mL of NaOH 1.6N) was added and the resulting solution was stirred 2 h at r.t. The mixture was neutralised with HCl 0.1 N and lyophilised. The components of the resulting E/Z-mixture were separated and purified by flash chromatography using same conditions as described above.

Example 3

(2S,4EZ)-1-([1,1'-biphenyl]-4-ylcarbonyl)-N-[2-(diethylamino)ethyl]-4-{[(4-methoxybenzyl)oxy]imino}-2-pyrrolidinecarboxamide Following the general method as outlined in Example 2, starting from (2S,4EZ)-1-(tert-butoxycarbonyl)-4-{[(4-methoxybenzyl)oxy]imino}-2-pyrrolidinecarboxylic acid, [1,1'-biphenyl]-4-carboxylic acid, and $N^1$,$N^1$-diethyl-1,2-ethanediamine the title compound was obtained after column chromatography as an off-white solid as a mixture of E/Z-isomers.

$^1$HNMR (400 MHz, CDCl3); 1.05–1.15 (m, 6H), 2.7–2.8 (m, 1H), 2.9–3.2 (m, 6H), 3.4 (m, 1H), 3.6 (s, 3H), 4.0–4.1 (m, 1H), 4.3–4.4 (m, 1H), 3.75 (m, 1H), 3.8 (m, 2H), 6.65 (m, 2H), 7.0–7.1(m, 2H) 7.2–7.3(m, 3H), 7.35–7.45(m, 6H), 8.8 (s/br, 0.5H). $M^+(APCI^+)$; 543.

Example 4

(2S,4EZ)-1-([1,1'-biphenyl]-4-ylcarbon)-4-(chloromethylene)-N-[(2RS)-2-hydroxy-2-phenethyl]-2-pyrrolidinecarboxamide Following the general method as outlined in Example 2, starting from (2S,4EZ)-1-(tert-butoxycarbonyl)-4-(chloromethylene)-2-pyrrolidinecarboxylic acid, [1,1'-biphenyl]-4-carboxylic acid, and (1RS)-2-amino-1-phenylethanol, the title compound was obtained after column chromatography as a mixture of E/Z-isomers as an off-white solid. The two isomers could be separated by another flash chromatographic purification step.

(2S,4E)-1-([1,1'-biphenyl]-4-ylcarbonyl)-4-(chloromethylene)-N-[(2RS)-2-hydroxy-2-phenethyl]-2-pyrrolidinecarboxamide: 1H NMR (400 Mz, CDCl3); 2.6–2.7 (m, 1H), 2.8–3.0 (m, 3H), 3.2 (m, 1H), 3.4–3.6 (m, 1H), 3.9 (m, 1H), 4.15 (t, 1H), 4.6 (m, 1H), 4.85 (m, 1H), 5.75 (s, 1H), 7.0–7.4 (m, 14H). $M^+(APCI^+)$; 461.

(2S,4Z)-1-([1,1'-biphenyl]ylcarbonyl)-4-(chloromethylene)-N-[(2RS)-2-hydroxy-2-phenethyl]-2-pyrrolidinecarboxamide: 1H NMR (400 MHz, CDCl3); 2.5–2.6 (m, 1H), 2.7–2.9 (m, 1H), 3.0 (m, 1H), 3.1–3.4 (m, 1H), 3.4–3.6 (m, 1H), 3.94–4.0 (m, 1H), 4.2–4.4 (m, 2H), 4.6 (m, 1H), 4.8–4.9 (m, 1H), 5.75 (s, 1H), 7.0–7.5 (m, 14H). $M^+(APCI^+)$; 461.

Example 5

(2S,4EZ)-N-[2-(diethylamino)ethyl]-1-(diphenylacetyl)-4-(methoxyimino)-2-pyrrolidinecarboxamide Following the general method as outlined in Example 2, starting from (2S,4EZ)-1-(tert-butoxycarbonyl)-4-(methoxyimino)-2-pyrrolidinecarboxylic acid, diphenylacetic acid, and $N^1$,$N^1$-diethyl-1,2-ethanediamine the title compound was obtained after column chromatography as an off-white solid as a mixture of E/Z-isomers.

$^1$HNMR (400 MHz, CDCl3); 0.9 (t, 3H), 1.0 (m, 3H), 2.6–3.1 (m, 7H), 3.15 (m, 1H), 3.4 (m, 1H), 3.75 (s, 3H), 3.95 (t, 1H), 4.4–4.7 (m, 4H), 5.1 (m, 1H), 7.0–7.3 (m, 10H), 9.1 (m, 1H). $M^+$($APCI^+$); 451.

Example 6

(2S,4EZ)-4-(ethoxyimino)-N-(9-ethyl-9H-carbazol-3-yl)-1-(-phenoxyacetyl)-2-pyrrolidinecarboxamide Following the general method as outlined in Example 2, starting from (2S,4EZ)-1-(tert-butoxycarbonyl)-4-(ethoxyimino)-2-pyrrolidinecarboxylic acid, phenoxyacetic acid, and 9-ethyl-9H-carbazol-3-amine the title compound was obtained after column chromatography as an off-white solid as a mixture of E/Z-isomers. The isomers were then separated using column chromatography.

(2S,4E)-4-(ethoxyimino)-N-(9-ethyl-9H-carbazol-3-yl)-1-(phenoxyacetyl)-2-pyrrolidinecarboxamide: 1H NMR (360 MHz, $CDCl_3$); 1.2 (m, 6H), 2.7 (m, 1H), 3.35 (d, 1H), 4.1 (m, 4H), 4.3 (d, 1H), 4.45 (d, 1H), 4.7 (m, 2H), 5.15 (d, 1H), 6.9–7.3 (m, 10H), 7.9 (d, 1H), 8.15 (m, 1H), 9.0 (br s, 1H). $M^+$($APCI^+$); 499.

(2S,4Z)-4-(ethoxyimino)-N-(9-ethyl-9H-carbazol-3-yl)-1-(phenoxyacetyl)-2-pyrrolidinecarboxamide: 1H NMR (360 MHz, $CDCl_3$); 1.2 (m, 6H), 2.7 (m, 1H), 3.2 (m, 1H), 4.1 (m, 4H), 4.35 (m, 2H), 4.7 (m, 2H), 5.1 (m, 1H), 6.9–7.3 (m, 10H), 7.9 (d, 1H), 8.15 (m, 1H), 9.0 (br s, 1H). $M^+$($APCI^+$); 499.

Example 7

(2S,4EZ)-N-(9-ethyl-9H-carbazol-3-yl)-4-(methoxyimino)-1-[(2-oxo-6pentyl-2H-pyran-3-yl)carbonyl]-2-pyrolidinecarboxamide Following the general method as outlined in Example 2, starting from (2S,4EZ)-1-(tert-butoxycarbonyl)-4-(methoxyimino)-2-pyrrolidinecarboxylic acid, 2-oxo-6-pentyl-2H-pyran-3-carboxylic acid, and 9-ethyl-9H-carbazol-3-amine the title compound was obtained after column chromatography as an off-white solid as a mixture of E/Z-isomers. The isomers were separated by column chromatography.

(2S,4E)-N-(9-ethyl-9H-carbazol-3-yl)-4-(methoxyimio)-1-[(2-oxo-6-pentyl-2H-pyran-3-yl)carbonyl]-2-pyrrolidinecarboxamide: 1H NMR (360 MHz, $CDCl_3$); 0.8 (m, 6H), 1.2 (m, 6H), 2.5 (m, 2H), 3.0 (m, 1H), 3.3 (m, 1H), 3.8 (s, 3H), 4.2 (m, 3H), 4.45 (m, 1H), 5.3 (m, 1H), 6.1 (d, 1H), 7.1 (m, 1H), 7.2 (m, 1H), 7.3 (d, 1H), 7.35 (m, 1H), 7.55 (m, 1H), 7.65 (m, 1H), 8.0 (d, 1H), 8.5 (m, 1H), 9.1 (br S, 1H). $M^+$($ES^+$); 543.

(2S,4Z)-N-(9-ethyl-9H-carbazol-3-yl)-4-(methoxyimino)-1-[(2-oxo-6-pentyl-2H-pyran-3-yl)carbonyl]-2-pyrrolidinecarboxamide: 1H NMR (360 MHz, $CDCl_3$); 0.8 (m, 6H), 1.2 (m, 6H), 2.5 (m, 2H), 3.05 (m, 1H), 3.25 (m, 1H), 3.75 (s, 3H), 4.1 (m, 3H), 4.45 (d, 1H), 5.3 (d, 1H), 6.1 (d, 1H), 7.1 (t, 1H), 7.2 (m, 1H), 7.3 (m, 1H), 7.4 (m, 1H), 7.6 (m, 1H), 7.7 (m, 1H), 8.0 (d, 1H), 8.45 (m, 1H), 9.1 (m, 1H). $M^+$($ES^+$); 543.

Example 8

(2S,4EZ)-4-[(allyloxy)imino]-1-benzoyl-N-(9-ethyl-9H-carbazol-3-yl)-2-pyrrolidinecarboxamide Following the general method as outlined in Example 2, starting from (2S,4EZ)-4-[(allyl-oxy)imino]-1-(tert-butoxycarbonyl)-2-pyrrolidinecarboxylic acid, benzoic acid, and 9-ethyl-9H-carbazol-3-amine the title compound was obtained after column chromatography as an off-white solid as a mixture of E/Z-isomers.

1H NMR (360 MHz, $CDCl_3$); 1.2 (m, 3H), 2.8 (m, 1H), 3.35 (m, 1H), 4.2 (m, 4H), 4.4 (m, 3H), 5.2 (m, 2H), 5.35 (m, 1H), 5.85 (m, 1H), 7.0–7.5 (m, 5H), 7.9 (m, 3H), 8.1 (m, 2H), 8.3 (m, 1H), 9.2 (br s, 1H). $M^+$($APCI^+$); 481.

Example 9

General Protocol for the Solution-Phase Synthesis of Oximether Pyrrolidine Derivatives of General Formula I Containing Additional Reactive Groups; (2S,4EZ)-1-([1,1'-biphenyl]-4-ylcarbonyl)-N-(2-hydroxyethyl)-4-(methoxyimino)-2-pyrrolidinecarboxamide a) Protocol for the Formation of the Amide Bond A solution was made containing the central building block, e.g. (2S,4EZ)-1-(tert-butoxycarbonyl)-4-(methoxyimino)-2-pyrrolidinecarboxylic acid (Intermediate 7) (575 mg, 2.2 mmol), the amine or amine salt containing the suitably protected reactive group, e.g. 2-aminoethyl acetate (Intermediate 12) (480 mg, 2.2 mmol) and DMAP (870 mg, 7.1 mmol) in DCM (20 ml). At 0° C., EDC (427 mg, 2.2 mmol) was slowly added portion-wise. The reaction was slowly allowed to reach room temperature and was stirred overnight. The DCM was evaporated and the crude purified by column chromatography using EtOAc/Hexane: 55/45 to collect the desired amide compound, e.g. tert-butyl (2S,4EZ)-2-({[2-(acetyloxy)ethyl]-amino}carbonyl)-4-(methoxyimino)-1-pyrrolidinecarboxylate (373 mg, 49%) as an oil.

1H NMR (400 MHz, CDCl3); 1.7 (m, 9H), 2.1–2.2 (m, 3H), 2.8–3.3 (m, 2H), 3.7–3.8 (m, 2H), 4.0–4.1 (m, 3H), 4.2–4.8 (m, 5H), 7.3 (s broad, 1H).

b) Protocol for the N-Deprotection Step

A solution was made containing the Boc-protected compound from the previous step, e.g. tert-butyl (2S,4EZ)-2-({[2-(acetyloxy)ethyl]amino}carbonyl)-4-(methoxyimino)-1-pyrrolidinecarboxylate (373 mg, 1.2 mmol) in anhydrous ether (40 ml). HCl gas was bubbled slowly through the reaction and the deprotection was followed by TLC. After approximately 20 minutes, the ether was evaporated. The product was concentrated in vacuo from DCM (2–3 times) to remove the HCl. The desired free NH product, e.g. 2-({[(2S,4EZ)-4-(methoxyimino)pyrrolidinyl]carbonyl}amino)ethyl acetate (300 mg, quant.) was isolated as a yellow oil and used without further purification.

1H NMR (400 MHz, $D_2O$); 1.75 (s, 3H), 2.55–2.65 (m, 1H), 2.8–3.3 (m, 3H), 3.45–3.55 (m, 3H), 3.8–4.0 (m, 4H), 4.25–4.35 (m, 1H).

c) Protocol for the N-Capping Step

A solution was made containing the amine-hydrochloride from the previous step, e.g. 2-({[(2S,4EZ)-4-(methoxyimino)pyrrolidinyl]carbonyl}amino)ethyl acetate (560 mg, 2 mmol) and an acid chloride, e.g. [1,1'-biphenyl]-4-carbonyl chloride (433 mg, 2 mmol) in DCM (20 ml). Triethylamine (0.7 ml, 5 mmol) was added and the reaction stirred overnight at room temperature. The DCM was evaporated and the crude-purified by column chromatography using EtOAc (100%) to collect the desired amide compound, e.g. 2-({[(2S,4EZ)-1-([1,1'-biphenyl]-4-ylcarbonyl)-4-(methoxyimino)pyrrolidinyl]carbonyl}amino)ethyl acetate (457 mg, 54%) as an oil.

1H NMR (400 MHz, CDCl3); 1.9 (s, 3H), 2.7–2.8 (m, 1H), 3.2–3.6 (m, 3H), 3.75–3.85 (m, 3H), 4.0–4.4 (m, 4H), 5.15–5.25 (m, 1H), 7.2–7.6 (m, 9H).

d) Protocol for the Deprotection of the Reactive Group

A solution was made containing the side-chain protected compound from the previous step, e.g. 2-({[(2S,4EZ)-1-([1,1'-biphenyl]-4-ylcarbonyl)-4-(methoxyimino)pyrrolidinyl]carbonyl}amino)ethyl acetate (450 mg, 10.6 mmol) in TBF (10 ml). An aqueous solution (10 ml) of sodium hydroxide (75 mg, 19 mmol) with methanol (5 ml) was added and the reaction stirred at room temperature for three hours. The solvent was removed in vacuo and the crude purified by column chromatography using THF (100%) to give the expected final product, e.g. (2S,4EZ)-1-([1,1'-biphenyl]-4-ylcarbonyl)-N-(2-hydroxyethyl)-4-(methoxyimino)-2-pyrrolidinecarboxamide (300 mg, 75%) as a white solid.

1H NMR (400 Mz, CDCl3); 2.85–3.0 (m, 1H), 3.3–3.6 (m, 3H), 3.7–3.8 (2H), 3.85–3.95 (m, 3H), 4.2–4.5 (m, 2H), 5.15–5.25 (m, 1H), 7.2–7.9 (m, 9H). $M^+$(APCI$^+$); 382.

Example 10

(2S,4EZ)-1-([1,1'-biphenyl]-4-ylcarbonyl)-N-[(2RS)-2-hydroxy-2-phenethyl]-4-(methoxyimino)-2-pyrrolidinecarboxamide Following the general method as outlined in Example 9, starting from (2S,4EZ)-1-(tert-butoxycarbonyl)-4-(methoxyimino)-2-pyrrolidinecarboxylic acid, [1,1'-biphenyl]-4-carbonyl chloride, and 2-amino-1-phenylethyl acetate, the title compound was obtained after column chromatography as a mixture of E/Z-isomers as an off-white solid. The two isomers could be separated by another flash chromatographic purification step.

(2S,4E)-1-([1,1'-biphenyl]-4-ylcarbonyl)-N-[(2RS)-2-hydroxy-2-phenethyl]-4-(methoxyimino)-2-pyrrolidinecarboxamide: 1H NMR (400 MHz, CDCl3); 2.75–2.9 (m, 1H), 3.1–3.25 (m, 2H), 3.35–3.6 (m, 1H), 3.7–3.8 (m, 1H), 3.75 (s, 3H), 4.1–4.3 (m, 2H), 4.8 (m, 1H), 5.1 (dd, 1H), 7.1–7.6 (m, 15H). $M^+$(APCI$^+$); 458.

(2S,4Z)-1-([1,1'-biphenyl]-4-ylcarbonyl)-N-[(2RS)-2-hydroxy-2-phenethyl)]-4-(methoxyimino)-2-pyrrolidinecarboxamide: 1H NMR (400 MHz, CDCl3); 2.7–2.85 (m, 1H), 3.05–3.25 (m, 2H), 3.35 (m, 1H), 3.65–3.8 (m, 1H), 3.8 (s, 3H), 4.15–4.25 (d, 1H), 4.25–4.4 (m, 1H), 4.75 (m, 1H), 5.1 (dd, 1H), 7.15–7.6 (m, 15H). $M^+$(APCI$^+$); 458.

Example 11

General Protocol for the Solution-Phase Synthesis of Oximether Pyrrolidine Derivatives of General Formula Ib (Scheme 5); (3EZ,5S)-5-(1H-benzimidazol-2-yl)-1-([1,1'-biphenyl]-4-ylcarbonyl)-3-pyrrolidinone-O-methyloxime a) Protocol for the Formation of the Amide Bond A solution was prepared containing the central building block, e.g. (2S,4EZ)-1-(tert-butoxycarbonyl)-4-(methoxyimino)-2-pyrrolidinecarboxylic acid (Intermediate 7) (2.1 g, 8.1 mmol), an ortho-substituted aromatic amine or amine salt, e.g. 1,2-benzenediamine (0.88 g, 8.1 mmol) and DMAP (1.59 g, 13.0 mmol). in dry dichloromethane (30 ml). This solution was cooled to 0° C. and treated with EDC (1.56 g, 8.2 mmol) before warming to room temperature and stirring for 2 days. The solvent was removed in vacuo and the product purified by silica gel chromatography, eluting with a gradient of 30–80% ethyl acetate in hexane to give the desired anilide product, e.g. tert-butyl (2S,4EZ)-2-[(2-aminoanilide)carbonyl]-4-(methoxyimino)-1-pyrrolidinecarboxylate 2.8 g, 97% as a colourless foam.

1H NMR (360 MHz, CDCl3); 1.7 (m, 9H), 2.5–3.5 (br, 4H), 3.4 (m, 1H), 4.0 (m, 3H), 4.2–4.4 (m, 2H), 4.9 (m, 1H), 6.9–7.5 (m, 4H), 8.5 (br, 1H).

b) Protocol for the Formation of the Fused Heterocyclic Ring

A solution of the anilide compound from the previous step, e.g. tert-butyl (2S,4EZ)-2-[(2-aminoanilino)carbonyl]-4-(methoxyimino)-1-pyrrolidinecarboxylate (0.8 g, 2.3 mmol) in dichloromethane (30 ml) and acetic acid (3 ml) was stirred at room temperature for 3 days. Saturated aqueous sodium bicarbonate (7 ml) was added to the reaction, the organic phase collected and dried over magnesium sulfate before filtering and removal of solvent in vacuo to give the desired product, e.g. tert-butyl (2S,4EZ)-2-(1H-benzimidazol-2-yl)-4-(methoxyimino)-1-pyrrolidinecarboxylate (740 mg, 97%) as an off-white foam.

1H NMR (360 MHz, CDCl3); 1.5 (m, 9H), 3.1 (m, 1H), 3.8 (m, 3H) 3.9–4.3 (m, 3H), 5.3 (m, 1H), 7.1–7.6 (m, 4H), 10–10.5 (br, 1H).

c) Protocol for the N-Deprotection Step

Hydrogen chloride gas was bubbled into a solution of the fused heterocyclic product from the previous step, e.g. tert-butyl (2S,4EZ)-2-(1H-benzimidazol-2-yl)-4-(methoxyimino)-1-pyrrolidinecarboxylate (740 mg, 2.2 mmol) in dry DCM (20 ml) for 30 min. The solvent was removed in vacuo to give the desired product, e.g. (3EZ,5S)-5-(1H-benzimidazol-2-yl)-3-pyrrolidinone O-methyloxime (0.58 g, 99%), as a brown amorphous powder which was used without further purification.

d) Protocol for the N-Capping Step

A solution of the free NH product from the previous step, e.g. (3EZ,5S)-5-(1H-benzimidazol-2-yl)-3-pyrrolidinone O-methyloxime (0.58 g, 2.2 mmol) in dry dichloromethane (25 ml) was treated with an acid chloride, e.g. [1,1'-biphenyl]-4-carbonyl chloride (0.48 g, 2.2 mmol) and triethylamine (0.9 ml, 6.6 mmol). The resulting solution was then stirred for 3 h at room temp before removal of solvent in vacuo and the desired isomers were isolated by flash chromatography on silica gel, eluting with a gradient of ethyl acetate (10–80%) in hexane to give the two isomers (120 mg of the less polar and 400 mg of the more polar) of the desired product, e.g. (3E,5S)- and (3Z,5S)-5-(1H-benzimidazol-2-yl)-1-([1,1'-biphenyl]-4-ylcarbonyl)-3-pyrrolidinone O-methyloxime, as off-white powders.

(3E,5S)-5-(1H-benzimidazol-2-yl)-1-([1,1'-biphenyl]-4-ylcarbonyl)-3-pyrrolidinone O-methyloxime: 1H NMR (360 MHz, CDCl3); 3.2 (m, 1H), 3.8 (s, 3H), 4.0 (m, 1H), 4.3 (m, 2H), 6.0 (m, 1H), 6.0 (m, 1H), 7.2–7.7 (m, 13H), 10–11 (br, 1H). $M^+$(APCI$^+$); 411. (3Z,5S)-5-(1H-benzimidazol-2-yl)-1-([1,1'-biphenyl]-4-ylcarbonyl)-3-pyrrolidinone O-methyloxime: 1H NMR (360 MHz, CDCl3); 3.1, (m, 1H), 3.8 (s, 3H), 3.9 (m, 1H), 4.3 (m, 2H), 6.0 (m, 1H), 6.0 (m, 1H), 7.2–7.7 (m, 13H), 10–11 (br, 1H). $M^+$(APCI$^+$); 411.

Example 12

(3EZ,5S)-5-(1H-benzimidazol-2-yl)-1-[(2'-methyl[1,1'-biphenyl]-4-yl)-carbonyl]-3-pyrrolidinone O-methyloxime Following the general method as outlined in Example 11, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 1,2-benzenediamine, the title compound was obtained in 91% purity by HPLC. MS(ESI+): m/z=425.

Example 13

(3EZ,5S)-5-(1-methyl-1H-benzimidazol-2-yl)-1-[(2'-methyl[1,1'-biphenyl]-4-yl)carbonyl]-3-pyrrolidinone O-methyloxime Following the general method as outlined in Example 11, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and $N^1$-methyl-1,2-benzenediamine, the title compound was obtained in 83% purity by HPLC. MS($ESI^+$): m/z=439.

Example 14

(3EZ,5S)-5-(7-hydroxy-1H-benzimidazol-2-yl)-1-[(2'-methyl[1,1'-biphenyl]-4-yl)carbonyl]-3-pyrrolidinone O-methyloxime Following the general method as outlined in Example 11, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 2,3-diaminophenol, the title compound was obtained in 91% purity by HPLC. MS(ESI+): m/z=441.

Example 15

(3EZ,5S)-5-(3,4-dihydro-2-quinazolinyl)-1-[(2'-methyl[1,1'-biphenyl]-4-yl)carbonyl]-3-pyrrolidinone O-methyloxime Following the general method as outlined in Example 11, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 2-(aminomethyl)aniline, the title compound was obtained in 77% purity by HPLC. MS(ESI+): m/z=439.

Example 16

(3EZ,5S)-1-([1,1'-biphenyl]-4-ylcarbonyl)-5-(1-methyl-1H-benzimidazol-2-yl)-3-pyrrolidinone O-methyloxime Following the general method as outlined in Example 11, starting from (2S,4EZ)-1-(tert-butoxycarbonyl)-4-(methoxyimino)-2-pyrrolidinecarboxylic acid, [1,1'-biphenyl]-4carbonyl chloride, and $N^1$-methyl-1,2-benzenediamine, the title compound was obtained in 88% purity by HPLC. MS(ESI+): m/z=425.

Example 17

General Protocol for the Solution-Phase Synthesis of Oxime or Hydrazone Pyrrolidine Derivatives of General Formula I (Scheme 6); (2S,4EZ)-1-([1,1'-biphenyl]-4-ylcarbonyl)-4-(hydroxyimino)-N-[(2RS)-2-hydroxy-2-phenethyl]-2-pyrrolidine-carboxamide a) Protocol for the Hydrolysis of the Oximether Group.

The starting oximether compounds, e.g. (2S,4EZ)-1-([1,1'-biphenyl]-4-ylcarbonyl)-N-[(2RS)-2-hydroxy-2-phenethyl]-4-(methoxyimino)-2-pyrrolidinecarboxamide, were obtained following the general methods as outlined, e.g., in Example 2, 11 or 22. A solution containing the oximether compound was prepared, e.g. (2S,4EZ)-1-([1,1'-biphenyl]-4-ylcarbonyl)-N-[(2RS)-2-hydroxy-2-phenethyl]-4-(methoxyimino)-2-pyrrolidinecarboxamide (64 mg, 0.14 mmol), paraformaldehyde powder (95%, 42 mg, 1.41 mmol) and Amberlyst® 15 (30 mg) in acetone containing 10% of water (2 mL). The reaction was stirred 4 h at 60° C. Insoluble materials were filtered off and washed with a small amount of acetone. The filtrate was concentrated and the residue was diluted with DCM (15 mL). The organic solution was washed with brine (10 mL), dried over $Na2SO_4$, and concentrated. The desired ketocarbonyl product, e.g. (2S)-1-([1,1'-biphenyl]-4-ylcarbonyl)-N-[(2RS)-2-hydroxy-2-phenylethyl]-4-oxo-2-pyrrolidinecarboxamide (56 mg, 92%) was isolated as a yellow oil and used without further purification.

b) Protocol for the Formation of Oxime and/or Hydrazone Compounds

A solution was made containing the keto-pyrrolidine derivative from the previous step, e.g. (2S)-1-([1,1'-biphenyl]-4-ylcarbonyl)-N-[(2RS)-2-hydroxy-2-phenethyl]-4-oxo-2-pyrrolidinecarboxamide (46 mg, 0.11 mmol) and hydroxylamine hydrochloride (12 mg, 0.17 mmol) in chloroform (1 ml) containing triethylamine (29 mg, 0.29 mmol). The reaction mixture was then stirred at ambient temperature for one day, prior to removal of solvent. The resultant crude reaction mixture was purified by column chromatography using DCM/MeOH (25:1) to collect the desired product, e.g. (2S,4EZ)-1-([1,1'-biphenyl]-4-ylcarbonyl)-4-hydroxyimino)-N-[(2RS)-2-hydroxy-2-phenethyl]-2-pyrrolidinecarboxamide as a mixture of two isomers as an off-white solid (46 mg, 96% yield).

$^1H$ NMR (300 MHz, $CDCl_3$); 2.6–3.3 (m, 4H), 4.0–4.7 (m, 4H), 4.9 (m, 1H), 5.5 (m, 1H), 7.1–7.5 (m, 8H), 7.6–7.8 (m, 5H), 8.1 (m, 1H), 10.9 (m, 1H). $M^+$($APCI^+$); 444.

Example 18

(2S,4EZ)-1-([1,1'-biphenyl]-4-ylcarbonyl)-4-(dimethylhydrazono)-N-[(2RS)-2-hydroxy-2-phenylethyl]-2-pyrrolidinecarboxamide Following the general method as outlined in Example 17, starting from (2S)-1-([1,1'-biphenyl]-4-ylcarbonyl)-N-[(2RS)-2-hydroxy-2-phenylethyl]-4-oxo-2-pyrrolidinecarboxamide and N,N-dimethylhydrazine, the resultant crude reaction mixture was purified by column chromatography using DCM/MeOH (30:1) to collect the desired product, e.g. (2S,4EZ)-1-([1,1'-biphenyl]-4-ylcarbonyl)-4-(dimethylhydrazono)-N-[(2RS)-2-hydroxy-2-phenylethyl]-2-pyrrolidinecarboxamide as a mixture of two isomers as a light yellow oil in 56% yield (90.2% purity by HPLC).

$^1$H NMR (300 MHz, $CDCl_3$); 2.35–2.55 (br s, 3H), 2.40–2.60 (m, 1H), 2.75–3.55 (m, 5H), 3.55–3.82 (m, 1H), 3.90–4.4 (m, 2H), 4.83 (m, 1H), 4.93–5.35 (m, 1H), 7.18–7.49 (m, 9H), 7.49–7.68 (m, 5H). $M^+$(APCI$^+$); 471. $M^-$(APCI$^-$); 469.

Example 19

(2S,4EZ)-1-([1,1'-biphenyl]-4-ylcarbonyl)-N-[(2RS)-2-hydroxy-2-phenylethyl]-4-(methylhydrazono)-2-pyrrolidinecarboxamide Following the general method as outlined in Example 17, starting from (2S)-1-([1,1'-biphenyl]-4-ylcarbonyl)-N-[(2RS)-2-hydroxy-2-phenylethyl]-4-oxo-2-pyrrolidinecarboxamide and N-methylhydrazine, the resultant crude reaction mixture was purified by column chromatography using DCM/MeOH (30:1) to collect the desired product, e.g. (2S,4EZ)-1-([1,1'-biphenyl]-4-ylcarbonyl)-N-[(2RS)-2-hydroxy-2-phenylethyl]-4-(methylhydrazono)-2-pyrrolidinecarboxamide as a mixture of two isomers as a colorless solid in 57% yield (95.2% purity by HPLC).

$^1$H NMR (300 MHz, $CDCl_3$); 2.45–2.70 (m, 1H), 2.85 (br s, 3H, $NNHCH_3$), 2.85–3.5 (m, 2H), 3.51–4.4 (m, 4H), 4.84 (br s, 1H, NNHMe), 4.95–5.35 (m, 1H), 7.18–7.67 (m, 14H). $M^+$(APCI$^+$); 457. $M^-$(APCI$^-$); 455.

Example 20

(2S,4EZ)-1-([1,1'-biphenyl]l-4-ylcarbonyl)-4-hydrazono-N-[(2RS)-2-hydroxy-2-phenylethyl]-2-pyrrolidinecarboxamide Following the general method as outlined in Example 17, starting from (2S)-1-([1,1'-biphenyl]-4-ylcarbonyl)-N-[(2RS)-2-hydroxy-2-phenylethyl]-4-oxo-2-pyrrolidinecarboxamide and hydrazine hydrate (4% in EtOH), the resultant crude reaction mixture was purified by column chromatography using DCM/MeOH (30:1) to collect the desired product, e.g. (2S,4EZ)-1-([1,1'-biphenyl]-4-ylcarbonyl)-4-hydrazono-N-[(2RS)-2-hydroxy-2-phenylethyl]-2-pyrrolidinecarboxamide as a mixture of two isomers as a colorless solid in 63% yield (95.3% purity by HPLC).

$^1$H NMR (300 MHz, DMSO-$d_6$, 80° C.); 2.55 (dd, J=9.8; 17.6 Hz, 1H), 2.73 (dd, J=9.8; 18.2 Hz, 1H), 3.28 (m, 2H), 4.12 (m, 2H), 4.61 (m, 1H), 4.85 (m, 1H), 5.15 (m, 1H), 5.70 (br s, 2H, $NH_2N{=}C$), 7.17–7.43 (m, 6H), 7.44–7.60 (m, 4H), 7.66–7.77 (m, 5H). $M^+$(APCI$^+$); 443. $M^-$(APCI$^-$) 441.

Example 21

(2S,4EZ)-4-(acetylhydrazono)-1-([1,1'-biphenyl]-4-ylcarbonyl)-N-[(2RS)-2-hydroxy-2-phenylethyl]-2-pyrrolidinecarboxamide A hydrazono pyrrolidine derivative obtained by the general method outlined in Example 17, e.g. (2S,4EZ)-1-([1,1'-biphenyl]-4-ylcarbonyl)-4-hydrazono-N-[(2RS)-2-hydroxy-2-phenylethyl]-2-pyrrolidinecarboxamide (51 mg, 0.11 mmol) was dissolved in pyridine (1 mL). Acetic anhydride (3 eq, 32 μl, 0.35 mmol) was added, and the mixture was stirred overnight. The solvent was evaporated and the resultant crude reaction mixture was purified by column chromatography using DCM/MeOH (20:1) to collect the desired product, e.g. (2S,4EZ)-4-(acetylhydrazono)-1-([1,1'-biphenyl]-4-ylcarbonyl)-N-[(2RS)-2-hydroxy-2-phenylethyl]-2-pyrrolidinecarboxamide as a mixture of two isomers as a colorless solid in 73% yield (98.4% purity by HPLC).

$^1$H NMR (300 MHz, DMSO-$d_6$, 80° C.); 1.99 (br, s, 3H, $CH_3CON$), 2.7–3.4 (m, 5H), 4.26 (m, 2H), 4.63 (m, 1H), 4.89 (m, 1H), 5.15 (m, 1H), 7.18–7.44 (m, 6H), 7.45–7.62 (m, 4H), 7.66–7.85 (m, 5H), 9.97 (br s, 1H, MeCONHN, major isomer), 10.04 (br s, 1H, MeCONHN, minor isomer). $M^+$(ESI$^+$); 485. $M^-$(ESI$^-$); 483.

Example 22

General Protocol for the Solid-Phase Synthesis of Pyrrolidine Derivatives of General Formula I a) Loading Step Kaiser oxime resin (16.5 g, loading 1.57 mmol/g) was added to a solution of the relevant pyrrolidine carboxylic acid building block (51.8 mmol) and diisopropylcarbodiimide (8.1 ml, 51.8 mmol) in dry dichloromethane (150 ml). The resulting suspension was shaken overnight before filtering at the pump and washing sequentially with DMF, DCM and finally diethyl ether before drying at room temperature in vacuo.

b) N-Deprotection Step

The resin obtained in the loading step was shaken with a 20% solution of trifluoroacetic acid in dichloromethane (200 ml) for 30 minutes prior to filtering at the pump and washing sequentially with aliquots of DMF, DCM and finally diethyl ether before drying at room temperature in vacuo.

c) N-Capping Step

The resin from the previous step was transferred into a 96-well filter-plate (approx. 50 mg of dry resin/well) and each well treated with an N-reactive derivatising agent, e.g. with either of the following solutions:

a) an acid chloride (0.165 mmol) and diisopropylethylamine (0.165 mmol) in dry dichloromethane (1 ml), overnight
b) an acid (0.165 mmol) and DIC (0.165 mmol) in, depending on the solubility of the carboxylic acid, dry dichloromethane or NMP (1 ml) overnight.
c) an isocyanate (0.165 mmol) in dry THF (1 ml), overnight
d) a sulfonyl chloride (0.165 mmol) and diisopropylethylamine (0.165 mmol) in NMP (1 ml), overnight.
e) a benzyl (alkyl) bromide (0.165 mmol) and diisopropylethylamine (0.165 mmol) in NMP (1 ml), overnight.
f) a vinyl ketone (0.165 mmol) in THF, overnight
g) diketene (0.165 mmol) in TBF, overnight The plate was then sealed and shaken overnight at ambient temperature. The resins were then filtered, washing the resin sequentially with aliquots of DMF, DCM and finally diethyl ether before drying at room temperature in vacuo.

d) Cleavage Step

A solution of amine (0.05 mmol) in 2% AcOH in dichloromethane (1 ml) was added to each well containing the resin from the previous step. The plate was then sealed and shaken for two days at ambient temperature. The wells were then filtered into a collection plate and the solvent removed in a vacuum centrifuge to yield 2–3 mg of the corresponding products, generally obtained as oils. The products were characterised by LC (205 nm) and mass spectrometry (ES+). All of the following examples were identified based on the observation of the correct molecular ion in the mass spectrum, and were shown to be at least 40% pure (usually 60–95% pure) by LC.

Example 23

(2S,4EZ)-$N^2$-(2-hydroxyethyl)-4-(methoxyimino)-$N^1$-pentyl-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, 1-isocyanatopentane, and 2-aminoethanol the title compound was obtained in 100% purity by LC/MS. MS(ESI+): m/z=315.2.

Example 24

(2S,4EZ)-4-benzylidene-1-([1,1'-biphenyl]-4-ylcarbonyl)-N-[2-(diethylamino)-ethyl]-2-pyrrolidinecarboxamide Following the general method as outlined in Example 22, starting from (2S,4EZ)-4-benzylidene-1-(tert-butoxycarbonyl)-2-pyrrolidinecarboxylic acid, [1,1'-biphenyl]-4-carbonyl chloride, and N1,N1-diethyl-1,2-ethanediamine the title compound was obtained in 90% purity by LC/MS. MS(ESI+): m/z=482.4.

Example 25

(2S,4EZ)-4[(allyloxy)imino]-1-(4-cyanobenzoyl)-N-[2-(1H-pyrrol-1-yl)phenyl]-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, 4-cyanobenzoyl chloride, and 2-(1H-pyrrol-1-yl)phenylamine the title compound was obtained in 51% purity by LC/MS. MS(ESI+): m/z=454.4.

Example 26

(2S,4EZ)-4-{[(3,4-dichlorobenzyl)oxy]imino}-N-(2-furylmethyl)-1-[(2-oxo-6-pentyl-2H-pyran-3-yl)carbonyl]-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, 2-oxo-6-pentyl-2H-pyran-3-carbonyl chloride, and 2-furylmethylamine the title compound was obtained in 92% purity by LC/MS. MS(ESI+): m/z=574.4.

Example 27

(2S,4EZ)-4-(methoxyimino)-$N^1$-(3-methoxyphenyl)-$N^2$-(2-thienylmethyl)-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, 1-isocyanato-3-methoxybenzene, and 2-thienylmethylamine the title compound was obtained in 79% purity by LC/MS. MS(ESI+): m/z=403.2.

Example 28

(2S,4EZ)-2-{[4-(1,3-benzodioxol-5-ylmethyl)-1-piperazinyl]carbonyl}-4-(methoxyimino)-N-pentyl-1-pyrolidinecarboxamide Following the general method as outlined in Example 22, starting from (2S,4EZ)-1-(tert-butoxycarbonyl)-4-(methoxyimino)-2-pyrrolidinecarboxylic acid, 1-isocyanatopentane, and 1-(1,3-benzodioxol-5-ylmethyl)piperazine the title compound was obtained in 72% purity by LC/MS. MS(ESI+): m/z=474.4.

Example 29

(2S,4EZ)-4-[(benzyloxy)imino]-1-(4-cyanobenzoyl)-N-(2-furylmethyl)-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, 4-cyanobenzoyl chloride, and 2-furylmethylamine the title compound was obtained in 49% purity by LC/MS. MS(ESI+): m/z=443.4.

Example 30

(2S,4EZ)-4-[(benzyloxy)imino]-N-[2-(diethylamino)ethyl]-1-(4-phenoxybenzoyl)-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, 4-phenoxybenzoyl chloride, and N1,N1-diethyl-1,2-ethanediamine the title compound was obtained in 86% purity by LC/MS. MS(FSI+): m/z=529.6.

Example 31

4-[((2S,4EZ)-4-[(benzyloxy)imino]-2-{[4-(3,4-dichlorophenyl)-1-piperazinyl]-carbonyl}pyrrolidinyl)carbonyl]benzonitrile Following the general method as outlined in Example 22, starting from (2S,4EZ)-4-[(benzyloxy)imino]-1-(tert-butoxycarbonyl)-2-pyrrolidinecarboxylic acid, 4-cyanobenzoyl chloride, and 1-(3,4-dichlorophenyl)piperazine the title compound was obtained in 43% purity by LC/MS. MS(ESI+): m/z=576.6.

Example 32

(2S,4EZ)-4-(methoxyimino)-$N^1$-pentyl-$N^2$-[2-(1H-pyrrol-1-yl)phenyl]-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, 1-isocyanatopentane, and 2-(1H-pyrrol-1-yl)phenylamine the title compound was obtained in 74% purity by LC/MS. MS(ESI+): m/z=412.2.

Example 33

(2S,4EZ)-1-acryloyl-4-{[(3,4-dichlorobenzyl)oxy]imino}-N-(2-furylmethyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, acryloyl chloride, and 2-furylmethylamine the title compound was obtained in 74% purity by LC/MS. MS(ESI+): m/z=436.8.

Example 34

(2S,4EZ)-4-(tert-butoxyimino)-$N^2$-cyclopropyl-$N^1$-(3,5-dichlorophenyl)-1,2-pyrrolidinedicarboxamide Following the general method as outlined in Example 22, starting from (2S,4EZ)-1-(tert-butoxycarbonyl)-4-(tert-butoxyimino)-2-pyrrolidinecarboxylic acid, 1,3-dichloro-5-isocyanatobenzene, and cyclopropylamine the title compound was obtained in 48% purity by LC/MS. MS(ESI+): m/z=427.6.

Example 35

(2S,4EZ)-4-[(allyloxy)imino]-N-[2-(diethylamino)ethyl]-1-[(2-oxo-6-pentyl-2H-pyran-3-yl)carbonyl]-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, 2-oxo-6-pentyl-2H-pyran-3-carbonyl chloride, and N1,N1-diethyl-1,2-ethanediamine the title compound was obtained in 93% purity by LC/MS. MS(ESI+): m/z=475.4.

Example 36

(2S,4EZ)-$N^2$-[(2-hydroxy-2-phenethyl]-4-(methoxyimino)-$N^1$-(3-methylphenyl)-1,2-pyrrolidinedicarboxamide Following the general method as outlined in Example 22, starting from (2S,4EZ)-1-(tert-butoxycarbonyl)-4-(methoxyimio)-2-pyrrolidinecarboxylic acid, 1-isocyanato-3-methylbenzene, and (1RS)-2-amino-1-phenylethanol the title compound was obtained in 100% purity by LC/MS. MS(ESI+): m/z=411.2.

Example 37

(2S,4EZ)-1-[(benzoylamino)carbonyl]-N-benzyl-4-[(benzyloxy)imino]-N-methyl-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, benzoyl isocyanate, and N-benzyl-N-methylamine the title compound was obtained in 40% purity by LC/MS. MS(ESI+): m/z=485.4.

Example 38

(2S,4EZ)-1-(4-cyanobenzoyl)-N-(9-ethyl-9H-carbazol-3-yl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-cyanobenzoyl chloride, and 9-ethyl-9H-carbazol-3-amine the title compound was obtained in 72% purity by LC/MS. MS(ESI+): m/z=480.4.

Example 39

(2S,4EZ)-4-(methoxyimino)-$N^1$-(3-methylphenyl)-$N^2$-(2-thienylmethyl)-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, 1-isocyanato-3-methylbenzene, and 2-thienylmethylamine the title compound was obtained in 98% purity by LC/MS. MS(ESI+): m/z=387.2.

Example 40

(2S,4EZ)-4-(tert-butoxyimino)-N-(2-methoxyethyl)-1-[(2-oxo-6-pentyl-2H-pyran-3yl)carbonyl]-2-pyrrolidinecarboxamide Following the general method as outlined in Example 22, starting from (2S,4EZ)-1-(tert-butoxycarbonyl)-4-(tert-butoxyimino)-2-pyrrolidinecarboxylic acid, 2-oxo-6-pentyl-2H-pyran-3-carbonyl chloride, and 2-methoxyethylamine the title compound was obtained in 75% purity by LC/MS. MS(ESI+): m/z=450.2.

Example 41

(3EZ,5S)-5-{[4-(1,3-benzodioxol-5-ylmethyl)-1-piperazinyl]carbonyl}-1-benzoyl-3-pyrrolidinone O-(3,4-dichlorobenzyl)oxime Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, benzoyl chloride, and 1-(1,3-benzodioxol-5-ylmethyl)piperazine the title compound was obtained in 71% purity by LC/MS. MS(ESI+): m/z=609.8.

Example 42 tert-butyl 3-[({(2S,4EZ)-4-(ethoxyimino)-1-[(2-oxo-6-pentyl-2H-pyran-3-yl)carbonyl]pyrrolidinyl}carbonyl)amino]-1-azetidinecarboxylate Following the general method as outlined in Example 22, starting from (2S,4EZ)-1-(tert-butoxycarbonyl)-4-(ethoxyimino)-2-pyrrolidinecarboxylic acid, 2-oxo-6-pentyl-2H-pyran-3-carbonyl chloride, and tert-butyl 3-amino-1-azetidinecarboxylate the title compound was obtained in 100% purity by LC/MS. MS(ESI+): m/z=519.6.

Example 43

(2S,4EZ)-4-1{[(4-methoxybenzyl)oxy]imino}-N-(3-methylphenyl)-2-(4-morpholinylcarbonyl)-1-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, 1-isocyanato-3-methylbenzene, and morpholine the title compound was obtained in 41% purity by LC/MS. MS(ESI+): m/z=467.4.

Example 44

(2S,4EZ)-$N^2$-cyclopropyl-4-{[(4-methoxybenzyl)oxy]imino}-$N^1$-pentyl-1,2-pyrrolidinedicarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, 1-isocyanatopentane, and cyclopropylamine the title compound was obtained in 75% purity by LC/MS. MS(ESI+): m/z=417.2.

Example 45

(3EZ,5S)-5-{[4-(3 4-dichlorophenyl)-1-piperazinyl]carbonyl}-1-[(2-oxo-6-pentyl-2H-pyran-3-yl)carbonyl]-3-pyrrolidinone O-benzyloxime Following the general method as outlined in Example 22, starting from (2S,4EZ)-4[(benzyloxy)imino]-1-(tert-butoxycarbonyl)-2-pyrrolidinecarboxylic acid, 2-oxo-6-pentyl-2H-pyran-3-carbonyl chloride, and 1-(3,4-dichlorophenyl)piperazine the title compound was obtained in 47% purity by LC/MS. MS(ESI+): m/z=639.8.

Example 46

(2S,4EZ)-4-(tert-butoxyimino)-N-[2-(1H-pyrrol-1-yl)phenyl]-2-pyrrolidinecarboxamide Following the general method as outlined in Example 22, starting from (2S,4EZ)-1-(tert-butoxycarbonyl)-4-(tert-butoxyimino)-2-pyrrolidinecarboxylic acid, and 2-(1H-pyrrol-1-yl)phenylamine the title compound was obtained in 83% purity by LC/MS. MS(ESI+): m/z=341.2.

Example 47

1-({(2S,4EZ)-4-(chloromethylene)-1-[(4-chlorophenoxy)acetyl]pyrrolidinyl}-carbonyl)-4-(3,4-dichlorophenyl)piperazine Following the general method as outlined in Example 22, starting from (2S,4EZ)-1-(tert-butoxycarbonyl)-4-(chloromethylene)-2-pyrrolidinecarboxylic acid, (4-chlorophenoxy)acetyl chloride, and 1-(3,4-dichlorophenyl)piperazine the title compound was obtained in 64% purity by LC/MS. MS(ESI+): m/z=543.6.

Example 48

(2S,4EZ)-4-[(benzyloxy)imino]-N-(4,6-dimethoxy-2-pyrimidinyl)-1-[(2-oxo-6-pentyl-2H-pyran-3-yl)carbonyl]-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, 2-oxo-6-pentyl-2H-pyran-3-carbonyl chloride, and 4,6-dimethoxy-2-pyrimidinamine the title compound was obtained in 62% purity by LC/MS. MS(ESI+): m/z=564.6.

Example 49

(2S,4EZ)-4-{[(3,4-dichlorobenzyl)oxy]imino}-1-[4-(diethylamino)butanoyl]-N-(1-naphthylmethyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, 4-(dimethylamino)butanoyl chloride, and 1-naphthylmethylamine the title compound was obtained in 62% purity by LC/MS. MS(ESI+): m/z=555.6.

Example 50

(2S)-$N^2$-(2,1,3-benzothiadiazol-4-yl)-$N^1$-(3,5-dichlorophenyl)-4-oxo-1,2-pyrrolidinedicarboxamide Following the general method as outlined in Example 22, starting from 1-(tert-butoxy-carbonyl)-4-oxoproline, 1,3-dichloro-5-isocyanatobenzene, and 2,1,3-benzothiadiazol-4-amine the title compound was obtained in 47% purity by LC/MS. MS(ESI+): m/z=450.6.

Example 51

(2S,4EZ)-N-benzyl-4-(chloromethylene)-N-methyl-1-(4-phenoxybenzoyl)-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, 4-phenoxybenzoyl chloride, and N-benzyl-N-methylamine the title compound was obtained in 61% purity by LC/MS. MS(ESI+): m/z=461.4.

Example 52

(2S,4EZ)-$N^2$-(9-ethyl-9H-carbazol-3-yl)-4-{[(4-methoxybenzyl)oxy]imino}-$N^1$-(3-methylphenyl)-1,2-pyrrolidinedicarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, 1-isocya-nato-3-methylbenzene, and 9-ethyl-9H-carbazol-3-amine the title compound was obtained in 72% purity by LC/MS. MS(ESI+): m/z=590.8.

Example 53

(2S)-N-(tert-butyl)-4-methylene-1-[(2-oxo-6-pentyl-2H-pyran-3-yl)carbonyl]-2-pyrrolidinecarboxamide Following the general method as outlined in Example 22, starting from 1-(tert-butoxycarbonyl)-4-methyleneproline, 2-oxo-6-pentyl-2H-pyran-3-carbonyl chloride, and tert-butylamine the title compound was obtained in 100% purity by LC/MS. MS(ESI+): m/z=375.4.

Example 54

(2S,4EZ)-4-benzylidene-1-[4-(dimethylamino)butanoyl]-N-(6-quinolinyl)-2-pyrrolidinecarboxamide Following the general method as outlined in Example 22, starting from (2S,4EZ)-4-benzylidene-1-(tert-butoxycarbonyl)-2-pyrrolidinecarboxylic acid, 4-(dimethylamino)butanoyl chloride, and 6-quinolinamine the title compound was obtained in 71% purity by LC/MS. MS(ESI+): m/z=443.6.

Example 55

(2S)-1-[4-(dimethylamino)butanoyl]-N-(9-ethyl-9H-carbazol-3-yl)-4-methylene-2-pyrrolidinecarboxamide Following the general method as outlined in Example 22, starting from 1-(tert-butoxycarbonyl)-4-methyleneproline, 4-(dimethylamino)butanoyl chloride, and 9-ethyl-9H-carbazol-3-amine the title compound was obtained in 51% purity by LC/MS. MS(ESI+): m/z=433.6.

Example 56

(2S,4EZ)-N-(1,3-benzodioxol-5-ylmethyl)-4-[(benzyloxy)imino]-1-(4-cyanobenzoyl)-2-pyrrolidinecarboxamide Following the general method as outlined in Example 22, starting from (2S,4EZ)-4-[(benzyl-oxy)imino]-1-(tert-butoxycarbonyl)-2-pyrrolidinecarboxylic acid, 4-cyanobenzoyl chloride, and 1,3-benzodioxol-5-ylmethylamine the title compound was obtained in 51% purity by LC/MS. MS(ESI+): m/z=497.6.

Example 57

(2S)-1-({1-[4-(dimethylamino)butanoyl]-4-methylene-2-pyrrolidinyl}carbonyl)-3-azetidinol Following the general method as outlined in Example 22, starting from 1-(tert-butoxycarbonyl)-4-methyleneproline, 4-(dimethylamino)butanoyl chloride, and 3-azetidinol the title compound was obtained in 100% purity by LC/MS. MS(ESI+): m/z=296.4.

Example 58

(2S,4EZ)-1-([1,1'-biphenyl]-4-ylcarbonyl)-4-{[(3,4-dichlorobenzyl)oxy]imino}-N-[2-(1H-pyrrol-1-yl)phenyl]-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, [1,1'-biphenyl]-4carbonyl chloride, and 2-(1H-pyrrol-1-yl)phenylamine the title compound was obtained in 54% purity by LC/MS. MS(ESI+): m/z=623.6.

Example 59

(2S,4EZ)-4-benzylidene-1-[(4-chlorophenoxy)acetyl]-N-(3,4-dimethoxy-benzyl)-2-pyrrolidinecarboxamide Following the general method as outlined in Example 22, starting from (2S,4EZ)-4-benzylidene-1-(tert-butoxycarbonyl)-2-pyrrolidinecarboxylic acid, (4-chlorophenoxy)acetyl chloride, and 3,4-dimethoxybenzylamine the title compound was obtained in 49% purity by LC/MS. MS(ESI+): m/z=521.6.

Example 60

(2S,4EZ)-4-{[(3,4-dichlorobenzyl)oxy]imino}-1-(diphenylacetyl)-N-(2-thienylmethyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, diphenylacetyl chloride, and 2-thienylmethylamine the title compound was obtained in 51% purity by LC/MS. MS(ESI+): m/z=592.6

Example 61

(2S,4EZ)-N-(3,4-dimethoxybenzyl)-(diphenylacetyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, diphenylacetyl chloride, and 3,4-dimethoxybenzylamine the title compound was obtained in 74% purity by LC/MS. MS(ESI+): m/z=502.6.

Example 62

(2S,4EZ)-$N^1$-(3,5-dichlorophenyl)(ethoxyimino)-$N^2$-[2-(1H-pyrrol-1-yl)phenyl-1,2-pyrrolidinedicarboxamide Following the general method as outlined in Example 22, starting from (2S,4EZ)-1-(tert-butoxycarbonyl)-4-(ethoxyimino)-2-pyrrolidinecarboxylic acid, 1,3-dichloro-5-isocyanatobenzene, and 2-(1H-pyrrol-1-yl)phenylamine the title compound was obtained in 54% purity by LC/MS. MS(ESI+): m/z=500.6.

Example 63

(2S,4EZ)-$N^2$-(1,3-benzodioxol-5-ylmethyl)-4-{[(4-methoxybenzyl)-oxy]imino}-$N^1$-pentyl-1,2-pyrrolidinedicarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, 1-isocyanatopentane, and 1,3-benzodioxol-5-ylmethylamine the title compound was obtained in 63% purity by LC/MS. MS(ESI+): m/z=511.4.

Example 64

(2S,4EZ)-N-benzol-4-[(benzyloxy)imino]-1-(diphenylacetyl)-N-methyl-2-pyrrolidinecarboxamide Following the general method as outlined in Example 22, starting from (2S,4EZ)-4[(benzyloxy)imino]-1-(tert-butoxycarbonyl)-2-pyrrolidinecarboxylic acid, diphenylacetyl chloride, and N-benzyl-N-methylamine the title compound was obtained in 42% purity by LC/MS. MS(ESI+): m/z=532.4.

Example 65

(2S,4EZ)-N-(2,1,3-benzothiadiazol-4-yl)-1-(1,1'-biphenyl]-4-ylcarbonyl)-4-(methoxyimio)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 2,1,3-benzothiadiazol-4-amine the title compound was obtained in 66% purity by LC/MS. MS(ESI+): m/z=472.4.

Example 66

(2S,4EZ)-1-([1,1'-biphenyl]-4-ylcarbonyl)-4-(methoxyimio)-N-(6-quinolinyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 6-quinolinamine the title compound was obtained in 79% purity by LC/MS. MS(ESI+): m/z=465.4.

Example 67

(2S,4EZ)-1-acetoacetyl-N-benzyl-4-(methoxyimino)-2-pyrrolidinecarboxamide

Following the general method as outlined in Example 22, starting from (2S,4EZ)-1-(tert-butoxycarbonyl)-4-(methoxyimino)-2-pyrrolidinecarboxylic acid, 2,4-oxetanedione, and benzylamine the title compound was obtained in 45% purity by LC/MS. MS(ESI+): m/z=332.2.

Example 68

(2S,4EZ)-1-([1,1'-biphenyl]-4-ylcarbonyl-4-(chloromethylene)-N-(2-furylmethyl-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, [1,1'-biphenyl]-4-carbo-nyl chloride, and 2-furylmethylamine the title compound was obtained in 70% purity by LC/MS. MS(ESI+): m/z=421.4.

Example 69

(2S,4EZ)-1-[(4-chlorophenoxy)acetyl]-4-{[(3,4-dichlorobenzyl)oxy]imino}-N-[(2RS)-2-hydroxy-2-phenethyl]-2-pyrrolidinecarboxamide Following the general method as outlined in Example 22, starting from (2S,4EZ)-1-(tert-butoxycarbonyl)-4-{[(3,4dichlorobenzyl)oxy]imino}-2-pyrrolidinecarboxylic acid, (4-chlorophenoxy)acetyl chloride, and (1RS)-2-amino-1-phenylethanol the title compound was obtained in 62% purity by LC/MS. MS(ESI+): m/z=590.8.

Example 70

(2S,4EZ)-N-allyl-1-[1'-biphenyl]-4-ylcarbonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and allylamine the title compound was obtained in 87% purity by LC/MS. MS(ESI+): m/z=378.2.

Example 71

(2S,4EZ)-1-[1,1'-biphenyl]-4-ylcarbonyl)-4-methoxyimino)-N-(2-thienylmethyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 2-thienylmethylamine the title compound was obtained in 78% purity by LC/MS. MS(ESI+): m/z=434.4.

Example 72

(2S,4EZ)-4-(cyanomethylene)-N-(2-furylmethyl)-1-[2-oxo-6-pentyl-2H-pyran-3-yl)carbonyl]-2-pyrrolidinecarboxamide Following the general method as outlined in Example 22, starting from (2S,4EZ)-1-(tent-butoxycarbonyl)-4-(cyanomethylene)-2-pyrrolidinecarboxylic acid, 2-oxo-6-pentyl-2H-pyran-3-carbonyl chloride, and 2-furylmethylamine the title compound was obtained in 34% purity by LC/MS. MS(ESI+): m/z=424.4.

Example 73

(2S,4EZ)-1-([1,1'-biphenyl]-4-ylcarbonyl)-N-(2-furylmethyl)-4-(methoxy-imino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 2-furylmethylamine the title compound was obtained in 75% purity by LC/MS. MS(ESI+): m/z=418.4.

Example 74

(2S,4EZ)-1-acetyl-N-cyclopropyl-4-{[(3,4-dichlorobenzyl)oxy]imino}-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, acetyl chloride, and cyclopropylamine the title compound was obtained in 52% purity by LC/MS. MS(ESI+): m/z=384.4.

Example 75

(2S,4EZ)-N-(2-furylmethyl)-4-(methoxyimino)-1-[(2-oxo-6-pentyl-2H-pyran-3-yl)carbonyl]-2-pyrolidinecarboxamide Following the general method as outlined in Example 22, starting from (2S,4EZ)-1-(tert-butoxycarbonyl)-4-(methoxyimino)-2-pyrrolidinecarboxylic acid, 2-oxo-6-pentyl-2H-pyran-3-carbonyl chloride, and 2-furylmethylamine the title compound was obtained in 62% purity by LC/MS. MS(ESI+): m/z=430.4.

Example 76

(2S,4EZ)-N-benzyl-1-([1,1'-biphenyl]-4-ylcarbonyl)-4-(methoximino)-N-methyl-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and N-benzyl-N-methylamine the title compound was obtained in 67% purity by LC/MS. MS(ESI+): m/z=442.4.

Example 77

(2S,4EZ)-1-(diphenylacetyl)-4-(ethoxyimino)-N-(2-thienylmethyl)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, diphenylacetyl chloride, and 2-thienylmethylamine the title compound was obtained in 74% purity by LC/MS. MS(ESI+): m/z=462.4.

Example 78

(2S,4EZ)-N-(2,1,3-benzothiadiazol-4-yl)-4-(cyanomethylene)-1-(diphenylacetyl)-2-pyrrolidinecarboxamide Following the general method as outlined in Example 22, startling from (2S,4EZ)-1-(tert-butoxycarbonyl)-4-(cyanomethylene)-2-pyrrolidinecarboxylic acid, diphenylacetyl chloride, and 2,1,3-benzothiadiazol-4-amine the title compound was obtained in 42% purity by LC/MS. MS(ESI+): m/z=480.4.

Example 79

(2!)-1-(diphenylacetyl)-N-(1-naphthlmethyl)-4-oxo-2-pyrrolidinecarboxamide

Following the general method as outlined in Example 22, starting from 1-(tert-butoxycarbonyl)-4-oxoproline, diphenylacetyl chloride, and 1-naphthylmethylamine the title compound was obtained in 60% purity by LC/MS. MS(ESI+): m/z=463.4.

Example 80

(3EZ,5S)-5-(1H-benzimidazol-2-yl)-1-(diphenylacetyl)-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, diphenylacetyl chloride, and 1,2-benzenediamine the title compound was obtained in 72% purity by LC/MS. MS(ESI+): m/z=425.4.

Example 81

(2S)-2-[1-([1,1'-biphenyl]-4-ylcarbonyl)-4-methylene-2-pyrrolidinyl]-1H-benzimidazole Following the general method as outlined in Example 22, starting from 1-(tert-butoxycarbonyl)-4-methyleneproline, [1,1'-biphenyl]-4-carbonyl chloride, and 1,2-benzenediamine the title compound was obtained in 73% purity by LC/MS. MS(ESI+): m/z=380.4.

Example 82

(2S,4EZ)-1-([1,1'-biphenyl]-4-ylcarbonyl-4-(chloromethylene)-N-(2-methoxyethyl)-2-pyrrolidinecarboxamide Following the general method as outlined in Example 22, starting from (2S,4EZ)-1-(tertbutoxycarbonyl)-4-(chloromethylene)-2-pyrrolidinecarboxylic acid, [1,1'-biphenyl]-4-carbonyl chloride, and 2-methoxyethylamine the title compound was obtained in 55% purity by LC/MS. MS(ESI+): m/z=399.6.

Example 83

(3EZ,5S)-5-(1H-benzimidazol-2-yl)-1-(diphenylacetyl)-3-pyrrolidinone O-allyloxime Following the general method as outlined in Example 22, starting from (2S,4EZ)-4-[(allyloxy)-imino]-1-(tert-butoxycarbonyl)-2-pyrrolidinecarboxylic acid, diphenylacetyl chloride, and 1,2-benzenediamine the title compound was obtained in 63% purity by LC/MS. MS(ESI+): m/z=451.4.

Example 84

(2S,4EZ)-1-([1,1'-biphenyl]-4-ylcarbonyl)-N-[2-(diethylamino)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4- carbonyl chloride, and N1,N1-diethyl-1,2-ethanediamiine the title compound was obtained in 90% purity by LC/MS. MS(ESI+): m/z=437.4.

Example 85

(2S,4EZ)-1-(diphenylacetyl)-4-{[(4-methoxybenzyl)oxy]imino}-N-(2-thienylmethyl)-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, diphenylacetyl chloride, and 2-thienylmethylamine the title compound was obtained in 63% purity by LC/MS. MS(ESI+): m/z=554.4.

Example 86

(2S,4EZ)-1-([1,1'-biphenyl]-4-ylcarbonyl)-N-(3,4-dimethoxybenzyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 3,4-dimethoxybenzylamine the title compound was obtained in 58% purity by LC/MS. MS(ESI+): m/z=488.4.

Example 87

(2S,4EZ)-1-acetoacetyl-4-(methoxyimino)-N-(1-naphthylmethyl)-2-pyrroli-dinecarboxamide Following the general method as outlined in Example 22, starting from (2S,4EZ)-1-(tert-butoxycarbonyl)-4-(methoxyimino)-2-pyrrolidinecarboxylic acid, 2,4-oxetanedione, and 1-naphthylmethylamine the title compound was obtained in 40% purity by LC/MS. MS(ESI+): m/z=382.2.

Example 88

(2S,4EZ)-N-allyl-4-{[(3,4-dichlorobenzyl)oxy]imino}-1-(diphenylacetyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, diphenylacetyl chloride, and allylamine the title compound was obtained in 54% purity by LC/MS. MS(ESI+): m/z=536.6.

Example 89

(2S,4EZ)-4-{[3,4-dichlorobenzyl)oxy]imino}-$N^1$-pentyl-$N^2$-(6-quinolinyl)-1,2-pyrrolidinedicarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, 1-isocyanatopentane, and 6-quinolinamine the title compound was obtained in 54% purity by LC/MS. MS(ESI+): m/z=542.6.

Example 90

(2S,4EZ)-4-(chloromethylene)-1-(diphenylacetyl)-N-[(2RS)-2-hydroxy-2-phenethyl]-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, diphenylacetyl chloride, and (1RS)-2-amino-1-phenylethanol the title compound was obtained in 87% purity by LC/MS. MS(ESI+): m/z=475.4.

Example 91

(2S)-1-([1,1'-biphenyl-4-ylcarbonyl)-N-[(2RS)-2-hydroxy-2-phenethyl]-4-methylene-2-pyrrolidinecarboxamide Following the general method as outlined in Example 22, starting from 1-(tert-butoxycarbonyl)-4-methyleneproline, [1,1'-biphenyl]-4-carbonyl chloride, and 2-amino-1-phenylethanol the title compound was obtained in 74% purity by LC/MS. MS(ESI+): m/z=427.4.

Example 92

(2S,4EZ)-1-([1,1'-biphenyl]-4-ylcarbonyl)-4-(chloromethylene)-N-(6-quinolinyl)-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, [1,1'-biphenyl]-4-carbo-nyl chloride, and 6-quinolinamine the title compound was obtained in 73% purity by LC/MS. MS(ESI+): m/z=468.4.

Example 93

(254EZ)-4-benzylidene-N-[2-(diethylamino)ethyl]-1-(diphenylacetyl)-2-pyrrolidinecarboxamide Following the general method as outlined in Example 22, starting from (2S,4EZ)-4-benzylidene-1-(tert-butoxycarbonyl)-2-pyrrolidinecarboxylic acid, diphenylacetyl chloride, and N1,N1-diethyl-1,2-ethanediamine the title compound was obtained in 71% purity by LC/MS. MS(ESI+): m/z=496.4.

Example 94

(2S,4EZ)-1-acetoacetyl-4-(methoxyimino)-N-(2-thienylmethyl)-2-pyrrolidinecar-boxamide Following the general method as outlined in Example 22, starting from (2S,4EZ)-1-(tert-butoxycarbonyl)-4-(methoxyimino)-2-pyrrolidinecarboxylic acid, 2,4-oxetanedione, and 2-thienylmethylamine the title compound was obtained in 42% purity by LC/MS. MS(ESI+): m/z=338.2.

Example 95

(2S,4EZ)-1-acetyl-4-{[(3,4-dichlorobenzyl)oxy]imino}-N-(2-hydroxy-2-phenylethyl)-2-pyrrolidinecarboxamide Following the general method as outlined in Example 22, starting from (2S,4EZ)-1-(tert-butoxycarbonyl)-4-{[(3,4- dichlorobenzyl)oxy]imino})-2-pyrrolidinecarboxylic acid, acetyl chloride, and (1RS)-2-amino-1-phenylethanol the title compound was obtained in 48% purity by LC/MS. MS(ESI+): m/z=464.6.

Example 96

(2S,4EZ)-4-{[(3,4-dichlorobenzyl)oxy]imino}-$N^1$-(3,5-dichlorophenyl-$N^2$-(6-quinolinyl)-1,2-pyrrolidinecarboxamide Following the general method as outlined in Example 22, starting from (2S,4EZ;)-1-(tertbutoxycarbonyl)-4-{[(3,4-dichlorobenzyl)oxy]imino}-2-pyrrolidinecarboxylic acid, 1,3-dichloro-5-isocyanatobenzene, and 6-quinolinamine the title compound was obtained in 66% purity by LC/MS. MS(ESI+): m/z=617.2.

Example 97

(2S,4EZ)-4-(methoxyimino)-N-(1-naphthylmethyl)-1-(phenoxyacetyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, phenoxyacetyl chloride, and 1-naphthylmethylamine the title compound was obtained in 99% purity by LC/MS. MS(ESI+): m/z=432.2.

Example 98

(2S,4EZ)-4-(chloromethylene)-N-(3,4-dimethoxybenzyl)-1-[(2-oxo-6-pentyl-2H-pyran-3-yl)carbonyl]-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, 2-oxo-6-pentyl-2H-pyran-3-carbonyl chloride, and 3,4-dimethoxybenzylamine the title compound was obtained in 51% purity by LC/MS. MS(ESI+): m/z=503.4.

Example 99

(2S,4EZ)-1-(diphenylacetyl)-4-(methoxyimino)-N-(2-thienylmethyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, diphenylacetyl chloride, and 2-thienylmethylamine the title compound was obtained in 88% purity by LC/MS. MS(ESI+): m/z=448.4.

Example 100

(2S,4EZ)-N-benzyl-1-(diphenylacetyl)-4-(methoxyimino)-2-pyrrolidinecarboxamide

Following the general method as outlined in Example 22, starting from (2S,4EZ)-1-(tert-butoxycarbonyl)-4-(methoxyimino)-2-pyrrolidinecarboxylic acid, diphenylacetyl chloride, and benzylamine the title compound was obtained in 82% purity by LC/MS. MS(ESI+): m/z=442.4.

Example 101

(2S,4EZ)-1-([1,1'-biphenyl]-4-ylcarbonyl)-4-{[(3,4-dichlorobenzyl)oxy]-imino}-N-[2-(diethylamino)ethyl]-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, [1,1'-biphenyl]-4-carbonyl chloride, and N1,N1-diethyl-1,2-ethanediamine the title compound was obtained in 74% purity by LC/MS. MS(ESI+): m/z=581.6.

Example 102

(2S,4EZ)-4-{[(3,4-dichlorobenzyl)oxy]imino}-1-[4-(dimethylamino)butanoyl]-N-(6-quinolinyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, 4-(dimethylamino)butanoyl chloride, and 6-quinolinamine the title compound was obtained in 95% purity by LC/MS. MS(ESI+): m/z=542.6.

Example 103

(2S,4EZ)-1-([1,1'-biphenyl]-4-ylcarbonyl)-N-(5-ethyl-1,3,4-thiadiazol-2-yl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]carbonyl chloride, and 5-ethyl-1,3,4-thiadiazol-2-amine the title compound was obtained in 89% purity by LC/MS. MS(ESI+): m/z=450.2.

Example 104

(2S,4EZ)-N-benzyl-1-([1,1'-biphenyl]-4-ylcarbonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and benzylamine the title compound was obtained in 72% purity by LC/MS. MS(ESI+): m/z=428.2.

Example 105

(2S,4EZ)-N-benzyl-1-(diphenylacetyl)-4-(ethoxyimino)-2-pyrrolidinecarboxamide

Following the general method as outlined in Example 22, starting from (2S,4EZ)-1-(tertbutoxycarbonyl)-4-(ethoxyimino)-2-pyrrolidinecarboxylic acid, diphenylacetyl chloride, and benzylamine the title compound was obtained in 53% purity by LC/MS. MS(ESI+): m/z=456.4.

Example 106

(2S,4EZ)-$N^2$-cyclopropyl-4-{[(3,4-dichlorobenzyl)oxy]imino}-$N^1$-(3-methoxyphenyl)-1,2-pyrrolidinedicarboxamide Following the general method as outlined in Example 22, starting from (2S,4EZ)-1-(tert-butoxycarbonyl)-4-{[(3,4- dichlorobenzyl)oxy]imino}-2-pyrrolidinecarboxylic acid, 1-isocyanato-3-methoxybenzene, and cyclopropylamine the title compound was obtained in 45% purity by LC/MS. MS(ESI+): m/z=491.6.

Example 107

(2S,4EZ)-1-(diphenylacetyl)-N-[(2RS)-2-hydroxy-2-phenethyl]-4-{[(4-methoxyben-zyl oxy]imino}-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, diphenylacetyl chloride, and (1RS)-2-amino-1-phenylethanol the title compound was obtained in 66% purity by LC/MS. MS(ESI+): m/z=578.4.

Example 108

(2S)-N-(2-furylmethyl)-4-methylene-1-(2-oxo-6-pentyl-2H-pyran-3-yl)carbonyl]-2-pyrolidinecarboxamide Following the general method as outlined in Example 22, starting from 1-(tert-butoxycarbonyl)-4-methyleneproline, 2-oxo-6-pentyl-2H-pyran-3-carbonyl chloride, and 2-furylmethylamine the title compound was obtained in 43% purity by LC/MS. MS(ESI+): m/z=399.2.

Example 109

(2S,4MZ)-N-(2,1,3-benzothiadiazol-4-yl)-1-(diphenylacetyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, diphenylacetyl chloride, and 2,1,3-benzothiadiazol-4-amine the title compound was obtained in 69% purity by LC/MS. MS(ESI+): m/z=486.4.

Example 110

(2S)-N1-(3,5-dichlorophenyl)-N2-(3,4-dimethoxybenzyl)-4oxo-1,2-pyrrolidinedicarboxamide Following the general method as outlined in Example 22, starting from 1-(tert-butoxycarbonyl)-4-oxoproline, 1,3-dichloro-5-isocyanatobenzene, and 3,4-dimethoxybenzylamine the title compound was obtained in 48% purity by LC/MS. MS(ESI+): m/z=466.6.

Example 111

(2S,4EZ)-N-benzyl-1-(diphenylacetyl)-4-{[(4-methoxybenzyl)oxy]imino}-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, diphenylacetyl chloride, and benzylamine the title compound was obtained in 60% purity by LC/MS. MS(ESI+): m/z=548.4.

Example 112

(2S,4EZ)-1-benzoyl)-4-{[(3,4-dichlorobenzyl)oxy]imino}-N-(6-quinolinyl)-2-pyrrolidinecarboxamide Following the general method as outlined in Example 22, starting from (2S,4EZ)-1-(tert-butoxycarbonyl)-4{[(3,4-dichlorobenzyl)oxy]imino}-2-pyrrolidinecarboxylic acid, benzoyl chloride, and 6-quinolinamine the title compound was obtained in 67% purity by LC/MS. MS(ESI+): m/z=533.6.

Example 113

(2S,4EZ)-1-acetoacetyl-N-cyclopropyl-4-{[(3,4-dichlorobenzyl)oxy]imino}-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, 2,4-oxetanedione, and cyclopropylamine the title compound was obtained in 76% purity by LC/MS. MS(ESI+): m/z=426.6.

Example 114

(2S,4EZ)-4-{[(3,4-dichlorobenzyl)oxy]imino}-$N^2$-[(2RS)-2-hydroxy-2-phenethyl]-$N^1$-pentyl-1,2-pyrrolidinedicarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, 1-isocyanatopentane, and (1RS)-2-amino-1-phenylethanol the title compound was obtained in 47% purity by LC/MS. MS(ESI+): m/z=535.6.

Example 115

(2S,4EZ)-4-[(benzyloxy)imino]-N-(1-naphthylmethyl)-1-(phenoxyacetyl)-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, phenoxyacetyl chloride, and 1-naphthylmethylamine the title compound was obtained in 74% purity by LC/MS. MS(ESI+): m/z=508.4.

Example 116

(2S)-1-([1,1'-biphenyl]-4-ylcarbonyl)-4-methylene-N-(6-quinolinyl)-2-pyrrolidinecarboxamide Following the general method as outlined in Example 22, starting from 1-(tert-butoxycarbonyl)-4-methyleneproline, [1,1'-biphenyl]-4-carbonyl chloride, and 6-quinolinamine the title compound was obtained in 88% purity by LC/MS. MS(ESI+): m/z=434.2.

Example 117

(2S,4EZ)-N-cyclopropyl-4-{[(3,4-dichlorobenzyl)oxy]imino}-1-(diphenylacetyl)-2-pyrrolidinecarboxamide Following the general method as outlined in Example 22, starting from (2S,4EZ)-1-(tert-butoxycarbonyl)-4-{[(3,4- dichlorobenzyl)oxy]imino}-2-pyrrolidinecarboxylic acid, diphenylacetyl chloride, and cyclopropylamine the title compound was obtained in 49% purity by LC/MS. MS(ESI+): m/z=536.6.

Example 118

(2S,4EZ)-1-(4-cyanobenzoyl)-4-{[(3,4-dichlorobenzyl)oxy]imino}-N-(6-quinolinyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, 4-cyanobenzoyl chloride, and 6-quinolinamine the title compound was obtained in 52% purity by LC/MS. MS(ESI+): m/z=558.6.

Example 119

(2S)-4-oxo-1-(phenoxyacetyl)-N-[2-(1H-pyrrol-1-yl)phenyl]-2-pyrrolidinecarboxamide Following the general method as outlined in Example 22, starting from 1-(tert-butoxycarbonyl)-4-oxoproline, phenoxyacetyl chloride, and 2-(1H-pyrrol-1-yl)phenylamine the title compound was obtained in 42% purity by LC/MS. MS(ESI+): m/z=404.2.

Example 120

(2S,4EZ)-N-cyclopropyl-4-{[(3,4-dichlorobenzyl)oxy]imino}-1-(methoxyacetyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, methoxyacetyl chloride, and cyclopropylamine the title compound was obtained in 54% purity by LC/MS. MS(ESI+): m/z=414.6.

Example 121

(2S,4EZ)-N-(1,3-benzodioxol-5-ylmethyl)-1-([1,1'-biphenyl]-4-ylcarbonyl)-4-(methoxyimino-2-pyrrolidinecarboxamide Following the general method as outlined in Example 22, staring from (2S,4EZ)-1-(tert-butoxycarbonyl)-4-(methoxyimino)-2-pyrrolidinecarboxylic acid, [1,1'-biphenyl]-4-carbonyl chloride, and 1,3-benzodioxol-5-ylmethylamine the title compound was obtained in 64% purity by LC/MS. MS(ESI+): m/z=472.4.

Example 122

(3EZ,5S)-5-[(4-acetyl-1-piperazinyl)carbonyl]-1-acryloyl-3-pyrrolidinone O-(3,4-dichlorobenzyl) oxime Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, acryloyl chloride, and 1-acetylpiperazine the title compound was obtained in 79% purity by LC/MS. MS(ESI+): m/z=467.6.

Example 123

(2S)-1-([1,1'-biphenyl]-4-ylcarbonyl)-N-(2-furylmethyl)-4-methylene-2-pyrrolidinecarboxamide Following the general method as outlined in Example 22, starting from 1-(tert-butoxycarbonyl)-4-methyleneproline, [1,1'-biphenyl]-4-carbonyl chloride, and 2-furylmethylamine the title compound was obtained in 94% purity by LC/MS. MS(ESI+): m/z=387.2.

Example 124

(2S,4EZ)-4-(cyanomethylene)-N-(3,4-dimethoxybenzyl)-1-[(2-oxo-6-pentyl-2H-pyran-3-yl)carbonyl]-2-pyrrolidinecarboxamide Following the general method as outlined in Example 22, starting from (2S,4EZ)-1-(tert-butoxycarbonyl)-4-(cyanomethylene)-2-pyrrolidinecarboxylic acid, 2-oxo-6-pentyl-2H-pyran-3-carbonyl chloride, and 3,4-dimethoxybenzylamine the title compound was obtained in 65% purity by LC/MS. MS(ESI+): m/z=494.4.

Example 125

(2S,4EZ)-1-[(benzoylamino)carbonyl]-4-(cyanomethylene)-N-(9-ethyl-9H-carbazol-3-yl)-2-pyrrolidinecarboxamide Following the general method as outlined in Example 22, starting from (2S,4EZ)-1-(tert-butoxycarbonyl)-4-(cyanomethylene)-2-pyrrolidinecarboxylic acid, benzoyl isocyanate, and 9-ethyl-9H-carbazol-3-amine the title compound was obtained in 74% purity by LC/MS. MS(ESI+): m/z=492.4.

Example 126

(2S,4EZ)-1-benzoyl-N-[2-(diethylamino)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, benzoyl chloride, and N1,N1-diethyl-1,2-ethanediamine the title compound was obtained in 80% purity by LC/MS. MS(ESI+): m/z=361.2.

Example 127

(2S,4EZ)-N-[2-(diethylamino)ethyl]-1-(diphenylacetyl)-4-(ethoxyimino)-2-pyrrolidinecarboxamide Following the general method as outlined in Example 22, starting from (2S,4EZ)-1-tert-butoxycarbonyl)-4-(ethoxyimino)-2-pyrrolidinecarboxylic acid, diphenylacetyl chloride, and N1,N1-diethyl-1,2-ethanediamine the title compound was obtained in 50% purity by LC/MS. MS(ESI+): m/z=465.4.

Example 128

(2S,4EZ)-N-(2,1,3-benzothiadiazol-4-yl)-4-[(benzyloxy)imino]-1-(4-cyanobenzoyl)-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, 4-cyanobenzoyl chloride, and 2,1,3-benzothiadiazol-4-amine the title compound was obtained in 55% purity by LC/MS. MS(ESI+): m/z=497.4.

Example 129

(2EZ)-[5-(1H-benzimidazol-2-yl)-1-([1,1'-biphenyl] 4-ylcarbonyl)-3-pyrrolidinylidene]ethanenitrile Following the general method as outlined in Example 22, starting from (2S,4EZ)-1-(tert-butoxycarbonyl)-4-(cyanomethylene)-2-pyrrolidinecarboxylic acid, [1,1'-biphenyl]-4-carbonyl chloride, and 1,2-benzenediamine the title compound was obtained in 70% purity by LC/MS. MS(ESI+): m/z=405.2.

Example 130

(2S,4EZ)-4-(chloromethylene)-N-(9-ethyl-9H-carbazol-3-yl)-1-(phenoxyacetyl)-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, phenoxyacetyl chloride, and 9-ethyl-9H-carbazol-3-amine the title compound was obtained in 63% purity by LC/MS. MS(ESI+): m/z=488.6.

Example 131

(2S)-$N^2$-(9-ethyl-9H-carbazol-3-yl)-$N^1$-(3-methoxyphenyl)-4-methylene-1,2-pyrrolidinedicarboxamide Following the general method as outlined in Example 22, starting from 1-(tert-butoxycarbonyl)-4-methyleneproline, 1-isocyanato-3-methoxybenzene, and 9-ethyl-9H-carbazol-3-amine the title compound was obtained in 47% purity by LC/MS. MS(ESI+): m/z=469.4.

Example 132

(2S,4EZ)-4-(cyanomethylene)-N-(9-ethyl-9H-carbazol-3-yl)-2-pyrrolidinecarboxamide Following the general method as outlined in Example 22, starting from (2S,4EZ)-1-(tert-butoxycarbonyl)-4-(cyanomethylene)-2-pyrrolidinecarboxylic acid, and 9-ethyl-9H-carbazol-3-amine the title compound was obtained in 36% purity by LC/MS. MS(ESI+): m/z=345.2.

Example 133

(2S,4EZ)-1-(4-cyanobenzoyl)-N-[2-(diethylamino) ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-cyanobenzoyl chloride, and N1,N1-diethyl-1,2-ethanediamine the title compound was obtained in 58% purity by LC/MS. MS(ESI+): m/z=386.2.

Example 134

4-{[(2S,4EZ)-2-(1H-benzimidazol-2-yl)-4-(cyanomethylene)pyrrolidinyl]-carbonyl}benzonitrile Following the general method as outlined in Example 22, starting from (2S,4EZ)-1-(tert-butoxycarbonyl)-4-(cyanomethylene)-2-pyrrolidinecarboxylic acid, 4-cyanobenzoyl chloride, and 1,2-benzenediamine the title compound was obtained in 84% purity by LC/MS. MS(ESI+): m/z=354.2.

Example 135

(2S,4EZ)-4-[(allyloxy)imino]-1-[4-(dimethylamino) butanoyl]-N-(9-ethyl-9H-carbazol-3-yl)-2-pyrrolidinecarboxamide Following the general method as outlined in Example 22, starting from (2S,4EZ)-4-[(allyloxy)imino]-1-(tert-butoxycarbonyl)-2-pyrrolidinecarboxylic acid, 4-(dimethylamino)-butanoyl chloride and 9-ethyl-9H-carbazol-3-amine the title compound was obtained in 40% purity by LC/MS. MS(ESI+): m/z=490.4.

Example 136

(2S,4EZ)-4-benzylidene-N-(9-ethyl-9H-carbazol-3-yl)-2-pyrrolidinecarboxamide

Following the general method as outlined in Example 22, starting from (2S,4EZ)-4-benzylidene-1-(tert-butoxycarbonyl)-2-pyrrolidinecarboxylic acid, and 9-ethyl-9H-carbazol-3-amine the title compound was obtained in 53% purity by LC/MS. MS(ESI+): m/z=396.2.

Example 137

(2S,4EZ)-4-benzylidene-1-[4-(dimethylamino)butanoyl]-N-(9-ethyl-9H-carbazol-3-yl)-2-pyrolidinecarboxamide Following the general method as outlined in Example 22, starting from (2S,4EZ)-4-benzylidene-1-(tert-butoxycarbonyl)-2-pyrrolidinecarboxylic acid, 4-(dimethylamino)butanoyl chloride, and 9-ethyl-9H-carbazol-3-amine the title compound was obtained in 74% purity by LC/MS. MS(ESI+): m/z=509.4.

Example 138

(2S,4EZ)-4(chloromethylene)-N-(9-ethyl-9H-carbazol-3-yl)-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, and 9-ethyl-9H-carbazol-3-amine the title compound was obtained in 73% purity by LC/MS. MS(ESI+): m/z=354.4.

Example 139

(2S)-N-(9-ethyl-9H-carbazol-3-yl)-4-methylene-2-pyrrolidinecarboxamide

Following the general method as outlined in Example 22, starting from 1-(tert-butoxycarbonyl)-4-methyleneproline, and 9-ethyl-9H-carbazol-3-amine the title compound was obtained in 71% purity by LC/MS. MS(ESI+): m/z=320.2.

Example 140

(2S, 4EZ)-4-(cyanomethylene)-N-(9-ethyl-9H-carbazol-3yl)-1-(4-phenoxybenzoyl)-2-pyrrolidinecarboxamide Following the general method as outlined in Example 22, starting from (2S,4EZ)-1-(tert-butoxycarbonyl)-4-(cyanomethylene)-2-pyrrolidinecarboxylic acid, 4-phenoxybenzoyl chloride, and 9-ethyl-9H-carbazol-3-amine the title compound was obtained in 37% purity by LC/MS. MS(ESI+): m/z=541.4.

Example 141

N-{[(2S,4EZ)-2-(1H-benzimidazol-2-yl)-4-(chloromethylene)pyrrolidinyl]-carbonyl}benzamide Following the general method as outlined in Example 22, starting from (2S,4EZ)-1-(tert-butoxycarbonyl)-4-(chloromethylene)-2-pyrrolidinecarboxylic acid, benzoyl isocyanate, and 1,2-benzenediamine the title compound was obtained in 51% purity by LC/MS. MS(ESI+): m/z=381.4.

Example 142

(2S)-$N^1$-(3,5-dichlorophenyl)-$N^2$-(9-ethyl-9H-carbazol-3-yl)-4-methylene-1,2-pyrrolidinedicarboxamide Following the general method as outlined in Example 22, starting from 1-(tert-butoxycarbonyl)-4-methyleneproline, 1,3-dichloro-5-isocyanatobenzene, and 9-ethyl-9H-carbazol-3-amine the title compound was obtained in 40% purity by LC/MS. MS(ESI+): m/z=507.6.

Example 143

(2)-1-(diphenylacetyl)-N-(9-ethyl-9H-carbazol-3-yl)-4-methylene-2-pyrrolidinecarboxamide Following the general method as outlined in Example 22, starting from 1-(tert-butoxycarbonyl)-4-methyleneproline, diphenylacetyl chloride, and 9-ethyl-9H-carbazol-3-amine the title compound was obtained in 42% purity by LC/MS. MS(ESI+): m/z=514.4.

Example 144

(2S,4EZ)-1-benzoyl-4-(chloromethylene)-N-(9-ethyl-9H-carbazol-3-yl-)-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, benzoyl chloride, and 9-ethyl-9H-carbazol-3-amine the title compound was obtained in 48% purity by LC/MS. MS(ESI+): m/z=458.4.

Example 145

(2S,4EZ)-1-([1,1'-biphenyl]-4-ylcarbonyl)-4-(cyanomethylene)-N-(9-ethyl-9H-carbazol-3-yl)-2-pyrrolidinecarboxamide Following the general method as outlined in Example 22, starting from (2S,4EZ)-1-(tert-butoxycarbonyl)-4-(cyanomethylene)-2-pyrrolidinecarboxylic acid, [1,1'-biphenyl]-4-carbonyl chloride, and 9-ethyl-9H-carbazol-3-amine the title compound was obtained in 32% purity by LC/MS. MS(ESI+): m/z=525.4.

Example 146

(2S,4EZ)-4-(cyanomethylene)-N-(9-ethyl-9H-carbazol-3-yl)-1-(3-oxobutyl)-2-pyrrolidinecarboxamide Following the general method as outlined in Example 22, starting from (2S,4EZ)-1-(tert-butoxycarbonyl)-4-(cyanomethylene)-2-pyrrolidinecarboxylic acid, 3-buten-2-one, and 9-ethyl-9H-carbazol-3-amine the title compound was obtained in 59% purity by LC/MS. MS(ESI+): m/z=415.2.

Example 147

(2S)-1-[(4-chlorophenoxy)acetyl]-N-(9-ethyl-9H-carbazol-3-yl)-4methylene-2-pyrrolidinecarboxamide Following the general method as outlined in Example 22, starting from 1-(tert-butoxycarbonyl)-4-methyleneproline, (4-chlorophenoxy)acetyl chloride, and 9-ethyl-9H-carbazol-3-amine the title compound was obtained in 100% purity by LC/MS. MS(ESI+): m/z=488.4.

Example 148

(2S)-1-([1,1'-biphenyl]-4-carbonyl)-N-(9-ethyl-9H-carbazol-3-yl)-4-methylene-2-pyrrolidinecarboxamide Following the general method as outlined in Example 22, starting from 1-(tert-butoxycarbonyl)-4-methyleneproline, [1,1'-biphenyl]-4-carbonyl chloride, and 9-ethyl-9H-carbazol-3-amine the title compound was obtained in 46% purity by LC/MS. MS(ESI+): m/z=500.4.

Example 149

2-[(2S,4EZ)-4-(chloromethylene)pyrrolidinyl]-1H-benzimidazole

Following the general method as outlined in Example 22, starting from (2S,4EZ)-1-(tert-butoxycarbonyl)-4-(chloromethylene)-2-pyrrolidinecarboxylic acid, and 1,2-benzenediamine the title compound was obtained in 43% purity by LC/MS. MS(ESI+): m/z=234.4.

Example 150

(2S,4EZ)-4-(ethoxyimino)-N-(9-ethyl-9H-carbazol-3-yl)-2-pyrrolidinecarboxamide

Following the general method as outlined in Example 22, starting from (2S,4EZ)-1-(tert-butoxycarbonyl)-4-(ethoxyimino)-2-pyrrolidinecarboxylic acid, and 9-ethyl-9H-carbazol-3-amine the title compound was obtained in 91% purity by LC/MS. MS(ESI+): m/z=365.2.

Example 151

(2S)-1-benzoyl-N-(9-ethyl-9H-carbazol-3-yl)-4methylene-2-pyrrolidinecarboxamide

Following the general method as outlined in Example 22, starting from 1-(tert-butoxycarbonyl)-4-methyleneproline, benzoyl chloride, and 9-ethyl-9H-carbazol-3-amine the title compound was obtained in 52% purity by LC/MS. MS(ESI+): m/z=424.2.

Example 152

(2S,4EZ)-N-[2-(diethylamino)ethyl]-1-(diphenylacetyl)-4-{[(4-methoxybenzyl)oxy]imino}-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, diphenylacetyl chloride, and N1,N1-diethyl-1,2-ethanediamine the title compound was obtained in 56% purity by LC/MS. MS(ESI+): m/z=557.4.

Example 144153

(2S,4EZ)-1-benzoyl-N-(2-furylmethyl)-4-{[(4-methoxybenzyl)oxy]-imino}-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, benzoyl chloride and 2-furylmethylamine the title compound was obtained in 40% purity by LC/MS. MS(ESI+): m/z=448.2.

Example 154

(2S,4EZ)-4-(tert-butoxyimino)-N-[2-(diethylamino)ethyl]-1-(diphenyl-acetyl)-2-pyrrolidinecarboxamide Following the general method as outlined in Example 22, starting from (2S,4EZ)-1-(tert-butoxycarbonyl)-4-(tert-butoxyimino)-2-pyrrolidinecarboxylic acid, diphenylacetyl chloride, and N1,N1-diethyl-1,2-ethanediamine the title compound was obtained in 80% purity by LC/MS. MS(ESI+): m/z=493.4.

Example 155

(2S)-1-([1,1'-biphenyl]-4-ylcarbonyl)-N-(3 4-dimethoxybenzyl)-4-methylene-2-pyrrolidinecarboxamide Following the general method as outlined in Example 22, starting from 1-(tert-butoxycarbonyl)-4-methyleneproline, [1,1'-biphenyl]-4-carbonyl chloride, and 3,4-dimethoxybenzylamine the title compound was obtained in 72% purity by LC/MS. MS(ESI+): m/z=457.2.

Example 156

(2S,4EZ)-4-(cyanomethylene)-$N^1$-(3,5-dichlorophenyl)-$N^2$-(9-ethyl-9H-carbazol-3-yl)-1,2-pyrrolidinedicarboxamide Following the general method as outlined in Example 22, starting from (2S,4EZ)-1-(tert-butoxycarbonyl)-4-(cyanomethylene)-2-pyrrolidinecarboxylic acid, 1,3-dichloro-5-isocyanatobenzene, and 9-ethyl-9H-carbazol-3-amine the title compound was obtained in 60% purity by LC/MS. MS(ESI+): m/z=532.8.

Example 157

(2S,4EZ)-4-[(allyloxy)imino]-$N^2$-(9-ethyl-9H-carbazol-3-yl)-$N^1$-phenyl-1,2-pyrrolidinedicarboxamide Following the general method as outlined in Example 22, starting from (2S,4EZ)-4-[(allyloxy)-imino]-1-(tert-butoxycarbonyl)-2-pyrrolidinecarboxylic acid, isocyanatobenzene, and 9-ethyl-9H-carbazol-3-amine the title compound was obtained in 67% purity by LC/MS. MS(ESI+): m/z=496.4.

Example 158

(2S)-$N^2$-(9-ethyl-9H-carbazol-3-yl)-4-methylene-$N^1$-phenyl-1,2-pyrrolidinecar-boxamide Following the general method as outlined in Example 22, starting from 1-(tert-butoxycarbonyl)-4-methyleneproline, isocyanatobenzene, and 9-ethyl-9H-carbazol-3-amine the title compound was obtained in 66% purity by LC/MS. MS(ESI+): m/z=439.2.

Example 159

(2S,4EZ)-$N^2$-(2,1,3-benzothiadiazol-4-yl)-$N^1$-(3,5-dichlorophenyl)-4-(methoxyimino)-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, 1,3-dichloro-5-isocyanatobenzene, and 2,1,3-benzothiadiazol-4-amine the title compound was obtained in 55% purity by LC/MS. MS(ESI+): m/z=479.6.

Example 160

(2EZ)-[5-(1H-benzimidazol-2-yl)-1-(4-phenoxybenzoyl)-3-pyrrolidinylidene]ethanenitrile Following the general method as outlined in Example 22, starting from (2S,4EZ)-1-(tertbutoxycarbonyl)-4-(cyanomethylene)-2-pyrrolidinecarboxylic acid, 4-phenoxybenzoyl chloride, and 1,2-benzenediamine the title compound was obtained in 90% purity by LC/MS. MS(ESI+): m/z=421.2.

Example 161

(2S,4EZ)-4-(tert-butoxyimino)-1-(2-ethoxy-1-naphthoyl)-N-(9-ethyl-9H-carbazol-3-yl)-2-pyrrolidinecarboxamide Following the general method as outlined in Example 22, starting from (2S,4EZ)-1-(tert-butoxycarbonyl)-4-(tert-butoxyimino)-2-pyrrolidinecarboxylic acid, 2-ethoxy-1-naphthoyl chloride, and 9-ethyl-9H-carbazol-3-amine the title compound was obtained in 47% purity by LC/MS. MS(ESI+): m/z=591.4.

Example 162

(2S,4EZ)-1-benzoyl-N-[2-(diethylamino)ethyl-4-(ethoxyimino)-2-pyrrolidinecarboxamide Following the general method as outlined in Example 22, starting from (2S,4EZ)-1-(tertbutoxycarbonyl)-4-(ethoxyimino)-2-pyrrolidinecarboxylic acid, benzoyl chloride, and N1,N1-diethyl-1,2-ethanediamine the title compound was obtained in 84% purity by LC/MS. MS(ESI+): m/z=375.2.

Example 163

(2S,4EZ)-$N^2$-(2,1,3-benzothiadiazol-4-yl)-4-[(benzyloxy)imino]-$N^1$-phenyl-1,2-pyrrolidinedicarboxamide Following the general method as outlined in Example 22, starting from (2S,4EZ)-4-[(benzyloxy)imino]-1-(tert-butoxycarbonyl)-2-pyrrolidinecarboxylic acid, isocyanatobenzene, and 2,1,3-benzothiadiazol-4-amine the title compound was obtained in 57% purity by LC/MS. MS(ESI+): m/z=487.4.

Example 164

(2S,4EZ)-1-(4-cyanobenzoyl)-4-{[(3,4-dichlorobenzyl)oxy]imino}-N-(1-naphthylmethyl-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, 4-cyanobenzoyl chloride, and 1-naphthylmethylamine the title compound was obtained in 39% purity by LC/MS. MS(ESI+): m/z=571.6.

Example 165

(2S,4EZ)-N-(2,1,3-benzothiadiazol-4-yl)-1-benzoyl-4-{[(4-methoxybenzyl)-oxy]imino}-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, benzoyl chloride, and 2,1,3-benzothiadiazol-4-amine the title compound was obtained in 61% purity by LC/MS. MS(ESI+): m/z=502.4.

Example 166

(2S,4EZ)-4-[(allyloxy)imino]-N-(2,1,3-benzothiadiazol-4-yl)-1-(diphenylacetyl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, diphenylacetyl chloride, and 2,1,3-benzothiadiazol-4-amine the title compound was obtained in 46% purity by LC/MS. MS(ESI+): m/z=512.4.

Example 167

(2S,4EZ)-4-(ethoxyimino)-N-(9-ethyl-9H-carbazol-3-yl)-1-[(2-oxo-6-pentyl-2H-pyran-3-yl)carbonyl]-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, 2-oxo-6-pentyl-2H-pyran-3-carbonyl chloride, and 9-ethyl-9H-carbazol-3-amine the title compound was obtained in 75% purity by LC/MS. MS(ESI+): m/z=557.4.

Example 168

(2S,4EZ)-1-benzoyl-4-(ethoxyimino)-N-(9-ethyl-9H-carbazol-3-yl)-2-pyrrolidinecarboxamide Following the general method as outlined in Example 22, starting from (2S,4EZ)-1-(tertbutoxycarbonyl)-4-(ethoxyimino)-2-pyrrolidinecarboxylic acid, benzoyl chloride, and 9-ethyl-9H-carbazol-3-amine the title compound was obtained in 74% purity by LC/MS. MS(ESI+): m/z=469.4.

Example 169

(2S,4EZ)-4-(ethoxyimino)-N-(9-ethyl-9H-carbazol-3-yl)-1-(methoxyacetyl)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, methoxyacetyl chloride, and 9-ethyl-9H-carbazol-3-amine the title compound was obtained in 88% purity by LC/MS. MS(ESI+): m/z=437.2.

Example 170

(2S,4EZ)-4-[(benzyloxy)imino]-$N^2$-(9-ethyl-9H-carbazol-3-yl)-$N^1$-pentyl-1,2-pyrrolidinedicarboxamide Following the general method as outlined in Example 22, starting from (2S,4EZ)-4-[(benzyloxy)imino]-1-(tert-butoxycarbonyl)-2-pyrrolidinecarboxylic acid, 1-isocyanatopentane, and 9-ethyl-9H-carbazol-3-amine the title compound was obtained in 63% purity by LC/MS. MS(ESI+): m/z=540.4.

Example 171

(3EZ,5S)-1-benzoyl-5-{[4(3,4-dichlorophenyl)-1-piperazinyl]carbonyl}-3-pyrrolidinone O-ethyloxime Following the general method as outlined in Example 22, starting from (2S,4EZ)-1-(tert-butoxycarbonyl)-4-(ethoxyimino)-2-pyrrolidinecarboxylic acid, benzoyl chloride, and 1-(3,4-dichlorophenyl)piperazine the title compound was obtained in 51% purity by LC/MS. MS(ESI+): m/z=489.6.

Example 172

(2S,4EZ)-4-[(allyloxy)imino]-N-(9-ethyl-9H-carbazol-3-yl)-1-[(2-oxo-6-pentyl-2H-pyran-3-yl)carbonyl]-2-pyrrolidinecarboxamide Following the general method as outlined in Example 22, starting from (2S,4EZ)-4-[(allyloxy)-imino]-1-tert-butoxycarbonyl)-2-pyrrolidinecarboxylic acid, 2-oxo-6-pentyl-2H-pyran-3-carbonyl chloride, and 9-ethyl-9H-carbazol-3-amine the title compound was obtained in 48% purity by LC/MS. MS(ESI+): m/z=569.4.

Example 173

(2S,4EZ)-4-{[(4-methoxybenzyl)oxy]imino}-N-(2-methoxyethyl)-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, and 2-methoxyethylamine the title compound was obtained in 52% purity by LC/MS. MS(ESI+): m/z=322.2.

Example 174

(2S,4EZ)-4-[(allyloxy)imino]-N-(3,4-dimethoxybenzyl)-1-(diphenylacetyl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, diphenylacetyl chloride, and 3,4-dimethoxybenzylamine the title compound was obtained in 63% purity by LC/MS. MS(ESI+): m/z=528.4.

Example 175

(2S,4EZ)-4-[(allyloxy)imino]-1-(4-cyanobenzoyl)-N-(9-ethyl-9H-carbazol-3-yl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, 4-cyanobenzoyl chloride, and 9-ethyl-9H-carbazol-3-amine the title compound was obtained in 43% purity by LC/MS. MS(ESI+): m/z=506.4.

Example 176

(2S,4EZ)-4-{[(4-methoxybenzyl)oxy]imino}-1-[(2-oxo-6-pentyl-2H-pyran-3-yl)carbonyl]-N-(6-quinolinyl)-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, 2-oxo-6-pentyl-2H-pyran-3-carbonyl chloride, and 6-quinolinamine the title compound was obtained in 61% purity by LC/MS. MS(ESI+): m/z=583.4.

Example 177

(2S,4EZ)-N-(9-ethyl-9H-carbazol-3-yl)-4-(methoxyimino)-2-pyrrolidinecarboxamide

Following the general method as outlined in Example 22, starting from (2S,4EZ)-1-(tert-butoxycarbonyl)-4-(methoxyimino)-2-pyrrolidinecarboxylic acid, and 9-ethyl-9H-carbazol-3-amine the title compound was obtained in 46% purity by LC/MS. MS(ESI+): m/z=351.2.

Example 178

(2S,4EZ)-$N^2$-(9-ethyl-9H-carbazol-3-yl)-4-(methoxyimino)-$N^1$-(3-methoxyphenyl)-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, 1-isocyanato-3-methoxybenzene, and 9-ethyl-9H-carbazol-3-amine the title compound was obtained in 100% purity by LC/MS. MS(ESI+): m/z=500.4.

Example 179

(2S,4EZ)-4-(ethoxyimino)-$N^2$-(9-ethyl-9H-carbazol-3-yl)-$N^1$-(3-methoxyphenyl)-1,2-pyrrolidinedicarboxamide Following the general method as outlined in Example 22, starting from (2S,4EZ)-1-(tert-butoxycarbonyl)-4-(ethoxyimino)-2-pyrrolidinecarboxylic acid, 1-isocyanato-3-methoxybenzene, and 9-ethyl-9H-carbazol-3-amine the title compound was obtained in 60% purity by LC/MS. MS(ESI+): m/z=514.4.

Example 180

(2S,4EZ)-1-[(4-chlorophenoxy)acetyl]-4(ethoxyimino)-N-(9-ethyl-9H-carbazol-3-yl)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, (4chlorophenoxy) acetyl chloride, and 9-ethyl-9H-carbazol-3-amine the title compound was obtained in 100% purity by LC/MS.MS (ESI+): m/z=533.4.

Example 181

(2S,4EZ)-4-[(allyloxy)imino]-N-(9-ethyl-9H-carbazol-3-yl)-1-(4-phenoxybenzoyl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, 4-phenoxybenzoyl chloride, and 9-ethyl-9H-carbazol-3-amine the title compound was obtained in 63% purity by LC/MS. MS(ESI+): m/z=573.4.

Example 182

(2S,4EZ)-$N^1$-benzoyl-$N^2$-(9-ethyl-9H-carbazol-3-yl)-4-(methoxyimino)-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, benzoyl isocyanate, and 9-ethyl-9H-carbazol-3-amine the title compound was obtained in 59% purity by LC/MS. MS(ESI+): m/z=498.4.

Example 183

(2S,4EZ)-4-[(benzyloxy)imino]-N-(9-ethyl-9H-carbazol-3-yl)-1-[(2-oxo-6-pentyl-2H-pyran-3-yl)carbonyl]-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, 2-oxo-6-pentyl-2H-pyran-3-carbonyl chloride, and 9-ethyl-9H-carbazol-3-amine the title compound was obtained in 93% purity by LC/MS. MS(ESI+): m/z=619.6.

Example 184

(2S,4EZ)-1-acetyl-4-(ethoxyimino)-N-(9-ethyl-9H-carbazol-3-yl)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, acetyl chloride, and 9-ethyl-9H-carbazol-3-amine the title compound was obtained in 87% purity by LC/MS. MS(ESI+): m/z=407.2.

Example 185

(2S,4EZ)-1-([1,1'-biphenyl]-4-ylcarbonyl)-4-(ethoxyimino)-N-(9-ethyl-9H-carbazol-3-yl)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, [1,1'-biphenyl]-4-carbonyl chloride, and 9-ethyl-9H-carbazol-3-amine the title compound was obtained in 70% purity by LC/MS. MS(ESI+): m/z=545.4.

Example 186

(2S,4EZ)-1-acetyl-N-(9-ethyl-9H-carbazol-3-yl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, acetyl chloride, and 9-ethyl-9H-carbazol-3-amine the title compound was obtained in 69% purity by LC/MS. MS(ESI+): m/z=393.2.

Example 187

(2S,4EZ)-1-(diphenylacetyl)-N-(9-ethyl-9H-carbazol-3-yl)-4-(methoxy-imino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, diphenylacetyl chloride, and 9-ethyl-9H-carbazol-3-amine the title compound was obtained in 77% purity by LC/MS. MS(ESI+): m/z=545.4.

Example 188

(2S,4EZ)-4-[(allyloxy)imino]-$N^1$-benzoyl-$N^2$-(9-ethyl-9H-carbazol-3-yl)-1,2-pyrrolidinedicarboxamide Following the general method as outlined in Example 22, starting from (2S,4EZ)-4-[(allyloxy)imino]-1-(tert-butoxycarbonyl)-2-pyrrolidinecarboxylic acid, benzoyl isocyanate, and 9-ethyl-9H-carbazol-3-amine the title compound was obtained in 63% purity by LC/MS. MS(ESI+): m/z=524.4.

Example 189

(2S,4EZ)-$N^2$-(9-ethyl-9H-carbazol-3-yl)-4-(methoxyimino)-$N^1$-(3-methylphenyl)-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, 1-isocyanato-3-methylbenzene, and 9-ethyl-9H-carbazol-3-amine the title compound was obtained in 89% purity by LC/MS. MS(ESI+): m/z=484.4.

Example 190

(2S,4EZ)-4-{[(4-methoxybenzyl)oxy]imino}-$N^1$-pentyl-$N^2$-(2-thienyl-methyl)-1,2-pyrrolidinedicarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, 1-isocyanatopentane, and 2-thienylmethylamine the title compound was obtained in 86% purity by LC/MS. MS(ESI+): m/z=473.2.

Example 191

(2S,4EZ)-4-(ethoxyimino)-1-(methoxyacetyl)-N-(6-quinolinyl)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, methoxyacetyl chloride, and 6-quinolinamine the title compound was obtained in 81% purity by LC/MS. MS(ESI+): m/z=371.2.

Example 192

(2S,4EZ)-4-[(allyloxy)imino]-N-(9-ethyl-9H-carbazol-3-yl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, and 9-ethyl-9H-carbazol-3-amine the title compound was obtained in 80% purity by LC/MS. MS(ESI+): m/z=377.2.

Example 193

(2S,4EZ)-4-[(benzyloxy)imino]-1-[(2-oxo-6-pentyl-2H-pyran-3-yl)carbonyl]-N-(6-quinolinyl)-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, 2-oxo-6-pentyl-2H-pyran-3-carbonyl chloride, and 6-quinolinamine the title compound was obtained in 48% purity by LC/MS. MS(ESI+): m/z=553.4.

Example 194

(2S,4EZ)-4-[(allyloxy)imino]-N-[2-(diethylamino)ethyl]-2-pyrrolidinecarboxamide

Following the general method as outlined in Example 22, starting from (2S,4EZ)-4-[(allyloxy)-imino]-1-(tert-butoxycarbonyl)-2-pyrrolidinecarboxylic acid, and N1,N1-diethyl-1,2-ethanediamine the title compound was obtained in 78% purity by LC/MS. MS(ESI+): m/z=283.0.

Example 195

(2S,4EZ)-1-[4-(dimethylamino)butanoyl]-N-(9-ethyl-9H-carbazol-3-yl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(dimethylamino)-butanoyl chloride, and 9-ethyl-9H-carbazol-3-amine the title compound was obtained in 42% purity by LC/MS. MS(ESI+): m/z=464.2.

Example 196

(2S)-2-[(3-hydroxy-1-azetidinyl)carbonyl]-N-(3-methoxyphenyl)-4-oxo-1-pyrrolidinecarboxamide Following the general method as outlined in Example 22, starting from 1-(tert-butoxycarbonyl)-4-oxoproline, 1-isocyanato-3-methoxybenzene, and 3-azetidinol the title compound was obtained in 87% purity by LC/MS. MS(ESI+): m/z=334.2.

Example 197

(2S,4EZ)-4-[(benzyloxy)imino]-N-(9-ethyl-9H-carbazol-3-yl)-1-(phenoxyacetyl)-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, phenoxyacetyl chloride, and 9-ethyl-9H-carbazol-3-amine the title compound was obtained in 65% purity by LC/MS. MS(ESI+): m/z=561.4.

Example 198

(2S)-N-(9-ethyl-9H-carbazol-3-yl)-4-methylene-1-[(2-oxo-6-pentyl-2H-pyran-3-yl)carbonyl]-2-pyrrolidinecarboxamide Following the general method as outlined in Example 22, starting from 1-(tert-butoxycarbonyl)-4-methyleneproline, 2-oxo-6-pentyl-2H-pyran-3-carbonyl chloride, and 9-ethyl-9H-carbazol-3-amine the title compound was obtained in 70% purity by LC/MS. MS(ESI+): m/z=512.4.

Example 199

(2S,4EZ)-N-(9-ethyl-9H-carbazol-3-yl)-1-(methoxyacetyl)-4-(methoxy-imino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, methoxyacetyl chloride, and 9-ethyl-9H-carbazol-3-amine the title compound was obtained in 73% purity by LC/MS. MS(ESI+): m/z=423.4.

Example 200

(2S,4EZ)-$N^2$-(9-ethyl-9H-carbazol-3-yl)-4-(methoxyimino)-$N^1$-pentyl-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, 1-isocyanatopentane, and 9-ethyl-9H-carbazol-3-amine the title compound was obtained in 81% purity by LC/MS. MS(ESI+): m/z=464.2.

Example 201

(2S,4EZ)-4-(ethoxyimino)-$N^1$-pentyl-$N^2$-[2(1H-pyrrol-1-yl)phenyl]-1,2-pyrrolidinedicarboxamide Following the general method as outlined in Example 22, starting from (2S,4EZ)-1-(tert-butoxycarbonyl)-4-(ethoxyimino)-2-pyrrolidinecarboxylic acid, 1-isocyanatopentane, and 2-(1H-pyrrol-1-yl)phenylamine the title compound was obtained in 83% purity by LC/MS. MS(ESI+): m/z=426.2.

Example 202

(2S,4EZ)-4-[(allyloxy)imino]-N-(2-methoxyethyl)-2-pyrrolidinecarboxamide

Following the general method as outlined in Example 22, starting from (2S,4EZ)-4-[(allyloxy)-imino]-1-(tert-butoxycarbonyl)-2-pyrrolidinecarboxylic acid, and 2-methoxyethyl-amine the title compound was obtained in 100% purity by LC/MS. MS(ESI+): m/z=242.0.

Example 203

(2S,4EZ)-4-(tert-butoxyimino)-$N^2$-(2-methoxyethyl)-$N^1$-(3-methoxyphenyl)-1,2-pyrrolidinedicarboxamide Following the general method as outlined in Example 22, starting from (2S,4EZ)-1-(tert-butoxycarbonyl)-4-(tert-butoxyimino)-2-pyrrolidinecarboxylic acid, 1-isocyanato-3-methoxybenzene, and 2-methoxyethylamine the title compound was obtained in 76% purity by LC/MS. MS(ESI+): m/z=407.2.

Example 204

(2S,4EZ)-4-[(allyloxy)imino]-$N^2$-(2-methoxyethyl)-$N^1$-(3-methylphenyl-1,2-pyrrolidinedicarboxamide Following the general method as outlined in Example 22, starting from (2S,4EZ)-4[(allyloxy)-imino]-1-(tert-butoxycarbonyl)-2-pyrrolidinecarboxylic acid, 1-isocyanato-3-methylbenzene, and 2-methoxyethylamine the title compound was obtained in 85% purity by LC/MS. MS(ESI+): m/z=375.2.

Example 205

(2S,4EZ)-1-benzoyl-4-benzylidene-N-(9-ethyl-9H-carbazol-3-yl)-2-pyrrolidinecarboxamide Following the general method as outlined in Example 22, starting from (2S,4EZ)-4benzylidene-1-(tert-butoxycarbonyl)-2-pyrrolidinecarboxylic acid, benzoyl chloride, and 9-ethyl-9H-carbazol-3-amine the title compound was obtained in 81% purity by LC/MS. MS(ESI+): m/z=500.4.

Example 206

(2S,4EZ)-$N^2$-benzyl-4-benzylidene-$N^2$-methyl-$N^1$-(3-methylphenyl)-1,2-pyrrolidinedicarboxamide Following the general method as outlined in Example 22, starting from (2S,4EZ)-4-benzylidene-1-(tert-butoxycarbonyl)-2-pyrrolidinecarboxylic acid, 1-isocyanato-3-methylbenzene, and N-benzyl-N-methylamine the title compound was obtained in 68% purity by LC/MS. MS(ESI+): m/z=440.2.

Example 207

(2S,4EZ)-4-(ethoxyimino)-N-(9-ethyl-9H-carbazol-3-yl)-1-(4phenoxybenzoyl)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, 4-phenoxybenzoyl chloride, and 9-ethyl-9H-carbazol-3-amine the title compound was obtained in 99% purity by LC/MS. MS(ESI+): m/z=561.4.

Example 208

(2S,4EZ)-4-(ethoxyimino)-$N^2$-(9-ethyl-9H-carbazol-3-yl)-$N^1$-(3-methylphenyl)-1,2-pyrrolidinedicarboxamide Following the general method as outlined in Example 22, starting from (2S,4EZ)-1-(tert-butoxycarbonyl)-4-(ethoxyimino)-2-pyrrolidinecarboxylic acid, 1-isocyanato-3-methylbenzene, and 9-ethyl-9H-carbazol-3-amine the title compound was obtained in 80% purity by LC/MS. MS(ESI+): m/z=498.4.

Example 209

(2S,4EZ)-4-(methoxyimino)-1-(phenoxyacetyl)-N-(6-quinolinyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, phenoxyacetyl chloride, and 6-quinolinamine the title compound was obtained in 100% purity by LC/MS. MS(ESI+): m/z=419.2.

Example 210

(2S,4EZ)-4-(tert-butoxyimino)-N-(3,4-dimethoxybenzyl)-1-[(2-oxo-6-pentyl-2H-pyran-3-yl)carbonyl]-2-pyrrolidinecarboxamide Following the general method as outlined in Example 22, starting from (2S,4EZ)-1-(tert-butoxycarbonyl)-4-(tert-butoxyimino)-2-pyrrolidinecarboxylic acid, 2-oxo-6-pentyl-2H-pyran-3-carbonyl chloride, and 3,4-dimethoxybenzylamine the title compound was obtained in 63% purity by LC/MS. MS(ESI+): m/z=542.4.

Example 211

(2S,4EZ)-4-(tert-butoxyimino)-N-cyclopropyl-1-(phenoxyacetyl)-2-pyrrolidinecarboxamide Following the general method as outlined in Example 22, starting from (2S,4EZ)-1-tert-butoxycarbonyl)-4-(tert-butoxyimino)-2-pyrrolidinecarboxylic acid, phenoxyacetyl chloride, and cyclopropylamine the title compound was obtained in 73% purity by LC/MS. MS(ESI+): m/z=374.2.

Example 212

(2S,4EZ)-4-[(benzyloxy)imino]-N-(tert-butyl)-1-(phenoxyacetyl)-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, phenoxyacetyl chloride, and tert-butylamine the title compound was obtained in 100% purity by LC/MS. MS(ESI+): m/z=424.2.

Example 213

(2S,4EZ)-N-(4,6-dimethoxy-2-pyrimidinyl-4-(ethoxyimino)-1-(4-phenoxybenzoyl)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, 4-phenoxybenzoyl chloride, and 4,6-dimethoxy-2-pyrimidinamine the title compound was obtained in 79% purity by LC/MS. MS(ESI+): m/z=506.4.

Example 214

(4ZE)-4-[(allyloxy)imino]-N-(9-ethyl-9H-carbazol-3-yl)-1-(phenoxyacetyl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, phenoxyacetyl chloride, and 9-ethyl-9H-carbazol-3-amine the title compound was obtained in 63% purity by LC/MS. MS(ESI+): m/z=511.4.

Example 215

(2S,4EZ)-1-([1,1'-biphenyl]-4-ylcarbonyl)-N-(9-ethyl-9H-carbazol-3-yl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 9-ethyl-9H-carbazol-3-amine the title compound was obtained in 66% purity by LC/MS. MS(ESI+): m/z=531.4.

Example 216

(3EZ,5S)-1-[4-(dimethylamino)butanoyl]-5-(1-piperidinylcarbonyl)-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 4(dimethylamino) butanoyl chloride, and piperidine the title compound was obtained in 100% purity by LC/MS. MS(ESI+): m/z=339.2.

Example 217

(2S,4EZ)-1-acetoacetyl-N-(9-ethyl-9H-carbazol-3-yl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2,4-oxetanedione, and 9-ethyl-9H-carbazol-3-amine the title compound was obtained in 42% purity by LC/MS. MS(ESI+): m/z=435.2.

Example 218

(2S,4EZ)-4-(methoxyimino)-1-[(2-oxo-6-pentyl-2H-pyran-3-yl)carbonyl]-N-(6-quinolinyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2-oxo-6-pentyl-2H-pyran-3-carbonyl chloride, and 6-quinolinamine the title compound was obtained in 57% purity by LC/MS. MS(ESI+): m/z=477.2.

Example 219

(2S,4EZ)-N-(9-ethyl-9H-carbazol-3-yl)-4-{[(4-methoxybenzyl)oxy]imino}-1-[(2-oxo-6-pentyl-2H)-pyran-3-yl)carbonyl]-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, 2-oxo-6-pentyl-2H-pyran-3-carbonyl chloride, and 9-ethyl-9H-carbazol-3-amine the title compound was obtained in 57% purity by LC/MS. MS(ESI+): m/z=649.4.

Example 220

(2S,4EZ)-$N^2$-allyl-$N^1$-benzoyl-4-(methoxyimino)-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, benzoyl isocyanate, and allylamine the title compound was obtained in 49% purity by LC/MS. MS(ESI+): m/z=345.0.

Example 221

(2S,4EZ)-4-[(benzyloxy)imino]-N-(9-ethyl-9H-carbazol-3-yl)-1-(methoxyacetyl)-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, methoxyacetyl chloride, and 9-ethyl-9H-carbazol-3-amine the title compound was obtained in 46% purity by LC/MS. MS(ESI+): m/z=499.2.

Example 222

(2S,4EZ)-$N^1$-(3,5-dichlorophenyl)-$N^2$-(9-ethyl-9H-carbazol-3-yl)-4-(methoxyimino)-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, 1,3-dichloro-5-isocyanatobenzene, and 9-ethyl-9H-carbazol-3-amine the title compound was obtained in 42% purity by LC/MS. MS(ESI+): m/z=538.2.

Example 223

(2S,4EZ)-N-(9-ethyl-9H-carbazol-3-yl)-4-(methoxyimino)-1-(4-phenoxybenzoyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-phenoxybenzoyl chloride, and 9-ethyl-9H-carbazol-3-amine the title compound was obtained in 43% purity by LC/MS. MS(ESI+): m/z=547.2.

Example 224

(2S,4EZ)-$N^1$-(3,5-dichlorophenyl)-4-(ethoxyimino)-$N^2$-(9-ethyl-9H-carbazol-3-yl)-1,2-pyrrolidinedicarboxamide Following the general method as outlined in Example 22, starting from (2S,4EZ)-1-(tert-butoxycarbonyl)-4-(ethoxyimino)-2-pyrrolidinecarboxylic acid, 1,3-dichloro-5-isocyanatobenzene, and 9-ethyl-9H-carbazol-3-amine the title compound was obtained in 43% purity by LC/MS. MS(ESI+): m/z=552.6.

Example 225

(3EZ,5S)-5-{[4-(1,3-benzodioxol-5-ylmethyl)-1-piperazinyl]carbonyl}-1-[(2-oxo-6-pentyl-2H-pyran-3-yl)carbonyl]-3-pyrrolidinone O-(tert-butyl)oxime Following the general method as outlined in Example 22, starting from (2S,4EZ)-1-(tert-butoxycarbonyl)-4-(tert-butoxyimino)-2-pyrrolidinecarboxylic acid, 2-oxo-6-pentyl-2H-pyran-3-carbonyl chloride, and 1-(1,3-benzodioxol-5-ylmethyl)piperazine the title compound was obtained in 59% purity by LC/MS. MS(ESI+): m/z=595.4.

Example 226

(2S,4EZ)-4-benzylidene-N-(9-ethyl-9H-carbazol-3-yl)-1-[(2-oxo-6-pentyl-2H-pyran-3-yl)carbonyl]-2-pyrrolidinecarboxamide Following the general method as outlined in Example 22, starting from (2S,4EZ)-4-benzylidene-1-(tert-butoxycarbonyl)-2-pyrrolidinecarboxylic acid, 2-oxo-6-pentyl-2H-pyran-3-carbonyl chloride, and 9-ethyl-9H-carbazol-3-amine the title compound was obtained in 47% purity by LC/MS. MS(ESI+): m/z=588.4.

Example 227

(2S,4EZ)-4-[(allyloxy)imino]-1-benzoyl-N-(6-quinolinyl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, benzoyl chloride, and 6-quinolinamine the title compound was obtained in 83% purity by LC/MS. MS(ESI+): m/z=415.2.

Example 228

(2S,4EZ)-4-[(allyloxy)imino]-1-(methoxyacetyl)-N-(6-quinolinyl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, methoxyacetyl chloride, and 6-quinolinamine the title compound was obtained in 71% purity by LC/MS. MS(ESI+): m/z=383.0.

Example 229

(2S,4EZ)-4-[(allyloxy)imino]-N-(9-ethyl-9H-carbazol-3-yl)-1-(methoxyacetyl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, methoxyacetyl chloride, and 9-ethyl-9H-carbazol-3-amine the title compound was obtained in 74% purity by LC/MS. MS(ESI+): m/z=449.2.

Example 230

(2S,4EZ)-4-[(allyloxy)imino]-1-(2-ethoxy-1-naphthoyl)-N-(9-ethyl-9H-carbazol-3-yl)-2pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, 2-ethoxy-1-naphthoyl chloride, and 9-ethyl-9H-carbazol-3-amine the title compound was obtained in 60% purity by LC/MS. MS(ESI+): m/z=575.4.

Example 231

(2S,4EZ)-4-[(allyloxy)imino]-1-[(4-chlorophenoxy)acetyl]-N-(9-ethyl-9H-carbazol-3-yl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, (4-chlorophenoxy)acetyl chloride, and 9-ethyl-9H-carbazol-3-amine the title compound was obtained in 78% purity by LC/MS. MS(ESI+): m/z=545.4.

Example 232

(2S,4EZ)-4-[(allyloxy)imino]-1-([1,1'-biphenyl]-4-ylcarbonyl)-N-(9-ethyl-9H-carbazol-3-yl)-2-pyrrolidinecarboxamide Following the general method as outlined in Example 22, starting from (2S,4EZ)-4-[(allyloxy)-imino]-1-(tert-butoxycarbonyl)-2-pyrrolidinecarboxylic acid, [1,1'-biphenyl]-4-carbonyl chloride, and 9-ethyl-9H-carbazol-3-amine the title compound was obtained in 51% purity by LC/MS. MS(ESI+): m/z=557.2.

Example 233

(2s,4EZ)-4-[(allyloxy)imino]-1-(diphenylacetyl)-N-(9-ethyl-9H-carbazol-3-yl)-2-pyrrolidinecarboxamide Following the general method as outlined in Example 22, staring from (2S,4EZ)-4-[(allyloxy)-imino]-1-(tert-butoxycarbonyl)-2-pyrrolidinecarboxylic acid, diphenylacetyl chloride, and 9-ethyl-9H-carbazol-3-amine the title compound was obtained in 43% purity by LC/MS. MS(ESI+): m/z=571.2.

Example 234

(2S,4EZ)-1-([1,1'-biphenyl]-4-ylcarbonyl)-N-(tert-butyl)-4-(chloromethylene)-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, [1,1'-biphenyl34-carbonyl chloride, and tert-butylamine the title compound was obtained in 80% purity by LC/MS. MS(ESI+): m/z=397.6.

Example 235 tert-butyl 3-[({4-methylene-1-[(pentylamino)carbonyl]-2-pyrrolidinyl}carbonyl)amino]-1-azetidinecarboxylate Following the general method as outlined in Example 22, starting from 1-(tert-butoxycarbonyl)-4-methyleneproline, 1-isocyanatopentane, and tert-butyl 3-amino-1-azetidinecarboxylate the title compound was obtained in 75% purity by LC/MS. MS(ESI+): m/z=395.2.

Example 236

(3EZ,5S)-1-acetyl-5-[(4-acetyl-1-piperazinyl)carbonyl]-3-pyrrolidinone O-(3,4-dichlorobenzyl)oxime Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, acetyl chloride, and 1-acetylpiperazine the title compound was obtained in 85% purity by LC/MS. MS(ESI+): m/z=455.2.

Example 237

(2S,4EZ)-$N^2$-benzyl-4-(methoxyimino)-$N^1$-pentyl-1,2-pyrrolidinedicarboxamide Following the general method as outlined in Example 22, starting from (2S,4EZ)-1-(tert-butoxycarbonyl)-4-(methoxyimino)-2-pyrrolidinecarboxylic acid, 1-isocyanatopentane, and benzylamine the title compound was obtained in 100% purity by LC/MS. MS(ESI+): m/z=361.0.

Example 238

(2S,4EZ)-1-acetyl-{[(3,4-dichlorobenzyl)oxy]imino}-N-(1naphthylmethyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, acetyl chloride, and 1-naphthylmethylamine the title compound was obtained in 60% purity by LC/MS. MS(ESI+): m/z=484.2.

Example 239

(2S,4EZ)-4-(tert-butoxyimino)-N-cyclopropyl-1-[(2-oxo-6-pentyl-2H-pyran-3-yl)carbonyl]-2-pyrrolidinecarboxamide Following the general method as outlined in Example 22, starting from (2S,4EZ)-1-(tert-butoxycarbonyl)-4-(tert-butoxyimino)-2-pyrrolidinecarboxylic acid, 2-oxo-6-pentyl-2H-pyran-3-carbonyl chloride, and cyclopropylamine the title compound was obtained in 75% purity by LC/MS. MS(ESI+): m/z=432.2.

Example 240

(2S,4EZ)-4-{[(4-methoxybenzyl)oxy]imino}-1-(4-phenoxybenzoyl)-N-[2-(1H-pyrrol-1-yl)phenyl]-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, 4-phenoxybenzoyl chloride, and 2-(1H-pyrrol-1-yl)phenylamine the title compound was obtained in 55% purity by LC/MS. MS(ESI+): m/z=601.4.

Example 241

(2S)-N-(1,3-benzodioxol-5-ylmethyl)-4-oxo-2-pyrrolidinecarboxamide

Following the general method as outlined in Example 22, starting from 1-(tert-butoxycarbonyl)-4-oxoproline, and 1,3-benzodioxol-5-ylmethylamine the title compound was obtained in 71% purity by LC/MS. MS(ESI+): m/z=263.0.

Example 242

(2S,4EZ)-N-(1,3-benzodioxol-5-ylmethyl)-1-([1,1'-biphenyl]-4-ylcarbonyl)-4-(chloromethylene)-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, [1,1'-biphenyl]-4-carbonyl chloride, and 1,3-benzodioxol-5-ylmethylamine the title compound was obtained in 63% purity by LC/MS. MS(ESI+): m/z=475.6.

Example 243

(2S,4EZ)-N-(3,4-dimethoxybenzyl-4-(ethoxyimino)-1-[(2-oxo-6-pentyl-2H-pyran-3-yl)carbonyl]-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, 2-oxo-6-pentyl-2H-pyran-3-carbonyl chloride, and 3,4-dimethoxybenzylamine the title compound was obtained in 41% purity by LC/MS. MS(ESI+): m/z=514.2.

Example 244

(2S)-2-[(3-hydroxy-1-azetidinyl)carbonyl]-N-(3-methylphenyl)-4-oxo-1-pyrrolidinecarboxamide Following the general method as outlined in Example 22, starting from 1-(tert-butoxycarbonyl)-4-oxoproline, 1-isocyanato-3-methylbenzene, and 3-azetidinol the title compound was obtained in 73% purity by LC/MS. MS(ESI+): m/z=318.0.

Example 245

(2S,4EZ)-4-[(benzyloxy)imino]-N-[(2RS)-2-hydroxy-2-phenethyl]-1-[(2-oxo-6-pentyl-2H-pyran-3-yl)carbonyl]-2-pyrrolidinecarboxamide Following the general method as outlined in Example 22, starting from (2S,4EZ)-4-[(benzyloxy)imino]-1-(tert-butoxycarbonyl)-2-pyrrolidinecarboxylic acid, 2-oxo-6-pentyl-2H-pyran-3-carbonyl chloride, and (1RS)-2-amino-1-phenylethanol the title compound was obtained in 55% purity by LC/MS. MS(ESI+): m/z=546.2.

Example 246

(2S,4EZ)-4-[(allyloxy)imino]-$N^2$-(3,4-dimethoxybenzyl)-$N^1$-(3-methoxyphenyl)-1,2-pyrrolidinedicarboxamide Following the general method as outlined in Example 22, starting from (2S,4EZ)-4-[(allyloxy)imino]-1-(tert-butoxycarbonyl)-2-pyrrolidinecarboxylic acid, 1-isocyanato-3-methoxybenzene, and 3,4-dimethoxybenzylamine the title compound was obtained in 97% purity by LC/MS. MS(ESI+): m/z=483.2.

Example 247

(2S,4EZ)-4-[(allyloxy)imino]-1-(4-cyanobenzoyl)-N-(2-methoxyethyl)-2-pyrrolidinecarboxamide Following the general method as outlined in Example 22, starting from (2S,4EZ)-4-[(allyloxy)imino]-1-(tert-butoxycarbonyl)-2-pyrrolidinecarboxylic acid, 4-cyanobenzoyl chloride, and 2-methoxyethylamine the title compound was obtained in 44% purity by LC/MS. MS(ESI+): m/z=371.0.

Example 248

(2S,4EZ)-N-benzyl-1-(methoxyacetyl)-4-{[(4-methoxybenzyl)oxy]imino}-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, methoxyacetyl chloride, and benzylamine the title compound was obtained in 49% purity by LC/MS. MS(ESI+): m/z=426.2.

Example 249

(2S,4EZ)-1-benzoyl-4-(chloromethylene)-N-(2-furylmethyl)-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, benzoyl chloride, and 2-furylmethylamine the title compound was obtained in 73% purity by LC/MS. MS(ESI+): m/z=345.6.

Example 250

(2S)-1-acetyl-4-methylene-N-(6-quinolinyl)-2-pyrrolidinecarboxamide

Following the general method as outlined in Example 22, starting from 1-(tert-butoxycarbonyl)-4-methyleneproline, acetyl chloride, and 6-quinolinamine the title compound was obtained in 87% purity by LC/MS. MS(ESI+): m/z=296.0.

Example 251

(2S,4EZ)-1-acetyl-4-{[(3,4-dichlorobenzyl)oxy]imino}-N-(2-furylmethyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, acetyl chloride, and 2-furylmethylamine the title compound was obtained in 199% purity by LC/MS. MS(ESI+): m/z=424.6.

Example 252

(2S)-$N^1$-(3,5-dichlorophenyl)-4-methylene-$N^2$-(6-quinolinyl)-1,2-pyrrolidinecarboxamide Following the general method as outlined in Example 22, starting from 1-(tert-butoxy-carbonyl)-4-methyleneproline, 1,3-dichloro-5-isocyanatobenzene, and 6-quinolinamine the title compound was obtained in 65% purity by LC/MS. MS(ESI+): m/z=441.0.

Example 253

(3EZ,5S)-1-(diphenylacetyl)-5-(1-piperidinylcarbonyl)-3-pyrrolidinone O-(4-methoxybenzyl)oxime Following the general method as outlined in Example 22, starting from (2S,4EZ)-1-(tert-butoxycarbonyl)-4-{[(4-methoxybenzyl)oxy]imino}-2-pyrrolidinecarboxylic acid, diphenylacetyl chloride, and piperidine the title compound was obtained in 87% purity by LC/MS. MS(ESI+): m/z=526.4.

Example 254

(2S,4EZ)-4-(chloromethylene)-N-(1-naphthylmethyl)-1-(phenoxyacetyl)-2-pyrrolidine-carboxamide Following the general method as outlined in Example 22, starting from (2S,4EZ)-1-(tert-butoxycarbonyl)-4-(chloromethylene)-2-pyrrolidinecarboxylic acid, phenoxyacetyl chloride, and 1-naphthylmethylamine the title compound was obtained in 75% purity by LC/MS. MS(ESI+): m/z=435.6.

Example 255

(2S,4EZ)-4[(allyloxy)imino]-N-benzoyl-2-(4-morpholinylcarbonyl)-1-pyrrolidinecarboxamide Following the general method as outlined in Example 22, starting from (2S,4EZ)-4-[(allyloxy)imino]-1-(tert-butoxycarbonyl)-2-pyrrolidinecarboxylic acid, benzoyl isocyanate, and morpholine the title compound was obtained in 46% purity by LC/MS. MS(ESI+): m/z=401.2.

Example 256

(2S,4EZ)-$N^1$-benzoyl-4-(chloromethylene)-$N^2$-cyclopropyl-1,2-pyrrolidinedicarboxamide Following the general method as outlined in Example 22, starting from (2S,4EZ)-1-(tertbutoxycarbonyl)-4-(chloromethylene)-2-pyrrolidinecarboxylic acid, benzoyl isocyanate, and cyclopropylamine the title compound was obtained in 76% purity by LC/MS. MS(ESI+): m/z=348.6.

Example: 257

(2S,4EZ)-4-{[(3,4-dichlorobenzyl)oxy]imino}-1-(methoxyacetyl)-N-(1-naphthylmethyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, methoxyacetyl chloride, and 1-naphthylmethylamine the title compound was obtained in 91% purity by LC/MS. MS(ESI+): m/z=514.8.

Example 258

(2S,4EZ)-1-benzoyl-N-benzyl-4-(chloromethylene)-N-methyl-2-pyrrolidinecarboxamide Following the general method as outlined in Example 22, starting from (2S,4EZ)-1-(tert-butoxycarbonyl)-4-(chloromethylene)-2-pyrrolidinecarboxylic acid, benzoyl chloride, and N-benzyl-N-methylamine the title compound was obtained in 62% purity by LC/MS. MS(ESI+): m/z=369.4.

Example 259

(2S)-$N^2$(2-furylmethyl)-$N^1$-(3-methoxyphenyl)-4-methylene-1,2-pyrrolidinedicarboxamide Following the general method as outlined in Example 22, starting from 1-(tert-butoxycarbonyl)-4-methyleneproline, 1-isocyanato-3-methoxybenzene, and 2-furylmethylamine the title compound was obtained in 95% purity by LC/MS. MS(ESI+): m/z=356.0.

Example 260

(3EZ,5S)-5-[(4-benzohydryl-1-piperazinyl)carbonyl]-1-(phenoxyacetyl)-3-pyrrolidinone O-ethyloxime Following the general method as outlined in Example 22, starting from (2S,4EZ)-1-(tert-butoxycarbonyl)-4-(ethoxyimino)-2-pyrrolidinecarboxylic acid, phenoxyacetyl chloride, and 1-benzhydrylpiperazine the title compound was obtained in 67% purity by LC/MS. MS(ESI+): m/z=541.2.

Example 261

(3EZ,5S)-1-benzoyl-5-(4-morpholinylcarbonyl)-3-pyrrolidinone O-(3,4-dichlorobenzyl)-oxime Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, benzoyl chloride, and morpholine the title compound was obtained in 69% purity by LC/MS. MS(ESI+): m/z=476.2.

Example 262

(2S)-$N^1$-(3-methoxyphenyl)-4-methylene-$N^2$-(1-naphthylmethyl)-1,2-pyrrolidine-dicarboxamide Following the general method as outlined in Example 22, starting from 1-(tert-butoxycarbonyl)-4-meth-yleneproline, 1-isocyanato-3-methoxybenzene, and 1-naphthylmethylamine the title compound was obtained in 55% purity by LC/MS. MS(ESI+): m/z=416.3.

Example 263

$N^2$-(2-methoxyethyl)-4-methylene-$N^1$-(3-methylphenyl)-1,2-pyrrolidinecarboxamide Following the general method as outlined in Example 22, starting from 1-(tert-butoxycarbonyl)-4-methyleneproline, 1-isocyanato-3-methylbenzene, and 2-methoxyethylamine the title compound was obtained in 85% purity by LC/MS. MS(ESI+): m/z=318.0.

Example 264

(2S,4EZ)-N-allyl-4-{[(4-methoxybenzyl)oxy]imino}-1-(phenoxyacetyl)-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, phenoxyacetyl chloride, and allylamine the title compound was obtained in 72% purity by LC/MS. MS(ESI+): m/z=438.2.

Example 265

(2S,4EZ)-1-benzoyl-4-(cyanomethylene)-N-(1-naphthylmethyl)-2-pyrrolidinecarboxamide Following the general method as outlined in Example 22, starting from (2S,4EZ)-1-(tert-butoxycarbonyl)-4-(cyanomethylene)-2-pyrrolidinecarboxylic acid, benzoyl chloride, and 1-naphthylmethylamine the title compound was obtained in 43% purity by LC/MS. MS(ESI+): m/z=396.0.

Example 266

(2S,4EZ)-4-{[(3,4-dichlorobenzyl)oxy]imino}-1-[(2-oxo-6-pentyl-2H-pyran-3-yl)carbonyl]-N-(6-quinolinyl)-2-pyrrolidinecarboxamide Following the general method as outlined in Example 22, starting from (2S,4EZ)-1-(tert-butoxycarbonyl)-4-{[(3,4-dichlorobenzyl)oxy]imino}-2-pyrrolidinecarboxylic acid, 2-oxo-6-pentyl-2H-pyran-3-carbonyl chloride, and 6-quinolinamine the title compound was obtained in 70% purity by LC/MS. MS(ESI+): m/z=621.2.

Example 267

(2S,4EZ)-N-[2-(diethylamino)ethyl]-1-[4-(dimethylamino)butanoyl]-4-{[(4-methoxybenzyl)oxy]imino}-2-pyrrolidinecarboxamide Following the general method as outlined in Example 22, starting from (2S,4EZ)-1-(tert-butoxycarbonyl)-4-{[(4-methoxybenzyl)oxy]imino}-2-pyrrolidinecarboxylic acid, 4-(dimethylamino)butanoyl chloride, and N1,N1-diethyl-1,2-ethanediamine the title compound was obtained in 100% purity by LC/MS. MS(ESI+): m/z=476.2.

Example 268

(2S,4EZ)-4-[(allyloxy)imino]-1-[4-(dimethylamino)butanoyl]-N-(1-naphthylmethyl)-2-pyrrolidinecarboxamide Following the general method as outlined in Example 22, starting from (2S,4EZ)-4-[(allyloxy)imino]-1-(tert-butoxycarbonyl)-2-pyrrolidinecarboxylic acid, 4-(dimethylamino)butanoyl chloride, and 1-naphthylmethylamine the title compound was obtained in 85% purity by LC/MS. MS(ESI+): m/z=437.2.

Example 269

(2S,4EZ)-N-[2-(diethylamino)ethyl]-4-(ethoxyimino)-2-pyrrolidinecarboxamide

Following the general method as outlined in Example 22, starting from (2S,4EZ)-1-(tert-butoxycarbonyl)-4-(ethoxyimino)-2-pyrrolidinecarboxylic acid, and N1,N1-diethyl-1,2-ethanediamine the title compound was obtained in 70% purity by LC/MS. (ESI+): m/z=271.0.

Example 270

(2S)-4-methylene-1-[(2-oxo-6-pentyl-2H-pyran-3-yl)carbonyl]-N-(6-quinolinyl)-2-pyrrolidinecarboxamide Following the general method as outlined in Example 22, starting from 1-(tert-butoxycarbonyl)-4-methyleneproline, 2-oxo-6-pentyl-2H-pyran-3-carbonyl chloride, and 6-quinolinamine the title compound was obtained in 48% purity by LC/MS. MS(ESI+): m/z=446.2.

Example 271

(2S,4EZ)-1-acryloyl-N-allyl-4-(methoxyimino)-2-pyrrolidinecarboxamide

Following the general method as outlined in Example 22, starting from (2S,4EZ)-1-(tert-butoxycarbonyl)-4-(methoxyimino)-2-pyrrolidinecarboxylic acid, acryloyl chloride, and allylamine the title compound was obtained in 81% purity by LC/MS. MS(ESI+): m/z=252.0.

Example 273 tert-butyl 3-({[(2S,4EZ)-1-acetyl-4-benzylidenepyrrolidinyl]carbonyl}-amino)-1-azetidinecarboxylate Following the general method as outlined in Example 22, starting from (2S,4EZ)-4-benzylidene-1-(tert-butoxycarbonyl)-2-pyrrolidinecarboxylic acid, acetyl chloride, and tert-butyl 3-amino-1-azetidinecarboxylate the title compound was obtained in 81% purity by LC/MS. MS(ESI+): m/z=400.2.

Example 273

(2S,4EZ)-4-[(allyloxy)imino]-1-[(2-oxo-6-pentyl-2H-pyran-3-yl)carbonyl]-N-(6-quinolinyl)-2-pyrrolidinecarboxamide Following the general method as outlined in Example 22, starting from (2S,4EZ)-4-[(allyloxy)imino]-1-(tert-butoxycarbonyl)-2-pyrrolidinecarboxylic acid, 2-oxo-6-pentyl-2H-pyran-3-carbonyl chloride, and 6-quinolinamine the title compound was obtained in 67% purity by LC/MS. MS(ESI+): m/z=503.2.

Example 274

(2S,4EZ)-4-(ethoxyimino)-N-(1-naphthlmethyl)-1-(phenoxyacetyl)-2-pyrrolidinecarboxamide Following the general method as outlined in Example 22, starting from (2S,4EZ)-1-(tert-butoxycarbonyl)-4-(ethoxyimino)-2-pyrrolidinecarboxylic acid, phenoxyacetyl chloride, and 1-naphthylmethylamine the title compound was obtained in 85% purity by LC/MS. MS(ESI+): m/z=446.3.

Example 275

(2S,4EZ)-N-[(2RS)-2-hydroxy-2-phenylethyl]-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (1RS)-2-amino-1-phenylethanol, the title compound was obtained in 96.4% purity by HPLC. MS(ESI+): m/z=472.

Example 276

(2S,4EZ)-1-([1,1'-biphenyl]-3-ylcarbonyl)-N-[(2RS)-2-hydroxy-2-phenyl-ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-3-carboxylic acid, and (1RS)-2-amino-1-phenylethanol, the title compound was obtained in 72% purity by HPLC. MS(ESI+): m/z=458.

Example 277

(2S,4EZ)-1-(4-benzoylbenzyl)-N-[(2RS)-2-hydroxy-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-benzoylbenzoic acid, and (1RS)-2-amino-1-phenylethanol, the title compound was obtained in 93% purity by HPLC. MS(ESI+): m/z=486.

Example 278

(2S,4EZ)-N-[(2RS)-2-hydroxy-2-phenylethyl]-4-(methoxyimino-1-(3-phenoxybenzoyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 3-phenoxybenzoic acid, and (1RS)-2-amino-1-phenylethanol, the title compound was obtained in 94% purity by HPLC. MS(ESI+): m/z=474.

Example 279

(2S,4EZ)-N-[(2RS)-2-hydroxy-2-phenylethyl]-4-(methoxyimino)-1-(2-phenoxybenzoyl)-2-pyrrolidinecarboxamide Following the general method as outlined in Example 22, starting from (2S,4EZ)-1-(tert-butoxycarbonyl)-4-(metboxyimino)-2-pyrrolidinecarboxylic acid, 2-phenoxybenzoic acid, and (1RS)-2-amino-1-phenylethanol, the title compound was obtained in 92% purity by HPLC. MS(ESI+): m/z=474.

Example 280

(2S,4EZ)-N-[(2S)-2-hydroxy-2-phenylethyl]-4-(methoxyimio)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (1S)-2-amino-1-phenylethanol, the title compound was obtained in 98% purity by HPLC. MS(ESI+): m/z=472.

Example 281

(2S,4EZ)-N-[(2R)-2-hydroxy-2-phenylethyl]-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (1R)-2-amino-1-phenylethanol, the title compound was obtained in 84% purity by HPLC. MS(ESI+): m/z=472.

Example 282

(2S,4EZ)-N-(2-hydroxyethyl)-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 2-aminoethanol, the title compound was obtained in 75% purity by HPLC. MS(ESI+): m/z=396.

Example 283

(2S,4EZ)-N-(2-hydroxyethyl)-4-(methoxyimino)-N-methyl-1-[(2'-methyl-[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 2-(methylamino)ethanol, the title compound was obtained in 78% purity by HPLC. MS(ESI+): m/z=410.

Example 284

(2S,4EZ)-1-([1,1'-biphenyl]-4-ylsulfonyl)-N-[(1S,2S,3R,4R)-3-hydroxy-methyl)bicyclo[2.2.1]hept-2-yl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and [(1R,2R,3S,4S)-3-aminobicyclo[2.2.1]hept-2-yl]methanol, the title compound was obtained in 79% purity by HPLC. MS(ESI+): m/z=498.

Example 285

(2S,4EZ)-1-([1,1'-biphenyl]-4-ylcarbonyl)-N-(trans-4-hydroxycyclohexyl)-4-methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and trans-4-aminocyclohexanol, the title compound was obtained in 62% purity by HPLC. MS(ESI+): m/z=436.

Example 286

(2S,4EZ)-1-([1,1'-biphenyl]-4-ylcarbonyl)-N-[(1R,2R)-2-(hydroxymethyl)-cyclohexyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and [(1R,2R)-2-aminocyclohexyl]methanol, the title compound was obtained in 65% purity by HPLC. MS(ESI+): m/z=450.

Example 287

(2S,4EZ)-1-([1,1'-biphenyl]-4-ylcarbonyl)-N-[(2RS)-2-hydroxy-3-phenoxypropyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (2RS)-1-amino-3-phenoxy-2-propanol, the title compound was obtained in 68% purity by HPLC. MS(ESI+): m/z=488.

Example 288

(2S,4EZ)-N-[(2RS)-2-hydroxy-3-phenoxypropyl]-4-(methoxyimino)-1-[4-(3-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl) benzoic acid, and (2RS)-1-amino-3-phenoxy-2-propanol, the title compound was obtained in 76% purity by HPLC. MS(ESI+): m/z=489.

Example 289

(2S,4EZ)-1-([1,1'-biphenyl]-4-ylsulfonyl)-N-[(2RS)-2-hydroxy-3-phenoxypropyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (2RS)-1-amino-3-phenoxy-2-propanol, the title compound was obtained in 78% purity by HPLC. MS(ESI+): m/z=524.

Example 290

(2S,4EZ)-1-([1,1'-biphenyl]-4-ylcarbonyl)-N-[(2RS)-2-hydroxy-2-2-(4-hydroxyphenyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 4-[(1RS)-2-amino-1-hydroxyethyl] phenol, the title compound was obtained in 63% purity by HPLC. MS(ESI+): m/z=474.

Example 291

(2S,4EZ)-1-([1,1'-biphenyl]-4-ylsulfonyl)-N-[(2RS)-2-hydroxy-2-(4-hydroxyphenyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chlonde, and 4-[(1RS)-2-amino-1-hydroxyethyl] phenol, the title compound was obtained in 72% purity by HPLC. MS(ESI+): m/z=510.

Example 292

(2S,4EZ)-1-([1,1'-biphenyl]-4-ylcarbonyl)-N-[(1-hydroxycyclohexyl)-methyl]-4-(methoxyimino)-2-pyrrolidinecarboxamide Following the general method as outlined in Example 22, starting from (2S,4EZ)-1-(tert-butoxycarbonyl)-4-(methoxyimio)-2-pyrrolidinecarboxylic acid, [1,1'-biphenyl]-4-carbonyl chloride, and 1-(aminomethyl)cyclohexanol, the title compound was obtained in 65% purity by HPLC. MS(ESI+): m/z=450.

Example 293

(2S,4EZ)-N-[(1-hydroxycyclohexyl)methyl]-4-(methoxyimino)-1-[4-(3-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl) benzoic acid, and 1-(aminomethyl)cyclohexanol, the title compound was obtained in 69% purity by HPLC. MS(ESI+): m/z=451.

Example 294

(2S,4EZ)-1-([1,1'-biphenyl]-4-ylsulfonyl)-N-[(1-hydroxycyclohexyl)methyl-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and 1-(aminomethyl)cyclohexanol, the title compound was obtained in 66% purity by HPLC. MS(ESI+): m/z=486.

Example 295

(2S,4EZ)-1-([1,1'-biphenyl]-4-ylcarbonyl-N-[(2RS)-2-(3,4-dihydroxy-phenyl)-2-hydroxyethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 4-[(1RS)-2-amino-1-hydroxyethyl]-1,2-benzenediol, the title compound was obtained in 66% purity by HPLC. MS(ESI+): m/z=490.

Example 296

(2S,4EZ)-N-(2S)-2-hydroxy-2-phenylethyl]-4-(methoxyimino)-1-[4-(4-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(4-pyridinyl) benzoic acid, and (1S)-2-amino-1-phenylethanol, the title compound was obtained in 65% purity by HPLC. MS(ESI+): m/z=459.

Example 297

(2S,4EZ)-N-[(2S)-2-hydroxy-2-phenylethyl]-4-(methoxyimino)-1-[4-(3-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl) benzoic acid, and (1S)-2-amino-1-phenylethanol, the title compound was obtained in 73% purity by HPLC. MS(ESI+): m/z=459.

Example 298

(2S,4EZ)-N-[(2S)-2-hydroxy-2-phenylethyl]-4-(methoxyimino)-1-[4-(2-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(2-pyridinyl) benzoic acid, and (1S)-2-amino-1-phenylethanol, the title compound was obtained in 69% purity by HPLC. MS(ESI+): m/z=459.

Example 299

(2S,4EZ)-1-([1,1'-biphenyl]-4-ylcarbonyl)-N-[(2RS)-2,3-dihydroxpropyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (2RS)-3-amino-1,2-propanediol, the title compound was obtained in 73% purity by HPLC. MS(ESI+): m/z=412.

Example 300

(2S,4EZ)-1-([1,1'-biphenyl]-4-ylsulfonyl)-N-[((2RS)-2,3-dihydroxypropyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (2RS)-3-amino-1,2-propanediol, the title compound was obtained in 64% purity by HPLC. MS(ESI+): m/z=448.

Example 301

(2S,4EZ)-1-([1,1'-biphenyl]-4-ylcarbonyl)-N-[(2RS)-2-hydroxy-3-(4-methoxyphenoxy)propyl]-4-(methoxyimino)-2-pyrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (2RS)-1-amino-3-(4-methoxyphenoxy)-2-propanol, the title compound was obtained in 81% purity by HPLC. MS(ESI+): m/z=518.

Example 302

(2S,4EZ)-N-[(2RS)-2-hydroxy-3-(4-methoxyphenoxy)propyl]-4-(methoxyimino)-1-[4-(3-pyridinyl) benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl) benzoic acid, and (2RS)-1-amino-3-(4-methoxyphenoxy)-2-propanol, the title compound was obtained in 63% purity by HPLC. MS(ESI+): m/z=519.

Example 303

(2S,4EZ)-1-([1,1'-biphenyl]-4-ylsulfonyl)-N-[(2RS)-2-hydroxy-3-(4-methoxyphenoxy)propyl]-4-(methoxyimino-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (2RS)-1-amino-3-(4-methoxyphenoxy)-2-propanol, the title compound was obtained in 69% purity by HPLC. MS(ESI+): m/z=554.

Example 304

(2S,4EZ)-1-([1,1'-biphenyl]-4-ylcarbonyl)-N-[(2RS)-2-hydroxypropyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (2RS)-1-amino-2-propanol, the title compound was obtained in 82% purity by HPLC. MS(ESI+): m/z=396.

Example 305

(2S,4EZ)-1-([1,1'-biphenyl]-4-ylsulfonyl)-N-[(2RS)-2-hydroxypropyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (2RS)-1-amino-2-propanol, the title compound was obtained in 75% purity by HPLC. MS(ESI+): m/z=432.

Example 306

(2S,4EZ)-1-([1,1'-biphenyl]-4-ylsulfonyl)-N-[(2RS)-2-hydroxy-2-(2-naphthyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecaxboxylic acid, [1,1'-biphenyl]-4-sulfonyl chloride, and (1RS)-2-amino-1-(2-naphthyl)ethanol, the title compound was obtained in 77% purity by HPLC. MS(ESI+): m/z=544.

Example 307

(2S,4EZ)-1-([1,1'-binhenyl]-4-ylcarbonyl)-N-[(2RS)-2-hydroxy-2-(4-nitrophenyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (1RS)-2-amino-1-(4-nitrophenyl) ethanol, the title compound was obtained in 84% purity by HPLC. MS(ESI+): m/z=503.

Example 308

(2S,4EZ)-N-[(2RS)-2-hydroxy-2-(4-nitrophenyl) ethyl]-4-(methoxyimino)-1-[4-(4-pyrdinyl)benzoyl]-2-pyrrolidinecarboxamide Following the general method as outlined in Example 22, starting from (2S,4EZ)-1-(tert-butoxycarbonyl)-4(methoxyimino)-2-pyrrolidinecarboxylic acid, 4-(4-pyridinyl)benzoic acid, and (1RS)-2-amino-1-(4-nitrophenyl)ethanol, the title compound was obtained in 89% purity by HPLC. MS(ESI+): m/z=504.

Example 309

(2S,4EZ)-N-[(2RS)-2-hydroxy-2-(4-nitrophenyl) ethyl]-4-(methoxyimino)-1-[4-(3-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl) benzoic acid, and (1RS)-2-amino-1-(4-nitrophenyl)ethanol, the title compound was obtained in 72% purity by HPLC. MS(ESI+): m/z=504.

Example 310

(2S,4EZ)-N-[(2RS)-2-hydroxy-2-(4-nitropheny) ethyl]-4-(methoxyimino)-1-[4-(2-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(2-pyridinyl) benzoic acid, and (1RS)-2-amino-1-(4-nitrophenyl)ethanol, the title compound was obtained in 63% purity by HPLC. MS(ESI+): m/z=504.

Example 311

(2S,4EZ)-1-([1,1'-biphenyl]-4-ylsulfonyl)-N-[(2RS)-2-hydroxy-2-(4-nitrophenyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (1RS)-2-amino-1-(4-nitrophenyl) ethanol, the title compound was obtained in 79% purity by HPLC. MS(ESI+): m/z=539.

Example 312

(2S-4EZ)-N-{(2RS)-3-[4-(acetylamino)phenoxy]-2-hydroxypropyl}-1-([1,1'-biphenyl]-4-ylcarbonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and N-(4-{[(2RS)-3-amino-2-hydroxypropyl]oxy}phenyl)acetamide, the title compound was obtained in 79% purity by HPLC. MS(ESI+): m/z=545.

Example 313

(2S,4EZ)-N-{(2RS)-3-[4-(acetylamino)phenoxy]-2-hydroxypropyl}-4-(methoxyimino)-1-[4-(4-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(4pyidinyl)benzoic acid, and N-(4-{[(2RS)-3-amino-2-hydroxypropyl] oxy}phenyl)acetamide, the title compound was obtained in 62% purity by HPLC. MS(ESI+): m/z=546.

Example 314

(2S,4EZ)-N-{(2RS)-3-[4-(acetylamino)phenoxy]-2-hydroxypropyl}-4-(methoxyimino)-1-[4-(3-pyrdinyl) benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl) benzoic acid, and N-(4-{[(2RS)-3-amino-2-hydroxypropyl] oxy}phenyl)acetamide, the title compound was obtained in 66% purity by HPLC. MS(ESI+): m/z=546.

Example 315

(2S,4EZ)-N-{(2RS)-3-([4-(acetylamino)phenoxy]-2-hydroxypropyl}-1-([1,1'-biphenyl]-4-ylsulfonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and N-(4-{[(2RS)-3-amino-2-hydroxypropyl]oxy}phenyl)acetamide, the title compound was obtained in 62% purity by HPLC. MS(ESI+): m/z=581.

Example 316

(2S,4EZ)-1-([1,1'-biphenyl]-4-ylcarbonyl)-N-[(2R)-2-hydroxy-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (1R)-2-amino-1-phenylethanol, the title compound was obtained in 84% purity by HPLC. MS(ESI+): m/z=458.

Example 317

(2S,4EZ)-N-[(2R)-2-hydroxy-2-phenylethyl]-4-(methoxyimino)-1-[4-(4-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(4-pyridinyl) benzoic acid, and (1R)-2-amino-1-phenylethanol, the title compound was obtained in 66% purity by HPLC. MS(ESI+): m/z=459.

Example 318

(2S,4EZ)-N-[(2R)-2-hydroxy-2-phenylethyl]-4-(methoxyimino)-1-[4-(3-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl) benzoic acid, and (1R)-2-amino-1-phenylethanol, the title compound was obtained in 76% purity by HPLC. MS(ESI+): m/z=459.

Example 319

(2S,4EZ)-N-[(2R)-2-hydroxy-2-phenylethyl]-4-(methoxyimino)-1-[4-(2-pyridin)benzoyl]-2-pyrrolidinecarboxamide Following the general method as outlined in Example 22, starting from (2S,4EZ)-1-(tert-butoxycarbonyl)-4-(methoxyimnino)-2-pyrrolidinecarboxylic acid, 4-(2-pyridinyl) benzoic acid, and (1R)-2-amino-1-phenylethanol, the title compound was obtained in 65% puity by HPLC. MS(ESI+): m/z=459.

Example 320

(2S,4EZ)-1-([1,1'-biphenyl]-4-ylsulfony)-N-[(2R)-2hydroxy-2-phenyl-ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (1R)-2-amino-1-phenylethanol, the title compound was obtained in 87% purity by HPLC. MS(ESI+): m/z=494.

Example 321

(2S,4EZ)-1-([1,1'-biphenyl]-4-ylcarbonyl)-N-(3-hydroxypropyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 3-amino-1-propanol, the title compound was obtained in 81% purity by HPLC. MS(ESI+): m/z=395.

Example 322

(2S,4EZ)-1-([1,1'-biphenyl]-4-ylsulfonyl)-N-(3-hydroxypropyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and 3-amino-1-propanol, the title compound was obtained in 64% purity by HPLC. MS(ESI+): m/z=432.

Example 323

(3EZ,5S)-1-([1,1'-biphenyl]-4-ylcarbonyl)-5-[(4-hydroxy-4-phenyl-1-piperidinyl)carbonyl]-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 4-phenyl-4-piperidinol, the title compound was obtained in 74% purity by HPLC. MS(ESI+): m/z=498.

Example 324

(3EZ,5S)-5-[(4-hydroxy-4-phenyl-1-piperidinyl) carbonyl]-1-[4-(4-pyrdinyl)benzoyl]-3-pyrrolidinone O-methyloxime Following the general method as outlined in Example 22, starting from (2S,4EZ)-1-(tert-butoxycarbonyl)-4-(methoxyinio)-2-pyrrolidinecarboxylic acid, 4-(4-pyridinyl)benzoic acid, and 4-phenyl-4-piperidinol, the title compound was obtained in 78% purity by HPLC. MS(ESI+): m/z=499.

Example 325

(3EZ,5S)-5-[(4-hydroxy-4-phenyl-1-piperidinyl) carbonyl]-1-[4-(3-pyridinyl)benzoyl]-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 4-(3-pyridinyl) benzoic acid, and 4-phenyl-4-piperidinol, the title compound was obtained in 79% purity by HPLC. MS(ESI+): m/z=499.

Example 326

(3EZ,5S)-1-([1,1'-biphenyl]-4-ylsulfonyl)-5-[(4-hydroxy-4-phenyl-1-piperidinyl)carbonyl]-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and 4phenyl-4-piperidinol, the title compound was obtained in 84% purity by HPLC. MS(ESI+): m/z=534.

Example 327

(2S,4EZ)-1-([1,1'-biphenyl]-4-ylcarbonyl)-N-[(1S, 2S)-2-hydroxycyclohexyl]-4-(methoximino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (1S,2S)-2-aminocyclohexanol, the title compound was obtained in 84% purity by HPLC. MS(ESI+): m/z=436.

Example 328

(2S,4EZ)-1-([1,1'-biphenyl]-4-ylsulfonyl)-N-[(1S, 2S)-2-hydroxycyclohexyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (1S,2S)-2-aminocyclohexanol, the title compound was obtained in 61% purity by HPLC. MS(ESI+): m/z=472.

Example 329

(2S,4EZ)-N-benzyl-1-([1,1'-biphenyl]-4-ylcarbonyl)-N-(2-hydroxyethyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 2-(benzylamino)ethanol, the title compound was obtained in 74% purity by HPLC. MS(ESI+): m/z=472.

Example 330

(2S,4EZ)-N-benzyl-N-(2-hydroxyethyl)-4-(methoxyimino)-1-[4-(3-pyri-dinyl-benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl) benzoic acid, and 2-(benzylamino)ethanol, the title compound was obtained in 82% purity by HPLC. MS(ESI+): m/z=473.

Example 331

(3EZ,5S)-1-([1,1'-biphenyl]-4-ylcarbonyl)-5-{[(3RS)-3-hydroxypiperidinyl]-carbonyl}-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (3RS)-3-piperidinol, the title compound was obtained in 78% purity by HPLC. MS(ESI+): m/z=422.

Example 332

(3EZ,5S)-5-{[(3RS)-3-hydroxypiperidinyl]carbonyl}-1-[4-(4-pyridinyl-benzoyl]-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 4-(4-pyridinyl) benzoic acid, and (3RS)-3-piperidinol, the title compound was obtained in 91% purity by HPLC. MS(ESI+): m/z=423.

Example 333

(3EZ,5S)-5-{[(3RS)-3-hydroxypiperidinyl]carbonyl}-1-[4-(3-pyridinyl)-benzoyl]-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 4-(3-pyridinyl) benzoic acid, and (3RS)-3-piperidinol, the title compound was obtained in 84% purity by HPLC. MS(ESI+): m/z=423.

Example 334

(3EZ,5S)-1-([1,1'-biphenyl]-4-ylsulfonyl)-5-{[(3RS)-3-hydroxypiperidin]-carbonyl}-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (3RS)-3-piperidinol, the title compound was obtained in 79% purity by HPLC. MS(ESI+): m/z=458.

Example 335

(2S,4EZ)-1-([1,1'-biphenyl]-4-ylcarbonyl)-N-[(1S, 2S)-2-hydroxy-1-(hydroxymethyl)-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4carbonyl chloride, and (1S,2S)-2-amino-1-phenyl-1,3-propanediol, the title compound was obtained in 88% purity by HPLC. MS(ESI+): m/z=488.

Example 336

(2S,4EZ)-N-[(1S,2S)-2hydroxy-1-(hydroxymethyl)-2-phenylethyl]-4-(methoxyimino)-1-[4-(4-pyridinyl) benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(4-pyridinyl) benzoic acid, and (1S,2S)-2-amino-1-phenyl-1,3-propanediol, the title compound was obtained in 64% purity by HPLC. MS(ESI+): m/z=489.

Example 337

(2S,4EZ)-N-[(1S,2S)-2-hydroxy-1-(hydroxymethyl)-2-phenylethyl]-4-(methoxyimino)-1-[4-(3-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl)benzoic acid, and (1S,2S)-2-amino-1-phenyl-1,3-propanediol, the title compound was obtained in 93% purity by HPLC. MS(ESI+): m/z=489.

Example 338

(2S,4EZ)-1-([1,1'-biphenyl]-4-ylsulfonyl)-N-[(1S,2S)-2-hydroxy-1-(hydroxemethyl)-2-phenylethyl-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (1S,2S)-2-amino-1-phenyl-1,3-propanediol, the title compound was obtained in 82% purity by HPLC. MS(ESI+): m/z=524.

Example 339

(2S,4EZ)-N-(2-anilinoethyl)-1-([1,1'-biphenyl]-4-ylcarbonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and $N^1$-phenyl-1,2-ethanediamine, the title compound was obtained in 93% purity by HPLC. MS(ESI+): m/z=457.

Example 340

(2S,4EZ)-N-(2-anilinoethyl)-4-(methoxyimio)-1-[4-(4-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(4-pyridinyl)benzoic acid, and $N^1$-phenyl-1,2-ethanediamine, the title compound was obtained in 85% purity by HPLC. MS(ESI+): m/z =458.

Example 341

(2S,4EZ)-N-(2-anilinoethyl)-4-(methoxyimino)-1-[4-(3-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(3-pyridinyl)benzoic acid, and $N^1$-phenyl-1,2-ethanediamine, the title compound was obtained in 85% purity by HPLC. MS (ESI+): m/z=458.

Example 342

(2S,4EZ)-N-(2-anilinoethyl)-4-(methoxyimino)-1-[4-(2-pyridinyl)benzoyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 4-(2-pyridinyl)benzoic acid, and $N^1$-phenyl-1,2-ethanediamine, the title compound was obtained in 67% purity by HPLC. MS(ESI+): m/z=458.

Example 343

(2S,4EZ)-N-(2-anilinoethyl)-1-([1,1'-biphenyl]-4-ylsulfonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and $N^1$-phenyl-1,2-ethanediamine, the title compound was obtained in 73% purity by HPLC. MS(ESI+): m/z=493.

Example 344

(3EZ,5S)-1-([1,1'-biphenyl]-4-ylcarbonyl)-5-[(4-hydroxy-1-piperidinyl)-carbonyl]-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 4-piperidinol, the title compound was obtained in 86% purity by HPLC. MS(ESI+): m/z=422.

Example 345

(3EZ,5S)-1-([1,1'-biphenyl]-4-ylsulfonyl)-5-[(4-hydroxy-1-piperidinyl)-carbonyl]-3-prolidinone O-methyloxime Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and 4-piperidinol, the title compound was obtained in 68% purity by HPLC. MS(ESI+): m/z=458.

Example 346

(2S,4EZ)-N-[(1S,2,R3S,4R)-3-(aminocarbonyl)bicyclo[2.2.1]hept-5-en-2-yl]-1-([1,1'-biphenyl]-4-ylsulfonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (1R,2S,3R,4S)-3-aminobicyclo[2.2.1]hept-5-ene-2-carboxamide, the title compound was obtained in 79% purity by HPLC. MS(ESI+): m/z=509.

Example 347

(2S,4EZ)-N-(3-amino-3-oxopropyl)-1-([1,1'-biphenyl]-4-ylcarbonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 3-aminopropanamide, the title compound was obtained in 71% purity by HPLC. MS(ESI+): m/z=409.

Example 348

(2S,4EZ)-N-[(1S,2S,3R,4R)-3-(aminocarbonyl)bicyclo[2.2.1]hept-5-en-2-yl]-1-([1,1'-biphenyl]-4-ylsulfonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and (1R,2R,3S,4S)-3-aminobicyclo[2.2.1]hept-5-ene-2-carboxamide, the title compound was obtained in 83% purity by HPLC. MS(ESI+): m/z=509.

Example 349

(2S,4EZ)-1-([1,1'-biphenyl]-4-ylcarbonyl)-N-(4-hydroxybutyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 4-amino-1-butanol, the title compound was obtained in 68% purity by HPLC. MS(ESI+): m/z=410.

Example 350

(2S,4EZ)-1-([1,1'-4-biphenyl]-4-ylsulfonyl)-N-(4-hydroxybutyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and 4-amino-1-butanol, the title compound was obtained in 78% purity by HPLC. MS(ESI+): m/z=446.

Example 351

(2S,4EZ)-1-([1,1'-biphenyl]-4-ylsulfonyl)-N-[(1R,2R)-2-(hydroxymethyl)-cyclohexyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and [(1R,2R)-2-aminocyclohexyl]methanol, the title compound was obtained in 40% purity by HPLC. MS(ESI+): m/z=486.

Example 352

(2S,4EZ)-1-([1,1'-biphenyl]-4-ylsulfonyl)-N-[(1R,2S,3R,4S)-3-(hydroxymethyl)bicyclo[2.2.1]hept-2-yl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and [(1S,2R,3S,4R)-3-aminobicyclo[2.2.1]hept-2-yl]methanol, the title compound was obtained in 58% purity by HPLC. MS(ESI+): m/z=498.

Example 353

(2S,4EZ)-1-([1,1'-biphenyl]-4-ylsulfonyl)-N-[(1R,2S)-2-(hydroxymethyl)-cyclohexyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-sulfonyl chloride, and [(1S,2R)-2-aminocyclohexyl]methanol, the title compound was obtained in 41% purity by HPLC. MS(ESI+): m/z=486.

Example 354

(2S,4E and 4Z)-N-[(2RS)-2-hydroxy-2-phenylethyl]-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (1RS)-2-amino-1-phenylethanol, the title compounds were obtained as a mixture of E/Z-isomers of the oxime functionality. Separation of the isomers by flash chromatography yielded (2S,4E)-N-[(2RS)-2-hydroxy-2-phenylethyl]-4-(methoxyimino)-1-[(2'-methyl[1,1'-biphenyl]-4-yl)carbonyl]-2-pyrrolidinecarboxamide in 98.9% purity and (2S,4Z)-N-[(2RS)-2-hydroxy-2-phenylethyl]-4-(methoxyimino)-1-[(2'-methyl[1,1'-biphenyl]-4-yl)carbonyl]-2-pyrrolidinecarboxamide in 99.9% purity by HPLC. MS(ESI+): m/z=472.

Example 355

(2S,4E and 4Z)-N-[(2S)-2-hydroxy-2-phenylethyl]-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecatboxylic acid, 2'-methyl[1,1'-biphenyl]-4-carboxylic acid, and (1S)-2-amino-1-phenylethanol, the title compounds were obtained as a mixture of E/Z-isomers of the oxime functionality. Separation of the isomers by flash chromatography yielded (2S,4E)-N-[(2S)-2-hydroxy-2-phenylethyl]-4-(methoxyimino)-1-[(2'-methyl[1,1'-biphenyl]-4-yl)carbonyl]-2-pyrrolidinecarboxamide in 98.9% purity and (2S,4Z)-N-[(2S)-2-hydroxy-2-phenylethyl])-4-(methoxyimino)-1-[(2'-methyl[1,1'-biphenyl]-4-yl)carbonyl]-2-pyrrolidinecarboxamide in 99.8% purity by HPLC. MS(ESI+): m/z=472.

Example 356

(2S,4E and 4Z)-N-[(2R)-2-hydroxy-2-phenylethyl]-4-(methoxyimino)-1-[(2'-methyl[1,1'-biphenyl]-4-yl) carbonyl]-2-pyrrolidinecarboxamide Following the general method as outlined in Example 22, starting from (2S,4EZ)-1-(tert-butoxycarbonyl)-4-(methoxyimino)-2-pyrrohidinecarboxylic acid, 2'-methyl[1,1'-biphenyl]-4-carboxylic acid, and (1R)-2-amino-1-phenylethanol, the title compounds were obtained as a mixture of E/Z-isomers of the oxime functionality. Separation of the isomers by flash chromatography yielded (2S,4E)-N-[(2R)-2-hydroxy-2-phenylethyl]-4-(methoxyimino)-1-[(2'-methyl [1,1'-biphenyl]-4-yl)carbonyl]-2-pyrrolidinecarboxamide in 99.7% purity and (2S,4Z)-N-[(2R)-2-hydroxy-2-phenylethyl]-4-(methoxyimino)-1-[(2'-methyl[1,1'-biphenyl]-4-yl) carbonyl]-2-pyrrolidinecarboxamide in 99.7% purity by HPLC. MS(ESI+): m/z=472.

Example 357

(2S,4EZ)-1-([1,1'-biphenyl]-4-ylcarbonyl)-N-[(1R, 2S)-2-(hydroxymethyl)-cyclohexyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and [(1S,2R)-2-aminocyclohexyl]methanol, the title compound was obtained in 63% purity by HPLC. MS(ESI+): m/z=450.

Example 358

(2S,4EZ)-1-([1,1'-biphenyl]-4-ylcarbonyl)-N-[2-hydroxy-1-(hydroxymethyl)-ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 2-amino-1,3-propanediol, the title compound was obtained in 61% purity by HPLC. MS(ESI+): m/z=412.

Example 359

(2S,4EZ)-N-[(1S,2R,3S,4R)-3-(aminocarbonyl)bicyclo[2.2.1]hept-5-en-2-yl]-1-([1,1'-biphenyl]-4-ylcarbonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (1R,2S,3R,4S)-3-aminobicyclo [2.2.1]hept-5-ene-2-carboxamide, the title compound was obtained in 68% purity by HPLC. MS(ESI+): m/z=473.

Example 360

(2S,4EZ)-N-[(1S,2S,3R,4R)-3-(aminocarbonyl)bicyclo[2.2.1.]hept-5-en-2-yl]1-([1,1'-biphenyl]-4-ylcarbonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (1R,2R,3S,4S)-3-aminobicyclo [2.2.1]hept-5-ene-2-carboxamide, the title compound was obtained in 78% purity by HPLC. MS(ESI+): m/z=473.

Example 361

(2S,4EZ)-1-([1,1'-biphenyl]-4-ylcarbonyl)-N-[(2S)-2-hydroxy-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (1S)-2-amino-1-phenylethanol, the title compound was obtained in 87% purity by HPLC. MS(ESI+): m/z=458.

Example 362

(2RS)-3-({[(2S,4EZ)-1-([1,1'-biphenyl]-4-ylcarbonyl)-4-(methoxyimino-pyrrolidinyl] carbonyl}amino)-2-hydroxypropanoic acid Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (2RS)-3-amino-2-hydroxypropanoic acid, the title compound was obtained in 44% purity by HPLC. MS(ESI+): m/z=426.

Example 363

(2S,4EZ)-N-[(1R,2S)-2-(aminocarbonyl)cyclohexyl]-1-([1,1'-biphenl]-4-ylcarbonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (1S,2R)-2-aminocyclohexanecarboxamide, the title compound was obtained in 89% purity by HPLC. MS(ESI+): m/z=463.

Example 364

(2S,4EZ)-1-([1,1'-biphenyl]-4-ylcarbony)-N-[(1RS)-2-hydroxy-1-methyl-ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (2RS)-2-amino-1-propanol, the title compound was obtained in 81% purity by HPLC. MS(ESI+): m/z=396.

Example 365

(2S,4EZ)-1-([1,1'-biphenyl]-4-ylcarbonyl)-N-[(1S, 2S)-2-hydroxy-1-(hydroxymethyl)-2-(4-nitrophenyl) ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (1S,2S)-2-amino-1-(4-nitrophenyl)-

1,3-propanediol, the title compound was obtained in 70% purity by HPLC. MS(ESI+): m/z=533.

Example 366

4-({[(2S,4EZ)-1-([1,1'-biphenyl]-ylcarbonyl)-4-(methoxyimino)pyrrolidinyl]carbonyl}amino)butanoic acid Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 4-aminobutanoic acid, the title compound was obtained in 57% purity by HPLC. MS(ESI+): m/z=424.

Example 367

(2S,4EZ)-N-[(2S)-2-hydroxy-2-phenylethyl]-1-[(2'-methoxy[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methoxy[1,1'-biphenyl]-4-carboxylic acid, and (1S)-2-amino-1-phenylethanol, the title compound was obtained in 90% purity by HPLC. MS(ESI+): m/z=488.

Example 368

(2S,4EZ)-N-[(2RS)-2-hydroxy-2-(2-naphthlyl)ethyl]-1-[(2'-methoxy[1,1'-biphenyl]4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methoxy[1,1'-biphenyl]-4-carboxylic acid, and (1RS)-2-amino-1-(2-naphthyl)ethanol, the title compound was obtained in 67% purity by HPLC. MS(ESI+): m/z=538.

Example 369

(2S,4EZ)-N-[(1RS)-2-hydroxy-1-methylethyl]-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (2RS)-2-amino-1-propanol, the title compound was obtained in 88% purity by HPLC. MS(ESI+): m/z=410.

Example 370

(2S,4EZ)-N-[(1S,2S)-2-hydroxy-1-(hydroxymethyl)-2-(4-nitrophenyl)ethyl]-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (1S,2S)-2-amino-1-(4-nitrophenyl)-1,3-propanediol, the title compound was obtained in 74% purity by HPLC. MS(ESI+): m/z=547.

Example 371

(2S,4EZ)-N-[(1S,2S)-2-hydroxy-1-(hydroxymethyl)-2-(4-nitrophenyl)ethyl]-4-(methoxyimino)-1-[(2'-methoxy[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxymino)-2-pyrrolidinecarboxylic acid, 2'-methoxy[1,1'-biphenyl]-4-carboxylic acid, and (1S,2S)-2-amino-1-(4-nitrophenyl)-1,3-propanediol, the title compound was obtained in 61% purity by HPLC. MS(ESI+): m/z=563.

Example 372

(3EZ,5S)-5-[(4-hydroxy-1-piperidinyl)carbonyl]-1-[(2'-methyl[1,1'-biphenyl]-4-yl)carbonyl]-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 4-piperidinol, the title compound was obtained in 86% purity by HPLC. MS(ESI+): m/z=436.

Example 373

(2S,4EZ)-N-[(1S,2S,3R,4R)-3-(aminocarbonyl)bicyclo[2.2.1]hept-5-en-2-yl]-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (1R,2R,3S,4S)-3-aminobicyclo[2.2.1]hept-5-ene-2-carboxamide, the title compound was obtained in 55% purity by HPLC. MS(ESI+): m/z=487.

Example 374

(2S,4EZ)-N-[(2RS)-2-hydroxy-2-phenylethyl]-1-[(2'-methoxy[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methoxy[1,1'-biphenyl]-4-carboxylic acid, and (1RS)-2-amino-1-phenylethanol, the title compound was obtained in 82% purity by HPLC. MS(ESI+): m/z=488.

Example 375

(2S,4EZ)-N-[(2RS)-2-hydroxypropyl]-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (2RS)-1-amino-2-propanol, the title compound was obtained in 90% purity by HPLC. MS(ESI+): m/z=410.

Example 376

(2S,4EZ)-N-[(2RS)-2,3-dihydroxypropyl]-4-(methoxyimino)-1-[(2'-methyl-[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (2RS)-3-amino-1,2-propanediol, the title compound was obtained in 67% purity by HPLC. MS(ESI+): m/z=426.

Example 377

(2S,4EZ)-N-(3-hydroxypropyl)-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 3-amino-1-propanol, the title compound was obtained in 90% purity by HPLC. MS(ESI+): m/z=410.

Example 378

(2S,4EZ)-N-(2-amino-2-oxoethyl)-1-([1,1'-biphenyl]-4-ylcarbonyl)-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 2-aminoacetamide, the title compound was obtained in 82% purity by HPLC. MS(ESI+): m/z=395.

Example 379

(2S,4EZ)-N-(2-amino-2-oxoethyl)-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 2-aminoacetamide, the title compound was obtained in 92% purity by HPLC. MS(ESI+): m/z=409.

Example 380

(2S,4EZ)-1-([1,1'-biphenyl]-4-ylcarbonol)-N-[(2RS)-2-hydroxy-2-(3-hydroxyphenyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and 3-[(1RS)-2-amino-1-hydroxyethyl]phenol, the title compound was obtained in 88% purity by HPLC. MS(ESI+): m/z=504.

Example 381

(2S,4EZ)-1-([1,1'-biphenyl]-4-ylcarbonyl)-N-[(1S,2R,3S,4R)-3-(hydroxymethyl)bicyclo[2.2.1]hept-2-yl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and [(1R,2S,3R,4S)-3-aminobicyclo[2.2.1]hept-2-yl]methanol, the title compound was obtained in 64% purity by HPLC. MS(ESI+): m/z=462.

Example 382

(2S,4EZ)-N-[(1R,2S,3R,4S)-3-(hydroxymethyl)bicyclo[2.2.1]hept-2-yl]-1-[(2'-methoxy[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methoxy[1,1'-biphenyl]-4-carboxylic acid, and [(1S,2R,3S,4R)-3-aminobicyclo[22.1]hept-2-yl]methanol, the title compound was obtained in 56% purity by HPLC. MS(ESI+): m/z=492.

Example.383

(2S,4EZ)-N-(trans-4-hydroxycyclohexyl)-1-[(2'-methoxy[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methoxy[1,1'-biphenyl]-4-carboxylic acid, and trans-4-aminocyclohexanol, the title compound was obtained in 61% purity by HPLC. MS(ESI+): m/z=466.

Example 384

(2S,4EZ)-N-[(1R,2R)-2-(hydroxymethyl)cyclohexyl]-1-[(2'-methoxy[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methoxy[1,1'-biphenyl]-4-carboxylic acid, and [(1R,2R)-2-aminocyclohexyl]methanol, the title compound was obtained in 68% purity by HPLC. MS(ESI+): m/z=480.

Example 385

(2S,4EZ)-N-[(2RS)-2-hydroxy-3-phenoxypropyl]-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (2RS)-1-amino-3-phenoxy-2-propanol, the title compound was obtained in 80% purity by HPLC. MS(ESI+): m/z=502.

Example 386

(2S,4EZ)-N-[(2RS)-2-hydroxy-2-(4-hydroxyphenyl)ethyl]-4-(methoxy-mino)-1-[(2'-methyl[1,1'-biphenyl]-4-yl)carbonyl]-2-pyrrolidinecarboxamide Following the general method as outlined in Example 22, staring from (2S,4EZ)-1-(tert-butoxycarbonyl)-4-(methoxyimino)-2-pyrrolidinecarboxylic acid, 2'-methyl[1,1'-biphenyl]-4-carboxylic acid, and 4-[(1RS)-2-amino-1-hydroxyethyl]phenol, the title compound was obtained in 76% purity by HPLC. MS(ESI+): m/z=488.

Example 387

(2S,4EZ)-N-](2RS)-2-hydroxy-2-(4-hydroxyphenyl)ethyl]-4-(methoxy-imino)-1-[(2'-methoxy[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methoxy[1,1'-biphenyl]-4-carboxylic acid, and 4-[(1RS)-2-amino-1-hydroxyethyl]phenol, the title compound was obtained in 90% purity by HPLC. MS(ESI+): m/z=504.

Example 388

(2S,4EZ)-N-[(2RS)-2-hydroxy-2-(4-hydroxy-3-methoxyphenyl)ethyl]-1-[(2'-methly[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 4-[(1RS)-2-amino-1-hydroxyethyl]-2-methoxyphenol, the title compound was obtained in 67% purity by HPLC. MS(ESI+): m/z=518.

Example 389

(2S,4EZ)-N-[(2RS)-2-hydroxy-2-(4-hydroxy-3-methoxyphenyl)ethyl]-1-[(2'-methoxy[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methoxy[1,1'-biphenyl]-4-carboxylic acid, and 4-[(1RS)-2-amino-1-hydroxyethyl]-2-methoxyphenol, the title compound was obtained in 87% purity by HPLC. MS(ESI+): m/z=534.

Example 390

(2S,4EZ)-N-[(2RS)-2-(3,4-dihydroxyphenyl)-2-hydroxyethyl]-1-(2'-methoxy[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methoxy[1,1'-biphenyl]-4-carboxylic acid, and 4-[(1RS)-2-amino-1-hydroxyethyl]-1,2-benzenediol, the title compound was obtained in 69% purity by HPLC. MS(ESI+): m/z=520.

Example 391

(2R,4EZ)-1-([1,1'-biphenyl]-4-ylcarbonyl)-N-[(2RS)-2-hydroxy-2-phenylethyl]-4-(methoxyimino)-2-pyrrolidinecarboxamide Following the general method as outlined in Example 22, starting from (2R,4EZ)-1-(tert-butoxycarbonyl)-4-(methoxy)-2-pyrrolidinecarboxylic acid, [1,1'-biphenyl]-4-carbonyl chloride, and (1RS)-2-amino-1-phenylethanol, the title compound was obtained in 90% purity by HPLC. MS(ESI+): m/z=456.

Example 392

(2R,4EZ)-N-[(2RS)-2-hydroxy-2-phenylethyl]-4-(methoxyimino)-1-[(2'-methyl[1,1'-biphenyl]-4-yl)carbonyl]-2-pyrrolidinecarboxamide Following the general method as outlined in Example 22, starting from (2R,4EZ)-1-(tert-butoxycarbonyl)-4-(methoxyimino)-2-pyrrolidinecarboxylic acid, 2'-methyl[1,1'-biphenyl]-4-carboxylic acid, and (1RS)-2-amino-1-phenylethanol, the title compound was obtained in 94% purity by HPLC. MS(ESI+): m/z=472.

Example 393

(2S,4EZ)-1-[(2'-cyano[1,1'-biphenyl]-4-yl)carbonyl]-N-[(2RS)-2-hydroxy-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-cyano[1,1'-biphenyl]-4-carboxylic acid, and (1RS)-2-amino-1-phenylethanol, the title compound was obtained in 86% purity by HPLC. MS(ESI+): m/z=483.

Example 394

(2S,4EZ)-1-[(3',4'-dichioro[1,1'-biphenyl]-4-yl)carbonyl]-N-[(2RS)-2-hydroxy-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 3',4'-dichloro[1,1'-biphenyl]-4-carboxylic acid, and (1RS)-2-amino-1-phenylethanol, the title compound was obtained in 89% purity by HPLC. MS(ESI+): m/z=527.

Example 395

(2S,4EZ)-1-[(2',6'-dimethyl[1,1'-biphenyl]-4-yl)carbonyl]-N-[(2RS)-2-hydroxy-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]-4-carboxylic acid, and (1RS)-2-amino-1-phenylethanol, the title compound was obtained in 95% purity by EPLC. MS(ESI+): m/z=486.

Example 396

(2S,4EZ)-1-[(2',3-dimethyl[1,1'-biphenyl]-4-yl)carbonyl]-N-[(2RS)-2-hydroxy-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]4-carboxylic acid, and (1RS)-2-amino-1-phenylethanol, the title compound was obtained in 83% purity by HPLC. MS(ESI+): m/z=486.

Example 397

(2S,4EZ)-N-[(2RS)-2-hydroxy-2-(3-hydroxyphenyl)ethyl]-4-(methoxy-imino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 3-[(1RS)-2-amino-1-hydroxyethyl]phenol, the title compound was obtained in 70% purity by HPLC. MS(ESI+): m/z=488.

Example 398

(2S,4EZ)-N-[(2RS)-2-hydroxy-2-(3-hydroxyphenyl)ethyl]-4-(methoxy-imino)-1-[(2'-cyano[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-cyano[1,1'-biphenyl]-4-carboxylic acid, and 3-[(1RS)-2-amino-1-hydroxyethyl]phenol, the title compound was obtained in 86% purity by HPLC. MS(ESI+): m/z=499.

Example 399

(2S,4EZ)-N-[(2RS)-2-hydroxy-2-(3-hydroxyphenyl)ethyl]-4-(methoxy-imino)-1-[(3',4'-dichloro[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 3',4'-dichloro[1,1'-biphenyl]-4-carboxylic acid, and 3-[(1RS)-2-amino-1-hydroxyethyl]phenol, the title compound was obtained in 91% purity by HPLC. MS(ESI+): m/z=543.

Example 400

(2S,4EZ)-N-[(2RS)-2 hydroxy-2-(3-hydroxyphenyl)ethyl]-4-(methoxy-imino)-1-[(2',6'-dimethyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]-4-carboxylic acid, and 3-[(1RS)-2-amino-1-hydroxyethyl]phenol, the title compound was obtained in 87% purity by HPLC. MS(ESI+): m/z=502.

Example 401

(2S,4EZ)-N-[(2RS)-2-hydroxy-2-(3-hydroxyphenyl)ethyl]-4-(methoxy-imino)-1-[(2',3-dimethyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]-4-carboxylic acid, and 3-[(1RS)-2-amino-1-hydroxyethyl]phenol, the title compound was obtained in 91% purity by HPLC. MS(ESI+): m/z=502.

Example 402

(2S,4EZ)-1-[(3',4'-dichloro[1,1'-biphenyl]-4-yl)carbonyl]-N-[(2RS)-2-hydroxy-2-(4-hydroxyphenyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 3',4'-dichloro[1,1'-biphenyl]-4-carboxylic acid, and 4-[(1RS)-2-amino-1-hydroxyethyl]phenol, the title compound was obtained in 86% purity by HPLC. MS(ESI+): m/z=543.

Example 403

(2S,4EZ)-1-[(2',6'-dimethyl[1,1'-biphenyl]-4-yl)carbonyl]-N-[(2RS)-2-hydroxy-2-(4-hydroxyphenyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]-4-carboxylic acid, and 4-[(1RS)-2-amino-1-hydroxyethyl]phenol, the title compound was obtained in 89% purity by HPLC. MS(ESI+): m/z=502.

Example 404

(2S,4MZ)-1-[(2',3-dimethyl[1,1'-biphenyl]-4-yl)carbonyl]-N-[(2RS)-2-hydroxy-2-(4-(hydroxyphenyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]-4-carboxylic acid, and 4-[(1RS)-2-amino-1-hydroxyethyl]phenol, the title compound was obtained in 90% purity by HPLC. MS(ESI+): m/z=502.

Example 405

(2S,4EZ)-1-[(2',6'-dimethyl[1 1'-biphenyl]-4-yl)carbonyl]-N-[(2RS)-2-hydroxy-3-(4-methoxyphenoxy)propyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]-4-carboxylic acid, and (2RS)-1-amino-3-(4-methoxyphenoxy)-2-propanol, the title compound was obtained in 87% purity by HPLC. MS(ESI+): m/z=546.

Example 406

(2S,4EZ)-1-[(2',3-dimethyl[1,1'-biphenyl]-4-yl)carbonyl]-N-[(2RS)-2-hydroxy-3-(4-methoxyphenoxy)propyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]-4-carboxylic acid, and (2RS)-1-amino-3-(4methoxyphenoxy)-2-propanol, the title compound was obtained in 77% purity by HPLC. MS(ESI+): m/z=546.

Example 407

(2S,4EZ)-N-(2-amino-2-oxyethyl)-1-[(2',6'-dimethyl[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]-4-carboxylic acid, and 2-aminoacetamide, the title compound was obtained in 88% purity by HPLC. MS(ESI+): m/z=423.

Example 408

(2S,4EZ)-N-(2-amino-2-oxyethyl)-1-[(2',3-dimethyl[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]-4-carboxylic acid, and 2-aminoacetamide, the title compound was obtained in 85% purity by HPLC. MS(ESI+): m/z=423.

Example 409

(2S,4EZ)-N-(3-amino-3-oxopropyl)-1-[(2',6'-dimethyl[1,1'-biphenyl]-4-yl)carbonyl]4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]-4-carboxylic acid, and 3-aminopropionamide, the title compound was obtained in 87% purity by HPLC. MS(ESI+): m/z=437.

Example 410

(2S,4EZ)-N-(3-amino-3-oxopropyl)-1-[(2',3-dimethyl[1,1'-biphenyl]-4-yl)carbonyl]-4-(methoxyimino)-2-prrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]-4-carboxylic acid, and 3-aminopropionamide, the title compound was obtained in 87% purity by HPLC. MS(ESI+): m/z=437.

Example 411

(2S,4EZ)-1-[(2',6'-dimethyl[1,1'-biphenyl]-4-yl)carbonyl]-N-[2-hydroxy-1-(hydroxymethyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-phenyl]-4-carboxylic acid, and 2-amino-1,3-propanediol, the title compound was obtained in 70% purity by HPLC. MS(ESI+): m/z=440.

Example 412

(2S,4EZ)-1-[(2',3-dimethyl[1,1'-biphenyl]-4-yl)carbonyl]-N-[2-hydroxy-1-(hydroxemethyl)ethyl]-4-(methoxyimino)-2-pyrrolidinecarboxaamide Following the general method as outlined in Example 22, starting from (2S,4EZ)-1-(tert-butoxycarbonyl)-4-(methoxyimino)-2-pyrrolidinecarboxyhc acid, 2',3-dimethyl[1,1'-biphenyl]-4-carboxylic acid, and 2-amino-1,3-propanediol, the title compound was obtained in 68% purity by HPLC. MS(ESI+): m/z=440.

Example 413

(2S,4EZ)-1-[(2'-cyano[1,1'-biphenyl]-4-yl)carbonyl]-N-[(1R,2R)-2-(hydroxymethyl)cyclohexyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-cyano[1,1'-biphenyl]-4-carboxylic acid, and [(1R,2R)-2-aminocyclohexyl]methanol, the title compound was obtained in 78% purity by HPLC. MS(ESI+): m/z=475.

Example 414

(3EZ,5S)-5-(3,4-dihydro-2(1H)-isoquinolinylcarbonyl)-1-[(2',3-dimethyl[1,1'-biphenyl]-4-yl)carbonyl]-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]-4-carboxylic acid, and 1,2,3,4-tetrahydroisoquinoline, the title compound was obtained in 77% purity by HPLC. MS(ESI+): m/z=482.

Example 415

(2S,4EZ)-N-[(1R)-2-hydroxy-1-phenylethyl]-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl-]4-carboxylic acid, and (2R)-2-amino-2-phenylethanol, the title compound was obtained in 91% purity by HPLC. MS(ESI+): m/z=472.

Example 416

(2S,4EZ)-1-[(2',6'-dimethyl[1,1'-biphenyl]-4-yl)carbonyl]-N-[2-(4-hydroxyphenyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]-4-carboxylic acid, and 4-(2-aminoethyl)phenol, the title compound was obtained in 87% purity by HPLC. MS(ESI+): m/z=486.

Example 417

(2S,4EZ)-1-[(2',3-dimethyl[1,1'-biphenyl]-4-yl)carbonyl]-N-[2-(4-hydroxyphenyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]-4-carboxylic acid, and 4-(2-aminoethyl)phenol, the title compound was obtained in 83% purity by HPLC. MS(ESI+): m/z=486.

Example 418

(2S,4EZ)-1-[(2',6'-dimethyl[1,1'-biphenyl]-4-yl)carbonyl]-N-[2-(3-hydroxyphenyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]-4-carboxylic acid, and 3-(2-aminoethyl)phenol, the title compound was obtained in 81% purity by HPLC. MS(ESI+): m/z=486.

Example 419

(2S,4EZ)-1-[(2',3-dimethyl[1,1'-biphenyl]-4-yl)carbonyl]-N-[2-(3-hydroxyphenyl)ethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]-4-carboxylic acid, and 3-(2-aminoethyl)phenol, the title compound was obtained in 89% purity by HPLC. MS(ESI+): m/z=486.

Example 420

(2S,4EZ)-1-[(2',3-dimethyl[1,1'-biphenyl]-4-yl)carbonyl]-N-[(1R,2S)-2-hydroxy-1,2-diphenylmethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]-4carboxylic acid, and (1S,2R)-2-amino-1,2-diphenylethanol, the title compound was obtained in 73% purity by HPLC. MS(ESI+): m/z=562.

Example 421

(2RS)-2-[({2S,4EZ)-4-(methoxyimino)-1-[(2'-methyl[1,1'-biphenyl]-4-yl)carbonyl]-pyrrolidinyl}carbonyl amino]-3-phenylpropane acid Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and DL-phenylalanine, the title compound was obtained in 62% purity by HPLC. MS(ESI+): m/z=500.

Example 422

(2S,4EZ)-N-[(1R,2S)-2-(aminocarbonyl)cyclohexyl]-1-[(2',6'-dimethyl[1,1'-biphenyl]-4-yl)carbonyl]-4-(methoxyimino) -2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',6'-dinethyl[1,1'-biphenyl]-4-carboxylic acid, and (1S,2R)-2-aminocyclohexanecarboxamide, the title compound was obtained in 92% purity by HPLC. MS(ESI+): m/z=491.

Example 423

(2S,4EZ)-N-[(1R,2S)-2-(aminocarbonyl)cyclohexyl]-1-[(2',3-dimethyl[1,1'-biphenyl]-4-yl)carbonyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]-4-carboxylic acid, and (1S,2R)-2-aminocyclohexanecarboxamide, the title compound was obtained in 91% purity by HPLC. MS(ESI+): m/z=491.

Example 424

4'-{[(2S,4EZ)-2-{[4-(2-hydroxyethyl)-1-piperazinyl]carbonyl}-4-(methoxyimino)pyrrolidinyl]carbonyl}[1,1'-biphenyl]-2-carbonitrile Following the general method as outlined in Example 22, starting from (2S,4EZ)-1-(tert-butoxycarbonyl)-4-(methoxyimino)-2-pyrrolidinecarboxylic acid, 2'-cyano[1,1'-biphenyl]-4-carboxylic acid, and 2-(1-piperazinyl)ethanol, the title compound was obtained in 89% purity by HPLC. MS(ESI+): m/z=476.

Example 425

(3EZ5S)-1-[(3',4'-dichloro[1,1'-biphenyl]-4-yl)carbonyl]-5-{[4-(2-hydroxyethyl)-1-piperazinyl]carbonyl}-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 3',4'-dichloro[1,1'-biphenyl]-4carboxylic acid, and 2-(1-piperazinyl)ethanol, the title compound was obtained in 86% purity by HPLC. MS(ESI+): m/z =520.

Example 426

(3EZ,5S)-1-[(2',6'-dimethyl[1,1'-biphenyl]-4-yl)carbonyl]-5-{[4-(2-hydroxyethyl)-1-piperazinyl]carbonyl}-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 2',6'-dimethyl[1,1'-biphenyl]-4carboxylic acid, and 2-(1-piperazinyl)ethanol, the title compound was obtained in 79% purity by HPLC. MS(ESI+): m/z=479.

Example 427

(3EZ,5S)-1-[(2',3-dimethyl[1,1'-biphenyl]-4-yl)carbonyl]-5-{[4-(2-hydroxyethyl)-1-piperazinyl]carbonyl}-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 2',3-dimethyl[1,1'-biphenyl]-4-carboxylic acid, and 2-(1-piperazinyl)ethanol, the title compound was obtained in 86% purity by HPLC. MS(ESI+): m/z=479.

Example 428

(3EZ,5S)-1-[(2'-methyl[1,1'-biphenyl]-4-yl)carbonyl]-5-({4-[4-(trifluoromethyl)phenyl]-1-piperazinyl}carbonyl)-3-pyrrolidinone O-methyloxime Following the general method as outlined in Example 22, staring from (2S,4EZ)-1-(tert-butoxycarbonyl)-4-(methoxyimino)-2-pyrrolidinecarboxylic acid, 2'-methyl[1,1'-biphenyl]-4-carboxylic acid, and 1-[4-(trifluoromethyl)phenyl] piperazine, the title compound was obtained in 89% purity by HPLC. MS(ESI+): m/z=565.

Example 429

(3EZ,5S)-1-[(2'-methyl[1,1'-biphenyl]-4yl)carbonyl]-5-({4-[3-(trifluoromethyl)phenyl]-1-piperazinyl}carbonyl)-3-pyrrolidinone O-methyloxime Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 1-[3-(trifluoromethyl)phenyl]piperazine, the title compound was obtained in 88% purity by HPLC. MS(ESI+): m/z=565.

Example 430

(2S,4EZ)-4-(methoxyimino)-1-[(2'-methyl[1,1'-biphenyl]-4-yl)carbonyl]-2-pyrrolidinecarboxamide Following the general method-as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and ammonia (0.5M in dioxane), the title compound was obtained in 88% purity by HPLC. MS(ESI+): m/z=352.

Example-431

(2S,4EZ)-4-(methoxyimino)-N-methyl-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and methylamine (2M in methanol), the title compound was obtained in 96% purity by HPLC. MS(ESI+): m/z=366.

Example 432

(2S,4EZ)-4-(methoxyimino)-N,N-dimethyl-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and dimethylamine (5.6M in ethanol), the title compound was obtained in 94% purity by HPLC. MS(ESI+): m/z=380.

Example 433

(2S,4EZ)-N-[(3R)-3-hydroxy-3-phenylpropyl]-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyl)-2-pyrrolidinecarboxylic acid, 2'-methyl[1,1'-biphenyl]-4-carboxylic acid, and (1R)-3-amino-1-phenyl-1-propanol, the title compound was obtained in 94% purity by HPLC. MS(ESI+): m/z=486.

Example 434

(2S,4EZ)-N-[(3S)-3-hydroxy-3-phenylpropyl]-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and (1S)-3-amino-1-phenyl-1-propanol, the title compound was obtained in 91% purity by HPLC. MS(ESI+): m/z=486.

Example 435

(2S,4EZ)-1-([1,1'-biphenyl]-4-ylcarbonyl)-N-[(3R)-3-hydroxy-3-phenylpropyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (1R)-3-amino-1-phenyl-1-propanol, the title compound was obtained in 94% purity by HPLC. MS(ESI+): m/z=472.

Example 436

(2S,4EZ)-1-([1,1'-biphenyl]-4-ylcarbonyl)-N-[(3S)-3-hydroxy-3-phenyl-propyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4-carbonyl chloride, and (1S)-3-amino-1-phenyl-1-propanol, the title compound was obtained in 93% purity by HPLC. MS(ESI+): m/z=472.

Example 437

(2S,4EZ)-N-[(2S)-2-hydroxy-2-phenylethyl]-4-(methoxyimino)-1-{[2'-(trifluoromethyl)[1,1'-biphenyl]-4-yl]carbonyl}-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-(trifluoromethyl)[1,1'-biphenyl]-4-carboxylic acid, and (1S)-2-amino-1-phenylethanol, the title compound was obtained in 87% purity by HPLC. MS(ESI+): m/z=526.

Example 438

(2S,4EZ)-N-[(2S)-2-hydroxy-2-phenylethyl]-4-(methoxyimino)-1-{[2'-chloro[1,1'-biphenyl]-4-yl]carbonyl}-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-chloro[1,1'-biphenyl]-4-carboxylic acid, and (1S)-2-amino-1-phenylethanol, the title compound was obtained in 89% purity by HPLC. MS(ESI+): m/z=492.

Example 439

(2S,4EZ)-N-(2-hydroxyphenyl)-4-(methoxyimino)-1-[(2'-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[1,1'-biphenyl]-4-carboxylic acid, and 2-aminophenol, the title compound was obtained in 88% purity by HPLC. MS(ESI+): m/z=444.

Example 440

(2S,4EZ)-N-[2-(hydroxyethyl)phenyl]-4-(methoxyimino)-1-[(2'-methyl-[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2'-methyl[l,1'-biphenyl]-4-carboxylic acid, and (2-aminophenyl)methanol, the title compound was obtained in 86% purity by HPLC. MS(ESI+): m/z=458.

Example 441

(2S,4EZ)-N-[(2S)-2-hydroxy-2-phenylethyl]-4-(methoxyimino)-1-[(2-methyl[1,1'-biphenyl]-4-yl)carbonyl]-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2-methyl[1,1'-biphenyl]-4-carboxylic acid, and (1S)-2-amino-1-phenylethanol, the title compound was obtained in 95% purity by HPLC. MS(ESI+): m/z=472.

Example 442

(2S,4E and 4Z)-1-([1,1'-biphenyl]-4-ylcarbonyl)-N-[(2S)-2-hydroxy-2-phenylethyl]-4-(methoxyimino)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, [1,1'-biphenyl]-4carbonyl chloride, and (1S)-2-amino-1-phenylethanol, the title compounds were obtained as a mixture of E/Z-isomers of the oxime functionality. Separation of the isomers by flash chromatography yielded (2S,4E)-1-([1,1'-biphenyl]-4-ylcarbonyl)-N-[(2S)-2-hydroxy-2-phenylethyl]-4-(methoxyimino)-2-pyrroidinecarboxamide in 98.8% purity and (2S,4Z)-1-([1,1'-biphenyl]-4-ylcarbonyl)-N-[(2S)-2hydroxy-2-phenylethyl]-4-(methoxyimino)-2-pyrrolidinecarboxamide in 97.4% purity by HPLC. MS(ESI+): m/z=458.

Example 443

(2S,4EZ)-4-(methoxyimino)-1-[(2'-methyl[1,1'-biphenyl]-4-yl)carbonyl]-N-(2-phenylethyl)-2-pyrrolidinecarboxamide Following the general method as outlined in Example 22, starting from (2S,4EZ)-1-(tert-butoxycarbonyl)-4-(methoxyimino)-2-pyrrolidinecarboxylic acid, 2-methyl[1,1'-biphenyl]-4-carboxylic acid, and 2-phenylethanamine, the title compound was obtained in 89% purity by HPLC. MS(ESI+): m/z=456.

Example 444

Preparation of a Pharmaceutical Formulation

The following formulation examples illustrate representative pharmaceutical compositions according to the present invention being not restricted thereto.

Formulation 1—Tablets

A pyrrolidine compound of formula I is admixed as a dry powder with a dry gelatin binder in an approximate 1:2 weight ration. A minor amount of magnesium stearate is added as a lubricant. The mixture is formed into 240–270 mg tablets (80–90 mg of active pyrrolidine compound per tablet) in a tablet press.

Formulation 2—Capsules

A pyrrolidine compound of formula I is admixed as a dry powder with a starch diluent in an approximate 1:1 weight ratio. The mixture is filled into 250 mg capsules (125 mg of active pyrrolidine compound per capsule).

Formulation 3—Liquid

A pyrrolidine compound of formula I (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A pyrrolidine compound of formula I is admixed as a dry powder with a dry gelatin binder in an approximate 1:2 weight ratio. A minor amount of magnesium stearate is added as a lubricant. The mixture is formed into 450–900 mg tablets (150–300 mg of active pyrrolidine compound) in a tablet press.

Formulation 5—Injection

A pyrrolidine compound of formula I is dissolved in a buffered sterile saline injectable aqueous medium to a concentration of approximately 5 mg/ml.

Example 445

Biological Assays a) In Vitro Binding Assay (SPA)

Membranes from HEK293EBNA cells expressing the hOT receptor were resuspended in buffer containing 50 mM Tris-HCl, pH 7.4,5 mM MgCl2 and 0.1% BSA (w/v). The membranes (2–4 μg) were mixed with 0.1 mg wheat-germ aglutinin (WGA) SPA bead (type A) and increasing concentrations of [$^{125}$I]-OVTA (for saturation binding experiments) or 0.2 nM [$^{125}$I]-OVTA (for competition binding experiments). Non specific binding was deter-mined in the presence of 1 μM Oxytocin. The total assay volume was 100 μl. The plates were incubated at room temperature for 30 min and counted on a Mibrobeta plate counter. The competition binding data were analysed using the iterative, nonlinear, curve-fitting program, Prism.

b) Biological Results—Discussion

The binding affinities to the oxytocin receptor of the pyrrolidine derivatives claimed in the formula I were assessed using the above described in vitro biological assay. Representative values for some example compounds are given in Table 1 below. The values refer to the binding capacity of the example compounds according to formula I to the Oxytocin receptor. From the values shown in Table 1 it can be derived that said test compounds according to formula I do show a significant binding to the Oxytocin receptor.

TABLE 1

| Structure | IUPAC-Name | Binding affinity human OT-R $IC_{50}$ (μM) |
|---|---|---|
| 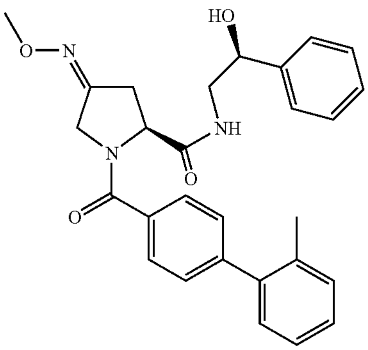 | (2S,4E)-N-[(2S)-2-hydroxy-2-phenylethyl]-4-(methoxyimino-1-[(2'-methyl[1,1'-biphenyl]-4-yl)carbonyl]-2-pyrrolidinecarboxamide | 0.13 |
| 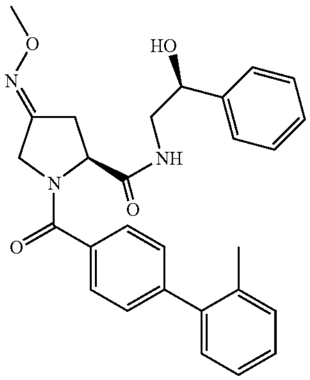 | (2S,4Z)-N-[(2S)-2-hydroxy-2-phenylethyl]-4-(methoxyimino-1-[(2'-methyl[1,1'-biphenyl]-4-yl)carbonyl]-2-pyrrolidinecarboxamide | 0.07 |

TABLE 1-continued

| Structure | IUPAC-Name | Binding affinity human OT-R $IC_{50}$ (μM) |
|---|---|---|
| 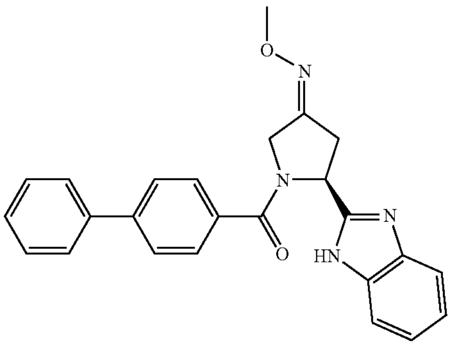 | (3Z,5S)-5-(1H-benzimidazol-2-yl)-1-([1,1'-biphenyl]-4-ylcarbonyl)-3-pyrrolidinone O-methyloxime | 0.63 |
| 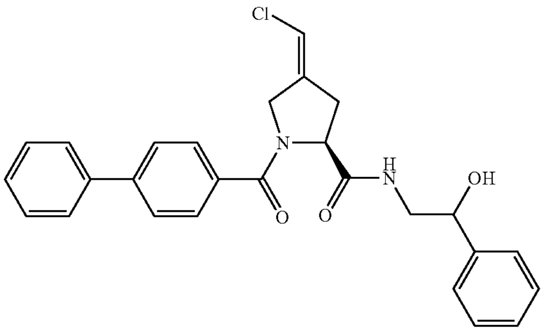 | (2S,4Z)-1-([1,1'-biphenyl]-4-ylcarbonyl)-4-(chloromethylene)-N-[(2RS)-2-hydroxy-2-phenylethyl]-2-pyrrolidinecarboxamide | 0.35 |
| 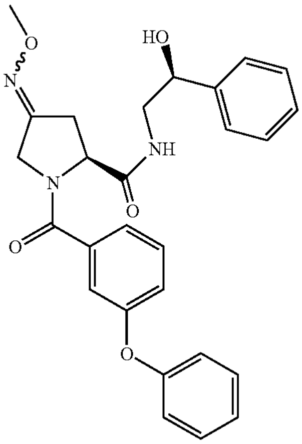 | (2S,4EZ)-N-[(2RS)-2-hydroxy-2-phenylethyl]-4-(methoxyimino-1-(3-phenoxybenzoyl)-2-pyrrolidinecarboxamide | 2.3 |
| 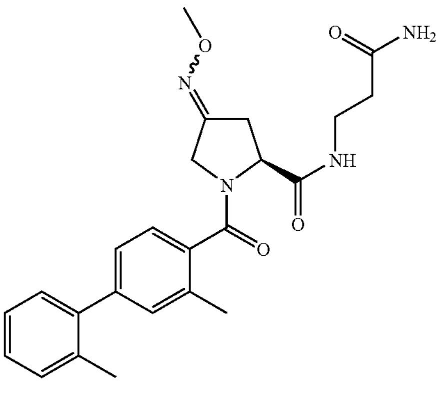 | (2S,4EZ)-N-(3-amino-3-oxopropyl)-1-[(2',3-dimethyl[1,1'-biphenyl]-4-yl)carbonyl]-4-(methoxyimino)-2-pyrrolidinecarboxamine | 0.54 |

TABLE 1-continued

| Structure | IUPAC-Name | Binding affinity human OT-R $IC_{50}$ (μM) |
|---|---|---|
| 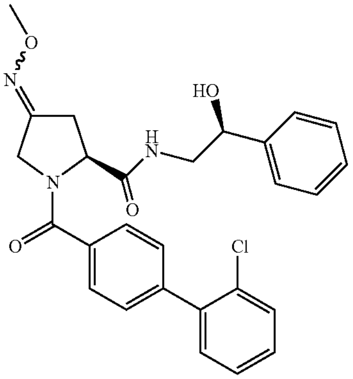 | (2S,4EZ)-1-[(2'-chloro[1,1'-biphenyl]-4-yl)carbonyl]-N-[(2S)-2-hydroxy-2-phenylethyl]-4-(methoxyimino)-2-pyrrolidinecarboxamide | 0.17 |
| 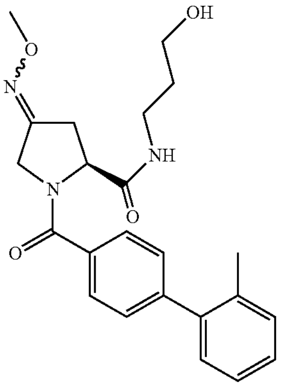 | (2S,4EZ)-N-(3-hydroxypropyl)-4-(methoxyimino)-1-[(2'-methyl[1,1'-biphenyl]-4-yl)carbonyl]-2-pyrrolidinecarboxamide | 0.37 |
| 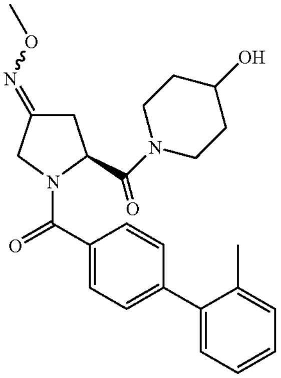 | (3EZ,5S)-5-[(4-hydroxy-1-piperidinyl)carbonyl]-1-[(2'-methyl[1,1'-biphenyl]-4-yl)carbonyl]-3-pyrrolidinone O-methyloxime | 0.30 |

TABLE 1-continued

| Structure | IUPAC-Name | Binding affinity human OT-R $IC_{50}$ (μM) |
|---|---|---|
| 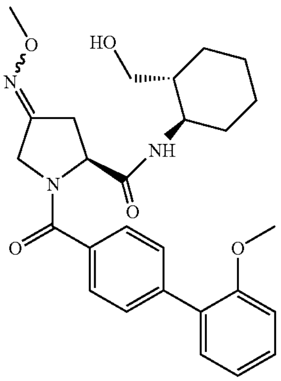 | (2S,4EZ)-N-[(1R,2R)-2-(hydroxymethyl)cyclohexyl]-1-[(2'-methoxy[1,1'-biphenyl]-4-yl)carbonyl]-4-(methoxyimino)-2-pyrrolidinecarboxamide | 0.55 |

According to a preferred embodiment, the compounds display binding affinities ($K_i$ (μM)) of less 0.40 μM, more preferred of less than 0.1 μM.

c) Functional Assay No. 1: Inhibition of $Ca^{2+}$-Mobilization by FLIPR

Preparing the plates: FLIPR-plates were pre-coated with PLL 10 μg/ml+0.1% gelatine for 30 min up to 2 days at 37° C. (for HEK-cells). The cells were plated out into 96-well plates (60000 cells/well).

Labelling with fluo-4: 50 μg fluo-4 were dissolved in 20 μl pluronic acid (20% in DMSO). The dissolved fluo-4 was then diluted in 10 ml DMEM-F12 medium without FCS. The medium was removed from the plates, followed by one wash with DMEM-F12 medium. Now, 100 μl of the DMEM-F12 medium containing fluo-4 were added and the cells incubated for 1–1.5 h (CHO-cells), and 1.5–2 h (HEK-cells).

Buffer: 145 mM NaCl, 5 mM KCl, 1 mM $MgCl_2$, 10 mM Hepes, 10 mM Glucose, EGTA. Adjust to pH 7.4.

Preparation of agonists and antagonists: A minimum of 80 μl/well of agonists and anta-gonists (5×) in the above buffer (1×) were prepared (96-well plates).

The activities of the pyrrolidine derivatives according to formula I were assessed using the above described in vitro biological assay. Representative values for some example compounds are given in Table 2 below. The values refer to the capacity of the example compounds according to formula I to effectively antagonize oxytocin-induced intracellular $Ca^{2+}$-mobilization mediated by the Oxytocin receptor. From the values shown in Table 2 it can be derived that said example test compounds according to formula I do exhibit a significant activity as Oxytocin receptor antagonists.

TABLE 2

| Structure | IUPAC-Name | Inhibition of $Ca^{2+}$ mobilization, hOT-R $IC_{50}$ (μM) |
|---|---|---|
| 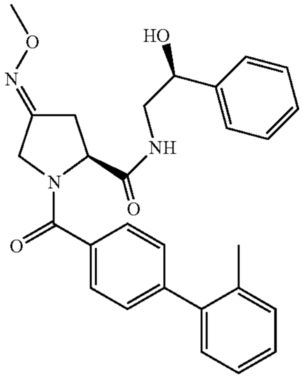 | (2S,4E)-N-[(2S)-2-hydroxy-2-phenylethyl]-4-(methoxyimino)-1-[(2'-methyl[1,1'-biphenyl]-4-yl)carbonyl]-2-pyrrolidinecarboxamide | 0.07 |

TABLE 2-continued

| Structure | IUPAC-Name | Inhibition of $Ca^{2+}$ mobilization, hOT-R $IC_{50}$ (μM) |
|---|---|---|
| 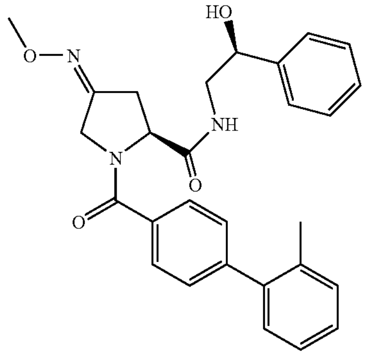 | (2S,4Z)-N-[(2S)-2-hydroxy-2-phenylethyl]-4-(methoxyimino)-1-[(2'-methyl[1,1'-biphenyl]-4-yl)carbonyl]-2-pyrrolidinecarboxamide | 0.03 |
| 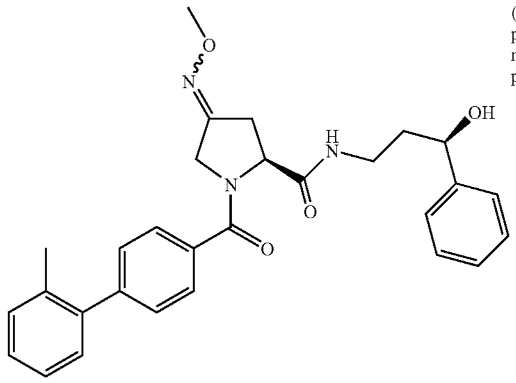 | (2S,4EZ)-N-[(3R)-3-hydroxy-3-phenylpropyl]-4-(methoxyimino)-1-[(2'-methyl[1,1'-biphenyl]-4-yl)carbonyl]-2-pyrrolidinecarboxamide | 0.32 |
| 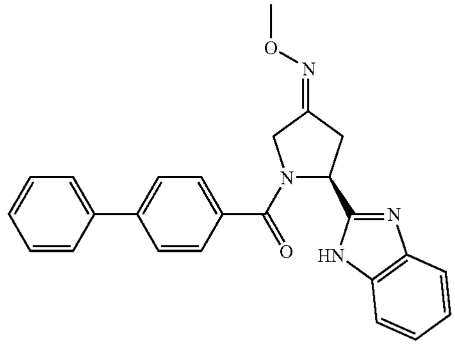 | (3Z,5S)-5-(1H-benzimidazol-2-yl)-1-([1,1'-biphenyl]-4-ylcarbonyl)-3-pyrrolidinone O-methyloxime | 0.4 |
| 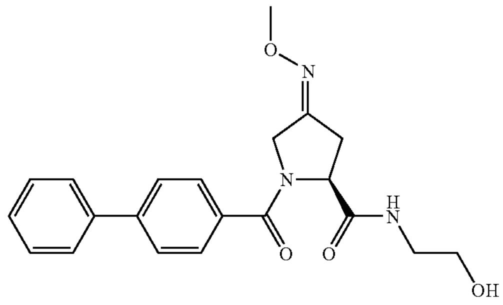 | (2S,4Z)-1-([1,1'biphenyl]-4-ylcarbonyl)-N-(2-hydroxyethyl)-4-(methoxyimino)-2-pyrrolidinecarboxamide | 0.65 |

d) Functional Assay No. 2: Inhibition of IP3-Synthesis in HEK/EBNA-OTR Cells

Stimulation of the cells: BEK/EBNA OTR(rat or human) cells were plated out into costar 12-well plates, and equilibrated for 15–24 h with [$^3$H]-inositol in medium without inositol supplement, with 1% FCS (0.5 ml/well). 4 µCi/ml were-used. After this, the medium containing the label was aspirated. Then was added DMEM (without FCS, inositol), 20 mM Hepes, 1 mg/ml BSA containing 10 mM LiCl (freshly prepared), for 10–15 min at 37° C. The agonists and antagonists were added for the time required (15–45 min), followed by aspiration of the medium. The reaction was stopped with 1 ml STOP-solution (0.4 M perchloric acid), and let sit for 5–10 min at RT (not longer). Then, 0.8 ml were transferred into tubes containing 0.4 ml of neutralizing solution (0.72 M KOH/0.6M $KHCO_3$), and the tubes vortexed and kept in the cold at least for 2 h. At this stage, samples could be kept over a prolonged period of time.

Separation of IP's: The samples were spun in a table top centrifuge at 3000–4000 rpm for 15 min. 1 ml of the supernatant was transferred to new tubes containing 2.5 ml $H_2O$. Packed resin (0.8 ml) was equilibrated with 20 ml $H_2O$, and the whole samples poured onto the columns. To discard free inositol, two washes with 10 ml $H_2O$ were carried out.

Elution of total IP's: The elution was achieved using 3 ml 1M ammonium formate/0.1M formic acid. The eluant was collected in scintillation counting tubes, followed by addition of 7 ml of scintillation liquid. Mixing and counting concluded the operation.

The activities of the pyrrolidine derivatives claimed in the formula I were assessed using the above described in vitro biological assay. Representative values for some example compounds are given in Table 3 below. The values refer to the capacity of the example compounds according to formula I to effectively antagonize oxytocin-induced IP3-synthesis mediated by the Oxytocin receptor. From the values shown in Table 3 it can be derived that said example test compounds according to formula I do exhibit a significant activity as Oxytocin receptor antagonists.

TABLE 3

| Structure | IUPAC-Name | Inhibition of IP3-synthesis, ratOT-R $IC_{50}$ (82 M) |
|---|---|---|
| 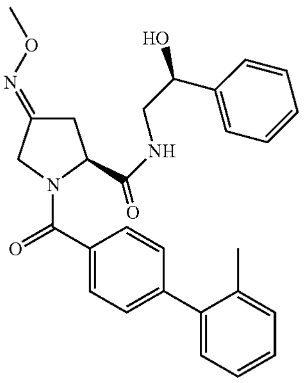 | (2S,4E)-N-[(2S)-2-hydroxy-2-phenylethyl]-4-(methoxyimino)-1-[(2'-methyl[1,1'-biphenyl]-4-yl)carbonyl]-2-pyrrolidinecarboxamide | 0.33 |
| 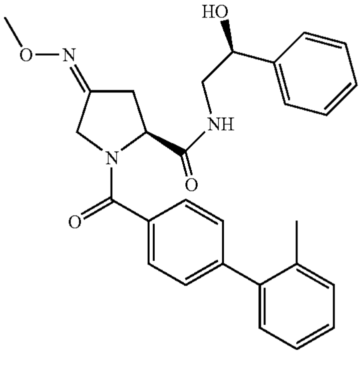 | (2S,4Z)-N-[(2S)-2-hydroxy-2-phenylethyl]-4-(methoxyimino)-1-[(2'-methyl[1,1'-biphenyl]-4-yl)carbonyl]-2-pyrrolidinecarboxamide | 0.03 |

TABLE 3-continued

| Structure | IUPAC-Name | Inhibition of IP3-synthesis, ratOT-R $IC_{50}$ (82 M) |
|---|---|---|
| 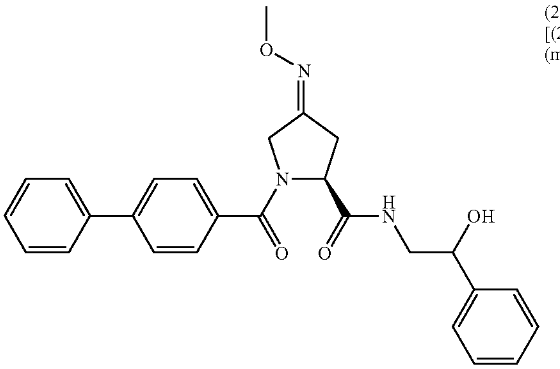 | (2S,4Z)-1-([1,1'-biphenyl]-4-ylcarbonyl)-N-[(2RS)-2-hydroxy-2-phenylethyl]-4-(methoxyimino)-2-pyrrolidinecarboxamide | 0.35 |

e) In Vivo Model for Inhibition of Uterine Contractions

Non-pregnant Charles River CD(SD) BR female rats (9–10 weeks old, 200–250 g) were treated at 18 and 24 hours before the experiment with 250 μg/kg, i.p. diethylstilbestrol (DES). For the assay, the animal was anaesthetised by urethane (1.75 g/kg, i.p.) and placed on an homeothermic operating table. The trachea was isolated and cannulated with a suitable polyethylene (PE) tubing. A midline incision at the hypogastrium level was made and one uterine horn exposed, its cephalic end cannulated with a PE240 tubing and, after filling the internal cavity with 0.2 ml of sterile physiological saline, connected to a "Gemini" amplifying/recording system via a P23ID Gould Statham pressure transducer. For the i.v. route of administration of the test compounds, one jugular vein was isolated and cannulated with a PE60 tubing connected to a butterfly needle to allow the administration by a dispensing syringe. In the case of intraduodenal administration of the test compounds, the duodenum was isolated and similarly cannulated through a small incision in its wall. One carotid artery was also isolated and cannulated with PE60 catheter and connected to a suitable syringe for blood sample collection (see below). After a stabilization period, the same dose of oxytocin was repeatedly injected intravenously at 30-min intervals. When comparable contractile responses of the uterus to the selected dose of oxytocin were obtained, the dose of the test or reference compound was administered. Further injections of the same dose of oxytocin were then made for a suitable time after treatment to assess inhibitory effects of the compounds under study. The contractile response of the uterus to oxytocin was quantified by measuring the intrauterine pressure and the number of contractions. The effect of the reference and test compounds were evaluated by comparing pre- and post-treatment pressure values. In addition, at 2, 30, 90 and 210 minutes after test compound administration, a 0.5-ml blood sample was withdrawn from the cannulated carotid artery of each experimental animal. Plasma was obtained by standard laboratory procedure and the resulting samples were stored at −20° C.

The activities of the pyrrolidine derivatives claimed in the formula I were assessed using the above described in vivo biological assay. Representative values for one example compound are given in Table 4 below. The values refer to the capacity of the example compound according to formula I to effectively antagonize oxytocin-induced -uterine contractions in the rat. From the values shown in Table 4 it can be derived that said example test compound according to formula I does exhibit a significant activity as tocolytic, i.e. uterine-relaxing, agent.

TABLE 4

| Structure | IUPAC-Name | Route of administration/ Vehicle | % Reduction of Utenne Contraction | Dose (mg/kg) |
|---|---|---|---|---|
| 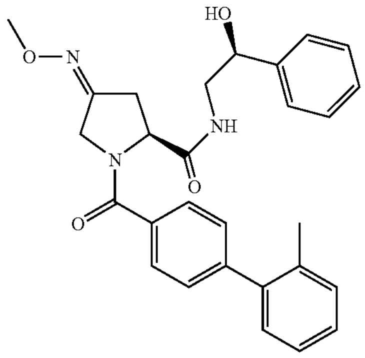 | (2S,4Z)-N-[(2S)-2-hydroxy-2-phenylethyl]-4-(methoxyimino)-1-[(2'-methyl[1,1'-biphenyl]-4-yl)carbonyl]-2-pyrrolidinecarboxamide | intravenous; PEG400/saline 50:50; 5 ml/kg infusion | −23.8 ± 4.1<br>−27.6 ± 4.6<br>−50.4 ± 5.8<br>−65.6 ± 6.4<br>−76.5 ± 4.24 | 0.3<br>1<br>3<br>10<br>30 |

The invention claimed is:

1. Pyrrolidine compounds according to formula I

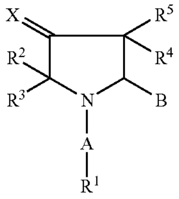

I as well as its geometrical isomers, its optically active forms as enantiomers, diastereomers and its racemate forms, as well as pharmaceutically acceptable salts thereof, wherein X is selected from the group consisting of $NOR^6$, and $NNR^6R^7$;

A is selected from the group consisting of —(C═O)—, —(C═O)—O—, —C(═NH)—, and —(C═O)—NH—, —(C═S)—NH, B is —(C═O)—$NR^8R^9$ $R^1$ is selected from the group consisting of unsubstituted or substituted $C_1$–$C_6$-alkyl, unsubstituted or substituted $C_2$–$C_6$-alkenyl, unsubstituted or substituted $C_2$–$C_6$-alkynyl, unsubstituted or substituted aryl, unsubstituted or substituted saturated or unsaturated 3–8-membered cycloalkyl, acyl, unsubstituted or substituted $C_1$–$C_6$-alkyl aryl, said cycloalkyl or aryl groups may be fused with 1–2 further cycloalkyl or aryl;

$R^2$, $R^3$, $R^4$ and $R^5$ are independently selected from each other from the group consisting of hydrogen, halogen, $C_1$–$C_6$-alkyl, $C_1$–$C_6$-alkoxy;

$R^6$ and $R^7$ are independently selected from the group comprising or consisting of hydrogen, unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted alkoxy, unsubstituted or substituted thioalkoxy, halogen, cyano, nitro, acyl, alkoxycarbonyl, aminocarbonyl, unsubstituted or substituted saturated or unsaturated 3–8-membered cycloalkyl, unsubstituted or substituted aryl, unsubstituted or substituted $C_1$–$C_6$-alkyl aryl;

$R^8$ and $R^9$ are independently selected from the group consisting of hydrogen, unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted saturated or unsaturated 3–8-membered cycloalkyl, unsubstituted or substituted aryl.

2. A pyrrolidine compound according to claim 1, wherein B is a group —(C═O)—$NHR^9$, in which $R^9$ is selected from the group consisting of unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted saturated or unsaturated 3–6-membered cycloalkyl, unsubstituted or substituted aryl, unsubstituted or substituted $C_1$–$C_2$-alkyl aryl.

3. A pyrrolidine compound according to any of the preceding claims, wherein X is $NOR^6$, and $R^6$ is selected from the group consisting of H, unsubstituted or substituted $C_1$–$C_6$ alkyl, unsubstituted or substituted $C_2$–$C_6$ alkenyl, unsubstituted or substituted $C_2$–$C_6$ alkynyl, unsubstituted or substituted acyl, unsubstituted or substituted aryl, unsubstituted or substituted saturated or unsaturated 3–8-membered cycloalkyl, unsubstituted or substituted $C_1$–$C_6$-alkyl aryl, said cycloalkyl, or aryl groups may be fused with 1–2 further cycloalkyl or aryl groups.

4. A pyrrolidine compound according to claim 3, wherein $R^6$ is H, $CH_3$, unsubstituted or substituted $CH_2$-phenyl or allyl.

5. A pyrrolidine compound according to claim 1, wherein A is —(C═O)—, or —(C═O)—NH.

6. A pyrrolidine compound according to claim 5, wherein A is —(C═O)—.

7. A pyrrolidine compound according to claim 1, wherein $R^1$ is an $C_1$–$C_6$-alkyl, $C_2$–$C_6$-alkenyl, unsubstituted or substituted $C_2$–$C_6$-alkynyl, aryl, saturated or unsaturated 3–8-membered cycloalkyl, $C_1$–$C_6$-alkyl aryl.

8. A pyrrolidine compound according to claim 7, wherein $R^1$ is an $C_1$–$C_6$-alkyl or aryl group.

9. A pyrrolidine compound according to claim 8, wherein $R^1$ is biphenyl.

10. A pyrrolidine compound according to claims 1 or 2, wherein X is ═$NOR^6$, $R^6$ is a $C_1$–$C_6$-alkyl or aryl or $C_1$–$C_6$-alkyl aryl group, A is —(C═O)— and $R^1$ is a $C_1$–$C_6$-alkyl or aryl or $C_1$–$C_6$-alkyl aryl group.

11. A pyrrolidine compound according claim 10, wherein X is =NOR$^6$, R$^6$ is methyl, B is an amido group of the formula —(C=O)NHR$^9$, wherein R$^9$ is an unsubstituted or substituted $C_1$–$C_6$-alkyl aryl group, A is —(C=O)— and R$^1$ is a biphenyl or an acetylmethyl group.

12. A pyrrolidine compound according to claim 11, wherein X is =NOCH$_3$, B is an amido group of the formula —(C=O)NHR$^9$, wherein R$^9$ is a substituted phenylethyl group, A is —(C=O)— and R$^1$ is a substituted biphenyl.

13. A pharmaceutical composition containing at least one pyrrolidine compound according to claim 1, and a pharmaceutically acceptable carrier, diluent or excipient thereof.

14. Process for the preparation of a pyrrolidine compound according to claim 1, wherein the following reaction is performed:

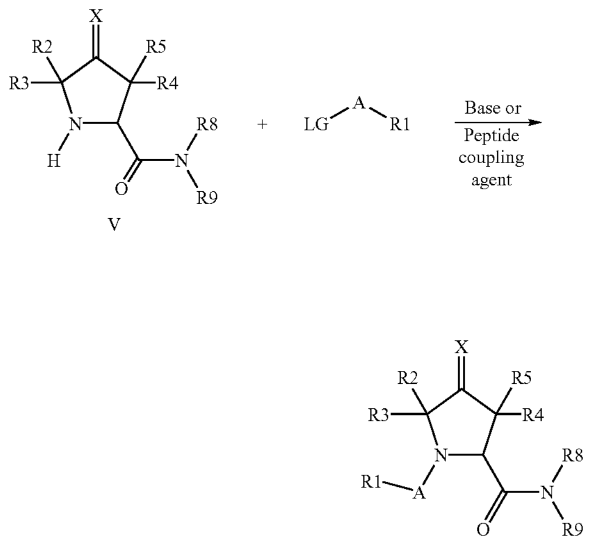

V

Ia whereby LG is a leaving group and the substituents R$^1$–R$^9$, A and X are as above defined.

15. Process for the preparation of a pyrrolidine compound according to claim 1, wherein the following reaction is performed:

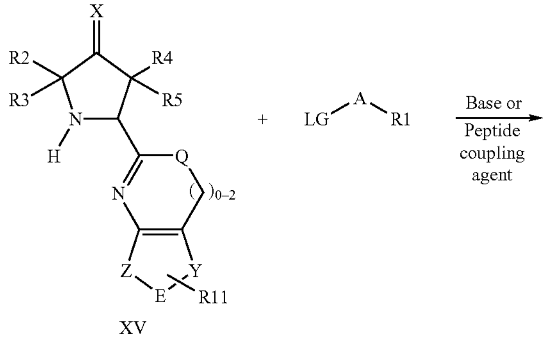

XV

-continued

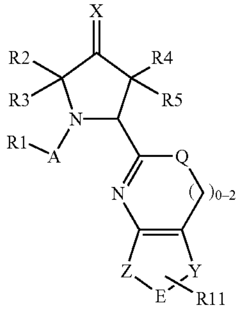

Ib whereby LG is a leaving group and the substituents R$^1$–R$^5$, R$^{11}$, A, E, Q, X, Y and Z are as above defined.

16. Process according to claim 15, wherein compound XV is obtained as follows:

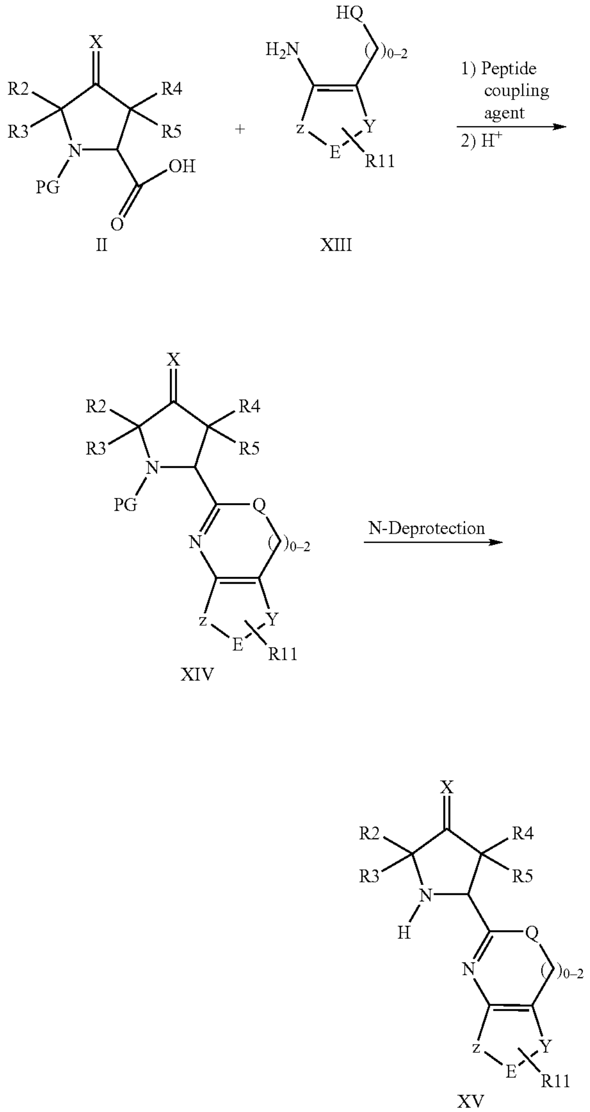

II

XIII

XIV

XV

17. A pyrrolidine compound according to claim 4, wherein $R^6$ is H or $CH_3$.

18. A method for treating premature labor, premature birth, and dysmenorrhea, comprising administering the pharmaceutical composition of claim 13 to a patient in need thereof.

19. A method according to claim 18, wherein said administering step administers the pharmaceutical composition orally to the patient.

20. A pyrrolidine compound according to claim 1, selected from the following group:

(2S,4EZ)-1-([1,1'-biphenyl]-4-ylcarbonyl)-N-(2-methoxyethyl)-4-(methoxyimino)-2-pyrrolidinecarboxamide (2S,4EZ)-1-([1,1'-biphenyl]-4-ylcarbonyl)-N-(2-hydroxyethyl)-4-(methoxyimino)-2-pyrrolidinecarboxamide (2S,4EZ)-1-([1,1'-biphenyl]-4-ylcarbonyl)-N-[(2RS)-2-hydroxy-2-phenylethyl]-4-(methoxyimino)-2-pyrrolidinecarboxamide (2S,4EZ)-1-acetoacetyl-N-benzyl-4-(methoxyimino)-2-pyrrolidinecarboxamide (2S,4EZ)-1-[(4-chlorophenoxy)acetyl]-4-{[(3,4-dichlorobenzyl)oxy]imino}-N-[(2RS)-2-hydroxy-2-phenylethyl]-2-pyrrolidinecarboxamide (2S,4EZ)-N-allyl-1-([1,1'-biphenyl]-4-ylcarbonyl)-4-(methoxyimino)-2-pyrrolidine-carboxamide (2S,4EZ)-1-acetyl-N-cyclopropyl-4-{[(3,4-dichlorobenzyl)oxy]imino}-2-pyrrolidine-carboxamide (2S,4EZ)-N-benzyl-1-([1,1'-biphenyl]-4-ylcarbonyl)-4-(methoxyimino)-N-methyl-2-pyrrolidinecarboxamide (2S,4EZ)-1-([1,1'-biphenyl]-4-ylcarbonyl)-N-[2-(diethylamino)ethyl]-4-(methoxyimino)-2-pyrrolidinecarboxamide (2S,4EZ)-1-([1,1'-biphenyl]-4-ylcarbonyl)-N-(3,4-dimethoxybenzyl)-4-(methoxyimino)-2-pyrrolidinecarboxamide (2S,4EZ)-1-acetoacetyl-4-(methoxyimino)-N-(1-naphthylmethyl)-2-pyrrolidinecarboxamide (2S,4EZ)-N-allyl-4-{[(3,4-dichlorobenzyl)oxy]imino}-1-(diphenylacetyl)-2-pyrrolidinecarboxamide (2S)-1-([1,1'-biphenyl]-4-ylcarbonyl)-N-[(2RS)-2-hydroxy-2-phenylethyl]-4-methylene-2-pyrrolidinecarboxamide (2S,4EZ)-4-benzylidene-N-[2-(diethylamino)ethyl]-1-(diphenylacetyl)-2-pyrrolidinecarboxamide (2S,4EZ)-1-acetyl-4-{[(3,4-dichlorobenzyl)oxy]imino}-N-[(2RS)-2-hydroxy-2-phenylethyl]-2-pyrrolidinecarboxamide (2S,4EZ)-4-(methoxyimino)-N-(1-naphthylmethyl)-1-(phenoxyacetyl)-2-pyrrolidinecarboxamide (2S,4EZ)-N-benzyl-1-(diphenylacetyl)-4-(methoxyimino)-2-pyrrolidinecarboxamide (2S,4EZ)-1-([1,1'-biphenyl]-4-ylcarbonyl)-4-{[(3,4-dichlorobenzyl)oxy]imino}-N-[2-(diethylamino)ethyl]-2-pyrrolidinecarboxamide (2S,4EZ)-N-benzyl-1-([1,1'-biphenyl]-4-ylcarbonyl)-4-(methoxyimino)-2-pyrrolidinecarboxamide (2S,4EZ)-N-benzyl-1-(diphenylacetyl)-4-(ethoxyimino)-2-pyrrolidinecarboxamide (2S,4EZ)-$N^2$-cyclopropyl-4-{[(3,4-dichlorobenzyl)oxy]imino }-$N^1$-(3-methoxyphenyl)-1,2-pyrrolidinedicarboxamide (2S,4EZ)-1-(diphenylacetyl)-N-[(2RS)-2-hydroxy-2-phenylethyl]-4-{[(4-methoxybenzyl)oxy]-imino}-2-pyrrolidinecarboxamide (2S,4EZ)-N-benzyl-1-(diphenylacetyl)-4-{[(4-methoxybenzyl)oxy]imino}-2-pyrrolidinecarboxamide (2S,4EZ)-1-acetoacetyl-N-cyclopropyl-4-{[(3,4-dichlorobenzyl)oxy]imino}-2-pyrrolidinecarboxamide (2S,4EZ)-4-{[(3,4-dichlorobenzyl)oxy]imino}-$N^2$-[(2RS)-2-hydroxy-2-phenylethyl]-$N^1$-pentyl-1,2-pyrrolidinedicarboxamide (2S,4EZ)-4-[(benzyloxy)imino]-N-(1-naphthylmethyl)-1-(phenoxyacetyl)-2-pyrrolidinecarboxamide (2S,4EZ)-N-cyclopropyl-4-{[(3,4-dichlorobenzyl)oxy]imino}-1-(diphenylacetyl)-2-pyrrolidinecarboxamide (2S,4EZ)-N-cyclopropyl-4-{[(3,4-dichlorobenzyl)oxy]imino}-1-(methoxyacetyl)-2-pyrrolidinecarboxamide (2s,4EZ)-N-[(2RS)-2-hydroxy-2-phenylethyl]-4-(methoxyimino)-1-[(2'-methyl[1,1'-biphenyl]-4-yl) carbonyl]-2-pyrrolidinecarboxamide (2S,4EZ)-1-([1,1'-biphenyl]-3-ylcarbonyl)-N-[(2RS)-2-hydroxy-2-phenylethyl]-4-(methoxyimino)-2-pyrrolidinecarboxamide (2S,4EZ)-1-(4-benzoylbenzyl)-N-[(2RS)-2-hydroxy-2-phenylethyl]-4-(methoxyimino)-2-pyrrolidinecarboxamide (2S,4EZ)-N-[(2RS)-2-hydroxy-2-phenylethyl]-4-(methoxyimino)-1-(3-phenoxybenzoyl)-2-pyrrolidinecarboxamide (2S,4EZ)-N-[(2RS)-2-hydroxy-2-phenylethyl]-4-(methoxyimino)-1-(2-phenoxybenzoyl)-2-pyrrolidinecarboxamide (2S,4EZ)-N-[(2S)-2-hydroxy-2-phenylethyl]-4-(methoxyimino)-1-[(2'-methyl[1,1'-biphenyl]-4-yl)carbonyl]-2-pyrrolidinecarboxamide (2S,4EZ)-N-[(2R)-2-hydroxy-2-phenylethyl]-4-(methoxyimino)-1-[(2'-methyl[1,1'-biphenyl]-4-yl)carbonyl]-2-pyrrolidinecarboxamide (2S,4EZ)-N-(2-hydroxyethyl)-4-(methoxyimino)-1-[(2'-methyl[1,1'-biphenyl]-4-yl)carbonyl]-2-pyrrolidinecarboxamide (2S,4EZ)-N-(2-hydroxyethyl)-4-(methoxyimino)-N-methyl-1-[(2'-methyl[1,1'-biphenyl]-4-yl)carbonyl]-2-pyrrolidinecarboxamide (2S,4EZ)-1-([1,1'-biphenyl]-4-ylcarbonyl)-N-(trans-4-hydroxycyclohexyl)-4-(methoxyimino)-2-pyrrolidinecarboxamide (2S,4EZ)-1-([1,1'-biphenyl]-4-ylcarbonyl)-N-[(1R,2R)-2-(hydroxymethyl)cyclohexyl]-4-(methoxyimino)-2-pyrrolidinecarboxamide (2S,4EZ)-1-([1,1'-biphenyl]-4-ylcarbonyl)-N-[(2RS)-2-hydroxy-3-phenoxypropyl]-4-(methoxyimino)-2-pyrrolidinecarboxamide (2S,4EZ)-1-([1,1'-biphenyl]-4-ylcarbonyl)-N-[(2RS)-2-hydroxy-2-(4-hydroxyphenyl)ethyl]-4-(methoxyimino)-2-pyrrolidinecarboxamide (2S,4EZ)-1-([1,1'-biphenyl]-4-ylcarbonyl)-N-[(1-hydroxycyclohexyl)methyl]-4-(methoxyimino)-2-pyrrolidinecarboxamide (2S,4EZ)-1-([1,1'-biphenyl]-4-ylcarbonyl)-N-[(2RS)-2-(3,4-dihydroxyphenyl)-2-hydroxyethyl]-4-(methoxyimino)-2-pyrrolidinecarboxamide (2S,4EZ)-1-([1,1'-biphenyl]-4-ylcarbonyl)-N-[(2RS)-2,3-dihydroxypropyl]-4-(methoxyimino)-2-pyrrolidinecarboxamide (2S,4EZ)-1-([1,1'-biphenyl]-4-ylcarbonyl)-N-[(2RS)-2-hydroxy-3-(4-methoxyphenoxy)propyl]-4-(methoxyimino)-2-pyrrolidinecarboxamide (2S,4EZ)-1-([1,1'-biphenyl]-4-ylcarbonyl)-N-[(2RS)-2-hydroxypropyl]-4-(methoxyimino)-2-pyrrolidinecarboxamide (2S,4EZ)-1-([1,1'-biphenyl]-4-ylcarbonyl)-N-[(2RS)-2-hydroxy-2-(4-nitrophenyl)ethyl]-4-(methoxyimino)-2-pyrrolidinecarboxamide (2S,4EZ)-N-{(2RS)-3-[4-(acetylamino)phenoxy]-2-hydroxypropyl}-1-([1,1'-biphenyl]-4-ylcarbonyl)-4-(methoxyimino)-2-pyrrolidinecarboxamide (2S,4EZ)-1-([1,1'-biphenyl]-4-ylcarbonyl)-N-[(2R)-2-hydroxy-2-phenylethyl]-4-(methoxyimino)-2-pyrrolidinecarboxamide (2S,4EZ)-1-([1,1'-biphenyl]-4-ylcarbonyl)-N-(3-hydroxypropyl)-4-(methoxyimino)-2-pyrrolidinecarboxamide (2S,4EZ)-1-([1,1'-biphenyl]-4-ylcarbonyl)-N-[(1S,2S)-2-hydroxycyclohexyl]-4-(methoxyimino)-2-pyrrolidinecarboxamide (2S,4EZ)-N-benzyl-1-([1,1'-biphenyl]-4-ylcarbonyl)-N-(2-hydroxyethyl)-4-(methoxyimino)-2-pyrrolidinecarboxamide (2S,4EZ)-1-([1,1'-biphenyl]-4-ylcarbonyl)-N-[(1S,2S)-2-hydroxy-1-(hydroxymethyl)-2-phenylethyl]-4-(methoxyimino)-2-pyrrolidinecarboxamide (2S,4EZ)-N-(2-anilinoethyl)-1-([1,1'-biphenyl]-4-ylcarbonyl)-4-(methoxyimino)-2-pyrrolidinecarboxamide (2S,4EZ)-N-(3-amino-3-oxopropyl)-1-([1,1'-biphenyl]-4-ylcarbonyl)-4-(methoxyimino)-2-pyrrolidinecarboxamide (2S,4EZ)-1-([1,1'-biphenyl]-4-ylcarbonyl)-N-(4-hydroxybutyl)-4-(methoxyimino)-2-pyrrolidinecarboxamide (2S,4E and 4Z)-N-[(2RS)-2-hydroxy-2-phenylethyl]-4-(methoxyimino)-1-[(2'-methyl[1,1'-biphenyl]-4-yl) carbonyl]-2-pyrrolidinecarboxamide (2S,4E and 4Z)-N-[(2S)-2-hydroxy-2-phenylethyl]-4-(methoxyimino)-1-[(2'-methyl[1,1'-biphenyl]-4-yl)carbonyl]-2-pyrrolidinecarboxamide (2S,4E and 4Z)-N-[(2R)-2-hydroxy-2-phenylmethyl]-4-(methoxyimino)-1-[(2'-methyl[1,1'-biphenyl]-4-yl)carbonyl]-2-pyrrolidinecarboxamide (2S,4EZ)-1-([1,1'-biphenyl]-4-ylcarbonyl)-N-[(1R,2S)-2-(hydroxymethyl)cyclohexyl]-4-(methoxyimino)-2-pyrrolidinecarboxamide (2S,4EZ)-1-([1,1'-biphenyl]-4-ylcarbonyl)-N-[2-hydroxy-1-(hydroxymethyl)ethyl]-4-(methoxyimino)-2-pyrrolidinecarboxamide (2S,4EZ)-N-[(1S,2R,3S,4R)-3-(aminocarbonyl)bicyclo[2.2.1]hept-5-en-2-yl]-1-([1,1'-biphenyl]-4-ylcarbonyl)-4-(methoxyimino)-2-pyrrolidinecarboxamide (2S,4EZ)-N-[(1S,2S,3R,4R)-3-(aminocarbonyl)bicyclo[2.2.1]hept-5-en-2-yl]-1-([1,1'-biphenyl]-4-ylcarbonyl)-4-(methoxyimino)-2-pyrrolidinecarboxamide (2S,4EZ)-1-([1,1'-biphenyl]-4-ylcarbonyl)-N-[(2S)-2-hydroxy-2-phenylethyl]-4-(methoxyimino)-2-pyrrolidinecarboxamide (2RS)-3-({[(2S,4EZ)-1-([1,1'-biphenyl]-4-ylcarbonyl)-4-(methoxyimino)pyrrolidinyl]-carbonyl}amino)-2-hydroxypropanoic acid (2S,4EZ)-N-[(1R,2S)-2-(aminocarbonyl)cyclohexyl[-1-([1,1'-biphenyl]-4-ylcarbonyl)-4-(methoxyimino)-2-pyrrolidinecarboxamide (2S,4EZ)-1-([1,1'-biphenyl]-4-ylcarbonyl)-N-[(1RS)-2-hydroxy-1-methylethyl]-4-(methoxyimino)-2-pyrrolidinecarboxamide (2S,4EZ)-1-([1,1'-biphenyl]-4-ylcarbonyl)-N-[(1S,2S)-2-hydroxy-1-(hydroxymethyl)-2-(4-nitrophenyl)ethyl]-4-(methoxyimino)-2-pyrrolidinecarboxamide 4-({[(2S,4EZ)-1-([1,1'-biphenyl]-4-ylcarbonyl)-4-(methoxyimino)pyrrolidinyl]-carbonyl}amino)butanoic acid (2S,4EZ)-N-[(2S)-2-hydroxy-2-phenylethyl]-1-[(2'-methoxy[1,1'-biphenyl]-4-yl)carbonyl]-4-(methoxyimino)-2-pyrrolidinecarboxamide (2S,4EZ)-N-[(2RS)-2-hydroxy-2-(2-naphthyl)ethyl]-1-[(2'-methoxy[1,1'-biphenyl]-4-yl)carbonyl]-4-(methoxyimino)-2-pyrrolidinecarboxamide (2S,4EZ)-N-[(1RS)-2-hydroxy-1-methylethyl]-4-(methoxyimino)-1-[(2'-methyl[1,1-biphenyl]-4-yl)carbonyl]-2-pyrrolidinecarboxamide (2S,4EZ)-N-[(1S,2S)-2-hydroxy-1-(hydroxymethyl)-2-(4-nitrophenyl)ethyl]-4-(methoxyimino)-1-[(2'-methyl[1,1'-biphenyl]-4-yl)carbonyl]-2-pyrrolidinecarboxamide (2S,4EZ)-N-[(1S,2S)-2-hydroxy-1-(hydroxymethyl)-2-(4-nitrophenyl)ethyl]-4-(methoxyimino)-1-[(2'-methoxy[1,1'-biphenyl]-4-yl)carbonyl]-2-pyrrolidinecarboxamide (2S,4EZ)-N-[(1S,2S,3R,4R)-3-(aminocarbonyl)bicyclo[2.2.1]hept-5-en-2-yl]-4-(methoxyimino)-1-[(2'-methyl[1,1'-biphenyl]-4-yl)carbonyl]-2-pyrrolidinecarboxamide (2S,4EZ)-N-[(2RS)-2-hydroxy-2-phenylethyl]-1-[(2'-methoxy[1,1'-biphenyl]-4-yl)carbonyl]-4-(methoxyimino)-2-pyrrolidinecarboxamide (2S,4EZ)-N-[(2RS)-2-hydroxypropyl]-4-(methoxyimino)-1-[(2'-methyl[1,1'-biphenyl]-4-yl)carbonyl]-2-pyrrolidinecarboxamide (2S,4EZ)-N-[(2RS)-2,3-dihydroxypropyl]-4-(methoxyimino)-1-[(2'-methyl[1,1'-biphenyl]-4-yl)carbonyl]-2-pyrrolidinecarboxamide (2S,4EZ)-N-(3-hydroxypropyl)-4-(methoxyimino)-1-[(2'-methyl[1,1'-biphenyl]-4-yl) carbonyl]-2-pyrrolidinecarboxamide (2S,4EZ)-N-(2-amino-2-oxyethyl)-1-([1,1'-biphenyl]-4-ylcarbonyl)-4-(methoxyimino)-2-pyrrolidinecarboxamide (2S,4EZ)-N-(2-amino-2-oxyethyl)-4-(methoxyimino)-1-[(2'-methyl[1,1'-biphenyl]-4-yl)carbonyl]-2-pyrrolidinecarboxamide (2S,4EZ)-1-([1,1'-biphenyl]-4-ylcarbonyl)-N-[(2RS)-2-hydroxy-2-(3-hydroxyphenyl)ethyl]-4-(methoxyimino)-2-pyrrolidinecarboxamide (2S,4EZ)-1-([1,1'-biphenyl]-4-ylcarbonyl)-N-[(1S,2R,3S,4R)-3-(hydroxymethyl)bicyclo[2.2.1]hept-2-yl]-4-(methoxyimino)-2-pyrrolidinecarboxamide (2S,4EZ)-N-](1R,2S,3R,4S)-3-(hydroxymethyl)bicyclo[2.2.1]hept-2-yl]-1-[(2'-methoxy[1,1'-biphenyl]-4-yl) carbonyl]-4-(methoxyimino)-2-pyrrolidinecarboxamide (2S,4EZ)-N-(trans-4-hydroxycyclohexyl)-1-[(2'-methoxy[1,1'-biphenyl]-4-yl)carbonyl]-4-(methoxyimino)-2-pyrrolidinecarboxamide (2S,4EZ)-N-[(1R,2R)-2-(hydroxymethyl)cyclohexyl]-1-[(2'-methoxy[1,1'-biphenyl]-4-yl)carbonyl]-4-(methoxyimino)-2-pyrrolidinecarboxamide (2S,4EZ)-N-[(2RS)-2-hydroxy-3-phenoxypropyl]-4-(methoxyimino)-1-[(2'-methyl[1,1'-biphenyl]-4-yl)carbonyl]-2-pyrrolidinecarboxamide (2S,4EZ)-N-[(2RS)-2-hydroxy-2-(4-hydroxyphenyl) ethyl]-4-(methoxyimino)-1-[(2'-methyl[1,1'-biphenyl]-4-yl) carbonyl]-2-pyrrolidinecarboxamide (2S,4EZ)-N-[(2RS)-2-hydroxy-2-(4-hydroxyphenyl) ethyl]-4-(methoxyimino)-1-[(2'-methoxy[1,1'-biphenyl]-4-yl) carbonyl]-2-pyrrolidinecarboxamide (2S,4EZ)-N-[(2RS)-2-hydroxy-2-(4-hydroxy-3-methoxyphenyl)ethyl]-1-[(2'-methyl[1,1'-biphenyl]-4-yl)carbonyl]-4-(methoxyimino)-2-pyrrolidinecarboxamide (2S,4EZ)-N-[(2RS)-2-hydroxy-2-(4-hydroxy-3-methoxyphenyl)ethyl]-1-[(2'-methoxy[1,1'-biphenyl]-4-yl)carbonyl]-4-(methoxyimino)-2-pyrrolidinecarboxamide (2S,4EZ)-N-[(2RS)-2-(3,4-dihydroxyphenyl)-2-hydroxyethyl]-1-[(2'-methoxy[1,1'-biphenyl]-4-yl)carbonyl]-4-(methoxyimino)-2-pyrrolidinecarboxamide (2R,4EZ)-1-([1,1'-biphenyl]-4-ylcarbonyl)-N-[(2RS)-2-hydroxy-2-phenylethyl]-4-(methoxyimino)-2-pyrrolidinecarboxamide (2R,4EZ)-N-[(2RS)-2-hydroxy-2-phenylethyl]-4-(methoxyimino)-1-[(2'-methyl[1,1'-biphenyl]-4-yl)carbonyl]-2-pyrrolidinecarboxamide (2S,4EZ)-1-[(2'-cyano[1,1'-biphenyl]-4-yl)carbonyl]-N-[(2RS)-2-hydroxy-2-phenylethyl]-4-(methoxyimino)-2-pyrrolidinecarboxamide (2S,4EZ)-1-[(3',4'-dichloro[1,1'-biphenyl]-4-yl)carbonyl]-N-[(2RS)-2-hydroxy-2-phenylethyl]-4-(methoxyimino)-2-pyrrolidinecarboxamide (2S,4EZ)-1-[(2',6'-dimethyl[1,1'-biphenyl]-4-yl)carbonyl]-N-[(2RS)-2-hydroxy-2-phenylethyl]-4-(methoxyimnino)-2-pyrrolidinecarboxamide (2S,4EZ)-1-[(2',3-dimethyl[1,1'-biphenyl]-4-yl)carbonyl]-N-[(2RS)-2-hydroxy-2-phenylethyl]-4-(methoxyimino)-2-pyrrolidinecarboxamide (2S,4EZ)-N-[(2RS)-2-hydroxy-2-(3-hydroxyphenyl) ethyl]-4-(methoxyimino)-1-[(2'-methyl[1,1'-biphenyl]-4-yl)carbonyl]-2-pyrrolidinecarboxamide (2S,4EZ)-N-[(2RS)-2-hydroxy-2-(3-hydroxyphenyl) ethyl]-4-(methoxyimino)-1-[(2'-cyano[1,1'-biphenyl]-4-yl) carbonyl]-2-pyrrolidinecarboxamide (2S,4EZ)-N-[(2RS)-2-hydroxy-2-(3-hydroxyphenyl) ethyl]-4-(methoxyimino)-1-[(3',4'-dichloro[1,1'-biphenyl]-4-yl)carbonyl]-2-pyrrolidinecarboxamide (2S,4EZ) N-[(2RS)-2-hydroxy-2-(3-hydroxyphenyl) ethyl]-4-(methoxyimino)-1-[(2',6'-dimethyl[1,1'-biphenyl]-4-yl)carbonyl]-2-pyrrolidinecarboxamide (2S,4EZ)-N-[(2RS)-2-hydroxy-2-(3-hydroxyphenyl) ethyl]-4-(methoxyimino)-1-[(2',3-dimethyl[1,1'-biphenyl]-4-yl)carbonyl]-2-pyrrolidinecarboxamide (2S,4EZ)-1-[(3',4'-dichloro[1,1'-biphenyl]-4-yl)carbonyl]-N-[(2RS)-2-hydroxy-2-(4-hydroxyphenyl)ethyl]-4-(methoxyimino)-2-pyrrolidinecarboxamide (2S,4EZ)-1-[(2',6'-dimethyl[1,1'-biphenyl]-4-yl)carbonyl]-N-[(2RS)-2-hydroxy-2-(4-hydroxyphenyl)ethyl]-4-(methoxyimino)-2-pyrrolidinecarboxamide (2S,4EZ)-1-[(2',3-dimethyl[1,1'-biphenyl]-4-yl)carbonyl]-N-[(2RS)-2-hydroxy-2-(4-hydroxyphenyl)ethyl]-4-(methoxyimino)-2-pyrrolidinecarboxamide (2S,4EZ)-1-[(2',6'-dimethyl[1,1'-biphenyl]-4-yl)carbonyl]N-[(2RS)-2-hydroxy-3-(4-methoxyphenoxy)propyl]-4-(methoxyimino)-2-pyrrolidinecarboxamide (2S,4EZ)-1-[(2',3-dimethyl[1,1'-biphenyl]-4-yl)carbonyl]-N-[(2RS)-2-hydroxy-3-(4-methoxyphenoxy)propyl]-4-(methoxyimino)-2-pyrrolidinecarboxamide (2S,4EZ)-N-(2-amino-2-oxyethyl)-1-[(2',6'-dimethyl[1,1'-biphenyl]-4-yl)carbonyl]-4-(methoxyimino)-2-pyrrolidinecarboxamide (2S,4EZ)-N-(2-amino-2-oxyethyl)-1-[(2',3-dimethyl[1,1'-biphenyl]-4-yl)carbonyl]-4-(methoxyimino)-2-pyrrolidinecarboxamide (2S,4EZ)-N-(3-amino-3-oxopropyl)-1-[(2',6'-dimethyl[1,1'-biphenyl]-4-yl)carbonyl]-4-(methoxyimino)-2-pyrrolidinecarboxamide (2S,4EZ)-N-(3-amino-3-oxopropyl)-1-[(2',3-dimethyl[1,1'-biphenyl]-4-yl)carbonyl]-4-(methoxyimino)-2-pyrrolidinecarboxamide (2S,4EZ)-1-[(2',6'-dimethyl[1,1'-biphenyl]-4-yl)carbonyl]-N-[2-hydroxy-1-(hydroxymethyl)ethyl]-4-(methoxyimino)-2-pyrrolidinecarboxamide (2S,4EZ)-1-[(2',3-dimethyl[1,1'-biphenyl]-4-yl)carbonyl]-N-[2-hydroxy-1-(hydroxymethyl)ethyl]-4-(methoxyimino)-2-pyrrolidinecarboxamide (2S,4EZ)-1-[(2'-cyano[1,1'-biphenyl]-4-yl)carbonyl]-N-[(1R,2R)-2-(hydroxymethyl)cyclohexyl]-4-(methoxyimino)-2-pyrrolidinecarboxamide (2S,4EZ)-N-[(1R)-2-hydroxy-1-phenylethyl]-4-(methoxyimino)-1-[(2'-methyl[1,1'-biphenyl]-4-yl)carbonyl]-2-pyrrolidinecarboxamide (2S,4EZ)-1-[(2',6'-dimethyl[1,1'-biphenyl]-4-yl)carbonyl]-N-[2-(4-hydroxyphenyl)ethyl]-4-(methoxyimino)-2-pyrrolidinecarboxamide (2S,4EZ)-1-[(2',3-dimethyl[1,1'-biphenyl]-4-yl)carbonyl] N-[2-(4-hydroxyphenyl)ethyl]-4-(methoxyimino)-2-pyrrolidinecarboxamide (2S,4EZ)-1-[(2',6'-dimethyl[1,1'-biphenyl]-4-yl)carbonyl]-N-[2-(3-hydroxyphenyl)ethyl]-4-(methoxyimino)-2-pyrrolidinecarboxamide (2S,4EZ)-1-[(2',3-dimethyl[1,1'-biphenyl]-4-yl)carbonyl]-N-[2-(3-hydroxyphenyl)ethyl]-4-(methoxyimino)-2-pyrrolidinecarboxamide (2S,4EZ)-1-[(2',3-dimethyl[1,1'-biphenyl]-4-yl)carbonyl]-N-[(1R,2S)-2-hydroxy-1,2-diphenylmethyl]-4-(methoxyimino)-2-pyrrolidinecarboxamide (2RS)-2-[({(2S,4EZ)-4-(methoxyimino)-1-[(2'-methyl[1,1'-biphenyl]-4-yl)carbonyl]pyrrolidinyl}carbonyl) amino]-3-phenylpropanoil acid (2S,4EZ)-N-[(1R,2S)-2-(aminocarbonyl)cyclohexyl]-1-[(2',6'-dimethyl[1,1'-bipheriyl]-4-yl)carbonyl]-4-(methoxyimino)-2-pyrrolidinecarboxamide (2S,4EZ)-N-[(1R,2S)-2-(aminocarbonyl)cyclohexyl]-1-[(2',3-dimethyl[1,1'-biphenyl]-4-yl)carbonyl]-4-(methoxyimino)-2-pyrrolidinecarboxamide (2S,4EZ)-4-(methoxyimino)-1-[(2'-methyl[1,1'-biphenyl]-4-yl)carbonyl]-2-pyrrolidinecarboxamide (2S,4EZ)-4-(methoxyimino)-N-methyl-1-[(2'-methyl[1,1'-biphenyl]-4-yl)carbonyl]-2-pyrrolidinecarboxamide (2S,4EZ)-4-(methoxyimino)-N,N-dimethyl-1-[(2'-methyl [1,1'-biphenyl]-4-yl)carbonyl]-2-pyrrolidinecarboxamide (2S,4EZ)-N-[(3R)-3-hydroxy-3-phenylpropyl]-4-(methoxyimino)-1-[(2'-methyl[1,1'-biphenyl]-4-yl)carbonyl]-2-pyrrolidinecarboxamide (2S,4EZ)-N-[(3S)-3-hydroxy-3-phenylpropyl]-4-(methoxyimino)-1-[(2'-methyl[1,1'-biphenyl]-4-yl)carbonyl]-2-pyrrolidinecarboxamide (2S,4EZ)-1-([1,1'-biphenyl]-4-ylcarbonyl)-N-[(3R)-3-hydroxy-3-phenylpropyl]-4-(methoxyimino)-2-pyrrolidinecarboxamide (2S,4EZ)-1-([1,1'-biphenyl]-4-ylcarbonyl)-N-[(3S)-3-hydroxy-3-phenylpropyl]-4-(methoxyimino)-2-pyrrolidinecarboxamide (2S,4EZ)-N-[(2S)-2-hydroxy-2-phenylethyl]-4-(methoxyimino)-1-{[2'-(trifluoromethyl)[1,1'-biphenyl]-4-yl]carbonyl}-2-pyrrolidinecarboxamide (2S,4EZ)-N-[(2S)-2-hydroxy-2-phenylethyl]-4-(methoxyimino)-1-{[2'-chloro[1,1'-biphenyl]-4-yl]carbonyl}-2-pyrrolidinecarboxamide (2S,4EZ)-N-(2-hydroxyphenyl)-4-(methoxyimino)-1-[(2'-methyl[1,1'-biphenyl]-4-yl)carbonyl]-2-pyrrolidinecarboxamide (2S,4EZ)-N-[2-(hydroxymethyl)phenyl]-4-(methoxyimino)-1-[(2'-methyl[1,1'-biphenyl]-4-yl)carbonyl]-2-pyrrolidinecarboxamide (2S,4EZ)-N-[(2S)-2-hydroxy-2-phenylethyl]-4-(methoxyimino)-1-[(2-methyl[1,1'-biphenyl]-4-yl)carbonyl]-2-pyrrolidinecarboxamide (2S,4E and 4Z)-1-([1,1'-biphenyl]-4-ylcarbonyl)-N-[(2S)-2-hydroxy-2-phenylethyl]-4-(methoxyimino)-2-pyrrolidinecarboxamide, and (2S,4EZ)-4-(methoxyimino)-1-[(2'-methyl[1,1'-biphenyl]-4-yl)carbonyl]-N-(2-phenylethyl)-2-pyrrolidinecarboxamide.

21. A pyrrolidine compound according to claim 1, selected from the following group:

(2S,4EZ)-1-([1,1'-biphenyl]-4-ylcarbonyl)-N-(2-hydroxyethyl)-4-(methoxyimino)-2-pyrrolidinecarboxamide (2S,4EZ)-1-([1,1'-biphenyl]-4-ylcarbonyl)-N-[(2RS)-2-hydroxy-2-phenylethyl]-4-(methoxyimino)-2-pyrrolidinecarboxamide (2S,4Z)-N-[(2S)-2-hydroxy-2-phenylethyl]-4-(methoxyimino)-1-[(2'-methyl[1,1'-biphenyl]-4-yl)carbonyl]-2-pyrrolidinecarboxamide, and (2S,4E)-N-[(2S)-2-hydroxy-2-phenylethyl]-4-(methoxyimino)-1-[(2'-methyl[1,1'-biphenyl]-4-yl)carbonyl]-2-pyrrolidinecarboxamide.

* * * * *